US007427616B2

(12) United States Patent
Luke et al.

(10) Patent No.: US 7,427,616 B2
(45) Date of Patent: Sep. 23, 2008

(54) CONDENSED PYRIDINES AND PYRIMIDINES WITH TIE2 (TEK) ACTIVITY

(75) Inventors: Richard William Arthur Luke, Macclesfield (GB); Clifford David Jones, Macclesfield (GB); William McCoull, Macclesfield (GB); Barry Raymond Hayter, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 436 days.

(21) Appl. No.: 10/523,401

(22) PCT Filed: Aug. 1, 2003

(86) PCT No.: PCT/GB03/03275

§ 371 (c)(1),
(2), (4) Date: Feb. 3, 2005

(87) PCT Pub. No.: WO2004/013141

PCT Pub. Date: Feb. 12, 2004

(65) Prior Publication Data

US 2005/0256140 A1    Nov. 17, 2005

(30) Foreign Application Priority Data

Aug. 6, 2002   (GB) ................................. 0218168.3
May 30, 2003   (GB) ................................. 0312356.9

(51) Int. Cl.
C07D 473/34 (2006.01)
C07D 513/04 (2006.01)
C07D 498/04 (2006.01)
C07D 495/04 (2006.01)
C07D 491/04 (2006.01)
C07D 487/04 (2006.01)
A61K 31/519 (2006.01)

(52) U.S. Cl. ............... 514/230.5; 514/233.8; 514/234.2; 514/234.8; 514/257; 514/260.1; 514/263.2; 514/265.1; 544/105; 544/116; 544/117; 544/255; 544/264; 544/266; 544/280

(58) Field of Classification Search ................. 544/105, 544/116, 117, 255, 264, 266, 280; 514/230.5, 514/233.8, 234.2, 234.8, 257, 260.1, 263.2, 514/265.1

See application file for complete search history.

(56) References Cited

U.S. PATENT DOCUMENTS

| 5,958,930 | A | 9/1999 | Gangjee |
| 6,169,091 | B1 | 1/2001 | Cockerill et al. |
| 6,492,383 | B1 | 12/2002 | Munchhof et al. |
| 2002/0068721 | A1 | 6/2002 | Weigele et al. |
| 2002/0091116 | A1 | 7/2002 | Zhu et al. |

FOREIGN PATENT DOCUMENTS

| DE | 287 503 A5 | 2/1991 |
| EP | 0 447 891 B1 | 4/1994 |
| EP | 0 716 855 A2 | 6/1996 |
| EP | 0 716 855 A3 | 6/1996 |
| JP | 2002/105081 A | 4/2002 |
| WO | WO 95/10513 A1 | 4/1995 |
| WO | WO 97/12615 A1 | 4/1997 |
| WO | WO 97/49706 | 12/1997 |
| WO | WO 98/07835 A2 | 2/1998 |
| WO | WO 98/07835 A3 | 2/1998 |
| WO | WO 98/41525 A1 | 9/1998 |
| WO | WO 99/24440 A1 | 5/1999 |
| WO | WO 99/58523 A1 | 11/1999 |
| WO | WO 99/62908 A2 | 12/1999 |
| WO | WO 99/62908 A3 | 12/1999 |
| WO | WO 00/09511 A1 | 2/2000 |
| WO | WO 00/17202 A1 | 3/2000 |
| WO | WO 00/17203 A1 | 3/2000 |
| WO | WO 00/44728 A1 | 8/2000 |
| WO | WO 00/59449 A2 | 10/2000 |
| WO | WO 00/59902 A2 | 10/2000 |
| WO | WO 00/69861 A1 | 11/2000 |
| WO | WO 00/75145 A1 | 12/2000 |
| WO | 01/19829 A | 3/2001 |
| WO | WO 01/19798 A2 | 3/2001 |
| WO | WO 01/19798 A3 | 3/2001 |
| WO | WO 01/19828 A2 | 3/2001 |
| WO | WO 01/19828 A3 | 3/2001 |
| WO | WO 01/25242 A1 | 4/2001 |
| WO | WO 01/37835 A1 | 5/2001 |
| WO | WO 01/44259 A1 | 6/2001 |
| WO | WO 01/47883 A1 | 7/2001 |
| WO | WO 01/49688 A1 | 7/2001 |
| WO | WO 01/58907 A1 | 8/2001 |
| WO | WO 01/72751 A1 | 10/2001 |
| WO | WO 01/72778 A2 | 10/2001 |
| WO | WO 01/72778 A3 | 10/2001 |
| WO | WO 02/00651 A2 | 1/2002 |
| WO | WO 02/00651 A3 | 1/2002 |
| WO | WO 02/20734 A2 | 3/2002 |
| WO | WO 02/20734 A3 | 3/2002 |
| WO | WO 02/39956 A2 | 5/2002 |
| WO | WO 02/39956 A3 | 5/2002 |

(Continued)

OTHER PUBLICATIONS

Sun, Li 'Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases' *J Med Chem* vol. 42, pp. 5120-5130, 1999.

*Primary Examiner*—Bruck Kifle

(57) ABSTRACT

A compound of the Formula (I), wherein A together with the carbon atoms to which it is attached forms a fused 5-membered heteroaryl ring, wherein said heteroaryl ring contains 1 or 2 heteroatoms selected from O, N and S, and wherein the 5-membered ring containing G is linked to the ring formed by A in the meta position to the bridgehead carbon marked # in Formula (I): G is selected from O, S and $NR^5$; Z is selected from N and $CR^6$; $Q^1$ is selected from optionally substituted aryl and heteroaryl, and the substituents $R^1$ to $R^6$ are as defined in the text for use in the production of an anti-angiogenic effect in a warm blooded animal such as man.

18 Claims, No Drawings

FOREIGN PATENT DOCUMENTS

| | | |
|---|---|---|
| WO | WO 02/44156 A2 | 6/2002 |
| WO | WO 02/44156 A3 | 6/2002 |
| WO | WO 02/076986 A1 | 10/2002 |
| WO | WO 02/080926 A1 | 10/2002 |
| WO | WO 02/083693 A1 | 10/2002 |
| WO | WO 02/085909 A1 | 10/2002 |
| WO | WO 03/000187 A2 | 1/2003 |
| WO | WO 03/000187 A3 | 1/2003 |
| WO | WO 03/000194 A2 | 1/2003 |
| WO | WO 03/000194 A3 | 1/2003 |
| WO | WO 03/011868 A1 | 2/2003 |
| WO | WO 03/022852 A2 | 3/2003 |
| WO | WO 03/022852 A3 | 3/2003 |
| WO | WO 03/027093 A1 | 4/2003 |
| WO | WO 03/035065 A1 | 5/2003 |
| WO | WO 03/055860 A1 | 7/2003 |
| WO | WO 03/070729 A1 | 8/2003 |
| WO | WO 03/074530 A1 | 9/2003 |

CONDENSED PYRIDINES AND PYRIMIDINES WITH TIE2 (TEK) ACTIVITY

This invention relates to compounds, or pharmaceutically acceptable salts thereof, which possess anti-angiogentic activity and are accordingly useful in methods of treatment of disease states associated with angiogenesis in the animal or human body. The invention also concerns processes for the preparation of the compounds, pharmaceutical compositions containing the compounds as active ingredient, and methods for the use of the compounds in the manufacture of medicaments for use in the production of anti-angiogenic effects in warm-blooded animals such as humans.

The Tie2 receptor tyrosine kinase (also known as TEK) is expressed predominantly in endothelial and haematopoietic cells and is essential for vessel formation and maintenance (Jones, N. et al. Nature Reviews Molecular Cell Biology. 2001: 2, 257-67).

Angiogenesis is a fundamental process defined as the generation of new blood vessels from existing vasculature. It is a vital yet complex biological process required for the formation and physiological functions of virtually all the organs. Normally it is transient in nature and is controlled by the local balance of angiogenic and angiostatic factors in a multi-step process involving vessel sprouting, branching and tubule formation by endothelial cells (involving processes such as activation of endothelial cells (ECs), vessel destabilisation, synthesis and release of degradative enzymes, EC migration, EC proliferation, EC organisation and differentiation and vessel maturation).

Normal angiogenesis plays an important role in a variety of processes and is under stringent control. In the adult, physiological angiogenesis is largely confined to wound healing and several components of female reproductive function and embryonic development. In undesirable or pathological angiogenesis, the local balance between angiogenic and angiostatic factors is dysregulated leading to inappropriate and/or structurally abnormal blood vessel formation. Pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacology. Science. 16: 57-66; Folkman, 1995, Nature Medicine 1: 27-31). In cancer, growth of primary and secondary tumours beyond 1-2 $mm^3$ requires angiogenesis (Folkman, J. New England Journal of Medicine 1995; 33, 1757-1763).

In diseases such as cancer in which progression is dependant on aberrant angiogenesis, blocking the process can lead to prevention of disease advancement (Folkman, J. 1995, Nature Medicine. 1: 27-31). Many factors are described in the scientific literature that are believed to play important critical roles in the regulation of angiogenesis. Two major classes of angiogenic factors are the vascular endothelial growth factor (VEGF) and the angiopoietins. These polypeptide moieties interact with their respective receptors (transmembrane tyrosine kinases which are predominantly endothelial cell specific) and induce cellular responses via ligand mediated signal transduction. It has been speculated that VEGF and the angiopoietins co-operate to regulate various aspects of the angiogenic process during both normal and pathological angiogenesis via signalling through their respective receptors.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 999-991; Terman et al, 1992, Biochem. Biophys. Res. Comm. 1992, 187:1579-1586). Binding of VEGF to these receptors expressed in heterologous cells has been associated with changes in the tyrosine phosphorylation status of cellular proteins and calcium fluxes.

Recently a second family of predominantly endothelial cell specific receptors that regulate vessel destabilisation and maturation have been identified. The Tie receptors and their ligands, the angiopoietins, co-operate closely with VEGF during both normal and pathological angiogenesis. The transmembrane receptors Tie1 and Tie2, constitute a family of endothelial cell specific tyrosine kinase receptors involved in maintenance of blood vessel integrity and which are involved in angiogenic outgrowth and vessel remodelling. Structurally Tie1 and Tie2 share a number of features (e.g. the intracellular domains of both these receptors each contain a tyrosine kinase domain interrupted by a kinase insert region) and thus constitute a distinct RTK subfamily. Overall sequence identity between Tie1 and Tie2 receptors at the amino acid level is 44% while their intracellular domains exhibit 76% homology. Targeted disruption of the Tie1 gene results in a lethal phenotype characterised by extensive haemorrhage and poor microvessel integrity (Puri, M. et al. 1995 EMBO Journal:14: 5884-5891). Transgenic mice deficient in Tie2 display defects in vessel sprouting and remodelling and display a lethal phenotype in mid gestation (E9.5-10.5) caused by severe defects in embryonic vasculature (Sato, T. et al. 1995 Nature 370: 70-74).

To date no ligands have been identified for Tie1 and little is known regarding its signalling abilities. However, Tie1 is believed to influence Tie2 signalling via heterodimerisation with the Tie2 receptor (hence potentially modulating the ability of Tie2 to autophosphorylate (Marron, M. et al. 2000 Journal of Biological Chemistry: 275, 39741-39746) and recent chimaeric Tie1 receptor studies have indicated that Tie-1 may inhibit apoptosis via the PI 3 kinase/Akt signal transduction pathway (Kontos, C. D., et al., 2002 Molecular and Cellular Biology: 22, 1704-1713). In contrast, a number of ligands, designated the angiopoietins have been identified for Tie2 of which Angiopoietin 1 (Ang1) is the best characterised. Binding of Ang1 induces tyrosine phosphorylation of the Tie2 receptor via autophosphorylation and subsequently activation of its signalling pathways via signal transduction. Ang2 has been reported to antagonise these effects in endothelial cells (Maisonpierre, P. et al. 1997 Science:277, 55-60). The knock-out-and transgenic manipulation of Tie2 and its ligands suggest that stringent spatial and temporal control of Tie2 signalling is imperative for the correct development of new vasculature. There are also reports of at least another two ligands (Ang3 and Ang4) as well as the possibility of heterodimerisation between the angiopoietin ligands that has the potential to modify their activity (agonistic/antagonistic) on association with the receptor. Activation of the Tie2 receptor by Ang1 inhibits apoptosis (Papapetropoulos, A., et al., 2000 Journal of Biological Chemistry: 275 9102-9105), promotes sprouting in vascular endothelial cells (Witzenbicher, B., et al., 1998 Journal of Biological Chemistry: 273, 18514-18521) and in vivo promotes blood vessel maturation during angiogenesis and reduces the permeability and consequent leakage from adult microvessels (Thurston, G. et al., 2000 Nature Medicine: 6, 460-463). Thus activated Tie2 receptor is reported to be involved in the branching sprouting and outgrowth of new vessels and recruitment and interaction of periendothelial support cells important in maintaining vessel integrity and overall appears to be consistent with promoting microvessel stability. Absence of Tie2 activation or inhibition of Tie2 auto phosphorylation may lead to a loss of vascular structure and matrix/cell contacts (Brindle, N., in press, 2002) and in turn may trigger endothelial cell death, especially in the absence of survival or growth stimuli. On the basis of the above reported effects due to Tie2 kinase activity, inhibiting Tie2 kinase may provide an anti-angiogenic effect and thus have application in the therapy of disease states associated with pathological angiogenesis. Tie2 expression has been shown to be up-regulated in the neovasculature of a variety of tumours (e.g. Peters, K. G. et al, (British Joural of Cancer 1998; 77,51-56) suggesting that inhibiting Tie2 kinase activity will result in anti-angiogenic activity. In support of this hypothesis, studies with soluble Tie2 receptor (extracellular domain) (Pengnian, L. et al., 1997, Journal of Clinical Investigation 1997: 100, 2072-2078 and Pengnian, L. et al., 1998, Proceedings of the National Academy of Sciences 1998: 95, 8829-8834) have shown anti-tumour activity in in vivo tumour models. In addition these experiments also indicate that disruption of the Tie2 signalling pathways in a normal healthy individual may be well tolerated as no adverse toxicities were observed in these studies.

Examination of human primary breast cancer samples and human and murine breast cancer cell lines (Stratmann, A., et al., 2001, International Journal of Cancer: 91,273-282) indicate that Tie2 dependant pathways of tumour angiogenesis may exist alongside KDR dependant pathways and, in fact, may operate both independently (Siemeister G., et al., 1999 Cancer Research: 59,3185-3191) as well as in concert with each other (e.g. VEGF A and Ang1 reported to collaborate to induce angiogenesis and produce non-leaky mature vessels Thurston, G, et al., 1999 Science: 286,2511-2514). It is quite possible that a mix of such angiogenic processes even exist within a single tumour.

Tie2 has also been shown to play a role in the vascular abnormality called venous malformation (VM) (Mulliken, J. B. & Young, A. E. 1998, Vascular Birthmarks: W. B. Saunders, Philadelphia). Such defects can either be inherited or can arise sporadically. VM's are commonly found in the skin or mucosal membranes but can affect any organ. Typically lesions appear as a spongy, blue to purple vascular masses composed of numerous dilated vascular channels lined by endothelial cells. Among the inherited forms of this disease the most common defect appears to be a Tie2 kinase mutation C2545T in the Tie2 coding sequence (Calvert, J. T., et al., 1999 Human Molecular genetics: 8, 1279-1289), which produces a R849W amino acid substitution in the kinase domain. Analysis of this Tie2 mutant indicates that it is constitutively activated even in the absence of ligand (Vikkula, M., et al., 1996 Cell: 87,1181-1190).

Upregulation of Tie2 expression has also been found within the vascular synovial pannus of arthritic joints in humans, which is consistent with the role of inappropriate neovascularisation.

Such examples provide further indications that inhibition of Tie2 phosphorylation and subsequent signal transduction will be useful in treating disorders and other occurrences of inappropriate neovascularisation. To date only a few inhibitors of Tie2 are known in the art. There is thus a need to identify additional Tie2 inhibitors that could exploit the full therapeutic potential of inhibiting/modulating the Tie2 signalling pathways.

Co-pending application WO03/035065 discloses benzimidazoles and analogues having Tie2 activity. Co-pending application WO 03/00194 discloses thienopyridines and thienopyrimidines that are inhibitors of KDR/VEGF and of the erbB family of protein tyrosine kinsases such as EGFR, erbB2 HER3 or HER4 and. Co-pending application WO03/22852 discloses furo- and thienopyrimidine derivatives which are useful as Tie2 and/or VEGFR2 Inhibitors. WO95/10513 and EP 716855 disclose that benzothiophenes and related compounds as estrogen agonists. WO97/12615 discloses benziridazbles derivatives that are 15-lipoxygenase inhibitors. WO00/17202, WO00/17203 and WO 01/72751 disclose pyrrolopyrimidines which are inhibitors of serine/threonine and tyrosine kinase activity. WO99/62908 and WO00/75145 disclose thienopyridines and thienopyrimidines that are cell adhesion-inhibiting antiinflammatory compounds. WO 00/59449 and WO 01/49688 disclose purine derivatives. EP 1162196 and US 2003/0050320 disclose benzimidazoles and related ring systems which have anti-hepatitis C virus activity. JP 2002/105081 discloses thienopyrimidines and related compounds which are TNF alpha inhibitors. WO 00/59902 discloses aryl sulphonyl compounds which are Factor X Inhibitors. US 2002/0091116 and WO 01/19798 disclose benzothienylpyrazoles that are Factor X inhibitors.

We have found that certain compounds possess inhibitory activity for the Tie2 receptor tyrosine kinase and accordingly have value in the treatment of disease states associated with pathological angiogenesis such as cancer, rheumatoid arthritis, and other diseases where active angiogenesis is undesirable.

According, to a first aspect of the present invention there is provided a compound of the Formula I:

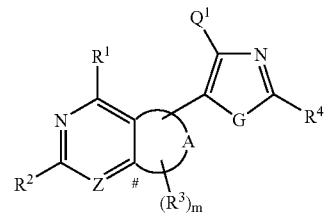

Formula I wherein:
A together with the carbon atoms to which it is attached forms a fused 5-membered heteroaryl ring, wherein said heteroaryl ring contains 1 or 2 heteroatoms selected from O, N and S,
and wherein the 5-membered ring containing G is linked to the ring formed by A in the meta position to the bridgehead carbon marked # in Formula I;
G is selected from O, S and $NR^5$;
Z is selected from N and $CR^6$;
$Q^1$ is selected from aryl and heteroaryl,
and wherein $Q^1$ is optionally substituted by one or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, 3-(1-6C)alkylureido, (1-6C)alkoxycarbonylamino from a group of the formula:

$$-X^1-R^7$$

wherein $X^1$ is a direct bond or is selected from O and N($R^8$), wherein $R^8$ is hydrogen or (1-6C)alkyl, and $R^7$ is halogeno-(1-6C)alkyl, hydroxy-(1-6C)alkyl, (1-6C)alkoxy-(1-6C)alkyl, cyano-(1-6C)alkyl, amino(1-6C)alkyl, (1-6C)alkylamino-(1-6C)alkyl or di-[(1-6C)alkyl]amino-(1-6C)alkyl, and from a group of the formula:

$$-X^2-Q^2$$

wherein $X^2$ is a direct bond or is selected from O, S, SO, $SO_2$, N($R^9$), CO, CH(O$R^9$), CON($R^9$), N($R^9$)CO, N($R^9$)CON (R), $SO_2$N($R^9$), N($R^9$)$SO_2$, C($R^9$)$_2$O, C($R^9$)$_2$S and N($R^9$)C($R^9$)$_2$, wherein $R^9$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1, 2 or 3 substituents, which may be the same or different, selected from trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$-X^3-R^{10}$$

wherein $X^3$ is a direct bond or is selected from O and N($R^{11}$), wherein $R^{11}$ is hydrogen or (1-6C)alkyl, and $R^{10}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino(1-6C)alkyl, and any heterocyclyl group within $Q^2$ optionally bears 1 or 2 oxo or thioxo substituents;

$R^1$ is selected from hydrogen, halogeno, trifluoromethyl, trifluoromethoxy, cyano, nitro, hydroxy, amino, mercapto, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, $R^2$ is selected from hydrogen, amino, hydroxy, halogeno, (1-6C)alkyl, (1-6C)alkoxy, formyl, (1-6C)alkylamino and di-[(1-6C)alkyl]amino;

$R^3$ is, independently, as defined for $R^4$ and $R^6$, provided that $R^3$ is not hydrogen, and when $R^3$ is attached to a nitrogen atom in A, $R^3$ is not halogeno;

$R^5$ is, independently, as defined for $R^4$ and $R^6$, provided that R is not halogeno;

$R^4$ and $R^6$ which may be the same or different, are selected from hydrogen, halogeno, trifluoromethyl, trifluoromethoxy, cyano, isocyano, nitro, hydroxy, mercapto, amino, formyl, carboxy, carbamoyl, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$Q^4\text{-}X^5-$$

wherein $X^5$ is a direct bond or is selected from O, S, SO, $SO_2$, N($R^{12}$), CO, CH(O$R^{12}$), CON($R^{12}$), N($R^{12}$)CO, $SO_2$N ($R^{12}$), N($R^{12}$)$SO_2$, OC($R^{12}$)$_2$, SC($R^2$)$_2$ and N($R^{12}$)C($R^{12}$)$_2$, wherein $R^{12}$ is hydrogen or (1-6C)alkyl, and $Q^4$ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^3$, $R^4$, $R^5$ or $R^6$ substituent are optionally separated by the insertion into the chain of a group selected from O, S, SO, $SO_2$, N($R^{13}$), CO, CH(O$R^{13}$), CON($R^{13}$), N($R^{13}$)CO, $SO_2$N($R^{13}$), N($R^{13}$)$SO_2$, CH=CH and C≡C wherein $R^{13}$ is hydrogen or (1-6C)alkyl, and wherein any $CH_2$=CH— or HC≡C— group within a $R^3$, $R^4$, $R^5$ or $R^6$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^5\text{-}X^6-$$

wherein $X^6$ is a direct bond or is selected from CO and N($R^{14}$)CO, wherein $R^{14}$ is hydrogen or (1-6C)alkyl, and Q is aryl, aryl-(1-6C)alkyl, (3-11C)cycloalkyl, heteroaryl, heteroaryl-(1-6C)alkyl, heterocyclyl or heterocyclyl-(1-6C)alkyl, and wherein any $CH_2$ or $CH_3$ group within a $R^3$, $R^4$, $R^5$ or $R^6$ substituent optionally bears on each said $CH_2$ or $CH_3$ group one or more halogeno or (1-6C)alkyl substituents or a substituent selected from oxo, hydroxy, cyano, amino, carboxy, carbamoyl, (1-6C)alkoxy, (1-6C)alkylthio, (1-6C)alkylsulfinyl, (1-6C)alkylsulfonyl, (1-6C)alkylamino, di-[(1-

6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, (1-6C)alkoxycarbonylamino, aminosulfonylamino, (1-6C)alkylaminosulfonylamino, di-[(1-6C)alkyl]aminosulfonylamino, or from a group of the formula:

—X⁷-Q⁶ wherein X⁷ is a direct bond or is selected from O, S, SO, SO₂, N(R¹⁵), CO, CH(OR¹⁵), CON(R¹⁵), N(R¹⁵)CO, SO₂N (R¹⁵), N(R¹⁵)SO₂, C(R¹⁵)₂O, C(R¹⁵)₂S and N(R¹⁵) C(R¹⁵)₂, wherein R¹⁵ is hydrogen or (1-6C)alkyl, and Q⁶ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl, and wherein any aryl, heteroaryl, heterocyclyl, cycloalkyl or cycloalkenyl group within a substituent on R³, R⁴, R⁵ or R⁶ optionally bears 1 or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, from a group of the formula:

—X⁸—R¹⁶ wherein X⁸ is a direct bond or is selected from O and N(R¹⁷), wherein R¹⁷ is hydrogen or (1-6C)alkyl, and R¹⁶ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

—X⁹-Q⁷ wherein X⁹ is a direct bond or is selected from O, S, SO, SO₂, N(R¹⁸), CO, CH(OR¹⁸), CON(R¹⁸), N(R¹⁸)CO, SO₂N (R¹⁸), N(R¹⁸)SO₂, C(R¹⁸)₂O, C(R¹⁸)₂S and N(R¹⁸) C(R¹⁸)₂, wherein R¹⁸ is hydrogen or (1-6C)alkyl, and Q⁷ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N, N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or when G is NR⁵, R⁴ and R⁵ together with the atoms to which they are attached form a fused 5- or 6- membered heteroaryl or heterocyclyl ring, and wherein said fused 5- or 6-membered ring optionally bears one or more substituents as defined for R⁴, and any fused 5- or 6- membered heterocyclyl ring so formed optionally bears 1 or 2 oxo or thioxo substituents, and wherein any heterocyclyl group within any R³, R⁴, R⁵ or R⁶ substituent optionally bears 1 or 2 oxo or thioxo substituents;

m is 0, 1 or 2, and wherein the values of R³ may be the same or different;

or a pharmaceutically-acceptable salt thereof.

According to a second aspect of the present invention there is provided a compound of the Formula I:

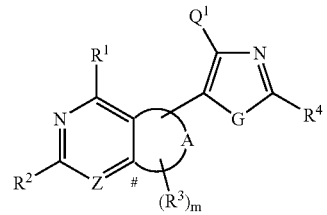

Formula I wherein:

A together with the carbon atoms to which it is attached forms a fused 5-membered heteroaryl ring, wherein said heteroaryl ring contains 1 or 2 heteroatoms selected from O, N and S, and wherein the 5-membered ring containing G is linked to the ring formed by A in the meta position to the bridgehead carbon marked # in Formula I;

G is selected from O, S and NR⁵;

Z is selected from N and CR⁶;

Q¹ is selected from aryl and heteroaryl, and wherein Q¹ is optionally substituted by one or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfsulfinyl, (1-6C)alkylsulfsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfsulfamoyl, N, N-di-[(1-6C)alkyl]sulfsulfamoyl, (1-6C)alkanesulfsulfonylamino, N-(1-6C)alkyl-(1-6C)alkanesulfsulfonylamino, from a group of the formula:

—X¹—R⁷ wherein X¹ is a direct bond or is selected from O and N(R⁸), wherein R⁸ is hydrogen or (1-6C)alkyl, and R⁷ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and from a group of the formula:

—X²-Q² wherein $X^2$ is a direct bond or is selected from O, S, SO, $SO_2$, $N(R^9)$, CO, $CH(OR^9)$, $CON(R^9)$, $N(R^9)CO$, $N(R^9)CON(R^9)$, $SO_2N(R^9)$, $N(R^9)SO_2$, $C(R^9)_2O$, $C(R^9)_2S$ and $N(R^9)C(R^9)_2$, wherein $R^9$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1, 2 or 3 substituents, which may be the same or different, selected from trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$—X^3—R^{10}$$

wherein $X^3$ is a direct bond or is selected from O and $N(R^{11})$, wherein $R^{11}$ is hydrogen or (1-6C)alkyl, and $R^{10}$ is halogeno-(1-6C)alkyl, hydroxy-(1-6C)alkyl, (1-6C)alkoxy-(1-6C)alkyl, cyano(1-6C)alkyl, amino-(1-6C)alkyl, (1-6C)alkylamino-(1-6C)alkyl or di-[(1-6C)alkyl]amino-(1-6C)alkyl, and any heterocyclyl group within $Q^2$ optionally bears 1 or 2 oxo or thioxo substituents;

$R^1$ is selected from hydrogen, halogeno, trifluoromethyl, trifluoromethoxy, cyano, nitro, hydroxy, amino, mercapto, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, $R^2$ is selected from hydrogen, amino, hydroxy, halogeno, (1-6C)alkyl, (1-6C)alkoxy, (1-6C)alkylamino and di-[(1-6C)alkyl]amino;

$R^3$ is, independently, as defined for $R^4$ and $R^6$, provided that $R^3$ is not hydrogen, and when $R^3$ is attached to a nitrogen atom in A, $R^3$ is not halogeno;

$R^5$ is, independently, as defined for $R^4$ and $R^6$, provided that $R^5$ is not halogeno;

$R^4$ and $R^6$ which may be the same or different, are selected from hydrogen, halogeno, trifluoromethyl, trifluoromethoxy, cyano, isocyano, nitro, hydroxy, mercapto, amino, formyl, carboxy, carbamoyl, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$Q^4-X^5—$$

wherein $X^5$ is a direct bond or is selected from O, S, SO, $SO_2$, $N(R^{12})$, CO, $CH(OR^{12})$, $CON(R^{12})$, $N(R^2)CO$, $SO_2N(R^{12})$, $N(R^{12})SO_2$, $OC(R^{12})_2$, $SC(R^{12})_2$ and $N(R^{12})C(R^{12})_2$, wherein $R^{12}$ is hydrogen or (1-6C)alkyl, and $Q^4$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^3$, $R^4$, $R^5$ or $R^6$ substituent are optionally separated by the insertion into the chain of a group selected from O, S, SO, $SO_2$, $N(R^{13})$, CO, $CH(OR^{13})$, $CON(R^{13})$, $N(R^{13})CO$, $SO_2N(R^{13})$, $N(R^{13})SO_2$, CH=CH and C≡C wherein $R^{13}$ is hydrogen or (1-6C)alkyl, and wherein any $CH_2$=CH— or HC≡C— group within a $R^3$, $R^4$, $R^5$ or $R^6$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^5-X^6—$$

wherein $X^6$ is a direct bond or is selected from CO and $N(R^{14})CO$, wherein $R^{14}$ is hydrogen or (1-6C)alkyl, and $Q^5$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^3$, $R^4$, $R^5$ or $R^6$ substituent optionally bears on each said $CH_2$ or $CH_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$—X^7-Q^6$$

wherein $X^7$ is a direct bond or is selected from O, S, SO, $SO_2$, $N(R^{15})$, CO, $CH(OR^{15})$, $CON(R^{15})$, $N(R^{15})CO$, $SO_2N(R^{15})$, $N(R^{15})SO_2$, $C(R^{15})_2O$, $C(R^{15})_2S$ and $N(R^{15})C(R^{15})_2$, wherein $R^{15}$ is hydrogen or (1-6C)alkyl, and $Q^6$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl, heterocyclyl, cycloalkyl or cycloalkenyl group within a substituent on $R^3$, $R^4$, $R^5$ or $R^6$ optionally bears 1 or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-1-6C)alkyl-(2-6C)alkanoylamino, N-(1-6C)alkylsulfamoyl, NN-di-[(1-6C)alkyl]sulfamoyl, (1-6C)alkanesulfonylamino, N-(1-6C)alkyl-(1-6C)alkanesulfonylamino, from a group of the formula:

$$-X^8-R^{16}$$

wherein $X^8$ is a direct bond or is selected from O and $N(R^{17})$, wherein $R^{17}$ is hydrogen or (1-6C)alkyl, and $R^{16}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[((1-6C)alkyl]amino-(1-6C)alkyl, (2-6C)alkanoylamino-(1-6C)alkyl or (1-6C) alkoxycarbonylamino-(1-6C)alkyl, and from a group of the formula:

$$-X^9-Q^7$$

wherein $X^9$ is a direct bond or is selected from O, S, SO, $SO_2$, $N(R^{18})$, CO, $CH(OR^{18})$, $CON(R^{18})$, $N(R^{18})CO$, $SO_2N(R^{18})$, $N(R^{18})SO_2$, $C(R^{18})_2O$, $C(R^{18})_2S$ and $N(R^{18})C(R^{18})_2$, wherein $R^{18}$ is hydrogen or (1-6C)alkyl, and $Q^7$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or when G is $NR^5$, $R^4$ and $R^5$ together with the atoms to which they are attached form a fused 5- or 6-membered heteroaryl or heterocyclyl ring, and wherein said fused 5- or 6-membered ring optionally bears one or more substituents as defined for $R^4$, and any fused 5- or 6-membered heterocyclyl ring so formed optionally bears 1 or 2 oxo or thioxo substituents, and wherein any heterocyclyl group within any $R^3$, $R^4$, $R^5$ or $R^6$ substituent optionally bears 1 or 2 oxo or thioxo substituents;

m is 0, 1 or 2, and wherein the values of $R^3$ may be the same or different;

or a pharmaceutically-acceptable salt thereof.

In this specification the generic term "alkyl" includes both straight-chain and branched-chain alkyl groups such as propyl, isopropyl and tert-butyl. However references to individual alkyl groups such as "propyl" are specific for the straight-chain version only, references to individual branched-chain alkyl groups such as "isopropyl" are specific for the branched-chain version only. An analogous convention applies to other generic terms, for example (1-6C)alkoxy includes methoxy, ethoxy, (1-6C)alkylamino includes methylamino and ethylamino, and di-[(1-6C)alkyl]amino includes dimethylamino and diethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^7$) when it is aryl or for the aryl group within a 'Q' group is, for example, phenyl or naphthyl, preferably phenyl.

A suitable value for any one of the 'Q' groups ($Q^4$, $Q^6$ or $Q^7$) when it is (3-11C)cycloalkyl or for the (3-11C)cycloalkyl group within a 'Q' group is, for example, cyclopropyl, cyclobutyl, cyclopentyl, cyclohexyl, cycloheptyl or bicyclo [2.2.1]heptyl and a suitable value for any one of the 'Q' groups ($Q^4$, $Q^6$ or $Q^7$) when it is (3-11C)cycloalkenyl or for the (3-11C)cycloalkenyl group within a 'Q' group is, for example, cyclobutenyl, cyclopentenyl, cyclohexenyl or cycloheptenyl. It will be understood that such cycloalkyl and cycloalkenyl groups may be monocyclic, bicyclic or tricyclic and may be bridged and/or spiro.

A suitable value for any one of the 'Q' groups ($Q^1$, $Q^2$ or $Q^4$ to $Q^7$) when it is heteroaryl or for the heteroaryl group within a 'Q' group is, for example, an aromatic 5- or 6-membered monocyclic ring or unless specified otherwise, a 9- or 10-membered bicyclic ring, with up to five ring heteroatoms selected from oxygen, nitrogen and sulfur, which may, unless otherwise specified be carbon or nitrogen linked. Preferably heteroaryl is an aromatic 5- or 6-membered monocyclic ring with up to five ring heteroatoms selected from oxygen, nitrogen and sulfur, which may, unless otherwise specified be carbon or nitrogen linked. Suitable heteroaryl rings include, for example furyl, pyrrolyl, thienyl, oxazolyl, isoxazolyl, imidazolyl, pyrazolyl, thiazolyl, isothiazolyl, oxadiazolyl, thiadiazolyl, triazolyl, totrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl. Preferably furyl, pyrrolyl, thenyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl or 1,3,5-triazenyl.

A suitable value for the fused 5-membered heteroaryl ring formed by A together with the carbon atoms to which it is attached includes for example furo, pyrrolo, thiopheno, oxazolo, imidazolo or thiazolo. As will be clear the ring formed by A is fused to the pyridine/pyrimidine ring in formula I to form a fused 6,5-bicyclic heteroaryl ring system, for example [1,3]thiazolo[5,4-d]pyrimidinyl, [1,3]oxazolo[5,4-d]pyrimidinyl, 9H-purinyl, 7H-purinyl, furo[3,2-d]pyrimidinyl, furo[2,3-d]pyrimidinyl, thieno[3,2-d]pyrimidinyl or thieno[2,3-d]pyrimidinyl. The fused ring formed by A optionally carries one or more substituents represented by $R^3$ which may be present on a ring carbon or ring nitrogen atom (provided that the nitrogen is not thereby quaternized)

A suitable value for any one of the 'Q' groups ($Q^2$ to $Q^7$) when it is heterocyclyl or for the heterocyclyl group within a 'Q' group is, for example, a non-aromatic saturated or partially saturated 3 to 10 membered monocyclic or bicyclic ring which may be bridged and/or spiro with up to five heteroatoms selected from oxygen, nitrogen and sulfur, which may, unless specified otherwise, be carbon or nitrogen linked, wherein a ring sulfur atom may be oxidized to form the S-oxide(s). Preferably a heterocyclyl is a non-aromatic saturated or partially saturated 5 or 6 membered monocyclic ring with 1, 2, 3 or 4 heteroatoms selected from oxygen, nitrogen and sulfur, which may, unless specified otherwise, be carbon or nitrogen linked, wherein a ring sulfur atom may be oxidized to form the S-oxide(s). Suitable heterocyclyls include, for example oxiranyl, oxetanyl, tetrahydrofuranyl, tetrahydropyranyl, 2,3-dihydro-1,3-thiazolyl, 1,3-thiazolidinyl, 1,3-oxazolidinyl, oxepanyl, pyrrolinyl, pyrolidinyl, morpholinyl, thiamorpholinyl (perhydro-1,4-thiazinyl), (8-oxa-3-azabicyclo[3.2.1]octyl), (7-oxa-3-azabicyclo[3.1.1]heptyl), perhydroazepinyl, perhydrooxazepinyl, tetrahydro-1,4-thiazinyl, 1-oxotetrahydrothienyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4$\underline{H}$-1,4-thiazinyl, piperidinyl or piperazinyl, more preferably tetrahydrofuran-3-yl, tetrahydropyran-4-yl, pyrrolidin-3-yl, morpholino, 1,1-dioxotetrahydro-4$\underline{H}$-1,4-thiazin-4-yl, piperidino, piperidin-4-yl or piperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopipendinyl, 2,5-dioxopyrrolidinyl, 2,5-dioxoimidazolidinyl or 2,6-dioxopiperidinyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl (such as phenyl-(1-6C)alkyl for example benzyl or phenylethyl), (3-7C)cycloalkyl-(1-6C)alkyl, (3-7C)cycloalkenyl-(1-6C)alkyl or heterocyclyl-(1-6C)alkyl group is present.

A suitable value when G is NR$^5$ and R$^4$ and R$^5$ together with the atoms to which they are attached form a fused 5- or 6-membered heteroaryl or heterocyclyl ring, include for example the divalent derivatives of the 5- and 6-membered heteroaryl and heterocyclyl rings mentioned hereinbefore for the "Q" groups that contain at least 1 nitrogen atom, for example, thiazolo, isothiazolo, 1,3-thiazolidino, pyrrolidino, pyrrolino, oxazolo, isoxazolo, pyrazolino, pyridino, pyrimidino or pyridazino. As will be understood the ring formed by R$^4$ and R$^5$ is fused to the ring containing G in formula I to form a 5,5 or 5,6 bicyclic ring structure, by way of example R$^4$ and R$^5$ together with the atoms to which they are attached may form, for example an imidazo[2,1-b][1,3]thiazolyl, 2,3-dihydroimidazo[2,1-b][1,3]thiazolyl fused bicyclic ring or imidazo[1,2-a]pyridinyl fused bicyclic ring.

For the avoidance of any doubt there are no substituents labelled X$^4$ or Q$^3$ included in this specification.

Suitable values for any of the 'R' groups (R$^1$ to R$^{18}$), or for various groups within an R$^1$ to R$^6$ substituent, or for various groups within Q$^1$:— for halogeno fluoro, chloro, bromo and iodo;
for (1-6C)alkyl: methyl, ethyl, propyl, isopropyl and tert-butyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulfinyl: methylsulfinyl and ethylsulfinyl;
for (1-6C)alkylsulfonyl: methylsulfonyl and ethylsulfonyl;
for (1-6C)alkylamino: methylamino, ethylamino, propylamino, isopropyl amino and butylamino;
for di-[(1-6C)alkyl]amino: dimethylamino, diethylamino, $\underline{N}$-ethyl-$\underline{N}$-methylamino and diisopropylamino;
for (1-6C)alkoxycarbonyl: meoxycarbonyl, ethoxycarbonyl, propoxycarbonyl and tert-butoxycarbonyl;
for $\underline{N}$-(1-6C)alkylcarbamoyl: $\underline{N}$-methylcarbamoyl, $\underline{N}$-ethylcarbamoyl and $\underline{N}$-propylcarbamoyl;
for $\underline{N},\underline{N}$-di-[(1-6C)alkyl]carbamoyl, $\underline{N}$-dimethylcarbamoyl, $\underline{N}$-ethyl-$\underline{N}$-methylcarbamoyl and $\underline{N}$-diethylcarbamoyl;
for (2-6C)alkanoyl: acetyl and propionyl;
for (2-6C)alkanoyloxy: acetoxy and propionyloxy;
for (2-6C)alkanoylamino: acetamido and propionamido;
for $\underline{N}$-(1-6C)alkyl-(2-6C)alkanoylamino: $\underline{N}$-methylacetamido and $\underline{N}$-methylpropionamido;
for $\underline{N}$-(1-6C)alkylsulfamoyl: $\underline{N}$-methylsulfamoyl and $\underline{N}$-ethylsulfamoyl;
for $\underline{N},\underline{N}$-di-[(1-6C)alkyl]sulfamoyl: $\underline{N},\underline{N}$-dimethylsulfamoyl;
for (1-6C)alkanesulfonylamino: methanesulfonylamino and ethanesulfonylamino;
for $\underline{N}$-(1-6C)alkyl-(1-6C)alkanesulfonylamino: $\underline{N}$-ethylmethanesulfonylamino and $\underline{N}$-methylethanesulfonylamino;
for (3-6C)alkenoylamino: acrylamido, methacrylamido and crotonamido;
for $\underline{N}$-(1-6C)alkyl-(3-6C)alkenoylamino: $\underline{N}$-methylacrylamido and $\underline{N}$-methylcrotonamido;
for (3-6C)alkynoylamino: propionamido;
for $\underline{N}$-(1-6C)alkyl-(3-6C)alkynoylamino: $\underline{N}$-methylpropionamido;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-ethylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;
for halogeno-(1-6C)alkyl: chloromethyl, 2-chloroethyl, 1-chloroethyl and 3-chloropropyl;
for hydroxy-(1-6C)alkyl: hydroxymethyl, 2-hydroxyethyl, 1-hydroxyethyl and 3-hydroxypropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for cyano-(1-6C)alkyl: cyanomethyl, 2-cyanoethyl, 1-cyanoethyl and 3-cyanopropyl;
for (1-6C)alkylthio-(1-6C)alkyl: methylthiomethyl, ethylthiomethyl, 2-methylthioethyl, 1-methylthioethyl and 3-methylthiopiopyl;
for (1-6C)alkylsulfinyl-(1-6C)alkyl: methylsulfinylmethyl, ethylsulfinylmethyl, 2-methylsulfinylethyl, 1-methylsulfinylethyl and 3-methylsulfinylpropyl;
for (1-6C)alkylsulfonyl-(1-6C)alkyl: methylsulfonylmethyl, ethylsulfonylmethyl, 2-methylsulfonylethyl, 1-methylsulfonylethyl and 3-methylsulfonylpropyl;
for (2-6C)alkanoylamino-(1-6C)alkyl: acetamidomethyl, propionamidomethyl and 2-acetamidoethyl; and
for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl.

When, as defined hereinbefore, an R⁶ group forms a group of the Formula Q⁴-X⁵— and, for example, X⁵ is a OC(R¹²)₂ linking group, it is the carbon atom, not the oxygen atom, of the OC(R¹²)₂ linking group which is attached to the pyridine ring and the oxygen atom is attached to the Q⁴ group. Similarly, when, for example a CH₃ group within a R³, R⁴, R⁵ or R⁶ substituent bears a group of the formula —X⁷-Q⁶ and, for example, X⁷ is a C(R¹⁵)₂O linking group, it is the carbon atom, not the oxygen atom, of the C(R¹⁵)₂O linking group which is attached to the CH₃ group and the oxygen atom is linked to the Q⁶ group.

As defined hereinbefore, adjacent carbon atoms in any (2-6C)alkylene chain within a R³, R⁴, R⁵ or R⁶ substituent may be optionally separated by the insertion into the chain of a group such as O, CON(R¹³) or C≡C. For example, insertion of a C≡C group into the ethylene chain within a 2-morpholinoethoxy group gives rise to a 4-morpholinobut-2-ynyloxy group and for example, insertion of a CONH group into the ethylene chain within a 3-methoxypropoxy group gives rise to, for example, a 2-(2-methoxyacetaimido)ethoxy group.

When, as defined hereinbefore, any CH₂=CH— or HC≡C— group within a R³, R⁴ R⁵ or R⁶ substituent optionally bears at the terminal CH₂= or HC≡ position a substituent such as a group of the formula Q⁵-X⁶— wherein X⁶ is, for example, NHCO and Q⁵ is a heterocyclyl-(1-6C)alkyl group, suitable R³, R⁴, R⁵ or R⁶ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethynyl groups such as N-(2-pyrrolidin-1-ylethyl)carbamoylethynyl.

When, as defined hereinbefore, any CH₂ or CH₃ group within a R³, R⁴, R⁵ or R⁶ substituent optionally bears on each said CH₂ or CH₃ group one or more halogeno or (1-6C)alkyl substituents, there are suitably 1 or 2 halogeno or (1-6C)alkyl substituents present on each said CH₂ group and there are suitably 1, 2 or 3 such substituents present on each said CH₃ group.

When, as defined hereinbefore, any CH₂ or CH₃ group within a R³, R⁴, R⁵ or R⁶ substituent optionally bears on each said CH₂ or CH₃ group a substituent as defined hereinbefore, suitable substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted amino-(2-6C)alkoxy groups such as 3-amino-2-hydroxypropoxy, hydroxy-substituted (1-6C)alkylamino-(2-6C)alkoxy groups such as 2-hydroxy-3-methylaminopropoxy, hydroxy-substituted di-[(1-6C)alkyl]amino-(2-6C)alkoxy groups such as 3-dimethylamino-2-hydroxypropoxy, hydroxy-substituted heterocyclyl-(1-6C)alkylamino groups such as 2-hydroxy-3-piperidinopropylamino and 2-hydroxy-3-morpholinopropylamino, hydroxy-substituted amino-(2-6C)alkylamino groups such as 3-amino-2-hydroxypropylamino, hydroxy-substituted (1-6C)alkylamino-(2-6C)alkylamino groups such as 2-hydroxy-3-methylaminopropylamino, hydroxy-substituted di-[(1-6C)alkyl]amino-(2-6C)alkylamino groups such as 3-dimethylamino-2-hydroxypropylamino, hydroxy-substituted (1-6C)alkoxy groups such as 2-hydroxyethoxy, (1-6C)alkoxy-substituted (1-6C)alkoxy groups such as 2-methoxyethoxy and 3-ethoxypropoxy, (1-C)alkylsulfonyl-substituted (1-6C)alkoxy groups such as 2-methylsulfonylethoxy and heterocyclyl-substituted (1-6C)alkylamino-(1-6C)alkyl groups such as 2-morpholinoethylaminomethyl, 2-piperazin-1-ylethylaminomethyl and 3-morpholinopropylaminomethyl.

When, as defined hereinbefore, any cycloalkyl or cycloalkenyl group within a R³, R⁴, R⁵ or R⁶ substituent optionally bears one or more substituent(s) as defined hereinbefore, the substituent may be present on any CH₂ or CH group within the cycloalkyl or cycloalkenyl group. Suitable substituents so formed include, for example, hydroxy-substituted (3-7C)cycloalkyl groups such as 1-hydroxycyclohex-1-yl or 1-hydroxycycloprop-1-yl, (3-7C)cycloalkyl-(1-6C)alkyl groups such as 2-(1-hydroxycyclohex-1-yl)ethyl, 2-(1-hydroxycyclohex-4-yl)ethyl 3-(1-hydroxycyclohex-1-yl)propyl or 3-(1-hydroxycyclopent-1-yl)propyl, or (3-7C)cycloalkyl-(1-6C) alkoxy groups such as 2-(1-hydroxycyclohex-1-yl)ethoxy or 3-(1-hydroxycyclohex-1-yl)propoxy.

For the avoidance of any doubt it is to be understood that when as hereinbefore defined, the ring containing G is linked to the ring formed by A in the meta position to the bridgehead carbon marked # in Formula I, the meta position refers to the second atom in the ring formed by A when moving around the ting A in an anti-clockwise direction from the bridgehead carbon marked # towards the bridgehead carbon atom adjacent to the carbon atom carrying R¹. By way of example when A together with the carbon atoms to which it is attached forms a thieno ring the ring containing G is attached to the thieno portion of the ring on the carbon atom marked "2" as shown below:

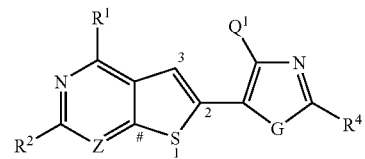

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulfuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morphohine or tris-(2-hydroxyethyl)amine.

Particular novel compounds of the invention include, for example, compounds of the Formula I, or pharmaceutically-acceptable salts thereof, wherein, unless otherwise stated, each of R¹, R², R³, R⁴, R⁵, R⁶, G, Z and Q¹ has any of the meanings defined hereinbefore or in paragraphs (a) to (ggg):

(a) A is selected from —CH=C*—O—, —O—C*=CH—, —CH=C*—S—, —S—C*=CH—, —CH=C*—NH—, —NH—C*=CH—, —N=C*—NH—, —NH—C*=N—, —O—C*—N—, —N=C—O—, —S—C*=N— and —N=C*—S— wherein * indicates the atom which forms the bond to the ring containing G in Formula I, and wherein A is optionally substituted on any available carbon or nitrogen atom (provided that the nitrogen is not thereby quaternized) by R³, wherein R³ is as hereinbefore defined;

(b) A is selected from —CH=C*—O—, —O—C*=CH—, —CH=C*—S—, —S—C*=CH—, —NH—C*=CH—, —N=C*—NH—, —NH—C*=N—, —O—C*=N—, —N=C*—O—, —S—C*=N— and —N=C*—S— wherein * indicates the atom which forms the bond to the ring containing G in Formula I and wherein A is optionally substituted on any available carbon or nitrogen atom (provided that the nitrogen is not thereby quaternized) by $R^3$, wherein $R^3$ is as hereinbefore defined;

(c) A is selected from —CH=C*—O—, —CH=C*—S—, —CH=C*—NH—, —N=C*—NH—, —N=C*—O— and —N=C*—S, wherein * indicates the atom which forms the bond to the ring containing G in Formula I, and wherein A is optionally substituted on a —NH— group by a substituent represented by $R^3$, wherein $R^3$ is as hereinbefore defined;

(d) A is selected from —CH=C*—O—, —CH=C*—S—, —S—C*=CH—, —CH=C*—NH—, —N=C*—NH—, —N=C*—O— and —N=C*—S—, wherein * indicates the atom which forms the bond to the ring containing G in Formula I;

(e) A is selected from —CH=C*—S—, —S—C*=CH—, —N=C*—S—, —S—C*=N—, —CH=C*—O—, —O—C*=CH—, —NH—C*=N— and —N=C*—NH—, wherein * indicates the atom which forms the bond to the ring containing G in Formula I; and wherein A is optionally substituted on any CH or NH group by $R^3$, wherein $R^3$ is as hereinbefore defined;

(f) A is selected from —CH=C*—S—, —S—C*=CH—, —N=C*—S—, —S—C*=N—, —CH=C*—O—, —O—C*=CH—, —NH—C*=N— and —N=C*—NH— wherein * indicates the atom which forms the bond to the ring containing G in Formula I, and wherein A is optionally substituted on a NH group by $R^3$, wherein $R^3$ is as hereinbefore defined;

(g) A is selected from —CH=C*—S—, —N=C*—NH— and —N=C*—S—, wherein * indicates the atom which forms the bond to the ring containing G in Formula I;

and wherein A is optionally substituted on any NH group by $R^3$, wherein $R^3$ is as hereinbefore defined;

(h) A is selected from —CH=C*—O— and —O—C*=CH—, wherein * indicates the atom which forms the bond to the ring containing G in Formula I;

(i) the fused 6,5-bicyclic heteroaromatic ring formed by A together with the pyridine/pyrimidine ring to which it is attached is a group of the Formula:

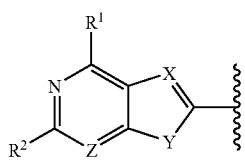

wherein $R^1$, $R^2$ and Z are as hereinbefore defined,
X is selected from CH and N,
Y is selected from O, S and NH,
and wherein any CH, NH group represented by X or Y optionally bears a substituent $R^3$ as hereinbefore defined;

(j) Z is N;
(k) Z is $CR^6$ wherein $R^6$ is as hereinbefore defined;
(l) $R^1$ is selected from hydrogen, trifluoromethyl, trifluoromethoxy, cyano, nitro, hydroxy, amino, mercapto, carbamoyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, and N-(1-6C)alkylcarbamoyl;

(m) $R^1$ is selected from hydrogen, cyano, hydroxy, amino, mercapto, (1-6C)alkyl, (1-6C)alkoxy, (1-6C)alkylthio, (1-6C)alkylsulfinyl, (1-6C)alkylsulfonyl and (1-6C)alkylamino;

(n) $R^1$ is selected from hydrogen, hydroxy, amino, mercapto, (1-3C)alkyl, (1-3C)alkoxy, (1-3C)alkylthio and (1-3C)alkylamino;

(o) $R^1$ is selected from amino, mercapto, (1-3C)alkylthio, and (1-3C)alkylamino;

(p) $R^1$ is selected from hydrogen, amino, mercapto, methyl, ethyl, propyl, iso-propyl, methoxy, ethoxy, methylthio, ethylthio, methylamino and ethylamino;

(q) $R^1$ is selected from hydrogen, amino; and methylamino;
(r) $R^1$ is hydrogen;
(s) $R^1$ is amino;
(t) $R^2$ is selected from hydrogen, amino, hydroxy, (1-3C)alkyl, (1-3C)alkoxy, (1-3C)alkylamino and di-[(1-3C)alkyl]amino;

(u) $R^2$ is selected from hydrogen and (1-3C)alkyl;
(v) $R^2$ is hydrogen;
(w) $R^1$ is selected from hydrogen, hydroxy, amino, mercapto, (1-3C)alkyl, (1-3C)alkoxy, (1-3C)alkylthio and (1-3C)alkylamino, and $R^2$ is selected from hydrogen and (1-3C)alkyl;

(x) $R^1$ is selected from hydrogen, hydroxy, amino, mercapto, (1-3C)alkyl, (1-3C)alkoxy, (1-3C)alkylthio and (1-3C)alkylamino, and $R^2$ is hydrogen;

(y) $R^1$ is selected from hydrogen, mercapto, methylthio, amino and methylamino, and $R^2$ is hydrogen;

(x) $R^1$ is selected from amino, methylamino and methylthio and $R^2$ is hydrogen;

(y) G is $NR^5$;
(z) G is selected from O and S;
(aa) $Q^1$ is selected from phenyl, naphthyl and thienyl which is optionally substituted by 1, 2 or 3 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, and from a group of the formula:

—$X^2$-$Q^2$ wherein $X^2$ is a direct bond or is selected from O, S, SO, $SO_2$, $N(R^9)$, CO, $CH(OR^9)$, $CON(R^9)$, $N(R^9)CO$, $N(R^9)CON(R^9)$, $SO_2N(R^9)$, $N(R^9)SO_2$, $C(R^9)_2O$, $C(R^9))_2S$ and $N(R^9)C(R^9)_2$, wherein $R^9$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1, 2 or 3 substituents, which may be the same or different, selected from trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)

alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and any heterocyclyl group within $Q^2$ optionally bears 1 or 2 oxo or thioxo substituents;

(bb) $Q^1$ is selected from phenyl and naphthyl which is optionally substituted by 1, 2 or 3 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino and from a group of the formula:

—$X^2$-$Q^2$ wherein $X^2$ is a direct bond or is selected from O, S, SO, $SO_2$, $N(R^9)$, CO, $CH(OR^9)$, $CON(R^9)$, $N(R^9)CO$, $N(R^9)CON(R^9)$, $SO_2N(R^9)$, $N(R^9)SO_2$, $C(R^9)_2O$, $C(R^9)_2S$ and $N(R^9)CR^9_2$, wherein $R^9$ is hydrogen or (1-6C)alkyl, and $Q^2$ is aryl, aryl-(1-6C)alkyl, heteroaryl, heteroaryl-(1-6C)alkyl, which optionally bears 1, 2 or 3 substituents, which may be the same or different, selected from trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

(cc) $Q^1$ is a group of the formula:

-$Q^{1a}$-$X^2$-$Q^2$ wherein $Q^{1a}$ is selected from phenyl and naphthyl which is optionally substituted by 1, 2 or 3 substituents, which may be the same or different, selected from fluoro, chloro, bromo, trifluoromethyl, trifluoromethoxy, cyano, nitro, hydroxy, amino, carboxy, carbamoyl, (1-3C)alkyl, (2-3C)alkenyl, (2-3C)alkynyl, (1-3C)alkoxy, (2-3C)alkenyloxy, (2-3C)alkynyloxy, (1-3C)alkylthio, (1-3C)alkylsulfinyl, (1-3C)alkylsulfonyl, (1-3C)alkylamino, di-[(1-3C)alkyl]amino, (1-3C)alkoxycarbonyl, N-(1-3C)alkylcarbamoyl, N,N-di-[(1-3C)alkyl]carbamoyl, (2-3C)alkanoyl, (2-3C)alkanoyloxy, (2-3C)alkanoylamino, N-(1-3C)alkyl-(2-3C)alkanoylamino, N-(1-3C)alkylsulfamoyl, N,N-di-[(1-3C)alkyl]sulfamoyl, (1-3C)alkanesulfonylamino and N-(1-3C)alkyl-(1-3C)alkane-sulfonylamino, $X^2$ is a direct bond or is selected from O, S, $SO_2$, $N(R^9)$, CO, $CON(R^9)$, $N(R^9)CO$, $N(R^9)CON(R^9)$, $SO_2N(R^9)$, $N(R^9)SO_2$, $C(R^9)_2O$, $C(R^9)_2S$ and $N(R^9)C(R^9)_2$, wherein $R^9$ is hydrogen or (1-6C)alkyl, and $Q^2$ is phenyl, phenyl-(1-6C)alkyl, furanyl, thienyl, oxazolyl, isoxazolyl, pyridyl, furanyl-(1-6C)alkyl, thienyl-(1-6C)alkyl, oxazolyl-(1-6C)alkyl, isoxazolyl-(1-6C)alkyl or pyridyl-(1-6C)alkyl, and wherein $Q^2$ optionally bears 1, 2 or 3 substituents, which may be the same or different, selected from trifluoromethyl, trifluoromethoxy, cyano, nitro, hydroxy, amino, carboxy, carbamoyl, (1-3C)alkyl, (2-3C)alkenyl, (2-3C)alkynyl, (1-3C)alkoxy, (1-3C)alkylthio, (1-3C)alkylsulfinyl, (1-3C)alkylsulfonyl, (1-3C)alkylamino, di-[(1-3C)alkyl]amino, (1-3C)alkoxycarbonyl, N-(1-3C)alkylcarbamoyl, N,N-di-[(1-3C)alkyl]carbamoyl, (2-3C)alkanoyl, (2-3C)alkanoyloxy, (2-3C)alkanoylamino, N-(1-3C)alkyl-(2-3C)alkanoylamino, N-(1-3C)alkylsulfamoyl, N,N-di-[(1-3C)alkyl]sulfamoyl, (1-3C)alkanesulfonylamino and N-(1-3C)alkyl-(1-3C)alkanesulfonylamino;

(dd) $Q^1$ is a group of the formula:

-$Q^{1a}$-$X^2$-$Q^2$ wherein $Q^{1a}$ is phenyl which is optionally substituted by 1 or 2 substituents which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl, $X^2$ is a direct bond or is selected from O, S, $SO_2$, $N(R^9)$, CO, $CON(R^9)$, $N(R^9)CO$, $N(R^9)CON(R^9)$, $SO_2N(R^9)$, $N(R^9)SO_2$, $C(R^9)_2O$, $C(R^9)_2S$ and $N(R^9)C(R^9)_2$, wherein $R^9$ is hydrogen or (1-3C)alkyl, and $Q^2$ is phenyl, phenyl-(1-3C)alkyl, thienyl, or thienyl-(1-3C)alkyl, and wherein $Q^2$ optionally bears 1, 2 or 3 substituents, which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl;

(ee) $Q^1$ is selected from phenyl and naphthyl which is optionally substituted by 1, 2 or 3 substituents, which may be the same or different, selected from fluoro, chloro, bromo, trifluoromethyl, trifluoromethoxy, cyano, nitro, hydroxy, amino, carboxy, carbamoyl, (1-3C)alkyl, (2-3C)alkenyl, (2-3C)alkynyl, (1-3C)alkoxy, (2-3C)alkenyloxy, (2-3C)alkynyloxy, (1-3C)alkylthio, (1-3C)alkylsulfinyl, (1-3C)alkylsulfonyl, (1-3C)alkylamino, di-[(1-3C)alkyl]amino, (1-3C)alkoxycarbonyl, N-(1-3C)alkylcarbamoyl, N,N-di-[(1-3C)alkyl]carbamoyl, (2-3C)alkanoyl, (2-3C)alkanoyloxy, (2-3C)alkanoylamino, N-(1-3C)alkyl-(2-3C)alkanoylamino, N-(1-3C)alkylsulfamoyl, N,N-di-[(1-3C)alkyl]sulfamoyl, (1-3C)alkanesulfonylamino and N-(1-3C)alkyl-(1-3C)alkanesulfonylamino;

(ff) $Q^1$ is selected from phenyl, and naphthyl optionally substituted by 1, 2 or 3 substituents selected from fluoro, chloro, bromo, methyl, ethyl, methoxy and ethoxy;

(gg) $Q^1$ is selected from 4-fluorophenyl, 2-fluorophenyl, 2,4-difluorophenyl, 4-methoxyphenyl, 3-methoxyphenyl, 2-naphthyl and 6-methoxy-2-naphthyl;

(hh) $Q^1$ is phenyl;

(ii) m is 0 or 1, and $R^5$ and any $R^3$ substituent which is attached to a ring nitrogen in A, which may be the same or different, are selected from trifluoromethyl, hydroxy, mercapto, formyl, carbamoyl, sulfamoyl, (1-6C)alkyl, (2-8C)alkenyl, (2-8C)alkynyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, N-(1-6C)alkylsulfamoyl, N,N-di-[(1-6C)alkyl]sulfamoyl, or from a group of the formula:

$$Q^4\text{-}X^5\text{—}$$

wherein $X^5$ is a direct bond or is selected from $SO_2$, $N(R^{12})$, CO, $CH(OR^{12})$, $CON(R^{12})$, $N(R^{12})CO$, $N(R^{12})SO_2$, $OC(R^{12})_2$, $SC(R^{12})_2$ and $N(R^{12})C(R^{12})_2$, wherein $R^2$ is hydrogen or (1-6C)alkyl, and $Q^4$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^3$, $R^4$, $R^5$ or $R^6$ substituent are optionally separated by the insertion into the chain of a group selected from O, S, SO, $SO_2$, $N(R^{13})$, CO, $CH(OR^{13})$, $CON(R^{13})$, $N(R^{13})CO$, $SO_2N(R^{13})$, $N(R^{13})SO_2$, CH=CH and C≡C wherein $R^{13}$ is hydrogen or (1-6C)alkyl, and wherein any $CH_2$=CH— or HC≡C— group within a $R^3$ or $R^5$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl, di-[(1-6C)alkyl]amino-(1-6C)alkyl and from a group of the formula:

$$Q^5\text{-}X^6\text{—}$$

wherein $X^6$ is a direct bond or is selected from CO and $NO(R^{14})CO$, wherein $R^{14}$ is hydrogen or (1-6C)alkyl, and $Q^5$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^3$ or $R^5$ substituent optionally bears on each said $CH_2$ or $CH_3$ group one or more halogeno or (1-6C)alkyl substituents or a substituent selected from hydroxy, cyano, amino, carboxy, carbamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino and a group of the formula:

$$-X^7\text{-}Q^6$$

wherein $X^7$ is a direct bond or is selected from O, S, SO, $SO_2$, $N(R^{15})$, CO, $CH(OR^{15})$, $CON(R^{15})$, $N(R^{15})CO$, $SO_2N(R^{15})$, $N(R^{15})SO_2$, $C(R^{15})_2O$, $C(R^{15})_2S$ and $N(R^{15})C(R^{15})_2$, wherein $R^{15}$ is hydrogen or (1-6C)alkyl, and $Q^6$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl, heterocyclyl, cycloalkyl or cycloalkenyl group within a substituent on $R^3$ or $R^5$ optionally bears 1 or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, from a group of the formula:

$$-X^8\text{—}R^{16}$$

wherein $X^8$ is a direct bond or is selected from O and $N(R^{17})$, wherein $R^{17}$ is hydrogen or (1-6C)alkyl, and $R^{16}$ is halogeno(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

$$-X^9\text{-}Q^7$$

wherein $X^9$ is a direct bond or is selected from O, S, SO, $SO_2$, $N(R^{18})$, CO, $CH(OR^{18})$, $CON(R^{18})$, $N(R^{18})CO$, $SO_2N(R^{18})$, $N(R^{18})SO_2$, $C(R^{18})_2O$, $C(R^{18})_2S$ and $N(R^{18})C(R^{18})_2$, wherein $R^{18}$ is hydrogen or (1-6C)alkyl, and $Q^7$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, and wherein R may also be hydrogen;

(jj) m is 0 or 1 and $R^3$, when present, is located in the ortho position relative to the bridgehead carbon marked # in formula I;

(kk) m is 0 or 1 and $R^3$, when present, is selected from is selected from cyano, nitro, fluoro, chloro, bromo, hydroxy, mercapto, amino, carbamoyl, sulfamoyl, methyl, ethyl, propyl, iso-propyl, methoxy, ethoxy, propoxy, acetyl, propionyl, methylthio, ethylthio, methylsulfonyl, ethylsulfonyl, methylamino, ethylamino, di-methylamino, di-ethylamino, N-methylcarbamoyl, N,N-di-methylcarbamoyl, N-methylsulfamoyl, N-di-methylsulfamoyl, methanesulfonylamino and N-methyl-methanesulfonylamino, or from a group of the formula:

$$Q^4\text{-}X^5\text{—}$$

wherein $X^5$ is a direct bond or is selected from O, S, $SO_2$, NH, N(methyl), CO, CONH, NHCO, $SO_2NH$, $NHSO_2$, $OCH_2$, $SCH_2$ and $NHCH_2$, $Q^4$ is phenyl; benzyl, 2-phenylethyl, cyclopropyl, cyclopentyl, cyclohexyl, cyclopropylmethyl, cyclopentylmethyl, cyclohexylmethyl, 2-(cyclopropyl)

ethyl, 2-(cyclopentylethyl, 2-cyclohexyl)ethyl, pyrrolinyl, pyrrolidinyl, piperidinyl, piperazinyl, morpholinyl, tetrahydro-1,4-thiazinyl, pyrrolinylmethyl, pyrrolidinylmethyl, piperidinylmethyl, piperazinylmethyl, morpholinylmethyl, tetrahydro-1,4-thiazinylmethyl, 2-pyrrolinylethyl, 2-pyrrolidinylethyl, 2-piperidinylethyl, 2-piperazinylethyl, 2-morpholinylethyl, 2-tetrahydro-1,4-thiazinylethyl, 3-pyrrolinylpropyl, 3-pyrrolidinylpropyl, 3-piperidinylpropyl, 3-piperazinylpropyl, 3-morpholinylpropyl or 3-tetrahydro-1,4-thiazinylpropyl, and wherein any $CH_2$ or $CH_3$ group within a $R^3$ substituent optionally bears on each said $CH_2$ or $CH_3$ group one or more fluoro, chloro, methyl or ethyl substituents or a substituent selected from hydroxy, cyano, amino, methylamino, di-methylamino, acetyl, acetoxy, methylsulfonyl and wherein any heterocyclyl or cycloalkyl group within a $R^3$ substituent optionally bears 1 or more substituents, which may be the same or different, selected from fluoro, chloro, bromo, trifluoromethyl, trifluoromethoxy, cyano, nitro, hydroxy, amino, methyl, ethyl, methoxy, methylamino and di-methylamino, and wherein any heterocyclyl group within a $R^3$ substituent optionally bears 1 or 2 oxo substituents, provided that when $R^3$ is present on a nitrogen atom in A, $R^3$ is not fluoro, chloro or bromo;

(ll) m is 0 or 1 and $R^3$, when present, is attached to a carbon atom in A and is selected from halogeno, cyano, hydroxy, nitro, amino, carbamoyl, (1-4C)alkyl, (1-4C)alkoxy, (2-4C)alkanoyl, (2-4C)alkanoyloxy, (1-4C)alkoxycarbonyl, (1-4C)alkylamino, di-[(1-4C)alkyl]amino, N-(1-4C)alkylcarbamoyl and N,N-di-[(1-4C)alkyl]carbamoyl;

(mm) m is 0 or 1 and $R^3$, when present, is attached to a carbon atom in A and is selected from fluoro, chloro, bromo, cyano, nitro, hydroxy, amino, carbamoyl, methyl, ethyl, propyl, iso-propyl, methoxy, ethoxy, propoxy, methylamino, ethylamino, di-methylamino, di-ethylamino, N-methylcarbamoyl and N,N-di-methylcarbamoyl;

(nn) m is 0 or 1 and $R^3$, when present, is attached to a nitrogen atom in A, provided that the ring formed by A is not thereby quaternized, and wherein $R^3$ is selected from hydroxy, carbamoyl, (1-4C)alkyl, (1-4C)alkylsulfonyl, (1-4C)alkoxycarbonyl, N-(1-4C)alkylcarbamoyl, N,N-di-[(1-4C)alkyl]carbamoyl and (2-4C)alkanoyl;

(oo) m is 0 or 1 and $R^3$, when present, is attached to a nitrogen atom in A, provided that the ring formed by A is not thereby quaternized, and wherein $R^3$ is selected from hydroxy, carbamoyl, methyl, ethyl, propyl, iso-propyl, acetyl, propionyl, methoxycarbonyl, ethoxycarbonyl, methylsulfonyl, N-methylcarbamoyl and N,N-di-methylcarbamoyl;

(pp) m is 0 or 1 and $R^3$, when present is (1-6C)alkyl;

(qq) m is 0, 1 or 2 and $R^3$ which may be the same or different is (1-4C)alkyl;

(rr) $R^5$ is selected from trifluoromethyl, hydroxy, formyl, carbamoyl, sulfamoyl, (1-6C)alkyl, (2-6C)alkenyl, (2-6C)alkynyl, (1-6C)alkylsulfonyl, (1-6C)alkyloxycarbonyl, N-(1-6C)alkylcarbamoyl, N,N-di-[(1-6C)alkyl]carbamoyl, (2-6C)alkanoyl, N-(1-6C)alkyl]sulfamoyl and N,N-di-[(1-6C)alkylsulfamoyl];

(ss) $R^5$ is selected from hydrogen, hydroxy, carbamoyl, sulfamoyl, methyl, ethyl, propyl, iso-propyl, methoxy, ethoxy, propoxy, acetyl, propionyl, methoxycarbonyl, methylsulfonyl, ethylsulfonyl, N-methylcarbamoyl, N,N-di-methylcarbamoyl, N-methylsulfamoyl, N,N-di-methylsulfamoyl, or from a group of the formula:

$Q^4-X^5—$ wherein $X^5$ is a direct bond or is selected from O, S, $SO_2$, NH, N(methyl), CO, CONH, NHCO, $SO_2NH$, $NHSO_2$, $OCH_2$, $SCH_2$ and $NHCH_2$, $Q^4$ is phenyl, benzyl, 2-phenylethyl, cyclopropyl, cyclopentyl, cyclohexyl, cyclopropylmethyl, cyclopentylmethyl, cyclohexylmethyl, 2-(cyclopropyl)ethyl, 2-(cyclopentyl)ethyl, 2-(cyclohexyl)ethyl, pyrrolinyl, pyrrolidinyl, piperidinyl, piperazinyl, morpholinyl, tetrahydro-1,4-thiazinyl, pyrrolinylmethyl, pyrrolidinylmethyl, piperidinylmethyl, piperazinylmethyl, morpholinylmethyl, tetrahydro-1,4-thiazinylmethyl, 2-pyrrolinylethyl, 2-pyrrolidinylethyl, 2-piperidinylethyl, 2-piperazinylethyl, 2-morpholinylethyl, 2-tetrahydro-1,4-thiazinylethyl, 3-pyrrolinylpropyl, 3-pyrrolidinylpropyl, 3-piperidinylpropyl, 3-piperazinylpropyl, 3-3-morpholinylpropyl or 3-tetrahydro-1,4-thiazinylpropyl, and wherein any $CH_2$ or $CH_3$ group within a $R^4$ substituent optionally bears on each said $CH_2$ or $CH_3$ group one or more fluoro, chloro, methyl or ethyl substituents or a substituent selected from hydroxy, cyano, acetyl, amino, methylamino and di-methylamino, and wherein any heterocyclyl or cycloalkyl group within a $R^3$ substituent optionally bears 1 or more substituents, which may be the same or different, selected from fluoro, chloro, bromo, trifluoromethyl, trifluoromethoxy, cyano, nitro, hydroxy, amino, methyl, ethyl, methoxy, methylamino and di-methylamino, and wherein any heterocyclyl group within a $R^3$ substituent optionally bears 1 or 2 oxo substituents;

(tt) $R^5$ is selected from hydrogen, hydroxy, (1-6C)alkyl, phenyl and phenyl-(1-6C)alkyl, wherein a phenyl group within $R^5$ optionally bears 1, 2 or 3 substituents selected from (1-3C)alkyl and (1-3C)alkoxy;

(uu) $R^5$ is selected from hydroxy, (1-6C)alkyl, phenyl and phenyl-(1-6C)alkyl, wherein a phenyl group within $R^5$ optionally bears 1, 2 or 3 substituents selected from (1-3C)alkyl and (1-3C)alkoxy;

(vv) $R^5$ is selected from methyl, ethyl, benzyl and 2-phenylethyl, wherein a phenyl group within $R^5$ optionally bears 1, 2 or 3 substituents selected from methyl, ethyl, methoxy and ethoxy;

(ww) $R^4$ and $R^6$, which may be the same or different, are selected from hydrogen, cyano, nitro, hydroxy, halogeno, mercapto, amino, carbamoyl, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino;

(xx) $R^4$ and $R^6$, which may be the same or different, are selected from hydrogen, cyano, nitro, hydroxy, amino, carbamoyl, sulfamoyl, (1-4C)alkyl, (2-4C)alkenyl, (2-4C)alkynyl, (1-4C)alkoxy, (1-4C)alkylamino, di-[(1-4C)alkyl]amino, N-(1-4C)alkylcarbamoyl and N,N-di-[(1-4C)alkyl]carbamoyl;

(yy) $R^4$ is selected from hydrogen, (1-4C)alkyl, (2-4C)alkenyl, (2-4C)alkynyl and (1-4C)alkoxy;

(zz) $R^4$ is hydrogen;

(aaa) $R^6$ is selected from hydrogen, (1-4C)alkyl, (2-4C)alkenyl, (2-4C)alkynyl and (1-4C)alkoxy;

(bbb) $R^6$ is hydrogen;

(ccc) $R^2$ is selected from hydrogen, and (1-3C)alkyl;

m is 0, 1 or 2 and $R^3$ which may be the same or different is (1-4C)alkyl; and $R^4$ and $R^6$, which may be the same or different, are selected from hydrogen, (1-4C)alkyl, (2-4C)alkenyl, (2-4C)alkynyl and (1-4C)alkoxy;

(ddd) $R^2$ is selected from hydrogen and (1-3C)alkyl;

m is 0 or 1 and $R^3$ is as hereinbefore defined;

$R^4$ and $R^6$, which may be the same or different, are selected from hydrogen, (1-4C)alkyl, (2-4C)alkenyl, (2-4C)alkynyl and (1-4C)alkoxy;

$R^5$ is selected from hydrogen, hydroxy and (1-4C)alkyl;

(eee) $R^2$ is selected from hydrogen and (1-3C)alkyl;

m is 0 or 1 and $R^3$ is (1-3C)alkyl;

$R^4$ and $R^6$, which may be the same or different, are selected from hydrogen, (1-4C)alkyl, (2-4C)alkenyl, (2-4C)alkynyl and (1-4C)alkoxy; and $R^5$ is selected from hydrogen, hydroxy and (1-6C)alkyl;

(fff) m is 0; and (ggg) $R^5$ is not hydrogen.

It is to be understood that in paragraphs (a) to (h) above, and hereinafter in this specification, the left-hand atom in the chain represented by A is attached to the bridgehead carbon atom adjacent to the carbon carrying $R^1$ in formula I and the right hand atom in the chain representing A is attached to the bridgehead carbon atom adjacent to Z in formula I. Accordingly when A is —N=C*—S—, A together with the pyridine/pyrimidine group to which it is attached forms a group of the formula:

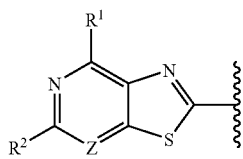

In an embodiment of the present invention there is provided a compound of formula (I) wherein:

A is selected from —N=C*—O—, —O—C*=N—, —N=C*—S—, —S—C*=N—, —N=C*—NH—, —NH—C*=NH—, —CH—C*—S—, —S—C*=CH—, —O—C*=CH—, —CH=C*—O—, —CH=C*—NH— and —NH—C*=CH—, wherein * indicates the atom which forms the bond to the ring containing G in Formula I, and wherein A is optionally substituted on any available carbon or nitrogen atom (provided that the nitrogen is not thereby quaternized) by $R^3$;

G is $NR^5$;

Z is N;

$Q^1$ is phenyl optionally substituted by halogeno, (1-4C)alkoxy, (1-4C)alkyl, trifluoromethyl, or trifluoromethoxy (preferably fluoro, chloro, bromo, methyl, methoxy or trifluoromethyl $R^1$ is selected from hydrogen, amino, hydroxy, (1-3C)alkoxy, mercapto, (1-3C)alkylthio and (1-3C)alkylamino;

$R^2$ is hydrogen;

$R^3$ is (1-6C)alkyl;

$R^4$ is selected from hydrogen and (1-6C)alkyl;

$R^5$ is selected from hydrogen, hydroxy, (1-6C)alkyl, phenyl and phenyl(1-6C)alkyl, wherein a phenyl group within $R^5$ optionally bears 1, 2 or 3 substituents selected from (1-3C)alkyl and (1-3C)alkoxy; and m is 0 or 1;

or a pharmaceutically-acceptable salt thereof.

In another embodiment of the present invention there is provided a compound of formula (I) wherein:

A is selected from —N=C*—S—, —S—C*=N—, —CH—C*—S—, —S—C*=CH—, —NH—C*=N—, —N=C*—NH—, —CH=C*—O— and —O—C*=CH—;

wherein * indicates the atom which forms the bond to the ring containing G in Formula I, and wherein A is optionally substituted on any NH group by $R^3$;

G is $NR^5$;

Z is N;

$Q^1$ is phenyl;

$R^1$ is selected from amino and (1-3C)alkylthio;

$R^2$ is hydrogen;

$R^3$ is (1-4C)alkyl;

$R^4$ is selected from hydrogen and (1-3C)alkyl;

$R^5$ is selected from (1-3C)alkyl, phenyl and benzyl, wherein a phenyl group within $R^5$ optionally bears 1 or 2 substituents selected from (1-3C)alkyl and (1-3C)alkoxy;

m is 0 or 1; and or a pharmaceutically-acceptable salt thereof.

In another embodiment of the present invention there is provided a compound of formula (I) wherein:

A is selected from —N=C*—S— or —CH=C*—S—, $R^2$ is H, Z is N, m is 0, G is $NR^5$ and $R^1$, $R^4$, $R^5$, and $Q^1$ are as previously defined.

In another embodiment of the present invention there is provided a compound of formula (I) wherein:

A is —CH=C*—O—, wherein * indicates the atom which forms the bond to the ring containing G in Formula I, and wherein A is optionally substituted on any available carbon atom by $R^3$;

G is $NR^5$;

Z is N;

$Q^1$ is phenyl;

$R^1$ is selected from hydrogen, mercapto, amino and (1-3C)alkylthio;

$R^2$ is hydrogen;

$R^4$ is selected from hydrogen and (1-3C)alkyl;

$R^5$ is selected from hydrogen, (1-3C)alkyl, phenyl and benzyl, wherein a phenyl group within $R^5$ optionally bears 1 or 2 substituents selected from (1-3C)alkyl and (1-3C)alkoxy; and m is 0;

or a pharmaceutically-acceptable salt thereof.

In another embodiment of the present invention there is provided a compound of formula (I) wherein:

A is selected from —N=C*—S— and —S—C*=N— wherein * indicates the atom which forms the bond to the ring containing G in Formula I, and wherein A is optionally substituted on any available carbon atom by $R^3$;

G is $NR^5$;

Z is N;

$Q^1$ is phenyl;

$R^1$ is selected from hydrogen, mercapto, amino and (1-3C)alkylthio;

$R^2$ is hydrogen;

$R^4$ is selected from hydrogen and (1-3C)alkyl;

$R^5$ is selected from hydrogen, (1-3C)alkyl, phenyl and benzyl, wherein a phenyl group within $R^5$ optionally bears 1 or 2 substituents selected from (1-3C)alkyl and (1-3C)alkoxy; and m is 0;

or a pharmaceutically-acceptable salt thereof.

In another embodiment of the present invention there is provided a compound of formula (I) wherein:

A is —N=C*—S— or —CH=C*—S—;

G is $NR^5$;

Z is N;

$R^1$ is selected from hydrogen, hydroxy, mercapto, amino, (1-6C)alkylamino, di(1-6C)alkylamino, (1-6C)alkanoylamino, aryl-(1-6C)alkylamino, (1-6C)alkoxy or (1-6C)alkylthio;

$R^2$ is hydrogen;

m is 0;

$R^4$ is selected from hydrogen, halogeno, amino, (1-6C)alkyl, (1-6C)alkoxy, (1-6C)alkylthio, aryl, heteroaryl, heterocyclyl, arylcarbonyl, heteroarylcarbonyl, aryl(1-6C)alkyl, heteroaryl(1-6C)alkyl, heterocyclyl(1-6C)alkyl, aryl(1-6C)alkylthio, heteroaryl(1-6C)alkylthio, (3-7C)cycloalkyl(1-6C)alkyl, (3-7C)cycloalkyl(1-6C)alkylthio, wherein each (1-6C)alkyl is optionally substituted by one or more of the following hydroxy, (1-6C)alkoxy, (1-6C)alkylthio, amino, (1-6C)alkylamino, di(1-6C)alkyl amino; or $R^4$ is (2-8C)alkynyl optionally substituted by amino, (1-6C)alkylamino, di(1-6C)alkyl amino, hydroxy, (1-6C)alkoxy, heteroaryl, or (3-7C)cycloalkyl in which thee cycloalkyl is optionally substituted by one or more amino or hydroxy;

$R^5$ is selected from hydrogen, (1-6C)alkyl, (2-C)alkenyl, (3-1C)cycloalkyl, (3-11C)cycloalkenyl, (3-11C)cycloalkyl(1-6C)alkyl, phenyl(1-6C)alkyl, [6-(8-oxa-3-azabicyclo[3.2.1]oct-3-yl)hexyl], (tetrahydro-1,1-dioxido-3-thienyl)amino]ethyl, piperidinyl, pyrrolidinyl, morpholinyl, piperazinyl, or tetrahydro-2H-pyranyl, 2-(benzylcarbonylamino)ethyl, 2-[(2-chloropyridin-3-yl)oxymethylcarbonylamino]ethyl, 2-(N,N-dimethylaminosulfonylamino)ethyl, (2-(2,4-dichlorobenzenesulfonamido)-phenyl)methyl, 2-(tert-butoxycarbonylamino)ethyl, 4-(tert-butoxycarbonylamino)butyl, 2-(2-propenylamino)ethyl and 5-(morpholinocarbonylamino)pent-1-yl, wherein a phenyl group within $R^5$ optionally bears 1 or 2 substituents selected from (1-3C)alkyl, (1-3C)alkoxy, halo, trifluoromethyl, piperidinyl, piperazinyl (optionally substituted by a (1-4C)alkyl), pyridinyloxy, amino, (1-6C)alkylamino, di(1-6C)alkylamino, or morpholino and wherein any wherein any (1-6C)alkyl or (3-11C)cycloalkyl is optionally substituted by 1 or more substituents selected from hydroxy, oxo, fluoro, amino, (1-6C)alkylamino, di(1-6C)alkylamino, anilino, methylsulfonyl, trifluoromethyl, carboxymethyl, (1-3C)alkoxy, (1-3C)alkylthio, pyridyl, pyrazolyl, imidazolyl, imidazo[1,2-a]pyridinyl, pyrrolidinyl, morpholinyl, piperidinyl, piperazinyl, 1,3-benzodioxinyl, 1,4-benzodioxinyl, (3,4-dihydro-1H-2-benzopyranyl), 1,4-dioxanyl, or tetrahydrofuryl and wherein any heterocyclic ring in $R^5$ is optionally substituted optionally substituted by one or more of the following: (1-4C)alkyl, halo, hydroxy, or phenyl;

$Q^1$ is phenyl, naphthyl, benzothienyl, indolyl, wherein any CH in $Q^1$ is optionally substituted by one or more halo, hydroxy, cyano, (1-6C)alkyl optionally substituted by one or more fluoro, (1-6C)alkoxy, (1-3C)alkylsulphonylamino, methanesulfonylamino, benzyloxy, phenylthio, a group $R^rNHCONH$— in which $R^r$ is selected from phenyl, phenyl(1-6C)alkyl or (1-6C)alkyl, or a group $R^s$—O—CO—NH— in which $R^s$ is selected from (1-6C)alkyl, phenyl or phenyl(1-6C)alkyl, wherein a phenyl ring in benzyloxy or phenylthio is optionally substituted by one or more (1-6C)alkyl or (1-6C)alkoxy;

or a pharmaceutically-acceptable salt thereof.

Preferably A is —N═C*—S—.

More preferably A is —N═C*—S—$R^2$ is H, Z is N, m is 0 and G is $NR^5$ and $R^1$, $R^4$, $R^5$, and $Q^1$ are as previously defined.

In another embodiment of the present invention there is provided a compound of formula (A) wherein:

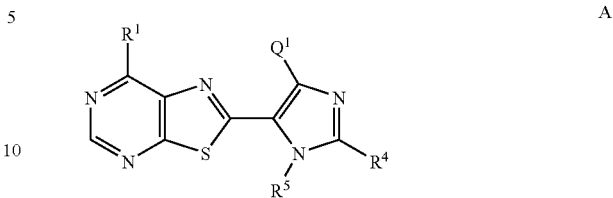

$R^1$ is selected from hydrogen, hydroxy, mercapto, amino, (1-6C)alkylamino, di(1-6C)alkylamino, (1-6C)alkanoylamino, aryl(1-6C)alkylamino, (1-6C)alkoxy or (1-6C)alkylthio;

$R^4$ is selected from hydrogen, halogeno, amino, (1-6C)alkyl, (1-6C)alkoxy, (1-6C)alkylthio, aryl, heteroaryl, heterocyclyl, arylcarbonyl, heteroarylcarbonyl, aryl(1-6C)alkyl, heteroaryl(1-6C)alkyl, heterocyclyl(1-6C)alkyl, aryl(1-6C)alkylthio, heteroaryl(1-6C)alkylthio, (3-7C)cycloalkyl(1-6C)alkyl, (3-7C)cycloalkyl(1-6C)alkylthio, wherein each (1-6C)alkyl is optionally substituted by one or more of the following hydroxy, (1-6C)alkoxy, (1-6C)alkylthio, amino, (1-6C)alkylamino, di(1-6C)alkyl amino; or $R^4$ is (2-8C)alkynyl optionally substituted by amino, (1-6C)alkylamino, di(1-6C)alkyl amino, hydroxy, (1-6C)alkoxy, heteroaryl, or (3-7C)cycloalkyl in which the cycloalkyl is optionally substituted by one or more amino or hydroxy;

$R^5$ is selected from hydrogen, (1-6C)alkyl, (2-6C)alkenyl, (3-7C)cycloalkyl, (3-7C)cycloalkyl(1-6C)alkyl and phenyl(1-6C)alkyl, wherein a phenyl group within $R^5$ optionally bears 1 or 2 substituents selected from halo, (1-3C)alkyl, (1-3C)alkoxy and morpholino and wherein any alkyl or cycloalkyl in $R^5$ is optionally substituted by 1 or 2 substituents selected from hydroxy, oxo, (1-3C)alkoxy, (1-3C)alkylthio, pyridyl, pyrrolidinyl, morpholinyl, piperidinyl, piperazinyl, tetrahydro-2H-pyranyl, tetrahydrofuryl which is optionally substituted by methyl;

$Q^1$ is phenyl or naphthyl optionally substituted by one or more of the following: halo, cyano, (1-6C)alkoxy, (1-3C)alkylsulphonylamino, (1-4C)alkyl-O—CO—NH— or benzyloxy or phenylthio wherein the phenyl ring in benzyloxy or phenylthio is optionally substituted by one or more (1-6C)alkyl or (1-6C)alkoxy;

or a pharmaceutically-acceptable salt thereof.

Particular values of the substituents $R^1$, $R^4$, $R^5$ and $Q^1$ are now given. It will be understood that such values may be used where appropriate with any of the definitions, claims or embodiments defined hereinbefore or hereinafter.

In one embodiment $R^5$ represents a phenyl(1-6C)alkyl group or a heteroaryl(1-6C)alkyl group in which the phenyl ring or the heteroaryl ring are optionally substituted on carbon by one or more of the following: halo, (1-3C)alkyl, (1-3C)alkoxy, heterocyclyl (optionally substituted by one or more (1-3C)alkyl), or a group $(CH_2)_zNR^jR^k$ in which z is 0, 1, 2, 3, 4, 5 or 6 and $R^j$ and $R^k$ are independently H or (1-4C)alkyl optionally substituted by one or more (1-3C)alkoxy or $R^5$ represents a (3-11C)cycloalkyl(1-6C)alkyl group in which the cycloalkyl group is optionally substituted by one or more of the following: halo, (1-3C)alkyl, (1-3C)alkoxy, hydroxy, oxo, heterocyclyl optionally substituted by one or more (1-3C)alkyl, or a group $(CH_2)_zNR^jR^k$ in which z is 0, 1, 2, 3, 4, 5 or 6 and $R^j$ and $R^k$ are independently H or (1-4C)alkyl optionally substituted by one or more (1-3C)alkoxy.

In another embodiment R⁵ represents a phenyl(1-6C)alkyl group in which the phenyl ring is optionally substituted by one or more of the following: halo, (1-3C)alkyl, (1-3C) alkoxy, heterocyclyl optionally substituted by one or more (1-3C)alkyl, or a group $(CH_2)_z NR^j R^k$ in which z is 0, 1, 2, 3, 4, 5 or 6 and $R^j$ and $R^k$ are independently H or (1-4C)alkyl optionally substituted by one or more (1-3C)alkoxy.

R¹ is selected from hydrogen, hydroxy, mercapto, methoxy, amino, methylamino, diisopropylamino, acetylamino, benzylamino, or methylthio.

R⁴ is selected from hydrogen, bromo, methoxy, amino, phenyl, 4-pyridyl, 3-thienyl, propylthio, 2-methoxyethylthio, 2-methoxyethyl, ethyl, hydroxy(2-thienyl)methyl, (2-thienyl)carbonyl, 2-furylcarbonyl, hydroxy(2-furyl)methyl, 5-methylisoxazol-3-ylcarbonyl, hydroxy(5-methylisoxazol-3-yl)methyl, hydroxy(1,3-dimethyl-1H-pyrazol-5-yl)methyl, (1,3-dimethyl-1H-pyrazol-5-yl)carbonyl, 2-(dimethylaminoethylthio, 2-[(methylthio)methyl]thio, (1H-imidazol-1-yl)ethyl]thio, (pyridin-3-ylmethyl)thio, cyclopropylmethylthio, benzylthio, 4-methylpiperazin-1-yl, 2-(1-aminocyclohexyl)ethynyl, 3-hydroxybut-1-yn-1-yl, 2-(1-hydroxycyclohexyl)ethynyl, pyridin-2-ylethynyl, 3-amino-3-methylbut-1-yn-1-yl, (3-methoxyprop-1-yn-1-yl), morpholin-4-yl, pyrimidin-5-yl, 3-(dimethylamino)prop-1-yn-1-yl, 1(2H)-(tert-butoxycarbonyl)-3,6-dihydropyridin-4-yl, (1,2,3,6-tetrahydropyridin-4-yl), hydroxy (phenyl)methyl, cyclopropyl(hydroxy)methyl, (1,3-benzodioxol-4-yl)(hydroxy)methyl, 1-hydroxy-3-methylbut-1-yl or (1-methyl-1H-imidazol-2-yl)(hydroxy) methyl.

R⁵ is selected from hydrogen, methyl, ethyl, butyl, cyclohexylmethyl, 2-hydroxyethyl, 2-methoxyethyl, 2-(hydroxymethyl)prop-1-yl, 4-oxocyclohex-1-ylmethyl, 4-hydroxycyclohex-1-ylmethyl, 1,4-dioxaspiro[4,5]dec-8-ylmethyl, 2- (morpholin-4-yl)benzyl or (2-(morpholin-4-yl) cyclohexyl)methyl.

Q¹ is phenyl.

Preferably in compounds of formula A

R¹ is selected from hydroxy, amino, mercapto or (1-6C)alkoxy or (1-6C)alkylthio;

R⁴ is selected from hydrogen, halogeno, amino, (1-6C)alkyl, (1-6C)alkoxy, (1-6C)alkylthio, aryl, heteroaryl, arylcarbonyl, heteroarylcarbonyl, aryl(1-6C)alkyl, heteroaryl(1-6C) alkyl or heterocyclyl(1-6C)alkyl wherein each (1-6C)alkyl is optionally substituted by one or more of the following hydroxy, (1-6C)alkoxy or (1-6C)alkylthio;

R⁵ is selected from hydrogen, (1-6C)alkyl, (2-6C)alkenyl, (3-7C)cycloalkyl, (3-7C)cycloalkyl(1-6C)alkyl and phenyl(1-6C)alkyl, wherein a phenyl group within R⁵ optionally bears 1 or 2 substituents selected from (1-3C)alkyl and (1-3C)alkoxy and morpholino and wherein any (1-6C) alkyl or (3-7C)cycloalkyl is optionally substituted by 1 or 2 substituents selected from hydroxy, oxo, (1-3C)alkoxy, (1-3C)alkylthio, pyridyl, pyrrolidinyl, morpholinyl, piperidinyl, or piperazinyl or dioxin or tetrahydrofuryl which is optionally substituted by methyl;

Q¹ is phenyl or naphthyl optionally substituted by one or more of the following: halo, cyano, (1-6C)alkoxy, (1-3C)alkylsulphonylamino, (1-4C)alkyl-O—CO—NH— or benzyloxy or phenylthio wherein the phenyl ring in benzyloxy or phenylthio is optionally substituted by one or more (1-6C) alkyl or (1-6C)alkoxy;

or a pharmaceutically-acceptable salt thereof.

Preferably in compounds of formula A, R⁵ is selected from hydrogen, (1-6C)alkyl(3-7C)cycloalkyl or (3-7C)cycloalkyl (1-6C)alkyl wherein each CH₂ is optionally substituted by one or more of the following hydroxy, (1-6C)alkoxy or oxo.

Preferably in compounds of formula A, Q¹ is phenyl.

In another embodiment of the present invention there is provided a compound of formula (I) wherein:

A is selected from —S—C*=CH— and —CH=C*—S— wherein * indicates the atom which forms the bond to the ring containing G in Formula I, and wherein A is optionally substituted on any available carbon atom by R³;

G is NR⁵;

Z is N;

Q¹ is phenyl;

R¹ is selected from hydrogen, mercapto, amino and (1-3C) alkylthio,

R² is hydrogen;

R⁴ is selected from hydro and (1-3C)alkyl;

R⁵ is selected from hydrogen, (1-3C)alkyl, phenyl and benzyl, wherein a phenyl group within R⁵ optionally bears 1 or 2 substituents selected from (1-3C)alkyl and (1-3C) alkoxy; and m is 0;

or a pharmaceutically-acceptable salt thereof.

Preferably A is selected from —CH=C*—S—.

More preferably A is —CH=C*—S—, R² is H, Z is N, m is 0, G is NR⁵ and R¹, R⁴, R⁵, and Q¹ are as previously defined.

In another embodiment of the present invention there is provided a compound of formula (B) wherein:

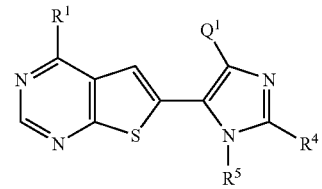

B

R¹ is selected from hydrogen, hydroxy, amino, (1-6C)alkylamino, di(1-6C)alkylamino benzylamino, (1-6C)alkanoylamino, (1-3C)alkylthio;

R⁴ is hydrogen; and

R⁵ is selected from hydrogen, (1-6C)alkyl, (2-6C)alkenyl, (3-11C)cycloalkyl, (3-11C)cycloalkenyl, (3-11C)cycloalkyl(1-6C)alkyl, phenyl(1-6C)alkyl, [6-(8-oxa-3-azabicyclo[3.2.1]oct-3-yl)hexyl], (tetrahydro-1,1-dioxido-3-thienyl)amino]ethyl, piperidinyl, pyrrolidinyl, morpholinyl, piperazinyl, or tetrahydro-2H-pyranyl, 2-(benzylcarbonylamino)ethyl, 2-[(2-chloropyridin-3-yl) oxymethylcarbonylamino]ethyl, 2-(N,N-dimethylaminosulfonylamino)ethyl, (2-(2,4-dichlorobenzenesulfonamido)-phenyl)methyl, 2-(tert-butoxycarbonylamino) ethyl, 4-(tert-butoxycarbonylamino)butyl, 2-(2-propenylamino)ethyl and 5-(morpholinocarbonylamino) pent-1-yl, wherein a phenyl group within R⁵ optionally bears 1 or 2 substituents selected from (1-3C)alkyl, (1-3C) alkoxy, halo, trifluoromethyl, piperidinyl, piperazinyl (optionally substituted by a (1-4C)alkyl), pyridinyloxy, amino, (1-6C)alkylamino, di(1-6C)alkylamino, or morpholino and wherein any wherein any (1-6C)alkyl or (3-11C)cycloalkyl is optionally substituted by 1 or more substituents selected from hydroxy, oxo, fluoro, amino, (1-6C)alkylamino, di(1-6C)alkylamino, anilino, methylsulfonyl, trifluoromethyl, carboxymethyl, (1-3C)alkoxy, (1-3C)alkylthio, pyridyl, pyrazolyl, imidazolyl, imidazo [1,2-a]pyridinyl, pyrrolidinyl, morpholinyl, piperidinyl, piperazinyl, 1,3-benzodioxinyl, 1,4-benzodioxinyl, (3,4-dihydro-1H-2-benzopyranyl), 1,4-dioxanyl, or tetrahydrofuryl and wherein any heterocyclic ring in $R^5$ is optionally substituted optionally substituted by one or more of the following: (1-4C)alkyl, halo, hydroxy, or phenyl;

$Q^1$ is phenyl, naphthyl, benzothienyl, indolyl, wherein any CH in $Q^1$ is optionally substituted by one or more halo, hydroxy, cyano, (1-6C)alkyl optionally substituted by one or more fluoro, (1-6C)alkoxy, (1-3C)alkylsulphonylamino, methansulfonylamino, benzyloxy, phenylthio, a group $R^t$NHCONH— in which $R^1$ is selected from phenyl, phenyl(1-6C)alkyl or (1-6C)alkyl, or a group $R^s$—O—CO—NH— in which $R^s$ is selected from (1-6C)alkyl, phenyl or phenyl(1-6C)alkyl;

or a pharmaceutically-acceptable salt thereof.

In a particular group of compounds of formula B:

$Q^1$ is phenyl or naphthyl optionally substituted by one or more of the following:halo, cyano, (1-6C)alkoxy, (1-3C)alkylsulphonylamino, (1-4C)alkyl-O—CO—NH— or benzyloxy or phenylthio wherein the phenyl ring in benzyloxy or phenylthio is optionally substituted by one or more (1-6C)alkyl or (1-6C)alkoxy;

$R^1$ is selected from amino, acetylamino and (1-3C)alkylthio;

$R^4$ is hydrogen; and $R^5$ is selected from (1-6C)alkyl, (2-6C)alkenyl, (3-7C)cycloalkyl, (3-7C)cycloalkyl(1-6C)alkyl and phenyl(1-6C)alkyl, wherein a phenyl group within $R^5$ optionally bears 1 or 2 substituents selected from (1-3C)alkyl and (1-3C)alkoxy and morpholino and wherein any (1-6C)alkyl or (3-7C)cycloalkyl is optionally substituted by 1 or 2 substituents selected from hydroxy, (1-3C)alkoxy, (1-3C)alkylthio, pyridyl, pyrrolidinyl, morpholinyl, piperidinyl, or piperazinyl or dioxin or tetrahydrofuryl which is optionally substituted by methyl;

or a pharmaceutically-acceptable salt thereof.

Particular values of the substituents $R^1$, $R^4$, $R^5$ and $Q^1$ are now given. It will be understood that such values may be used where appropriate with any of the definitions, claims or embodiments defined hereinbefore or hereinafter.

In one embodiment $R^5$ represents a phenyl(1-6C)alkyl group or a heteroaryl(1-6C)alkyl group in which the phenyl ring or the heteroaryl ring are optionally substituted on carbon by one or more of the following: halo, (1-3C)alkyl, (1-3C)alkoxy, heterocyclyl (optionally substituted by one or more (1-3C)alkyl), or a group $(CH_2)_zNR^jR^k$ in which z is 0, 1, 2, 3, 4, 5 or 6 and $R^j$ and $R^k$ are independently H or (1-4C)alkyl optionally substituted by one or more (1-3C)alkoxy or $R^5$ represents: a (3-11C)cycloalkyl(1-6C)alkyl group in which the cycloalkyl group is optionally substituted by one or more of the following: halo, (1-3C)alkyl, (1-3C)alkoxy, hydroxy, oxo, heterocyclyl optionally substituted by one or more (1-3C)alkyl, or a group $(CH_2)_zNR^jR^k$ in which z is 0, 1, 2, 3, 4, 5 or 6 and $R^j$ and $R^k$ are independently H or (1-4C)alkyl optionally substituted by one or more (1-3C)alkoxy.

In another embodiment $R^5$ represents a phenyl(1-6C)alkyl group in which the phenyl ring is optionally substituted by one or more of the following: halo, (1-3C)alkyl, (1-3C)alkoxy, heterocyclyl optionally substituted by one or more (1-3C)alkyl, or a group $(CH_2)_zNR^jR^k$ in which z is 0, 1, 2, 3, 4, 5 or 6 and $R^j$ and $R^k$ are independently H or (1-4C)alkyl optionally substituted by one or more (1-3C)alkoxy.

$R^1$ is selected from hydrogen, hydroxy, amino, methylamino, acetylamino, benzylamino, or methylthio.

$R^4$ is hydrogen.

$R^5$ is selected from hydrogen, methyl, ethyl, 1-methylethyl, 1-methylpropyl, 1,2-dimethylpropyl, butyl, isobutyl, 2-methylbutyl, 1,3-dimethylbutyl, 2-hydroxyethyl, 2-hydroxy-1-methylethyl, 2-hydroxyprop-1-yl, 3-hydroxyprop-1-yl, 2,3-dihydroxy-prop-1-yl, 3,3,3-trifluoro-2-hydroxyprop-1-yl, 1-hydroxyhex-2-yl, 1-hydroxybut-2-yl, 2-methoxyethyl, 2-methoxy-1-methylethyl, 2,2-dimethoxyethyl, 3-methoxypropyl, 2-methoxy-2-methylpropyl, 2-fluoroethyl, 2-(methylsulfonyl)ethyl, 4-aminobutyl, 4-(diethylamino)-1-methylbutyl, 2-(phenylamino)ethyl, 3-(dimethylamino)-2,2-dimethylpropyl, cyclopropyl, 4-hydroxycyclohex-1-yl, 2-hydroxycyclohex-1-ylmethyl, cyclohexylmethyl, cycloheptylmethyl, spiro[bicyclo[2.2.1]hept-2-ene-7,1'-cyclopropan]-5-ylmethyl, [(1S,5S)-6,6-dimethylbicyclo[3.1.1]hept-2-yl]methyl, 2-(carboxymethyl)cyclohex-1-ylmethyl, 2-propenyl, 2-methyl-2-propenyl, 2-(2-propenylamino)ethyl, (3-methylbut-2-en-1-yl), benzyl, 3,4-dimethoxybenzyl, (2-fluorophenyl)methyl, (2-methylphenyl)methyl, (3-fluorophenyl)methyl, phenylmethyl, (2-methoxyphenyl)methyl, [[2-(1-piperidinyl)phenyl]methyl], [[2-(2-pyridinyloxy)phenyl]methyl], 2-(morpholin-4-yl)benzyl, [2-(4-methyl-1-piperazinyl)phenyl]methyl, (2-aminophenyl)methyl, 2-hydroxy-2-(4-trifluoromethylphenyl)ethyl, pyridin-3-ylmethyl, (1H-imidazol-2-ylmethyl), (imidazo[1,2-a]pyridin-2-ylmethyl), 2-(methylpiperazin-1-yl)ethyl, 3-(4-methyl-1-piperazinyl)propyl, 3-(hexahydro-1H-azepin-1-yl)propyl, (tetrahydro-2-furanyl)methyl, 2-(4-morpholinyl)ethyl, 2-(3,5-dimethyl-1H-pyrazol-4-yl)ethyl, 2-(1H-imidazol-1-yl)ethyl, (3,4-dihydro-1H-2-benzopyran-1-yl)methyl, (1,4-ioxan-2-ylmethyl), [6-(8-oxa-3-azabicyclo[3.2.1]oct-3-yl)hexyl], [[2-(4-morpholinyl)phenyl]methyl], [(6-fluoro-4H-1,3-benzodioxin-8-yl)methyl], [3-[4-(2-methoxyphenyl)-1-piperazinyl]propyl], 2-(2,3-dihydro-1,4-benzodioxin-6-yl)-2-hydroxyethyl, pyrrolidin-3-yl, tetrahydro-2,2-dimethyl-2H-pyran-4-yl, 2,2,6,6-tetramethyl-4-piperidinyl, 2-(4-(hydroxymethyl)piperidin-1-yl), (1-methylpyrrolidin-3-yl), 2-[[(4-fluorophenyl)methyl]amino]ethyl, 2-[(tetrahydro-1,1-dioxido-3-thienyl)amino]ethyl, 2-(benzylcarbonylamino)ethyl, 2-[(2-chloropyridin-3-yl)oxymethylcarbonylamino]ethyl, 2-(N,N-dimethylaminosulfonylamino)ethyl, (2-(2,4-dichlorobenzenesulfonamido)-phenyl)methyl, 2-(tert-butoxycarbonylamino)ethyl, 4-(tert-butoxycarbonylamino)butyl, or 5-(morpholinocarbonylamino)pent-1-yl.

$Q^1$ is selected from phenyl, 2-chlorophenyl, 3-chlorophenyl, 4-chlorophenyl, 3-fluorophenyl, 4-fluorophenyl, 3-iodophenyl, 3-bromophenyl, 2,5-dichlorophenyl, 2,5-difluorophenyl, 2-methylphenyl, 3-butoxyphenyl, 3-(4-methylphenylthio)phenyl, 4-(benzyloxy)phenyl, 4-butoxyphenyl, 4-methanesulfonylaminophenyl, 1-naphthyl, 2-naphthyl, 1-benzothien-2-yl, 1H-indol-5-yl, 4-(benzyloxy)-2-methylphenyl, 3-(benzyloxy)phenyl, 3-hydroxyphenyl, 3-cyanophenyl, 4-[(3,4-dichlorobenzyl)oxyphenyl, 3-(tert-butoxycarbonylamino)phenyl, 3-(phenylaminocarbonylamino)phenyl, 3-(benzylaminocarbonylamino)phenyl, 4-(phenylaminocarbonylamino)phenyl, 4-(benzylaminocarbonylamino)phenyl, 3-[2-fluoro-5-(trifluoromethyl)phenylaminocarbonylamino]phenyl, 4-[2-fluoro-5-(trifluoromethyl)phenylaminocarbonylamino]phenyl, 4-(benzylcarbonylaminophenyl)phenyl, 3-(benzylcarbonylaminophenyl)phenyl, 3-(benzyloxycarbonylamino)phenyl, 3-(butyloxycarbonylamino)phenyl or 3-(phenyloxycarbonylamino)phenyl.

In another embodiment of the present invention there is provided a compound of formula (I) wherein:

A is selected from —NH—C*═N— and —N═C*—NH— wherein * indicates the atom which forms the bond to the ring containing G in Formula I, and wherein A is optionally substituted on any available carbon atom by $R^3$;

G is NR⁵;
Z is N;
Q¹ is phenyl;
R¹ is selected from hydrogen, mercapto, amino and (1-3C) alkylthio;
R² is hydrogen;
R³ is (1-3C)alkyl;
R⁴ is selected from hydrogen and (1-3C)alkyl;
R⁵ is selected from hydrogen, (1-3C)alkyl, phenyl and benzyl, wherein a phenyl group within R⁵ optionally bears 1 or 2 substituents selected from (1-3C)alkyl and (1-3C) alkoxy; and
m is 0 or 1;

or a pharmaceutically-acceptable salt thereof.

A particular compound according to the present is any one of the compounds described in the Examples or a pharmaceutically acceptable salt thereof. Particular groups of such compounds are described below.

A compound selected from:
8-(1-methyl-4-phenyl-1H-imidazol-5-yl)-9H-purin-6-amine
9-methyl-8-(1-methyl-4-phenyl-1H-imidazol-5-yl)-9H-purin-6-amine
7-methyl-8-(1-methyl-4-phenyl-1H-imidazol-5-yl)-7H-purin-6-amine or
8-(4-phenyl-1H-imidazol-5-yl)-9H-purin-6-amine or a pharmaceutically acceptable salt thereof.

A compound selected from:
6-(1-methyl-4-phenyl-1H-imidazol-5-yl)-4-(methylthio) thieno[3,2-d]pyrimidine
6-(1-methyl-4-phenyl-1H-imidazol-5-yl)thieno[3,2-d]pyrimidin-4-amine or
5-[4-(methylthio)thieno[3,2-d]pyrimidin-6-yl]-1H-imidazol-1-ol.

or a pharmaceutically acceptable salt thereof.

A compound selected from:
5-[4-(methylthio)thieno[3,2-d]pyrimidin-6-yl]-1H-imidazol-1-ol or
9-Cyclohexyl-8-(1-methyl-4-phenyl-1H-imidazol-5-yl)-9-purin-6-amine.

or a pharmaceutically acceptable salt thereof.

A compound selected from:
6-(1-methyl-4-phenyl-1H-imidazol-5-yl)furo[2,3-d]pyrimidine
6-(1-methyl-4-phenyl-1H-imidazol-5-yl)furo[2,3-d]pyrimidin-4-amine or
6-[-(4-methoxybenzyl)-4-phenyl-1H-imidazol-5-yl]furo[2,3-d]pyrimidine or a pharmaceutically acceptable salt thereof.

A compound selected from:
6-(1-methyl-4-phenyl-1H-imidazol-5-yl)-7H-pyrrolo[2,3-d]pyrimidine
6-(4-phenyl-1H-imidazol-5-yl)thieno[3,2-d]pyrimidine
2-(1-methyl-4-phenyl-1H-imidazol-5-yl)[1,3]oxazolo[5,4-d]pyrimidin-7-amine
2-[1-(4-methoxybenzyl)-4-phenyl-1H-imidazol-5-yl]furo[3,2-d]pyridine
6-(1-Methyl-4-phenyl-1H-imidazol-5-yl)-5H-pyrrolo[3,2-d]pyrimidin-4-amine or or a pharmaceutically acceptable salt thereof.

A compound of formula A selected from one or more of:
2-(1-methyl-4-phenyl-1H-imidazol-5-yl)[1,3]thiazolo[5,4-d]pyrimidin-7-amine
2-(4-phenyl-1H-imidazol-5-yl)[1,3]thiazolo[5,4-d]pyrimidin-7-amine
2-(4-phenyl-1H-imidazol-5-yl)[1,3]thiazolo[5,4-d]pyrimidine
2-(2-Bromo-1-methyl-4-phenyl-1H-imidazol-5-yl)[1,3]thiazolo[5,4-d]pyrimidin-7-amine
2-(2-Amino-1-methyl-4-phenyl-1H-imidazol-5-yl)[1,3]thiazolo[5,4-d]pyrimidin-7-amine
2-(2-Methoxy-1-methyl-4-phenyl-1H-imidazol-5-yl)[1,3]thiazolo[5,4-d]pyrimidin-7-amine
2-(1-Methyl-2,4-diphenyl-1H-imidazol-5-yl)[1,3]thiazolo[5,4-d]pyrimidin-7-amine
2-(1-methyl-4-phenyl-1H-imidazol-5-yl)[1,3]thiazolo[5,4-d]pyrimidine-7-thiol
7-methoxy-2-(1-methyl-4-phenyl-1H-imidazol-5-yl)[1,3]thiazolo[5,4-d]pyrimidine
2-[1-methyl-4-phenyl-2-(3-thienyl)-1H-imidazol-5-yl][1,3]thiazolo[5,4-d]pyrimidin-7-amine
2-(1-methyl-4-phenyl-2-pyridin-4-yl-1H-imidazol-5-yl)[1,3]thiazolo[5,4-d]pyrimidin-7-amine
2-(2-ethyl-1-methyl-4-phenyl-1H-imidazol-5-yl)[1,3]thiazolo[5,4-d]pyrimidin-7-amine
2-[1-methyl-4-phenyl-2-(propylthio)-1H-imidazol-5-yl][1,3]thiazolo[5,4-d]pyrimidin-7-amine
2-(2-[(methoxymethyl)thio]-1-methyl-4-phenyl-1H-imidazol-5-yl][1,3]thiazolo-[5,4-d]pyrimidin-7-amine
[5-(7-amino[1,3]thiazolo[5,4-d]pyrimidin-2-yl)-1-methyl-4-phenyl-1H-imidazol-2-yl](5-methylisoxazol-3-yl)methanone
[5-(7-amino[1,3]thiazolo[5,4-d]pyrimidin-2-yl)-1-methyl-4-phenyl-1H-imidazol-2-yl](5-methylisoxazol-3-yl)methanol
[5-(7-amino[1,3]thiazolo[5,4-d]pyrimidin-2-yl)-1-methyl-4-phenyl-1H-imidazol-2-yl](2-furyl)methanone
[5-(7-amino[1,3]thiazolo[5,4-d]pyrimidin-2-yl)-1-methyl-4-phenyl-1H-imidazol-2-yl](2-furyl)methanol
(5-(7-amino[1,3]thiazolo[5,4-d]pyrimidin-2-yl)-1-methyl-4-phenyl-1H-imidazol-2-yl](1,3-dimethyl-1H-pyrazol-5-yl)methanone
[5-(7-amino[1,3]thiazolo[5,4-d]pyrimidin-2-yl)-1-methyl-4-phenyl-1H-imidazol-2-yl](1,3-dimethyl-1H-pyrazol-5-yl)methanol or
[5-(7-amino[1,3]thiazolo[5,4-d]pyrimidin-2-yl)-1-methyl-4-phenyl-1H-imidazol-2-yl](2-thienyl)methanol
2-(1-Ethyl-4-phenyl-1H-imidazol-5-yl)[1,3]thiazolo[5,4-d]pyrimidin-7-amine
2-[1-(cyclohexylmethyl)-4-phenyl-1H-imidazol-5-yl][1,3]thiazolo[5,4-d]pyrimidin-7-amine
7-(Diisopropylamino)-2-(1-methyl-4-phenyl-1H-imidazol-5-yl)[1,3]thiazolo[5,4-d]pyrimidine-5-carbaldehyde
2-(2-{[2-(Dimethylamino)ethyl]thio}-1-methyl-4-phenyl-1H-imidazol-5-yl)[1,3]thiazolo[5,4-d]pyrimidin-7-amine
2-(1-Methyl-2-{[(methylthio)methyl]thio}-4-phenyl-1H-imidazol-5-yl)[1,3]thiazolo[5,4-d]pyrimidin-7-amine
2-(2-{[2-(1H-Imidazol-1-yl)ethyl]thio}-1-methyl-4-phenyl-1H-imidazol-5-yl)[1,3]thiazolo[5,4-d]pyrimidin-7-amine
2-{1-Methyl-4-phenyl-2-[(pyridin-3-ylmethyl)thio]-1H-imidazol-5-yl}[1,3]thiazolo[5,4-d]pyrimidin-7-amine
2-{2-[(Cyclopropylmethyl)thio]-1-methyl-4-phenyl-1H-imidazol-5-yl}[1,3]thiazolo[5,4-d]pyrimidin-7-amine
2-[2-(Benzylthio)-1-methyl-4-phenyl-1H-imidazol-5-yl][1,3]thiazolo[5,4-d]pyrimidin-7-amine
2-[1-Methyl-2-(4-methylpiperazin-1-yl)-4-phenyl-1H-imidazol-5-yl][1,3]thiazolo[5,4-d]pyrimidin-7-amine
2-{2-[(1-Aminocyclohexyl)ethynyl]-1-methyl-4-phenyl-1H-imidazol-5-yl}[1,3]thiazolo[5,4-d]pyrimidin-7-amine
4-[5-(7-Amino[1,3]thiazolo[5,4-d]pyrimidin-2-yl)-1-methyl-4-phenyl-1H-imidazol-2-yl]but-3-yn-2-ol 1-{[5-(7-Amino[1,3]thiazolo[5,4-d]pyrimidin-2-yl)-1-methyl-4-phenyl-1H-imidazol-2-yl]ethynyl}cyclohexanol
2-[1-Methyl-4-phenyl-2-(pyridin-2-ylethynyl)-1H-imidazol-5-yl][1,3]thiazolo[5,4-d]pyrimidin-7-amine
2-[2-(3-Amino-3-methylbut-1-yn-1-yl)-1-methyl-4-phenyl-1H-imidazol-5-yl][1,3]thiazolo[5,4-d]pyrimidin-7-amine
2-[2-(3-Methoxyprop-1-yn-1-yl)-1-methyl-4-phenyl-1H-imidazol-5-yl][1,3]thiazolo[5,4-d]pyrimidin-7-amine
2-(1-Methyl-2-morpholin-4-yl-4-phenyl-1H-imidazol-5-yl)[1,3]thiazolo[5,4-d]pyrimidin-7-amine
2-(1-Methyl-4-phenyl-2-pyrimidin-5-yl-1H-imidazol-5-yl)[1,3]thiazolo[5,4-d]pyrimidin-7-amine
2-{2-[3-Dimethylamino)prop-1-yn-1-yl]-1-methyl-4-phenyl-1H-imidazol-5-yl}[1,3]thiazolo[5,4-d]pyrimidin-7-amine
tert-Butyl 4-[5-(7-amino[1,3]thiazolo[5,4-d]pyrimidin-2-yl)-1-methyl-4-phenyl-1H-imidazol-2-yl]-3,6-dihydropyridine-1(2H)-carboxylate
2-[1-Methyl-4-phenyl-2-(1,2,3,6-tetrahydropyridin-4-yl)-1H-imidazol-5-yl][1,3]thiazolo[5,4-d]pyrimidin-7-amine
[5-(7-Amino[1,3]thiazolo[5,4-d]pyrimidin-2-yl)-1-methyl-4-phenyl-1H-imidazol-2-yl](phenyl)methanol
[5-(7-Amino[1,3]thiazolo[5,4-d]pyrimidin-2-yl)-1-methyl-4-phenyl-1H-imidazol-2-yl](cyclopropyl)methanol
(5-(7-Amino[1,3]thiazolo[5,4-d]pyrimidin-2-yl)-1-methyl-4-phenyl-1H-imidazol-2-yl](1,3-benzodioxol-4-yl)methanol
1-[5-(7-Amino[1,3]thiazolo[5,4-d]pyrimidin-2-yl)-1-methyl-4-phenyl-1H-imidazol-2-yl]-3-methylbutan-1-ol
[5-7-Amino[1,3]thiazolo[5,4-d]pyrimidin-2-yl)-1-methyl-4-phenyl-1H-imidazol-2-yl]-(1-methyl-1-H-imidazol-2-yl)methanol
2-(5-(7-Amino[1,3]thiazolo[5,4-d]pyrimidin-2-yl)-4-phenyl-1H-imidazol-1-yl]ethanol
2-[1-(2-Methoxyethyl)-4-phenyl-1H-imidazolo-5-yl][1,3]thiazolo[5,4-d]pyrimidin-7-amine
2-[5-(7-Amino[1,3]thiazolo[5,4-d]pyrimidin-2-yl)-4-phenyl-1H-imidazol-1-ylbutan-1-ol
2-(1-Butyl-4-phenyl-1H-imidazol-5-yl)[1,3]thiazolo[5,4-d]pyrimidin-7-amine
2-[1-(1,4-Dioxaspiro[4,5]dec-8-ylmethyl)-4-phenyl-1H-imidazol-5-yl][1,3]thiazolo[5,4-d]pyrimidin-7-amine
4-{[5-(7-Amino[1,3]thiazolo[5,4-d]pyrimidin-2-yl)-4-phenyl-1H-imidazol-1-yl]methyl}cyclohexanol
4-{[5-(7-Amino[1,3]thiazolo[5,4-d]pyrimidin-2-yl)-4-phenyl-1-imidazol-1-yl]methyl}cyclohexanone or
2-[1-(2-morpholin-4-ylbenzyl)-4-phenyl-1H-imidazol-5-yl)[1,3]thiazolo[5,4-d]pyrimidin-7-amine or a pharmaceutically acceptable salt thereof.

A compound of formula B selected from one or more of:
6-[1-(3,4-Dimethoxybenzyl)-4-phenyl-1H-imidazol-5-yl]thieno[2,3-d]pyrimidine
6-(1-Methyl-4-phenyl-1H-imidazol-5-yl)-4-(methylthio)thieno[2,3-d]pyrimidine
6-(1-Methyl-4-phenyl-1H-imidazol-5-yl)thieno(2,3-d]pyrimidin-4-amine
6-[1-(3,4-dimethoxybenzyl)-4-phenyl-1H-imidazol-5-yl]-4-(methylthio)thieno[2,3-d]pyrimidine
6-[1-(3,4-Dimethoxybenzyl)-4-phenyl-1H-imidazol-5-yl]thieno[2,3-d]pyrimidin-4-amine
N-methyl-6-(1-methyl-4-phenyl-1H-imidazol-5-yl)thieno[2,3-d]pyrimidin-4-amine
N-[6-(1-methyl-4-phenyl-1H-imidazol-5-yl)thieno2,3-d]pyrimidin-4-yl]acetamide
6-[4-(4-Fluorophenyl)-1-methyl-1H-imidazol-5-yl]thieno[2,3-d]pyrimidin-4-amine
6-(1-Benzyl-4-phenyl-1H-imidazol-5-yl)thieno[2,3-d]pyrimidine
6-[4-(3-Iodophenyl)-1-methyl-1H-imidazol-5-yl]thieno[2,3-d]pyrimidin-4-amine
6-[4-(3-Bromophenyl)-1-methyl-1H-imidazol-5-yl]thieno[2,3-d]pyrimidin-4-amine
6-[4-(3-Butoxyphenyl)-1-methyl-1H-imidazol-5-yl]thieno[2,3-d]pyrimidin-4-amine
6-{1-Methyl-4-[3-(4-methylphenylthio)phenyl]-1H-imidazol-5-yl}thieno[2,3-d]pyrimidin-4-amine
6-{4-[4-(Benzyloxy)phenyl]-1-methyl-1H-imidazol-5-yl}thieno[2,3-d]pyrimidin-4-amine
6-{4-[4-Butoxyphenyl]-1-methyl-1H-imidazol-5-yl}thieno[2,3-d]pyrimidin-4-amine
N-{4-[5-(4-aminothieno[2,3-d]pyrimidin-6-yl)-1-methyl-1H-imidazol-4-yl]phenyl}methanesulfonamide
6-(1-ethyl-4-phenyl-1H-imidazol-5-yl)thieno[2,3-d]pyrimidin-4-amine
6-[1-(3-Methoxypropyl)-4-phenyl-1H-imidazol-5-yl]thieno[2,3-d]pyrimidin-4-amine
6-(1-Isobutyl-4-phenyl-1H-imidazol-5-yl)thieno[2,3-d]pyrimidin-4-amine
2-[5-(4-Aminothieno[2,3-d]pyrimidin-6-yl)-4-phenyl-1H-imidazol-1-yl]ethanol
6-(1-Cyclopropyl-4-phenyl-1H-imidazol-5-yl)thieno[2,3-d]pyrimidin-4-amine
6-[1-(2-Methoxyethyl)-4-phenyl-1H-imidazol-5-yl]thieno[2,3-d]pyrimidin-4-amine
6-(1-Butyl-4-phenyl-1H-imidazol-5-yl)thieno[2,3-d]pyrimidin-4-amine
6-[4-Phenyl-1-(pyridin-3-ylmethyl)-1H-imidazol-5-yl]thieno[2,3-d]pyrimidin-4-amine
6-[1-(2,2-Dimethoxyethyl)-4-phenyl-1H-imidazol-5-yl]thieno[2,3-d]pyrimidin-4-amine
6-(4-Phenyl-1-pyrrolidin-3-yl)-1H-imidazol-5-yl)thieno[2,3-d]pyrimidin-4-amine
2-[5-(4-aminothieno[2,3-d]pyrimidin-6-yl)-4-phenyl-1H-imidazol-1-yl]hexan-1-ol
2-[5-(4-Aminothieno[2,3-d]pyrimidin-6-yl)-4-phenyl-1H-imidazol-1-yl]butan-1-ol
6-{1-[2-(4-Methylpiperazin-1-yl)ethyl]-4-phenyl-1H-imidazol-5-yl}thieno[2,3-d]pyrimidin-4-amine
2-(1-Ethyl-4-phenyl-1H-imidazol-5-yl)[1,3]thiazolo[5,4-d]pyrimidin-7-amine
2-[1-(cyclohexylmethyl)-4-phenyl-1H-imidazol-5-yl][1,3]thiazolo[5,4-d]pyrimidin-7-amine
6-(1-methyl-4-phenyl-1H-imidazol-5-yl)furo[3,2-d]pyrimidin-4-amine
6-[1-(2-Fluoroethyl)-4-phenyl-1H-imidazol-5-yl]thieno[2,3-d]pyrimidin-4-amine
6-[4-(2-Chlorophenyl)-1-methyl-1H-imidazol-5-yl]thieno[2,3-d]pyrimidin-4-amine
6-[4-(3-Chlorophenyl)-1-methyl-1H-imidazol-5-yl]thieno[2,3-d]pyrimidin-4-amine
6-[4-(4-Chlorophenyl)-1-methyl-1H-imidazol-5-yl]thieno[2,3-d]pyrimidin-4-amine
6-[1-Methyl-4-(2-naphthyl)-1H-imidazol-5-yl]thieno[2,3-d]pyrimidin-4-amine
6-[4-(1-Benzothien-2-yl)-1-methyl-1H-imidazol-5-yl]thieno[2,3-d]pyrimidin-4-amine
6-[4-(3-Fluorophenyl)-1-methyl-1H-imidazol-5-yl]thieno[2,3-d]pyrimidin-4-amine
6-[1-Methyl-4-(2-methylphenyl)-1H-imidazol-5-yl]thieno[2,3-d]pyrimidin-4-amine
6-[4-(2,5-Difluorophenyl)-1-methyl-1H-imidazol-5-yl]thieno[2,3-d]pyrimidin-4-amine 6-[(2,5-Dichlorophenyl)-1-methyl-1H-imidazol-5-yl]thieno[2,3-d]pyrimidin-4-amine
6-[1-Methyl-4-(1-naphthyl)-1H-imidazol-5-yl]thieno[2,3-d]pyrimidin-4-amine
6-[4-(1H-Indol-5-yl)-1-methyl-1H-imidazol-5-yl]thieno[2,3-d]pyrimidin-4-amine
6-{4-[4-(Benzyloxy)-2-methylphenyl]-1-methyl-1H-imidazol-5-yl}thieno[2,3-d]pyrimidin-4-amine
6-[1-(Cyclohexylmethyl)-4-phenyl-1H-imidazol-5-yl]-thieno[2,3-d]pyrimidin-4-amine
6-[1-[3-(4-Methyl-1-piperazinyl)propyl]-4-phenyl-1H-imidazol-5-yl]-thieno[2,3-d]pyrimidin-4-amine
6-[1-[3-(Hexahydro-1H-azepin-1-yl)propyl]-4-phenyl-1H-imidazol-5-yl]-thieno[2,3-d]pyrimidin-4-ol
6-[4-phenyl-1-(tetrahydro-2,2-dimethyl-2H-pyran-4-yl)-1H-imidazol-5-yl]-thieno[2,3-d]pyrimidin-4-amine
5-(4-aminothieno[2,3-d]pyrimidin-6-yl)-beta-methyl-4-phenyl-1H-imidazole-1-ethanol
6-[1-(2-methoxy-1-methylethyl)-4-phenyl-1H-imidazol-5-yl]thieno[2,3-d]pyrimidin-4-amine
6-[1-(1-methylethyl)-4-phenyl-1H-imidazol-5-yl]-thieno[2,3-d]pyrimidin-4-amine
6-[1-(1,2-dimethylpropyl)-4-phenyl-1H-imidazol-5-yl]-thieno[2,3-d]pyrimidin-4-amine
6-[1-(1,3-dimethylbutyl)-4-phenyl-1H-imidazol-5-yl]-thieno[2,3-d]pyrimidin-4-amine
6-[4-phenyl-1-(2-propenyl)-1H-imidazol-5-yl]-thieno[2,3-d]pyrimidin-4-amine
6-[4-phenyl-1-(2,2,6,6-tetrametyl-4-piperidinyl)-1H-imidazol-5-yl]-thieno[2,3-d]pyrimidin-4-amine
6-[1-(1-methylpropyl)-4-phenyl-1H-imidazol-5-yl]-thieno[2,3-d]pyrimidin-4-amine
4-[5-(4-aminothieno[2,3-d]pyrimidin-6-yl)-4-phenyl-1H-imidazol-1-yl]-cyclohexanol
6-[4-phenyl-1-[(tetrahydro-2-furanyl)methyl]-1H-imidazol-5-yl]-thieno[2,3-d]pyrimidin-4-amine
6-[1-[2-(4-morpholinyl)ethyl]-4-phenyl-1H-imidazol-5-yl]-thieno[2,3-d]pyrimidin-4-amine
6-[1-[4-(diethylamino)-1-methylbutyl]-4-phenyl-1H-imidazol-5-yl]-thieno[2,3-d]pyrimidin-4-amine
6-[1-[(2-fluorophenyl)methyl]-4-phenyl-1H-imidazol-5-yl]-thieno[2,3-d]pyrimidin-4-amine
6-[1-[(2-methylphenyl)methyl]-4-phenyl-1H-imidazol-5-yl]-thieno[2,3-d]pyrimidin-4-amine
6-[1-[(3-fluorophenyl)methyl]-4-phenyl-1H-imidazol-5-yl]-thieno[2,3-d]pyrimidin-4-amine
5-(4-aminothieno[2,3-d]pyrimidin-6-yl)-alpha-methyl-4-phenyl-1H-imidazole-1-ethanol
3-[5-(4-aminothieno[2,3-d]pyrimidin-6-yl)-4-phenyl-1H-imidazol-1-yl]-1,2-propanediol
6-[1-(2-methylbutyl)-4-phenyl-1H-imidazol-5-yl]-thieno[2,3-d]pyrimidin-4-amine
6-[4-phenyl-1-[2-(phenylamino)ethyl]-1H-imidazol-5-yl]-thieno[2,3-d]pyrimidin-4-amine
5-(4-aminothieno[2,3-d]pyrimidin-6-yl)-4-phenyl-1H-imidazole-1-propanol
6-[1-[3-(dimethylamino)-2,2-dimethylpropyl]-4-phenyl-1H-imidazol-5-yl]-thieno[2,3-d]pyrimidin-4-amine
6-[1-(2-methyl-2-propenyl)-4-phenyl-1H-imidazol-5-yl]-thieno[2,3-d]pyrimidin-4-amine
N-[2-[5-(4-aminothieno[2,3-d]pyrimidin-6-yl)-4-phenyl-1H-imidazol-1-yl]ethyl]-4-hydroxy-benzeneacetamide
6-[1-(2-methoxy-2-methylpropyl)-4-phenyl-1H-imidazol-5-yl]-thieno[2,3-d]pyrimidin-4-amine
6-[4-phenyl-1-(spiro[bicyclo[2.2.1]hept-2-ene-7,1'-cyclopropan]-5-ylmethyl)-1H-imidazol-5-yl]-thieno[2,3-d]pyrimidin-4-amine
6-[1-[2-(3,5-dimethyl-1H-pyrazol-4-yl)ethyl]-4-phenyl-1H-imidazol-5-yl]-thieno[2,3-d]pyrimidin-4-amine
6-[1-[2-(1H-imidazol-1-yl)ethyl]-4-phenyl-1H-imidazol-5-yl]-thieno[2,3-d]pyrimidin-4-amine
6-[1-[2-[[(4-fluorophenyl)methyl]amino]ethyl]-4-phenyl-1H-imidazol-5-yl]-thieno[2,3-d]pyrimidin-4-amine
6-[1-[(3,4-dihydro-1H-2-benzopyran-1-yl)methyl]-4-phenyl-1H-imidazol-5-yl]-thieno[2,3-d]pyrimidin-4-amine
6-[1-[2-(methylsulfonyl)ethyl]-4-phenyl-1H-imidazol-5-yl]-thieno[2,3-d]pyrimidin-4-amine
N-[2-[5-(4-aminothieno[2,3-d]pyrimidin-6-yl)-4-phenyl-1H-imidazol-1-yl]ethyl]-2-[(2-chloro-3-pyridinyl)oxy]-acetamide
6-[4-phenyl-1-[2-[(tetrahydro-1,1-dioxido-3-thienyl)amino]ethyl]-1H-imidazol-5-yl]-thieno[2,3-d]pyrimidin-4-amine
5-(4-aminothieno[2,3-d]pyrimidin-6-yl)-4-phenyl-alpha-(trifluoromethyl)-1H-imidazole-1-ethanol
5-(4-aminothieno[2,3-d]pyrimidin-6-yl)-4-phenyl-alpha-[3-(trifluoromethyl)phenyl]-1H-imidazole-1-ethanol
6-[4-phenyl-1-[2-(2-propenylamino)ethyl]-1H-imidazol-5-yl]-thieno[2,3-d]pyrimidin-4-amine
N-[5-[5-(4-aminothieno[2,3-d]pyrimidin-6-yl)-4-phenyl-1H-imidazol-1-yl]pentyl]-4-morpholinecarboxamide
5-(4-aminothieno[2,3-d]pyrimidin-6-yl)-alpha-(2,3-dihydro-1,4-benzodioxin-6-yl)-4-phenyl-1H-imidazole-1-ethanol
6-[1-[3-[4-(2-methoxyphenyl)-1-piperazinyl]propyl]-4-phenyl-1H-imidazol-5-yl]-thieno[2,3-d]pyrimidin-4-amine
N'-[2-[5-(4-aminothieno[2,3-d]pyrimidin-6-yl)-4-phenyl-1H-imidazol-1-yl]ethyl]-N,N-dimethyl-sulfamide
6-[1-[6-(8-oxa-3-azabicyclo[3.2.1]oct-3-yl)hexyl]-4-phenyl-1H-imidazol-5-yl]-thieno[2,3-d]pyrimidin-4-amine
6-[1-[[2-(4-morpholinyl)phenyl]methyl]-4-phenyl-1H-imidazol-5-yl]-thieno[2,3-d]pyrimidin-4-amine
6-[1-(1,4-dioxan-2-ylmethyl)-4-phenyl-1H-imidazol-5-yl]-thieno[2,3-d]pyrimidin-4-amine
2-[[5-(4-aminothieno[2,3-d]pyrimidin-6-yl)-4-phenyl-1H-imidazol-1-yl]methyl]-(1S,2R)-cyclohexanol
6-[1-cycloheptylmethyl)-4-phenyl-1H-imidazol-5-yl]-thieno[2,3-d]pyrimidin-4-amine
6-[1-[[(1S,5S)-6,6-dimethylbicyclo[3.1.1]hept-2-yl]methyl]-4-phenyl-1H-imidazol-5-yl]-thieno[2,3-d]pyrimidin-4-amine
1-[[5-(4-aminothieno[2,3-d]pyrimidin-6-yl)-4-phenyl-1H-imidazol-1-yl]methyl]-cyclohexaneacetic acid
6-[4-phenyl-1-(phenylmethyl)-1H-imidazol-5-yl]-thieno[2,3-d]pyrimidin-4-amine
6-[1-[(2-methoxyphenyl)methyl]-4-phenyl-1H-imidazol-5-yl]-thieno[2,3-d]pyrimidin-4-amine
6-[4-phenyl-1-[[2-(1-piperidinyl)phenyl]methyl]-1H-imidazol-5-yl]-thieno[2,3-d]pyrimidin-4-amine
6-[4-phenyl-1-[[2-(2-pyridinyloxy)phenyl]methyl]-1H-imidazol-5-yl]-thieno[2,3-d]pyrimidin-4-amine
6-[1-[[2-(4-methyl-1-piperazanyl)phenyl]methyl]-4-phenyl-1H-imidazol-5-yl]-thieno[2,3-d]pyrimidin-4-amine
1-[2-[[5-(4-aminothieno[2,3-d]pyrimidin-6-yl)-4-phenyl-1H-imidazol-1-yl]methylphenyl)-4-piperidinemethanol
6-[1-[(2-aminophenyl)methyl]-4-phenyl-1H-imidazol-5-yl]-thieno[2,3-d]pyrimidin-4-amine
N-[2-[[5-(4-aminothieno[2,3-d]pyrimidin-6-yl)-4-phenyl-1H-imidazol-1-yl]methyl]phenyl]-2,4-dichloro-benzenesulfonamide
6-[1-(1H-imidazol-2-ylmethyl)-4-phenyl-1H-imidazol-5-yl]-thieno[2,3-d]pyrimidin-4-amine
6-[1-[(6-fluoro-4H-1,3-benzodioxin-8-yl)methyl]-4-phenyl-1H-imidazol-5-yl]-thieno[2,3-d]pyrimidin-4-amine 6-[1-(imidazol[1,2-a]pyridin-2-ylmethyl)-4-phenyl-1H-imidazol-5-yl]-thieno[2,3-d]pyrimidin-4-amine N-Benzyl-6-(1-methyl-4-phenyl-1H-imidazol-5-yl)thieno[2,3-d]pyrimidin-4-amine 6-[1-(1-Methylpyrrolidin-3-yl)-4-phenyl-1H-imidazol-5-yl]thieno[2,3-d]pyrimidin-4-amine tert-Butyl {2-[5-(4-aminothieno[2,3-d]pyrimidin-6-yl)-4-phenyl-1H-imidazol-1-yl]ethyl}carbamate tert-Butyl {4-[5-(4-aminothieno[2,3-d]pyrimidin-6-yl)-4-phenyl-1H-imidazol-1-yl]butyl}carbamate 6-{4-[3-(Benzyloxy)phenyl]-1-methyl-1H-imidazol-5-yl}thieno[2,3-d]pyrimidin-4-amine 4-[5-(4-Aminothieno[2,3-d]pyrimidin-6-yl)-1-methyl-1H-imidazol-4-yl]phenol 3-[5-(4-Aminothieno[2,3-d]pyrimidin-6-yl)-1-methyl-1H-imidazol-4-yl]benzonitrile tert-Butyl {3-[5-(4-aminothieno[2,3-d]pyrimidin-6-yl)-1-methyl-1H-imidazol-4-yl]phenyl}carbamate 6-(4-{4-[(3,4-Dichlorobenzyl)oxy]phenyl}-1-methyl-1H-imidazol-5-yl)thieno[2,3-d]pyrimidin-4-amine N-{3-[5-(4-Aminothieno[2,3-d]pyrimidin-6-yl)-1-methyl-1H-imidazol-4-yl]phenyl}-N'-phenylurea N-{3-[5-(4-Aminothieno[2,3-d]pyrimidin-6-yl)-1-methyl-1H-imidazol-4-yl]phenyl}-N'-benzylurea N-{3-[5-(4-Aminothieno[2,3-d]pyrimidin-6-yl)-1-methyl-1H-imidazol-4-yl]phenyl}-N'-[2-fluoro-5-(trifluoromethyl)phenyl]urea N-{4-[5-(4-Aminothieno-2,3-d]pyrimidin-6-yl)-1-methyl-1H-imidazol-4-yl]phenyl}-N'-phenylurea N-{4-[5-(4-Aminothieno[2,3-d]pyrimidin-6-yl)-1-methyl-1H-imidazol-4-yl]phenyl}-N'-2-benzylurea N-{4-[5-(4-Aminothieno[2,3-d]pyrimidin-6-yl)-1-methyl-1H-imidazol-4-yl]phenyl}-N'-[2-fluoro-5-(trifluoromethyl)phenyl]urea 6-[1-(4-aminobutyl)-4-phenyl-1H-imidazol-5-yl]-thieno[2,3-d]pyrimidin-4-amine 6-[1-(3-methylbut-2-en-1-yl)-4-phenyl-1H-imidazol-5-yl]-thieno[2,3-d]pyrimidin-4-amine 6-[4-(4-fluorophenyl)-1-(2-morpholin-4-ylbenzyl)-1H-imidazol-5-yl]thieno[2,3-d]pyrimidin-4-amine phenyl {3-[5-(4-aminothieno[2,3-d]pyrimidin-6-yl)-1-methyl-1H-imidazol-4-yl]phenyl}carbamate or benzyl {3-[5-(4-aminothieno[2,3-d]pyrimidin-6-yl)-1-methyl-1H-imidazol-4-yl]phenyl}carbamate or a pharmaceutically acceptable salt thereof.

A compound of the Formula I, or a pharmaceutically-acceptable salt thereof, may be prepared by any process known to be applicable to the preparation of chemically-related compounds. Such processes, when used to prepare a compound of the Formula I are provided as a further feature of the invention and are illustrated by the following representative process variants. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

According to a further aspect of the present invention provides a process for preparing a compound of formula I or a pharmaceutically acceptable salt thereof (wherein A, $R^1$, $R^2$, $R^3$, $R^4$, $Q^1$, G and m are, unless otherwise specified, as defined in formula I) which process comprises:

(a) For the preparation of those compounds of the Formula I wherein G is $NR^5$ the reaction, conveniently in the presence of a base, of the imine of the Formula II

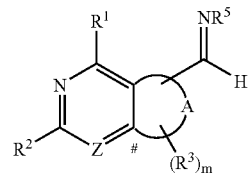

II wherein A, $R^1$, $R^2$, $R^3$, $R^5$, Z and m are as hereinbefore defined except any functional group is protected if necessary, and wherein the imine is attached to A in a meta position to the bridgehead carbon marked #, with a compound of the Formula III

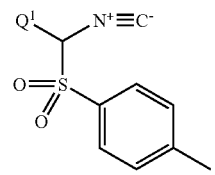

III wherein $Q^1$ is as hereinbefore defined except any functional group is protected if necessary;

(b) For the preparation of those compounds of the Formula I wherein Z is N, $R^1$ is amino and A together with the carbon atoms to which it is attached form an oxazoyl ring the reaction of the compound of the formula IV

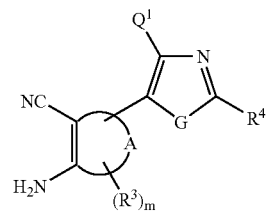

IV wherein A is —NH=C*—O— * indicates the atom which forms the bond to the ring containing G in Formula IV, and $R^3$, $R^4$, G, $Q^1$ and m are as hereinbefore defined except any functional group is protected if necessary, and wherein the ring containing G is attached to A in the meta-position to the amino group in Formula IV with an amidine, or a salt thereof;

(c) For the preparation of those compounds of the Formula I wherein A is —N=C*—S— or —S—C*=N—, wherein * indicates the atom which forms the bond to the ring containing G in Formula I, the sulfurisation and cyclisation of the compound of the Formula V by heating the compound of formula V in the presence of a suitable thionating agent:

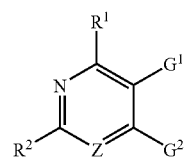

V wherein $R^1$, $R^2$ and Z are as hereinbefore defined except any functional group is protected if necessary, $G^1$ is a group of the formula VI and $G^2$ is OH, or $G^1$ is OH and $G^2$ is a group of the formula VI:

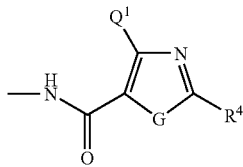

VI wherein $Q^1$, G and $R^4$ are as hereinbefore defined except any functional group is protected if necessary;

(d) For the preparation of those compounds of the Formula I wherein A is —N=C*—NH— or —NH—C*=N—, wherein * indicates the atom which forms the bond to the ring containing G in Formula I, the dehydration and cyclisation of a compound of the formula VII, in the presence of a suitable dehydrating agent:

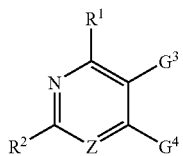

VII wherein $R^1$, $R^2$ and Z are as hereinbefore defined except any functional group is protected if necessary, $G^3$ is a group of the formula VI as hereinbefore defined and $G^4$ is amino;

(e) For the preparation of those compounds of the Formula I wherein G is N—OH, the reaction, under acidic conditions, of the ketooxime of the formula VIII with ammonium acetate and paraformaldehyde, conveniently in the presence of Lewis acid:

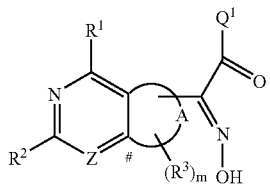

VIII wherein A, $R^1$, $R^2$, $R^3$, Z, $Q^1$ and m are as hereinbefore defined except any functional group is protected if necessary, and wherein the group carrying the ketooxime group in formula VIII is attached to A in the meta position relative to the bridgehead carbon marked #;

(f) For the preparation of those compounds of the Formula I wherein A is —CH=C*—NH—, —NH—C*=CH—, —CH—C*—O—, —O—C*=CH—, —CH=C*—S— or —S—C*=CH—, wherein * indicates the atom which forms the bond to the ring containing G in Formula I, the cyclisation of the alkyne of the Formula IX:

Formula IX

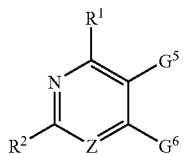

wherein $R^1$, $R^2$ and Z are as hereinbefore defined except any functional group is protected if necessary, and $G^5$ is a group of the Formula X and $G^6$ is amino, or
$G^5$ is amino and $G^6$ is a group of the Formula X, or
$G^5$ is a group of the Formula X and $G^6$ is hydroxy, or
$G^5$ is hydroxy and $G^6$ is a group of the Formula X, or
$G^5$ is a group of the Formula X and $G^6$ is mercapto, or
$G^5$ is mercapto and $G^6$ is a group of the Formula X, Formula X

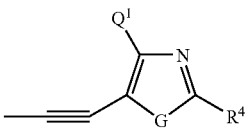

wherein $Q^1$, G and $R^4$ are as hereinbefore defined except any functional group is protected if necessary;

(g) Converting one compound of the Formula I into another compound of the Formula I; or (h) For the preparation of those compounds of the Formula I wherein A is —N=C*—S— or —S—C*=N—, wherein * indicates the atom which forms the bond to the ring containing G in Formula I, the cyclisation of the compound of the Formula XXVI by heating the compound of formula XVI in the presence of a suitable acid or dehydrating agent:

XXVI wherein $R^1$, $R^2$ and Z are as hereinbefore defined except any functional group is protected if necessary, $G^7$ is a group of the formula VI and $G^8$ is SH, or
$G^7$ is SH and $G^8$ is a group of the formula VI;

wherein the compound of formula VI is as hereinbefore defined; and thereafter, if necessary, removing any protecting groups and/or forming a pharmaceutically acceptable salt thereof.

Process (a)

Process (a) is conveniently carried out in the presence of a base. A suitable base for process (a) is, for example, an organic amine base such as, for example, piperazine, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxyde, for example sodium carbonate, potassium carbonate, cesium carbonate, calcium carbonate, sodium hydroxyde or potassium hydroxyde, or, for example, an alkali metal hydride, for example sodium hydride, or a metal alkoxide such as sodium ethoxide.

Process (a) is conveniently carried out in a suitable inert solvent or diluent such as an ether, for example tetrahydrofuran or 1,4-dioxan, an ester such as ethyl acetate, an alcohol or alcohol-water solution, for example methanol, ethanol or isopropylalcohol, or a dipolar aprotic solvent such as N,N-dimethylformamide, N,N-dimethylacetamide, N-methylpyrrolidin-2-one or N,N-dimethylsulfoxide. Process (a) is preferably carried out at a temperature of less than 50° C., for example 0 to 30° C., preferably at ambient temperature.

The compound of formula II may be prepared by the reaction of the aldehyde of the Formula XI:

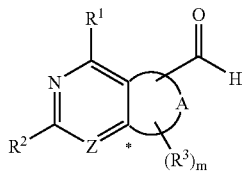

Formula XI wherein A, $R^1$ $R^2$, $R^3$, Z and m are as hereinbefore defined except any functional group is protected if necessary, with an amine of the formula $R^5NH_2$, wherein $R^5$ is as hereinbefore defined except any functional group is protected if necessary.

The reaction of the aldehyde of formula XI is preferably carried out in the presence of a suitable inert solvent, such as a chlorinated solvent, for example dichloromethane. The reaction is conveniently performed under reflux conditions. The reaction may be carried out in the presence of a suitable molecular sieve, for example a 4 Å molecular sieve.

In a variant to process (a) the compound of the Formula I wherein G is $NR^5$ may be prepared directly starting from the aldehyde of the formula XI, by combining the process steps described above without isolating the imine of the formula XI; namely by reaction of the aldehyde of formula XI with the amine of the formula $R^5NH_2$ as described above, followed directly by reaction of the resulting compound of Formula II as hereinbefore defined with the compound of the Formula III as described above in relation to process (a).

The aldehyde of the Formula XI may be prepared using conventional techniques. For example when $R^1$ is hydrogen or (1-6C)alkylthio in Formula I, the aldehyde of formula XI wherein $R^1$ is hydrogen or (1-6C)alkylthio may be prepared in accordance with Reaction Scheme 1:

Reaction Scheme 1

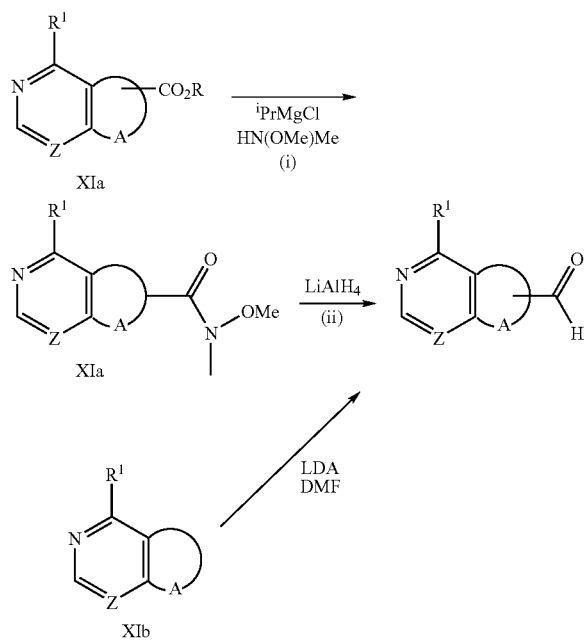

wherein Z and A are as hereinbefore defined, $R^1$ is hydrogen or (1-6C)alkylthio and R is a suitable displaceable group, for example (1-6C)alkyl or benzyl.

In step (i) of Reaction Scheme 1 the ester of the formula XIa is reacted with methoxy(methyl)amine in the presence of a suitable base, for example iso-propylmagnesium chloride. Conveniently the reaction is carried out in an inert solvent, such as an ether, for example tetrahydrofuran.

In step (ii) of Reaction Scheme (i) the carboxamide is reduced to the aldehyde of the formula XI using a suitable reducing agent, for example lithium aluminium hydride.

Additional substituents (for example $R^2$ and $R^3$) may be added to the compounds shown in Reaction Scheme 1 at any stage of the reaction or alternatively following Process (a) using conventional chemical modification methods, for example as described in process (g) herein.

The compounds of formula XIa and XIb are commercially available, or they are known in the literature, or they are prepared by standard processes known in the art. For example compounds of the formulae XIa and XIb in which $R^1$ is (1-6C)alkylthio may be prepared by reaction of the appropriate compound of the formula XIc or XId with a suitable alkali metal thio(1-6C)alkoxide (for example sodium thiomethoxide when $R^1$ is methylthio):

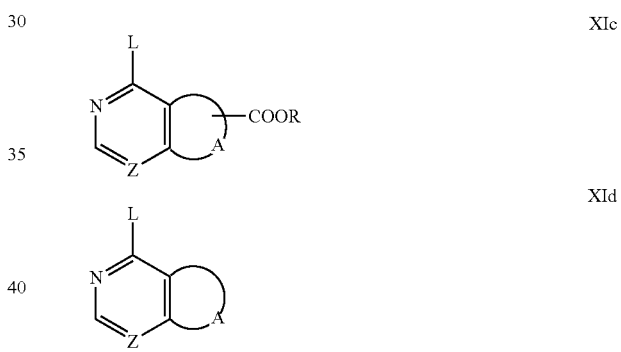

wherein L is a displaceable group and A, Z and R are as hereinbefore defined. Suitable displaceable groups represented by L include, for example halogeno (preferably chloro or bromo) or phenoxy.

Process (b)

Process (b) is conveniently carried out using a suitable amidine, or salt thereof, for example formamidine acetate. The process is conveniently carried out under anhydrous conditions, preferably in a suitable inert solvent or diluent, for example a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, 30 to 150° C., preferably in the range 50 to 120° C.

The compound of Formula (IV) used in Process (b) may be prepared using conventional methods for example as illustrated by Reaction Scheme 2, wherein A is —N═C*—O— and * indicates the atom which forms the bond to the ring containing G in Formula IV:

Reaction Scheme 2

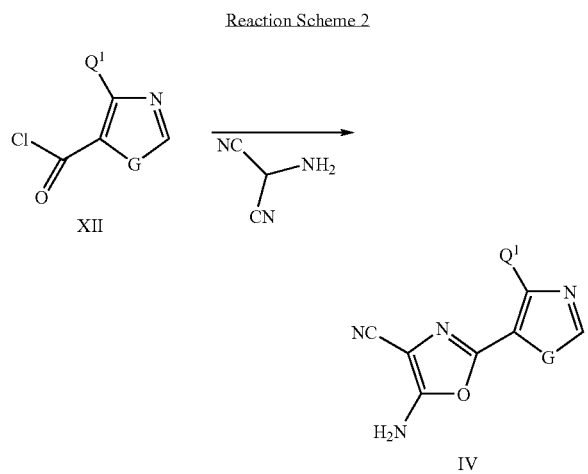

In Reaction Scheme 2 the carbonyl chloride of Formula XII is reacted with aminomalonitrile.para-toluenesulfonate in a suitable inert solvent or diluent, for example N-2-methylpyrrolidinone.

The compound of Formula XII may be prepared using conventional procedures. For example when G is $NR^5$ in Formula XII, the imidazole derivative of Formula XII may be prepared for example, using Reaction Scheme 3:

Reaction Scheme 3

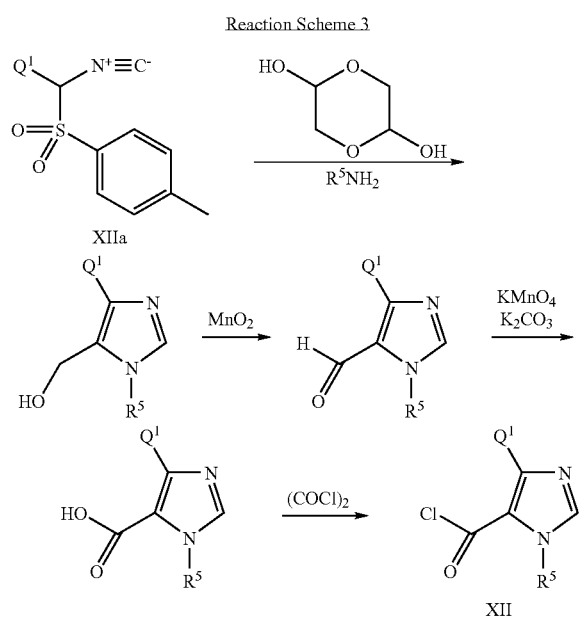

In Reaction Scheme 3 the isocyano compound of the formula XIIa is reacted with methylamine and glyoaldehyde to form the imidazol-5-yl methanol derivative. The alcohol is oxidized to the corresponding aldehyde using a mild oxidizing agent such as manganese dioxide. The aldehyde is then further oxidized to the carboxylic acid using a suitable oxidizing agent, for example potassium permanganate, or manganese dioxide, optionally in the presence of a suitable base such as potassium carbonate. The carboxylic acid is then reacted with a suitable acid chloride such as oxalyl chloride to give a compound of Formula XII in which G is $NR^5$.

Alternatively, in Reaction Scheme 3 the imidazol-5-yl-methanol derivative may be oxidized directly to the aldehyde using a suitable oxidizing agent such as potassium permanganate, preferably in the presence of a base as described above;

Compounds of the Formula XIIa are commercially available, or they are known in the literature, or they are prepared by standard processes known in the art (for example as described in Org. React. 77 198-205).

Compounds of the Formula XII in which G is O or S are known or may be prepared using known processes (for example J. Org. Chem. 2000, 65, 1516-1524).

Process (c)

Suitable thionating agents which may be used in Process (c) are well known in the art, for example phosphorus pentasulfide, Lawesson's reagent or Davy's reagent. The reaction is preferably carried out under anhydrous conditions in an inert solvent, for example a hydrocarbon solvent such as toluene or xylene. Preferably, however, the reaction is carried out in an inert basic organic solvent, for example pyridine or picoline). Process (c) is preferably performed at a temperature of 50 to 120° C., for example 80 to 110° C.

Compounds of the Formula V used in Process (c) may be prepared using conventional techniques, for example compounds of he Formula V wherein $R^1$ is amino and $R^2$ is H may be prepared by reacting the aniline of the formula XIII with a compound of the Formula XII as hereinbefore defined:

Formula XIII

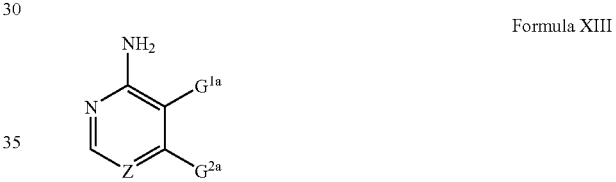

wherein $G^{1a}$ is amino and $G^{2a}$ is hydroxy, or
$G^{1a}$ is hydroxy and $G^{2a}$ is amino.

The reaction is conveniently carried out in an inert solvent or diluent, for example N-methylpyrrolidinone, preferably under anhydrous conditions.

The reaction is conveniently carried out in the presence of a base. Suitable bases are as described above in relation to process (a): for example triethylamine or pyridine.

Compounds of the formula XIII are commercially available, or they are known in the literature, or they are prepared by standard processes known in the art.

Process (d)

A suitable dehydrating agent which may be used in Process (d) is, for example phosphorous pentoxide, phosphorous oxychloride, polyphosphoric acid, phosphoric acid and/or a strong acid. Suitable strong acids include, for example concentrated hydrochloric acid or concentrated sulfuric acid. In embodiments a mixture of dehydrating agents may be used for example a phosphorous pentoxide and an acid, for example phosphorous pentoxide and phosphoric acid.

Conveniently process (d) is performed in a suitable inert solvent, for example water or an inert organic solvent (for example a suitable hydrocarbon solvent such as toluene or xylene).

Process (d) is conveniently performed at a temperature of −10 to 200° C., preferably at or near ambient temperature.

The compound of the Formula VII used in process (d) may be prepared using conventional methods. For example for the preparation of those compounds of the Formula I in which $R^1$ is amino and $R^2$ is hydrogen, by reaction of a compound of the Formula XIV

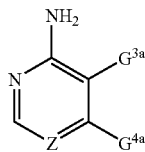

Formula XIV wherein $G^{3a}$ and $G^{4a}$ are both amino and Z is as hereinbefore defined,
with a compound of the Formula XII as hereinbefore defined.

The reaction is conveniently carried out in an inert solvent or diluent, for example N-methylpyrrolidinone, preferably under anhydrous conditions.

Conveniently the reaction is carried out in the presence of a suitable base. Suitable bases include, for example those described above in relation to process (a).

Compounds of the formula XIV are commercially available, or they are known in the literature, or they are prepared by standard processes known in the art.

As will be realized, the purine compound formed in process (c) will tautomerise between the 7-H and 9-H purine isomers. If required resulting isomers may be fixed in a particular isomeric form by substituting the NH groups in the mixture of purines with a substituent $R^3$, for example by alkylating with a suitable alkylating agent such as an alkylhalide (for example iodomethane). The two isomers may then be separated using a conventional technique, for such as HPLC.

Process (e)

Process (e) is conveniently carried out at a temperature of from 90 to 150° C. The reaction is conveniently performed over a period of from 1 to 48 hours, for example about 2 hours. Preferably, the reaction is carried out by adding the ammonium acetate to the ketooxime of formula VIII and heating the resulting mixture. The paraformaldehyde is then added to the reaction mixture. During the reaction the ketooxime of the formula VIII is converted to the corresponding imineoxime, which reacts in-situ with the paraformaldehyde to give a compound of the formula I in which G is N—OH.

The acidic conditions required for Process (e) may be generated by carrying out the reaction in the presence of a suitable acid such as an inorganic acid, for example HCl, or preferably in the presence of an organic acid such as acetic acid.

The ketooxime of the formula VIII may be prepared using conventional methods. For example compounds of the Formula I wherein $R^1$ is methylthio, $R^2$ is hydrogen, A is —S—C*=CH— and * indicates the atom which forms the bond to the ring containing G in Formula I, may be prepared according to Reaction Scheme 4:

Reaction Scheme 4

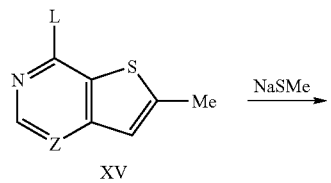

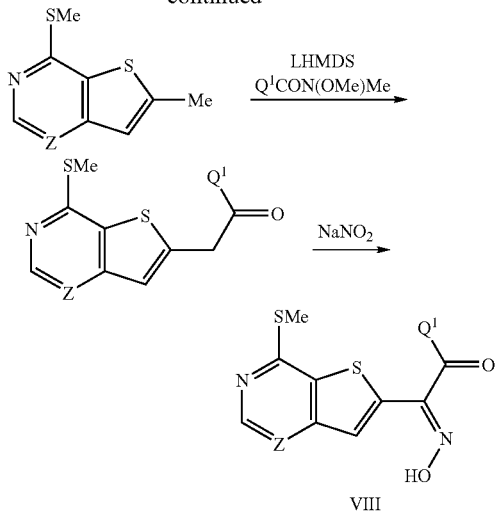

wherein Z and $Q^1$ are as hereinbefore defined and L is a displaceable group as hereinbefore defined, such as halogeno, for example chloro or bromo.

In Reaction Scheme 4 the compound of the formula XV is reacted with an alkali metal thiomethoxide such as sodium thiomethoxide. The resulting compound is then reacted with the Weinreb amide of an aryl or heteroaryl acid ($Q^1$-CON(OMe)Me) to give the ketone. The reaction with the Weinreb amide is preferably carried out in the presence of a suitable base such as lithium bis(trimethylsilyl)amide or lithium diisopropylamide. The reaction is preferably carried out in a suitable inert solvent or diluent, for such as an ether, for example tetrahydrofuran. The reaction is suitable performed at a temperature of −78° C. to 10° C., for example at approximately 0° C.

The resulting ketone is oxidized to the ketooxime by reaction with sodium nitrite to give the compound of the Formula VIII.

Compounds of the Formula XV are commercially available, or they are known in the literature, or they are prepared by standard processes known in the art.

As will be realized an analogous process to that shown in Reaction Scheme 4 may be used to prepare other compounds of the Formula I wherein A is other than a thieno ring by starting with an appropriate compound of the formula:

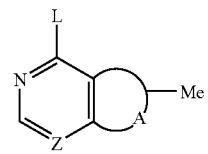

wherein L, A and Z are as hereinbefore defined. Such compounds are commercially available, or they are known in the literature, or may be prepared by standard processes known in the art.

Process (f)

When A together with the carbon atoms to which it is attached forms a furano or thieno fused ring, process (f) is conveniently carried out by heating the compound of the Formula IX (wherein $G^5$ is a group of the Formula X and $G^6$ is hydroxy, or $G^5$ is hydroxy and $G^6$ is a group of the Formula X, $G^5$ is a group of the Formula X and $G^6$ is mercapto, or $G^5$ is mercapto and $G^6$ is a group of the Formula X). A suitable reaction temperature is, for example from 0 to 80° C. preferably from 20 to 50° C.

When A together with the carbon atoms to which it is attached forms a pyrrolo fused ring, process (f) is conveniently performed by heating the compound of the Formula IX (wherein $G^5$ is a group of the Formula X and $G^6$ is amino, or $G^5$ is amino and $G^6$ is a group of the Formula X), in the presence of a suitable base, for example a base as described above in relation to process (a), preferably an alkali metal alkoxide (such a potassium tert-butoxide) or hydride (such as potassium or sodium hydride). A suitable reaction temperature is, for example from 0 to 80° C., preferably from 20 to 65° C.

Process (f) is conveniently carried out in a suitable inert solvent or diluent, for example a dipolar aprotic solvent such as N,N-dimethylformamide, N,N-dimethylacetamide or N-methylpyrrolidin-2-one.

As will be recognised when any of $G^5$ or $G^6$ are mercapto or hydroxy, the compound of the Formula IX may exist in the form of the corresponding oxo (=O) or thioxo (=S) tautomer.

The compound of the Formula IX may be prepared using conventional techniques, for example by coupling the compound of the Formula XVI

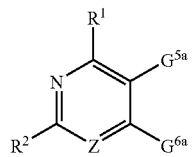

Formula XVI wherein $R^1$, $R^2$ and Z are as hereinbefore defined,
$G^{5a}$ is a displaceable group and $G^{6a}$ is selected from amino, hydroxy or mercapto, or
$G^{6a}$ is a displaceable group and $G^{5a}$ is selected from amino, hydroxy or mercapto,
with the ethynyl compound of the Formula XVII

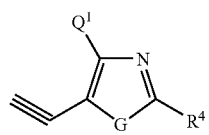

Formula XVII

The coupling process is conveniently carried out using the Sonogashira coupling technique (Org. Prep. Proc. Int. 1995, 129-160). The coupling process is conveniently carried out in the presence of a source of copper(I) ions, for example from copper(I)iodide in the presence of a suitable base, for example an organic amine base such as triethylamine. The reaction is conveniently carried out using a suitable metal catalyst, for example bis(triphenylphosphine)palladium dichloride, tetrakis triphenyl phosphine palladium(0) or palladium(II) acetate. The reaction may be carried out is a suitable inert solvent or diluent, for example a dipolar aprotic solvent such as N,N-dimethylformamide. The reaction is conveniently carried out at a temperature of from 0 to 150° C., preferably 20 to 80° C. Suitable displaceable groups that may be represented by $G^{5a}$ and $G^{6a}$ include, for example halogeno such as chloro, bromo and iodo.

Compounds of the Formula XVII may be prepared, for example, by converting the aldehyde of the Formula XVIII

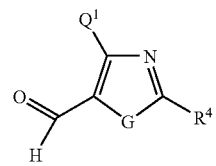

Formula XVIII wherein $Q^1$, G and $R^4$ are as hereinbefore defined,
to the corresponding ethyne of the Formula XVII.

The conversion may be carried out using known conversion methods, for example using the Ohira procedure (Chem. Commun. 1992, 721-722), wherein the compound of the Formula XVIII is reacted with n-butyllithium and trimethylsilyldiazomethane. The reaction is conveniently cared out in a suitable inert solvent or diluent, for example a hydrocarbon solvent such as pentane or hexane, or an ether such as tetrahydrofuran. The reaction may be carried out at a temperature of, for example from −78 to 30° C.

Compounds of the Formula XVI and XVIII are commercially available, or they are known in the literature, or may be prepared by standard processes known in the art. For example compounds of the Formula XVIII in which G is $NR^5$ can be prepared, for example using the initial stages of the procedure shown in Reaction Scheme 3 to give the required aldehyde of formula XVIII.

Process (g)

A compound of the Formula I may be prepared by converting one compound of the Formula I into another compound of the Formula I using conventional chemical modification techniques. For example when $R^1$ is an alkylthio group such as methylthio, it may be oxidized to the corresponding alkylsulfonyl, using a suitable oxidizing agent for such reactions, for example meta-chloroperbenzoic acid (m-CPBA). The alkylsulfonyl group may then be displaced by nucleophilic substitution using a suitable nucleophile, such as ammonia or an amine to give, $R^1$ as amino or substituted amino. Alternatively, the alkylthio group may displaced directly by reaction with a suitable nucleophile such as ammonia. For example by beating the compound in which $R^1$ is methyl thio with ammonium chloride solution in a suitable inert solvent such as N-methylpyrrolidinone. When $R^1$ is (1-6C)alkylthio or halogeno in Formula I, the $R^1$ group may be reduced to give a compound of the Formula I in which $R^1$ is hydrogen. Suitable conditions for such reductions are well known, for example by hydrogenation in the presence of a Raney nickel catalyst. The 1-hydroxy imidazole resulting from Process (e) may be converted to the corresponding imidazole by reduction. For example by heating with a tri-alkyl phosphite, or by hydrogenation in the presence of a suitable catalyst, for example a Raney nickel catalyst. A substituent $R^3$ or $R^5$ may be introduced to an NH group in the compound of Formula I using conventional techniques. For example by alkylation with an appropriate alkylating agent, for example an alkylhalide, alkyl sulfonate ester (such as a tosylate or mesylate), optionally in the presence of a suitable base and appropriate inert solvent.

Process (h)

The cyclisation reaction is conveniently performed at a temperature at a temperature of 50 to 120° C., for example 80 to 110° C. Suitable acids for use in the reaction include, for example aqueous hydrochloric acid. Suitable dehydrating agents that may be used include, for example $POCl_3$. Conveniently the reaction is carried out under an inert organic solvent, for example a hydrocarbon solvent such as toluene or xylene.

The compound of formula XVIX used in process (h) may be prepared using conventional methods. For example using an analogous process to that described above the preparation of compounds of the formula V in relation to process (c), except using a compound of the Formula XIII in which $G^{1a}$ is amino and $G^{2a}$ is mercapto, or $G^{1a}$ is mercapto and $G^{2a}$ is amino.

When a pharmaceutically acceptable salt of a compound of formula I is required, for example an acid addition salt, it may be obtained by, for example reaction of a compound of the Formula I with a suitable acid such as hydrochloric acid,: using a conventional procedure. When it the free-base form of the compound of Formula I is required an acid addition salt of the compound of Formula I may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7ene, or, for example, an alkali or alkaline earth metal carbonate or hydroxide, for example sodium carbonate, potassium carbonate, calcium carbonate, sodium hydroxide or potassium hydroxide.

Certain compounds of Formula I are capable of existing in stereoisomeric forms. It will be understood that the invention encompasses all geometric and optical isomers of the compounds of formula I and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

It will be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T.W. Green, Protective Groups in Organic Synthesis, John Wiley and Sons, 1991). Thus, if reactants include groups such as amino, carboxy or hydroxy it may be desirable to protect the group in some of the reactions mentioned herein. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example—methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

It will also be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of art aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It is believed that certain intermediate compounds of Formulae II to XXVI are novel and are herein claimed as another aspect of the present invention. Also certain of the Intermediate compounds 1 to 108 are believed to be novel and one or more of these Intermediate compounds is herein claimed as a further aspect of the present invention.

Biological Assays

The following assays can be used to measure the effects of the compounds of the present invention as Tie2 inhibitors in vitro and as inhibitors of Tie2 autophosphorylation in whole cells.

a. In Vitro Receptor Tyrosine Kinase Inhibition Assay

To test for inhibition of Tie2 receptor tyrosine kinase, compounds are evaluated in a non-cell based protein kinase assay by their ability to inhibit the protein kinase enzyme phosphorylation of a tyrosine containing polypeptide substrate in an ELISA based microtitre plate assay. In this particular case, the assay was to determine the $IC_{50}$, for three different recombinant human tyrosine kinases Tie2, KDR and Flt.

To facilitate production of the tyrosine kinases, recombinant receptor genes were produced using standard molecular biology cloning and mutagenesis techniques. These recombinant proteins fragments encoded within these genes consist of only the intracellular portion C-terminal portion of the respective receptor, within which is found the kinase domain. The recombinant genes encoding the kinase domain containing fragments were cloned and expressed in standard baculovirus/Sf21 system (or alternative equivalent).

Lysates were prepared from the host insect cells following protein expression by treatment with ice-cold lysis buffer (20 mM N-2-hydroxyethylpiperizine-N'-2-ethanesulphonic acid (HEPES) pH 7.5, 150 mM NaCl, 10% glycerol, 1% Triton X-100, 1.5 mM $MgCl_2$, 1 mM ethylene glycol-bis (β-aminoethyl ether) N',N',N',N'-tetraacetic acid (EGTA), plus protease inhibitors and then cleared by centrifugation. Tie2, KDR and Flt1 lysates were stored in aliquots at −80° C.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Nunc Maxisorb™ 96-well immunoplates were coated with 100 microlitres of synthetic peptide Sigma P3899 (1 mg/ml stock solution in PBS diluted 1:500 in PBS prior to plate coating) and incubated at 4° C. overnight. Plates were washed in 50 mM APES pH 7.4 at room temperature to remove any excess unbound synthetic peptide.

Tie2, KDR or Flt1 activities were assessed by incubation of the appropriate freshly diluted lysates (1:200, 1:400 and 1:1000 respectively) in peptide coated plates for 60 minutes Tie2) or 20 minutes for (KDR, Flt) at room temperature in 100 mM HEPES pH 7.4, adenosine trisphosphate (ATP) at 5 micromolor (or Km concentration for the respective enzyme, 10 mM $MnCl_2$, 0.1 mM $Na_3VO_4$, 0.2 mM DL-dithiothreitol (DTT), 0.1% Triton X-100 together with the test compound(s) in dissolved in DMSO (final concentration of 2.5%) with final compound concentrations ranging from 0.05 micromolar-100 micromolar. Reactions were terminated by the removal of the liquid components of the assay followed by washing of the plates with PBS-T (phosphate buffered saline with 0.5% Tween 20) or an alternative equivalent wash buffer.

The immobilised phospho-peptide product of the reaction was detected by immunological methods. Firstly, plates were incubated for 4 hours at room temperature with murine monoclonal anti-phosphotyrosin-HRP (Horseradish Peroxidase) conjugated antibodies (4G10 from Upstate Biotechnology UBI 16-105). Following extensive washing with PBS-T, HRP activity in each well of the plate was measured colorimetrically using 22'-Azino-di-[3-ethylbenzthiazoline sulfonate (6)] diammonium salt crystals ABTS (Sigma P4922—prepared as per manufactures instructions) as a substrate incubated for 30-45 minutes to allow colour development, before 100 ul of 1M $H_2MO_4$ was added to stop the reaction.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b. Cellular Tie2 Autophosphorylation Assay

This assay is based on measuring the ability of compounds to inhibit autophosphorylation of the Tie2 receptor which normally leads to the production of "activated" receptor that in turn initiates the particular signal transduction pathways associated with the receptor function.

Autophosphorylation can be achieved by a number of means. It is known that expression of recombinant kinase domains in baculoviral systems can lead to the production of phosphorylated and activated receptor. It is also reported that over expression of receptors in recombinant cell lines can itself lead to receptor autophosphorylation in the absence of the ligand (Heldin C-H. 1995 Cell: 80, 213-223; Blume-J. P, Hunter T. 2001 Nature: 411, 355-65). Furthermore, there are numerous literature examples in which chimaeric receptors have been constructed. In these cases the natural, external cell surface domain of the receptor has been replaced with that of a domain which is known to be readily dimerised via the addition of the appropriate ligand (e.g. TrkA-Tie2/NGF ligand (Marron, M. B., et al., 2000 Journal of Biological Chemistry: 275:39741-39746) or C-fms-Tie-1/CSF-1 ligand (Kontos, C. D., et al., 2002 Molecular and Cellular Biology: 22, 1704-1713). Thus when the chimaeric receptor expressed in a host cell line and the respective ligand is added, this induces autophosphorylation of the chimeric receptor's kinase domain. This approach has the advantage of often allowing a known (and often easily obtained) ligand to be used instead of having to identify and isolate the natural ligand for each receptor of interest.

Naturally if the ligand is available one can use natural cell lines or primary cells which are known to express the receptor of choice and simply stimulate with ligand to achieve ligand induced phosphorylation. The ability of compounds to inhibit autophosphorylation of the Tie2 receptor, which is expressed for example in EA.hy926/B3 cells (supplied by J. McLean/ B. Tuchi, Univ. of N. Carolina at Chapel Hill, CB-4100, 300 Bynum Hall, Chapel Hill, N.C. 27599-41000, USA) or primary HUVEC (human umbilical vein endothelial cells—available from various commercial sources), can measured by this assay.

Natural Ang1 ligand can be isolated using standard purification technology from either tumour cell supernatants or alternatively the Ang1 gene can be cloned and expressed recombinantly using stand molecular biology techniques and expression systems. In this case one can either attempt to produce the ligand either in its native state or as recombinant protein which for example may have been genetically engineered to contain additional of purification tags (eg. polyhistidine peptides, antibody Fc domains) to facilitate the process.

Using the ligand stimulation of either EA.hy926/B3 or HUVEC cellular Tie2 receptor as the example, a Ang1 ligand stimulated cellular receptor phosphorylation assay can be constructed which can be used to analyse to determine the potential of compounds to inhibit this process. For example EA.hy926/B3 cells were grown in the appropriate tissue culture media plus 10% foetal calf serum (FCS) for two days in 6 well plates starting with an initial seeding density of $5\times10^5$ cells/well. On the third day the cells were serum starved for a total of 2 hours by replacing the previous media with media containing only 1% FCS. After 1 hour 40 minutes of serum starvation the media was removed and replace with 1 ml of the test compound dilutions (compound dilutions made in serum starvation media yet keeping the DMSO concentration below 0.8%). After 1.5 hours of serun starvation orthovanidate was added to a final concentration of 0.1 mM for the final 10 minutes of serum starvation.

Following a total of 2 hours of serum starvation, the ligand plus orthovandiate was added to stimulate autophosphorylation of the cellular Tie2 receptor (ligand can be added either as purified material diluted in serum starvation media or non-purified cell supernatant containing ligand e.g. when recombinantly expressed mammalian cells).

After 10 minutes incubation at 37° C. with the ligand, the cells were cooled on ice washed with approximately 5 mls with cold PBS containing 1 mM orthovanadate, after which 1 ml of ice cold lysis buffer ((20 mM Tris pH 7.6, 150 mM NaCl, 50 mM NaF, 0.1% SDS, 1% NP40, 0.5% DOC, 1 mM orthovanadate, 1 mM EDTA, 1 mM PMSF, 30 µl/ml Aprotinin, 10 µg/ml Pepstatin, 10 µg/ml Lrupeptin) was added the cells and left on ice for 10-20 minutes. The lysate was removed and transferred to a 1.5 ml Eppendorf tube and centrifuged for 3 minutes at 13000 rpm at 4° C. 800 µl of each lysate was transferred to fresh 2 ml Eppendorf tubes for the immuno-precipitation. 3 mg=15 µl of anti-phospho-tyrosine antibody (Santa Cruz PY99—sc-7020) was added to the lysates and left to incubate for 2 hours at 4° C. 600 µl washed MagnaBind beads (goat anti-mouse IgG, Pierce 21354) were added to the lysates and the tubes left to rotate over night at 4° C.

Samples were treated for 1 minute in the magnet before carefully removing the lysis supernatant. 1 ml of lysis buffer was then added to the beads and this step repeated twice more. The beads were suspended in 25 µl of 94° C. hot 2× Laemmli loading buffer plus beta-mercaptoethanol and left to stand for 15 minutes at room temperature.

The beads were removed by exposing the tubes for 1 minutes in the magnet, and the total liquid separated from the beads from each immuno-precipitate loaded onto Polyacrylamide/SDS protein gels (pre-cast 4-12% BisTris NUPAGE/MOPS 12 well gels from Novex). Protein gels were run at 200 V and then blotted onto NC membrane for 1 hours 30 minutes at 50 V/250 mA. All blots were treated with 5% Marvel in PBS-Tween for 1 hour at room temperature to reduce non-specific binding of the detection antibody. A rabbit anti-Tie2 (Santa Cruz sc-324) was added in a 1:500 dilution in 0.5% Marvel/PBS-Tween and left to incubate overnight at 4° C. The blots were rigorously washed with PBS-Tween before adding the goat anti rabbit-POD conjugate (Dako P0448) at a 1:5000 dilution in 0.5% Marvel/PBS-Tween. The antibody was left on for 1 hour at room temperature before subsequently washing the blots with PBS-Tween. The western blots of the various immunoprecipitated samples were developed the blots with LumiGLO (NEB 7003). And transferred to an X-Ray cassette and films exposed for 15 sec/30 sec and 60 sec. The relative strength of the protein band which pertains to the phosphorylated Tie2 receptor was evaluated using a FluorS BioRad image analyser system. The percentage phosphorylation for each test compound dilution series was determined from which $IC_{50}$ values were calculated by standard methods using the appropriate control samples as reference.

Although the pharmacological properties of the compounds of the Formula I vary with structural change as expected, in general activity possessed by compounds of the Formula I, may be demonstrated at the following concentrations or doses in one or more of the above tests (a) and (b):
1(a):—$IC_{50}$ in the range, for example, <100 µM;
Test (b):—$IC_{50}$ in the range, for example, <50 µM;

For example Example 2 had an $IC_{50}$ of 2.7 µM and Example 7 had an $IC_{50}$ of 2.2 µM in Test (b).

According to a further aspect of the invention there is provided a pharmaceutical composition which comprises a compound of the Formula I, or a pharmaceutically acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to,the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

The compounds according to the present invention as defined herein are of interest for, amongst other things, their antiangiogenic effect. The compounds of the invention are expected to be useful in the treatment or prophylaxis of a wide range of disease states associated with undesirable or pathological angiogenesis, including cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. Cancer may affect any tissue and includes leukaemia, multiple myeloma and lymphoma. In particular such compounds of the invention are expected to slow advantageously the growth of primary and recurrent solid tumours of, for example, the colon, breast, prostate, lungs and skin.

We believe that the antiangiogenic properties of the compounds according to the present invention arise from their Tie2 receptor tyrosine kinase inhibitory properties. Accordingly, the compounds of the present invention are expected be useful to produce a Tie2 inhibitory effect in a warm-blooded animal in need of such treatment. Thus the compounds of the present invention may be used to produce an antiangiogenic effect mediated alone or in part by the inhibition of Tie2 receptor tyrosine kinase.

More particularly the compounds of the invention are expected to inhibit any form of cancer associated with Tie2. For example, the growth of those primary and recurrent solid tumours which are associated with Tie2, especially those tumours which are significantly dependent on Tie2 receptor tyrosine kinase for their growth and spread.

According to a further aspect of the invention there is provided a compound of the Formula I, or a pharmaceutically-acceptable salt thereof, as defined hereinbefore, for use as a medicament.

According to another aspect of the invention, there is provided the use of a compound of the formula I, or a pharmaceutically acceptable salt thereof, as defined hereinbefore, in the manufacture of a medicament for use as a Tie2 receptor tyrosine kinase inhibitor in a warm-blooded animal such as man.

According to another aspect of the invention, there is provided the use of a compound of the formula I, or a pharmaceutically acceptable salt thereof, as defined hereinbefore, in the manufacture of a medicament for use in the production of an anti-angiogenic effect in a warm-blooded animal such as man.

According to another aspect of the invention, there is provided the use of a compound of the formula I, or a pharmaceutically acceptable salt thereof, as defined hereinbefore in the manufacture of a medicament for use in the treatment of cancers in a warm-blooded animal such as man.

According to another aspect of the invention, there is provided the use of a compound of the formula I, or a pharmaceutically acceptable salt thereof, as defined hereinbefore in the manufacture of a medicament for use in the treatment of a cancer selected from leukaemia, breast, lung, colon, rectal, stomach, prostate, bladder, pancreas, ovarian, lymphoma, testicular, neuroblastoma, hepatic, bile duct, renal cell, uterine, thyroid and skin cancer in a warm-blooded animal such as man.

According to another aspect of the invention there is provided a method of inhibiting Tie2 receptor tyrosine kinase in a warm-blooded animal, such as man, in need of such treatment, which comprises administering to said animal an effective amount of a compound of the formula I, or a pharmaceutically acceptable salt hereof, as defined hereinbefore.

According to another aspect of the invention there is provided a method for producing an anti-angiogenic effect in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a method of treating cancers in a warm-blooded animal, such as man, in need of such treatment, which comprises administering to said animal an effective amount of a compound of the formula I, or a pharmaceutically acceptable salt thereof, as defined hereinbefore.

According to another aspect of the-invention there is provided a method of treating a cancer selected from leukaemia, breast, lung, colon, rectal, stomach, prostate, bladder, pancreas, ovarian, lymphoma, testicular, neuroblastoma, hepatic, bile duct, renal cell, uterine, thyroid or skin cancer, in a warm-blooded animal, such as man, in need of such treatment, which comprises administering to said animal an effective amount of a compound of the formula I, or a pharmaceutically acceptable salt thereof, as defined hereinbefore.

According to another aspect of the invention there is provided a compound of the formula I, or a pharmaceutically acceptable salt thereof, as defined hereinbefore, for use in inhibiting Tie2 receptor tyrosine kinase in a warm-blooded animal, such as man.

According to an another aspect of the invention there is provided a compound of the formula I, or a pharmaceutically acceptable salt thereof, as defined hereinbefore, for use in producing an anti-angiogenic effect in a warm-blooded animal, such as man.

According to another aspect of the invention there is provided a compound of the formula I, or a pharmaceutically acceptable salt thereof, as defined hereinbefore, for use in the treatment of cancer.

According to another aspect of the invention there is provided a compound of the formula I, or a pharmaceutically acceptable salt thereof, as defined hereinbefore, for use in the treatment of a cancer selected from leukaemia, breast, lung, colon, rectal, stomach, prostate, bladder, pancreas, ovarian, lymphoma, testicular, neuroblastoma, hepatic, bile duct, renal cell, uterine, thyroid or skin cancer.

As hereinbefore mentioned it is further expected that a compound of the present invention will possess activity against other diseases mediated by undesirable or pathological angiogenesis including psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

The anti-angiogenic activity defined herein may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may include one or more of the following categories of anti-tumour agents:

(i) anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-[2,7-dimethyloxo-3,4-dihydroquinazolin-6-ylmethyl]-N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5 α-reductase such as finasteride;

(iv) inhibitors of growth factor function, for example such inhibitors include growth factor antibodies, growth factor receptor antibodies, farnesyl transferase inhibitors, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents that work by different mechanisms to those defined hereinbefore, such as those which inhibit vascular endothelial growth factor such as the compounds disclosed in International Patent Applications WO 971/22596, WO 97/30035, WO 97/32856 and WO 98/13354 and those that work by other mechanisms (for example linomide, inhibitors of integrin αvβ3 function and angiostatin);

(vi) biotherapeutic therapeutic approaches for example those which use peptides or proteins (such as antibodies or soluble external receptor domain constructions) which either sequest receptor ligands, block ligand binding to receptor or decrease receptor signalling (e.g. due to enhanced receptor degradation or lowered expression levels)

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene-therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a compound of the Formula I as defined hereinbefore and an additional anti-tumour substance as defined hereinbefore for the conjoint treatment of cancer.

In addition to their use in therapeutic medicine, the compounds of Formula I and their pharmaceutically acceptable salts, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LC-MS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm)

relative to tetramethylsilane (TMS) as an internal standard, determined at 300 MHz using perdeuterio dimethyl sulphoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra (MS) were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is MH$^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example;

(xvi) the following abbreviations have been used:
AcOH Acetic acid
AIBN 2,2'-Azobisisobutyronitrile
DCM Dichloromethane
DIPEA Diisopropylethylamime
DMA N,N-Dimethylacetamide
DMF N,N-Dimethylformamide
DMSO Dimethylsulfoxide
DMTMM 4-(4,6-Dimethoxy-1,3,5-triazin-2-yl)-4-methylmorpholin-4-ium chloride
dppf 1,1'-Bis(diphenylphosphino)ferrocene
EtOAc Ethylacetate
HATU O-(7-Azabenzotriazol-1-yl)-N,N,N',N'-tetramethyluronium hexafluorophosphate
$^i$PrMgCl Isopropylmagnesium chloride
LDA Lithium diisopropylamide
LHMDS Lithium bis(trimethylsilyl)amide
m-CPBA meta-Chloroperbenzoic acid
MeOH Methanol
MeCN Acetonitrile
MCX Mixed cation exchange resin
MTBE Methyl tert-butyl ether
LCMS Liquid Chromatograpy—Mass Spectrometry
NMP 1-Methyl-2-pyrrolidinone
PhTosMIC α-Tosylbenzyl isocyanide
POCl$_3$ Phosphorus oxychloride
RRHPLC Reversed phase high peformance liquid chromatography
TFA Trifluoroacetic acid
THF Tetrahydrofuran (xvii) where a synthesis is described as leading to an acid addition salt (e.g. HCl salt), no comment is made on the stoichiometry of this salt. Unless otherwise stated, all NMR data is reported on free-base material, with isolated salts converted to the free-base form prior to characterisation.

EXAMPLE 1

2-(1-Methyl-4-phenyl-1H-imidazol-5-yl)[1,3]oxazolo[5,4-d]pyrimidin-7-amine

5-Amino-2-(1-methyl-4-phenyl-1H-imidazol-5-yl)-1,3-oxazole-4-carbonitrile (intermediate 5) (650 mg) in anhydrous DMF (2.0 mL) was added to formamidine acetate (2.55 g) suspended in anhydrous DMF (20 mL), and heated at 100° C. for 0.5 hours. After evaporation of solvent, purification by flash chromatography on silica eluting with DCM:MeOH (100:0 to 95:5) then DCM:MeOH:NH$_3$ (94:5:1) gave the title compound as a beige solid (221 mg, 31%);

$^1$H NMR (DMSO-$d_6$) δ 3.95 (s, 3H), 7.24-7.41 (m, 3H), 7.63-7.69 (m, 4H), 8.02 (s, 1H), 8.2 (s, 1H); MS m/e M$^+$ 293.

The starting materials used were prepared as follows:

Intermediate 1

(1-Methyl-4-phenyl-1H-imidazol-5-yl)methanol

Methylamine (33% in industrial methylated spirits, 60.3 mL) was added to a solution of glycolaldehyde dimer (2.7 g) in THF (320 mL). After 75 minutes 1-{[isocyano(phenyl)methyl]sulfonyl}-4-methylbenzene (PhTosMIC) (*Org. Syn.*, 77, 198-205) (10.8 g) was added, cooling to keep the reaction temperature below 30° C. The reaction was stirred for 90 minutes and the solvent evaporated to a volume of 100 mL. Water (500 mL) was added, and the title compound (4.94 g, 66%) collected by filtration as a white solid. The filtrate was extracted into EtOAc, dried, and the solvent removed in vacuo. The residue was triturated with EtOAc to give a further 1.06 g (14%) as a white solid.

$^1$H NMR (DMSO-$d_6$) δ 3.66 (s, 3H), 4.53 (d, 2H), 5.16 (t, 1H), 7.25 (t, 1H), 7.36 (d, 2H), 7.61-7.64 (m, 3H). MS m/e MH$^+$ 189.

Intermediate 2

1-Methyl-4-phenyl-1H-imidazole-5-carbaldehyde

Manganese dioxide (11.5 g) was added to a suspension of (1-methyl-4-phenyl-1H-imidazol-5-yl)methanol (intermediate 1) (5.75 g) in dioxane (100 mL), and the resulting mixture heated to 80° C. for 8 hours, and allowed to cool to ambient temperature overnight. The mixture was reheated to 80° C., filtered through diatomaceous earth and the cake washed well with acetone. Purification by flash chromatography on silica eluting with EtOAc:hexane (50:50 to 100:0) gave the title compound (4.90 g, 86%) as a pale solid.

$^1$H NMR (DMSO-$d_6$) δ 3.89 (s, 3H), 7.43-7.50 (m, 3H), 7.72 (d, 2H), 8.03 (s, 1H), 9.83 (s, 1H). MS m/e MH$^+$ 187

Intermediate 3

1-Methyl-4-phenyl-1H-imidazole-5-carboxylic acid

Potassium carbonate (3.13 g) was added to 1-methyl-4-phenyl-1H-imidazole-5-carbaldehyde (intermediate 2) (2.33 g) dissolved in acetone (125 mL) and water (25 mL). Once dissolved, potassium permanganate (4.23 g) was added and the mixture stirred for 24 hours. The mixture was filtered through diatomaceous earth and the cake washed with water (2×20 mL). Acetone was evaporated from the filtrate which was extracted with EtOAc (50 mL). The aqueous layer was acidified with acetic acid to pH 5, reduced to half volume and a cream precipitate filtered and dried at 60° C. in vacuo to give the title compound as a cream solid (1.74 g, 69%);

$^1$H NMR (DMSO-$d_6$) δ 3.8 (s, 3H), 7.3-7.4 (m, 3H), 7.65 (m, 2H), 7.9 (s, 1H); MS m/e MH$^+$ 203.

Intermediate 4

1-Methyl-4-phenyl-1H-imidazole-5-carbonyl chloride

Oxalyl chloride (0.35 mL) followed by one drop of DMF was added to 1-methyl-4-phenyl-1H-imidazole-5-carboxylic acid (intermediate 3) (732 mg) suspended in anhydrous DCM (6 mL). After stirring for 1 hour under inert atmosphere the mixture was evaporated to dryness and used immediately without further purification (800 mg, 100%).

Intermediate 5

5-Amino-2-(1-methyl-4-phenyl-1H-imidazol-5-yl)-1,3-oxazole-4-carbonitrile

A suspension of 1-methyl-4-phenyl-1H-imidazole-5-carbonyl chloride (intermediate 4) (0.80 g) in anhydrous NMP (2 mL) was added to aminomalononitrile p-toluenesulfonate (0.92 g) in anhydrous NMP (10 mL). The resultant mixture was stirred for 24 hours. The mixture was poured into water (10 mL), extracted with EtOAc (3×20 mL), organics combined and further washed with water (10 mL), aqueous sodium hydrogen carbonate solution (10 mL) then brine (10 mL). Organics were dried (MgSO$_4$) and evaporated to give a pale gum. Trituration with isohexane (5 mL) gave the title compound as a white solid (650 mg, 68%);
$^1$H NMR (DMSO-d$_6$) δ 3.74 (s, 3H), 7.3-7.4 (m, 3H), 7.6 (m, 2H), 7.9 (b s, 3H); MS m/e MH$^+$ 266.

EXAMPLE 2

2-(1-Methyl-4-phenyl-1H-imidazol-5-yl)[1,3]thiazolo[5,4-d]pyrimidin-7-amine

Phosphorous pentasulfide (411 mg) was added to N-(4-amino-6-hydroxypyrimidin-5-yl)-1-methyl-4-phenyl-1H-imidazole-5-carboxamide (intermediate 6) (0.185 g) suspended in anhydrous pyridine (1.0 mL) under an inert atmosphere and heated at 110° C. for 24 hours. The solvent was evaporated and the residue pre-absorbed onto silica gel and purified by column chromatography eluting with DCM:MeOH (100:0 to 90:10) then DCM:MeOH:NH$_3$ (89:10:1). Trituration with water and drying at 60° C. in vacuo gave the title compound as a yellow solid (32 mg, 19%);
$^1$H NMR (DMSO-d$_6$) δ 3.92 (s, 3H), 7.35-7.42 (m, 3H), 7.48-7.52 (m, 2H), 7.74 (bs, 2H), 7.99 (s, 1H), 8.26 (s, 1H); MS m/e MH$^+$ 309.

The starting material used was prepared as follows:

Intermediate 6

N-(4-Amino-6-hydroxypyrimidin-5-yl)-1-methyl-4-phenyl-1H-imidazole-5-carboxamide 1-Methylphenyl-1H-imidazole-5-carbonyl chloride (intermediate 4) (0.50 g) in anhydrous NMP (1 mL) was added to 4,5-diamino-6-hydroxy-pyrimidin (312 mg) in anhydrous NMP (5 mL) and stirred for 24 hours. The reaction mixture was poured into water (15 mL), adjusted to pH 9 with aqueous NH$_3$ and stirred for 15 minutes until precipitation was complete. The solid was filtered off, washed with water and dried at 60° C. in vacuo to give the title compound as a white solid (185 mg, 24%);
$^1$H NMR (DMSO d-$_6$) δ 3.76 (s, 3H), 6.17 (bs, 2H), 7.19-7.33 (m, 3H), 7.73 (s, 1H), 7.78 (s, 1H), 7.94 (dd, 2H), 8.70 (s, 1H), 11.72 (bs, 1H).

EXAMPLE 3

8-(1-Methyl-4-phenyl-1H-imidazol-5-yl)-9H-purin-6-amine

Phosphorous pentoxide (1.06 g) was added to N-(4,6diaminopyrimidin-5-yl)-1-methyl-4-phenyl-1H-imidazole-5-carboxamide (intermediate 7) (171 mg) followed by phosphoric acid (85%, 0.76 mL) and heated at 160° C. for 72 hours. Ice was added to the cooled mixture, which was then adjusted to pH 5 with aqueous NH$_3$, the resultant precipitate filtered off, washed with water and dried at 60° C. in vacuo to give the title compound as a cream solid (156 mg, 89%);
$^1$H NMR (DMSO-d$_6$+AcOH-d$_4$) δ 3.64 (s, 3H), 7.15-7.28 (m, 3H), 7.43 (dd, 2H), 7.89 (s, 1H), 8.14 (s, 1H); MS m/e MH$^+$ 292.

The starting material used was prepared as follows:

Intermediate 7

N-(4,6-Diaminopyrimidin-5-yl)-1-methyl-4-phenyl-1H-imidazole-5-carboxamide

A suspension of 1-methyl-4-phenyl-1H-imidazole-5-carbonyl chloride (intermediate 4) (0.30 g) in anhydrous NMP (1 mL) was added to 4,5,6-triaminopyrimidine (358 mg) in anhydrous NMP (2 mL). The resultant mixture was stirred for 24 hours, poured into water (10 mL), adjusted to pH 9 with aqueous NH$_3$ and allowed to stir for 10 minutes until precipitation was complete. The solid was filtered off, washed with water and dried at 60° C. in vacuo to give the title compound as a cream solid (171 mg, 37%)
$^1$H NMR (DMSO-d$_6$) δ 3.77 (s, 3H), 5.79 (s, 4H), 7.26-7.38 (m, 3H), 7.68 (dd, 2H), 7.76 (s, 1H), 7.78 (s, 1H), 8.75 (s, 1H); MS m/e MH$^+$ 309.

EXAMPLES 4 AND 5

9-Methyl-8-(1-methyl-4-phenyl-1H-imidazol-5-yl)-9H-purin-6-amine & 7-Methyl-8-(1-methyl-4-phenyl-1H-imidazol-5-yl)-7H-purin-6-amine Sodium hydride (60% dispersion in oil) (0.026 g) was added to a solution of 8-(1-methyl-4-phenyl-1H-imidazol-5-yl)-9H-purin-6-amine (example 3) (0.18 g) in DMF (25 ml) at 30° C. After stirring at 30° C. for one hour, iodomethane (0.088 g) was added and the reaction stirred for 5 hours. The solvent was evaporated and saturated aqueous sodium carbonate (20 mL) and chloroform (20 mL) added. The aqueous layer was re-extracted into chloroform (3×20 mL) and the combined organics dried (MgSO$_4$), filtered and evaporated in vacuo to give a brown oil. Purification by flash chromatography on silica eluting with DCM:MeOH (99:1) gave separation of the title compounds as white solids:
higher R$_f$ isomer; 0.081 g, 43%.
$^1$H NMR (CDCl3) δ 3.28 (s, 3H), 3.75 (s, 3H), 5.72 (s, b, 2H), 7.27 (m, 3H), 7.38 (d, 2H), 7.71 (s, 1H), 8.41 (s, 1H); MS m/e MH$^+$ 306.
lower R$_f$ isomer; 0.004 g, 2%.
$^1$H NMR (CDCl3) δ 3.42 (s, 3H), 3.83 (s, 3H), 5.05 (s, b, 2H), 7.31 (m, 3H), 7.41 (m, 2H), 7.75 (s, 1H), 8.55 (s, 1H); MS m/e MH$^+$ 306.

The identity of the specific isomer in the higher and lower retained fractions was not determined.

EXAMPLE 6

6-[1-(3,4Dimethoxybenzyl)-4-phenyl-1H-imidazol-5-yl]thieno[2,3-d]pyrimidin

N-(3,4Dimethoxybenzyl)-N-[thieno[2,3-d]pyrimidin-6-ylmethylidene]amine (intermediate 14) (76 mg), PhTosMIC (99 mg) and piperazine (31 mg) in THF (5 mL) were stirred under an inert atmosphere for 6 days. The reaction mixture was diluted with EtOAc and water. The organic layer was separated and the aqueous layer extracted with EtOAc (2×15 mL). The combined organics were dried (MgSO$_4$), filtered and concentrated in vacuo. Purification by flash chromatography on silica eluting with hexane:EtOAc (1:4) afforded the title compound as a pale yellow solid (50 mg, 48%);

$^1$H NMR (CDCl$_3$) δ 3.74 (s, 3H), 3.87 (s, 3H), 5.07 (s, 2H), 6.53-6.60 (m, 2H), 6.76-6.79 (m, 1H), 7.15 (s, 1H), 7.22-7.30 (m, 3H), 7.56-7.59 (m, 2H), 7.74 (s, 1H), 9.08 (s, 1H), 9.12 (s, 1H); MS m/e MH$^+$ 429.

The starting materials used were prepared as follows:

Intermediate 8

4,6-Dichloropyrimidine-5-carbaldehyde

DMP (7 mL) was added dropwise to POCl$_3$ (22 mL) keeping the internal temperature below 30° C. 4,6-Dihydroxypyrimidine (5.0 g) was added maintaining the temperature below 30° C. The reaction mixture was stirred for 20 minutes and then heated to reflux for 4 hours. Excess POCl$_3$ was removed by evaporation and the resulting viscous mixture was poured into a stirred ice solution. The product was extracted with diethyl ether (6×50 mL). The combined organics were concentrated in vacuo and then purified by flash chromatography on silica eluting with hexane:EtOAc (7:1 to 2:1) to afford the title compound as a white crystalline solid (4.42 g, 56%);

$^1$H NMR (CDCl$_3$) δ 8.89 (s, 1H), 10.46 (s, 1H).

Intermediate 9

Methyl [(6-chloro-5-formylpyrimidin-4-yl)thio]acetate

DIPEA (4.1 mL) was added to a solution of 4,6-dichloropyrimidine-5-carbaldehyde (intermediate 8) (4.2 g) in DCM (85 mL) under an inert atmosphere. The solution was cooled to −10° C. and methylthioglycolate (2.1 mL) in DCM (40 mL) was added dropwise over 30 minutes. The reaction mixture was allowed to warm to ambient temperature over 2 hours, washed with water (4×50 mL), dried (MgSO$_4$), filtered and concentrated in vacuo to give the title compound as an orange oil which later solidified (5.4 g, 92%);

$^1$H NMR (CDCl$_3$) δ 3.75 (s, 3H), 3.99 (s, 2H), 8.76 (s, 1H), 10.56 (s, 1H).

Intermediate 10

Methyl 4-chlorothieno[2,3-d]pyrimidine-6-carboxylate

DIPEA (2.1 mL) was added to methyl [(6chloro-5-formylpyrimidin-4-yl)thio]acetate (intermediate 9) (2.9 g) in cyclohexanol (50 mL) under an inert atmosphere. The reaction mixture was heated at 120° C. for 90 minutes. The solvent was evaporated and the product purified by flash chromatography on silica eluting with hexane:diethyl ether (4:1) to afford the title compound as a pale yellow solid (1.45 g, 53%);

$^1$H NMR (CDCl$_3$) δ 4.01 (s, 3H), 8.13 (s, 1H), 8.94 (s, 1H).

Intermediate 11

Methyl thieno[2,3-d]pyrimidine-6-carboxylate

Methyl 4-chlorothieno[2,3-d]pyrimidine-6-carboxylate (intermediate 10) (114 mg), magnesium oxide (40 mg) and Pd/C (12 mg) in isopropanol (10 mL) were stirred under hydrogen for 48 hours. The solution was filtered through diatomaceous earth, washed with DCM (3×10 mL) and then concentrated in vacuo. Purification by flash chromatography on silica eluting with hexane:EtOAc (2:1) afforded the title compound as a white crystalline solid (76 mg, 78%);

$^1$H NMR (CDCl$_3$) δ 4.00 (s, 3H), 8.07 (s, 1H), 9.19 (s, 1), 9.25 (s, 1H); MS m/e MH$^+$ 195.

Intermediate 12

N-Methoxy-N-methylthieno[2,3-d]pyrimidine-6-carboxamide $^i$PrMgCl (2M in THF, 1.1 mL) was added dropwise to a solution of methyl thieno[2,3-d]pyrimidine-6-carboxylate (intermediate 11) (138 mg) and N-methoxy-N-methylamide (104 mg) in THF at −20° C. maintaining the internal temperature below −5° C. The reaction was allowed to stir at −10° C. for 30 minutes and then quenched with NH$_4$Cl (sat. aq). The solution was diluted with EtOAc and the organic layer was separated. The aqueous layer was extracted with EtOAc (2×15 mL) and then the combined organics dried (MgSO$_4$), filtered and concentrated in vacuo. Purification by flash chromatography on silica eluting with hexane:EtOAc (1:1 to 1:4) afforded the title compound as a pale yellow solid (107 mg, 67%);

$^1$H NMR (CDCl$_3$) δ 3.46 (s, 3H), 3.86 (s, 3H), 8.22 (s, 1H), 9.19 (s, 1H), 9.26 (s, 1H);

Intermediate 13

Thieno[2,3-d]pyrimidine-6-carbaldehyde

LiAlH$_4$ (1M in THF, 0.26 mL) was added dropwise to N-methoxy-N-methylthieno[2,3-d]pyrimidine-6-carboxamide (intermediate 12) (117 mg) in THF (6 mL) at −78° C. under an inert atmosphere. The reaction was allowed to stir at −78° C. for 30 minutes and then allowed to warm to 0° C. Saturated aqueous-ammonium chloride (2 mL) was added and allowed to stir at 0° C. for 10 minutes. The organic layer was separated and the aqueous layer extracted with diethyl ether (2×15 mL). The combined organics were dried (MgSO$_4$), filtered and concentrated in vacuo. Purification by flash chromatography on silica eluting with hexane:EtOAc (1:4) afforded the title compound as a white solid (60 mg, 70%);

$^1$H NMR (CDCl$_3$) δ 8.06 (s, 1H), 9.22 (s, 1H), 9.33 (s, 1H), 10.15 (s, 1H); MS m/e MH$^+$ 165.

Intermediate 14

N-(3,4-dimethoxybenzyl)-N-[thieno[2,3-d]pyrimidin-6-ylmethylidene]amine

Thieno[2,3-d]pyrimidine-6-carbaldehyde (intermediate 13) (40 mg), 3,4-dimethoxybenzylamine (0.04 ml) and 4 Å molecular sieves (150 mg) were heated at reflux in DCM (5 ml) for 3 hours under an inert atmosphere. The molecular sieves were removed by filtration and the solvent evaporated to afford the title compound as a pale yellow solid (76 mg, 100%);

$^1$H NMR (CDCl$_3$) δ 3.87-3.90 (m, 6H), 4.84 (s, 2H), 6.84-6.88 (m, 3H), 7.51 (s, 1H), 8.50 (s, 1H), 9.10 (s, 1H), 9.11 (s, 1H).

EXAMPLE 7

6-(1-Methyl-4-phenyl-1H-imidazol-5-yl)-4-(methylthio)thieno[2,3d]pyrimidine

The title compound was prepared by a similar process to that described for Example 6 but using N-[4-(methylthio) thieno[2,3-d]pyrimidin-6-ylmethylidene]methanamine (intermediate 16) in place of N-(3,4-dimethoxybenzyl)-N-[thieno[2,3-d]pyrimidine-6-ylmethylidene]amine (intermediate 14). Off white solid (105 mg 81%);

$^1$H (CDCl$_3$) δ 2.73 (s, 3H), 3.65 (s, 3H), 7.19-7.30 (m, 3H), 7.57-7.61 (m, 2H), 7.66 (s, 1H), 8.86 (s, 1H); MS m/e MH$^+$ 339.

The starting materials used were prepared as follows:

Intermediate 15

4-(Methylthio)thieno[2,3-d]pyrimidine-6-carbaldehyde 4-(Methylthio)thieno[2,3-d]pyrimidine (*J. Heterocycl. Chem.* 1975, 12, 921-924) (1 g) in THF (5 mL) was added to a preformed solution of LDA (BuLi (1.6M in hexanes, 3.8 mL) and di-isopropylamine (0.85 mL)] in THF (20 mL) at −78° C. The reaction mixture was allowed to stir for 1 hour at −78° C. and then DMF (1.1 mL) was added. The reaction mixture was stirred at −78° C. for 30 minutes then allowed to warm to ambient temperature and stirred for a further 3 hours. The reaction mixture was diluted with water and the; product was extracted with EtOAc (4×30 mL). The combined organic extracts were washed with brine (30 mL), dried (MgSO$_4$), filtered and concentrated in vacuo. Purification by flash chromatography on silica eluting with DCM afforded the title compound as a white solid (1.17 g, 51%);

$^1$H NMR (CDCl$_3$) δ 2.76 (s, 3H), 8.03 (s, 1H), 8.90 (s, 1H), 10.10 (s, 1H); MS m/e MH$^+$ 211

Intermediate 16

N-[4-(Methylthio)thieno[2,3-d]pyrimidin-6-ylmethylidene]methanamine

The title compound was prepared by a similar process to that described for Intermediate 14 but using 4-(methylthio) thieno[2,3-d]pyrimidine-6-carbaldehyde (Intermediate 15) in place of thieno[2,3-d]pyrimidine-6-carbaldehyde (intermediate 13) and methylamine (33% in methylated spirits) in place of 3,4-dimethoxybenzylamine. Colourless solid (73 mg, 98%);

$^1$H NMR (CDCl$_3$) δ 2.73 (s, 3H), 3.57 (s, 3H), 7.48 (s, 1H), 8.45 (s, 1H), 8.83 (s, 1H).

EXAMPLE 8

6-(1-Methyl-4-phenyl-1H-imidazol-5-yl)thieno[2,3-d]pyrimidin-4-amine 6-(1-Methyl-4-phenyl-1H-imidazol-5-yl)-4-(methylsulfonyl)thieno[2,3-d]pyrimidine (intermediate 17) (30 mg) and concentrated NH$_3$ (0.75 mL) were stirred in 1,4-dioxane (3 mL) for 1 hour. The solvent was evaporated and the resultant residue dissolved in a small volume of DCM. Isohexane was then added and the resultant solid filtered and dried in vacuo to give the title compound as a pale yellow solid (25 mg, 100%);

$^1$H NMR (CDCl$_3$) δ 3.61 (s, 3H), 5.44 (b s, 2H), 7.10 (s, 1H), 7.21-7.31 (m, 3H), 7.58-7.61 (m, 2H), 7.66 (s, 1H), 8.53 (s, 1H); MS m/e MH$^+$ 308.

The starting material used was prepared as follows:

Intermediate 17

6-(1-Methyl-4-phenyl-1H-imidazol-5-yl)-4-(methylsulfonyl)thieno[2,3-d]pyrimidine m-CPBA (70-75%, 105 mg) was added to a stirred solution of 6-(1-methyl-4-phenyl-1H-imidazol-5-yl)-4-(methylthio) thieno[2,3-d]pyrimidine (example 7) (72 mg) in DCM (5 mL), stirred for 6 hours then 2M Na$_2$S$_2$O$_3$ (2.5 mL) was added. The organic layer was separated and the aqueous layer extracted with DCM (2×15 mL). The combined organics were washed with saturated aqueous NaHCO$_3$ (10 mL), dried (MgSO$_4$), filtered and concentrated in vacuo. Purification by flash chromatography on silica eluting with hexane:EtOAc (1:4) afforded the title compound as a yellow solid (44 mg, 56%);

$^1$H NMR (CDCl$_3$) δ 3.45 (s, 3H), 3.73 (s, 3H), 7.25-7.34 (m, 3H), 7.54-7.57 (m, 2H); 7.70 (s, 1H), 8.04 (s, 1H), 9.16 (s, 1H); MS m/e MH$^+$ 371.

EXAMPLE 9

6-[1-(3,4-Dimethoxybenzyl)-4-phenyl-1H-imidazol-5-yl]-4-(methylthio)thieno[2,3-d]pyrimidine The title compound was prepared in 55% yield using a procedure similar to the one described for example 6 above but starting from N-(3,4-dimethoxybenzyl)-N-{[4-(methylthio)thieno[2,3-d]pyrimidin-6-yl]methylidene}amine (intermediate 18) (76 mg), in place of N-(3,4-dimethoxybenzyl)-N-[thieno[2,3d]pyrimidin-6-ylmethylidene]amine (intermediate 14);

$^1$H NMR (CDCl$_3$) δ 2.71 (s, 3H), 3.75 (s, 3H), 3.87 (s, 3H), 5.05 (s, 2H), 6.54-6.62 (m, 2H), 6.79 (d, 1H), 7.11 (s, 1H), 7.22-7.30 (m, 3H), 7.58-7.61 (m, 2H), 7.74 (s, 1H), 8.84 (s, 1H); MS m/e MH$^+$ 475.

The starting material used was prepared as follows:

Intermediate 18

N-(3,4-Dimethoxybenzyl)-N-{[4-(methylthio)thieno[2,3-d]pyrimidin-6-yl]methylidene}amine The title compound was prepared by a similar process to that described for Intermediate 14 but using 4-(methylthio) thieno[2,3-d]pyrimidine-6-carbaldehyde (intermediate 15) in place of thieno[2,3-d]pyrimidine-6-carbaldehyde (intermediate 13). White solid (76 mg, 97%);

$^1$H NMR (CDCl$_3$) δ 2.71 (s, 3H), 3.87-3.89 (m, 6H), 4.81 (d, 2H), 6.83-6.87 (m, 3H), 7.50 (s, 1H), 8.45 (t, 1H), 8.82 (s, 1H).

EXAMPLE 10

6-[1-(3,4-Dimethoxybenzyl)-4-phenyl-1H-imidazol-5-yl]thieno[2,3-d]pyrimidin-4-amine The title compound was prepared by a similar process to that described for Example 8 but using 6-[1-(3,4-dimethoxybenzyl)-4-phenyl-1H-imidazol-5-yl]-4-(methylsulfonyl)-thieno[2,3-d]pyrimidine (intermediate 19) in place of 6-(1-methyl-4-phenyl-1H-imidazol-5-yl)-4-(methylsulfonyl)thieno[2,3-d]pyrimidine (intermediate 17). White solid (35 mg, 91%);

$^1$H NMR (CDCl$_3$) δ 3.72 (s, 3H), 3.84 (s, 3H), 4.96 (s, 2H), 5.47 (b s, 2H), 6.49-6.50 (m, 1H), 6.54-6.58 (m, 1H), 6.75 (d, 1H), 6.83 (s, 1H), 7.32-7.51 (m, 3H), 7.57-7.60 (m, 2H), 7.69 (s, 1H), 8.49 (s, 1H); MS m/e MH$^+$ 444.

The starting material used was prepared as follows:

Intermediate 19

6-[1-(3,4-Dimethoxybenzyl)-4-phenyl-1H-imidazol-5-yl]-4-(methylsulfonyl)thieno[2,3-d]pyrimidine The title compound was prepared in 75% yield according to a procedure similar to the one described for intermediate 17 above but starting from 6-[1-(3,4-dimethoxybenzyl)-4-phenyl-1H-imidazol-5-yl]-4-(methylthio)thieno[2,3-d]pyrimidine (example 9) in place of 6-(1-methyl-4-phenyl-1H-imidazol-5-yl)-4-(methylthio)thieno[2,3-d]pyrimidine (example 7);

$^1$H NMR (CDCl$_3$) δ 3.41 (s, 3H), 3.74 (s, 3H), 3.84 (s, 3H), 5.11 (s, 2H), 6.54-6.60 (m, 2H), 6.77 (d, 1H), 7.12-7.31 (m, 3H), 7.53-7.56 (m, 2H), 7.74 (s, 1H), 7.91 (s, 1H), 9.12 (s, 1H); MS m/e MH$^+$ 507.

EXAMPLE 11

6-(1-Methyl-4-phenyl-1H-imidazol-5-yl)-4-(methylthio)thieno[3,2-d]pyrimidine

Methylamine (2M in THF, 2.5 mL) was added to a solution of 4-(methylthio)thieno[3,2-d]pyrimidine-6-carbaldehyde (intermediate 21) (105 mg) in DCM (10 mL) containing 4 Å molecular sieves (1 g). The reaction mixture was stirred for 2.5 hours, at which point PhTosMIC (149 mg) and piperazine (90 mg) were added. The reaction was stirred for a further 72 hours then additional PhTosMIC (30 mg) was added. After stirring for a further 1.5 hours the mixture was poured into water and extracted into DCM, washed with water and brine, dried, and the solvent removed. Purification by flash chromatography on silica eluting with EtOAc:hexane (25:75 to 0:1Q0) gave the title compound as a pale solid foam (95 mg, 56%);

$^1$H NMR (CDCl$_3$) δ 2.77 (s, 3H), 3.66 (s, 3H), 7.22-7.28 (m, 3H), 7.47 (s, 1H), 7.55 (dd, 2H), 7.67 (s, 1H), 8.99 (s, 1H). MS m/s MH$^+$ 339.

The starting materials used were prepared as follows:

Intermediate 20

4-(Methylthio)thieno[3,2-d]pyrimidine

Sodium thiomethoxide (9.1 g) was added to a solution of 4-chlorothieno[3,2-d]pyrimidine (WO9849899, example 3A; WO9924440, example 1C) (17.0 g) in DMF (100 mL). After stirring for 90 minutes the mixture was poured into water (400 mL), extracted into EtOAc, washed with water, dried (MgSO$_4$), and the solvent removed. Purification by flash chromatography on silica eluting with DCM:EtOAc (4:1) gave the title compound as a pale yellow solid (16.5 g, 69%);

$^1$H NMR (CDCl$_3$) δ 2.76 (s, 3H), 7.50 (d, 1H), 7.85 (d, 1H), 8.97 (s, 1H). MS m/e MH$^+$ 182.

Intermediate 21

4-(Methylthio)thieno[3,2-d]pyrimidine-6-carbaldehyde

The title compound was prepared by a similar process to that described for Intermediate 15 but using 4-(methylthio)thieno[3,2-d]pyrimidine (intermediate 20) in place of 4-(methylthio)thieno[2,3-d]pyrimidine. Yellow solid (434 mg, 38%);

1H NMR (DMSO-d$_6$) δ 3.76 (s, 3H), 8.52 (s, 1H), 9.09 (s, 1H), 10.25 (s, 1H). MS m/e MH$^+$ 211.

EXAMPLE 12

6-(1-Methyl-4-phenyl-1H-imidazol-5-yl)thieno[3,2-d]pyrimidin-4-amine

Concentrated aqueous NH$_3$ (0.5 mL) and saturated ammonium chloride solution (one drop) were added to a solution of 6-(1-methyl-4-phenyl-1H-imidazol-5-yl)-4-(methylthio)thieno[3,2-d]pyrimidine (example 11) (40 mg) in NMP (2 mL). The vessel was sealed and heated in a microwave (CEM explorer, 200-210° C., 110 W) for 35 minutes. Dilution with water (1.5 mL) and purification by RPHPLC eluting with MeCN:H$_2$O (2:98 to 40:60) gave the title compound as a pale brown solid (24 mg, 67.%);

$^1$H NMR (DMSO-d$_6$) δ 3.73 (s, 3H), 7.30-7.50 (m, 5H), 7.78 (s, 1H), 8.74 (s, b, 2H), 9.03 (s, b, 2H). MS m/e MH$^+$ 308.

EXAMPLE 13

5-[4-(Methylthio)thieno[3,2-d]pyrimin-6-yl]-1H-imidazol-1-ol

A mixture of 1-[4-(methylthio)thieno[3,2-d]pyrimidin-6-yl]-2-phenylethane-1,2-dione 1-oxime (intermediate 23) (300 mg), cupric acetate (290 mg) and ammonium acetate (690 mg) in acetic acid (20 mL) was heated to 95° C. Paraformaldehyde in acetic acid (0.9 M) was added in small portions over 4 hours. After the addition of 1.2 mL of the paraformaldehyde stock solution, the reaction was complete. After evaporation of the solvent, the residual solid was suspended in a mixture of acetonitrile (8 mL) and water (8 mL) and filtered. The title compound was obtained as a brown solid, which was washed with water (10 mL), and diethyl ether (20 mL), and air-dried (189 mg, 62%) Preparative RPHPLC (eluting with a gradient of MeCN and water containing 0.1% TFA) of the filtrate and washes afforded a sample of the title compound as white solid (47 mg, 15%);

$^1$H NMR (CDCl$_3$) δ 2.72 (s, 3H), 7.4 (m, 3H), 7.56 (d, 2H), 7.59 (s, 1H), 8.36 (s, 1H), 8.95 (s, 1H). MS m/e MH$^+$ 341.

The starting materials used were prepared as follows:

Intermediate 22

6-Methyl-4-(methylthio)thieno[3,2-d]pyrimidine

A solution of sodium thiomethoxide (24S mg) and 6-methyl-4-chlorothieno[3,2-d]pyrimidine (Acta Pol. Pharm. (1986), 43(2), 97-100) (650 mg) in acetonitrile (50 mL) was stirred overnight. The mixture was filtered and the solid was washed with acetonitrile. The combined filtrate and washes were evaporated to give the title compound as a white solid (665 mg, 97%);

MS m/e MH$^+$ 197.

Intermediate 23

1-[4-(Methylthio)thieno[3,2-d]pyrimidin-6-yl]-2-phenylethane-1,2-dione 1-oxime

6-Methyl-4-(methylthio)thieno[3,2-d]pyrimidine, (intermediate 22) (665 mg) was dissolved in THF (10 mL) and added slowly, over 15 minutes, to a stirred solution of LHMDS in THF (1M, 3.39 mL) at −78° C. After 10 minutes, N-methoxy-N-methylbenzamide (616 mg) was added and the reaction mixture warmed to 0° C. After 2 hours at 0° C. the resultant solution of 2-[4-(methylthio)thieno[3,2-d]pyrimidin-6-yl]-1-phenylethanone was acidified with acetic acid (10 mL), diluted with water (10 mL) and re-cooled to 0° C. Sodium nitrite (280 mg) was added and the mixture was stirred overnight. After evaporation of the solvents, the solid residue was collected with water by filtration, and dried to give the title compound as a brown solid (959 mg, 86%);

MS m/e MH$^+$ 330.

EXAMPLE 14

6-(4-Phenyl-1H-imidazol-5-yl)furo[2,3-d]pyrimidine

A suspension of 5-[4-methylthio)furo[2,3-d]pyrimidin-6-yl]-4-phenyl-1H-imidazol-1-ol (intermediate 25) (375 mg) and Raney Nickel (Aldrich, suspension in water, 0.5 mL) in ethanol (75 mL) and water (75 mL) was stirred under reflux under a balloon of hydrogen. After 4 days the mixture was filtered through a pad of diatomaceous earth and the solids washed with a mixture of ethanol and water. The combined filtrate and washings were evaporated and the residue was purified by preparative RPHPLC (eluting with a gradient of MeCN and water containing 0.1% TFA) to afford the title compound as a white solid (105 mg, 35%);

$^1$H NMR (DMSO-$d_6$) δ 7.16 (s, 1H), 7.5 (m, 3H), 7.6 (d, 2H), 8.5 (s, 1H), 8.9 (s, 1H), 9.13 (s, 1H); MS m/e MH$^+$ 263.

The starting materials used were prepared as follows:

Intermediate 24

6-Methyl-4-(methylthio)furo[2,3-d]pyrimidine

A solution of 6-methyl-4-chlorofuro[2,3-d]pyrimidine (U.S. Pat. No. 3,577,420, example IG) (219 mg) in acetonitrile (25 mL) was heated under reflux with sodium thiomethoxide (190 mg) for 16 hours. The mixture was filtered and the solids washed with acetonitrile. Evaporation of the solvent afforded the title compound as a white solid (230 mg, 90%);

MS m/e MH$^+$ 181.

Intermediate 25

5-[4-(Methylthio)furo[2,3d]pyrimidin-6-yl]-4-phenyl-1H-imidazol-1-ol

The title compound was prepared in 35% yield using a similar process to that described for the preparation of intermediate 23 followed by a similar process to that described for the preparation of example 13 but starting from 6-methyl-4-(methylthio)furo[2,3-d]pyrimidine (intermediate 24) (230 mg) in place of 6-methyl-4-(methylthio)thieno[3,2-d]pyrimidine (intermediate 22). The title compound was used without further purification;

MS m/e MH$^+$ 325.

EXAMPLE 15

6-(1-Methyl-4-phenyl-1H-imidazol-5-yl)furo[2,3-d]pyrimidine

Copper(I) iodide (2 mg), bis(triphenylphosphine)palladium dichloride (4 mg) and 4-hydroxy-5-iodopyrimidine (*Coll. Czech. Chem. Commun.*, 1962, 27, 2550-2560) (51.9 mg) were stirred in a mixture of DMF (6 mL) and NEt$_3$ (2 mL) then degassed with nitrogen for 30 minutes. 5-Ethynyl-1-methyl-4-phenyl-1H-imidazole (intermediate 26) (42.6 mg) was added, the reaction mixture was then stirred for 16 hours and then heated at 50° C. for 8 hours. Water (10 mL) was added and the mixture extracted with DCM (3×10 mL), organics combined, washed with brine (2×10 mL) and water (4×10 mL), dried (MgSO$_4$), filtered and concentrated in vacuo. Purification by flash chromatography on silica eluting with DCM-MeOH (40:1) afforded the title compound as a white solid (17.1 mg, 26%);

$^1$H NMR (CDCl$_3$) δ 3.87 (s, 3H), 6.78 (s, 1H), 7.29-7.40 (m, 3H), 7.60-7.66 (m, 2H), 8.97 (s, 1H), 9.00 (s, 1H); MS m/e MH$^+$ 277

The starting material used was prepared as follows:

Intermediate 26

5-Ethynyl-1-methyl-4-phenyl-1H-imidazole n-Butyllithium (2M in pentane, 650 μL) was added dropwise to trimethylsilyldiazomethane (2M in hexane, 750 μL) in THF (1 mL), cooled to −78° C. and stirred for 30 minutes. 1-Methyl-4-phenyl-1H-imidazole-5-carbaldehyde (intermediate 2) (186 mg) was added dropwise over 5 minutes and stirring continued at −78° C. for 30 minutes, then warmed to 0° C. over 30 minutes and stirred for a further 30 minutes at 0° C. Saturated aqueous ammonium chloride (3 mL) was added, mixture extracted with diethyl ether (3×5 mL), organics combined dried (MgSO$_4$), filtered and concentrated in vacuo. Purification by flash chromatography on silica eluting with DCM:MeOH (50.1) afforded the title compound as yellow solid (61.3 mg, 34%);

$^1$H NMR (DMSO-$d_6$) δ 3.68 (s, 3H), 5.00 (b s, 1H), 7.27-7.32 (m, 1), 7.40-7.49 (m, 2H), 7.81 (b s, 1H), 8.04-8.06 (m, 2H); MS m/e MH$^+$ 183.

EXAMPLE 16

6-(1-Methyl-4-phenyl-1H-imidazol-5-yl)furo[2,3d]pyrimidin-4-amine

The title compound was prepared in 13% yield according to a procedure similar to the one described for example 15 above but starting from 4-amino-5-iodo-6-hydroxypyrimidine (intermediate 27) in place of 4-hydroxy-5-iodopyrimidine;

$^1$H NMR (CDCl$_3$) δ 3.80 (s, 3H), 5.25 (b s, 2H), 6.61 (s, 1H), 7.29-7.38 (m, 3H), 7.61-7.64 (m, 3H), 8.42 (s, 1H); MS m/e MH$^+$ 292.

The starting material used was prepared as follows:

Intermediate 27

4-Amino-5-iodo-6-hydroxypyrimidine

4-Amino-6-hydroxypyrimidine (1.77 g) was stirred in aqueous sodium hydroxide (1.5N, 12.7 mL) and heated to 60° C. for 30 minutes. After cooling to ambient temperature, iodine (4.04 g) was added and the mixture refluxed for 2 hours. The mixture was cooled in an ice bath, filtered, washed with ice-cold water (10 mL), dried by suction then in a vacuum oven over P$_2$O$_5$ at 60° C. for 16 hours to afford the title compound as a white solid (886 mg, 23%);

$^1$H NMR (DMSO-$d_6$) δ 6.65 (b s, 1H), 7.76 (s, 1H), 11.34 (b s, 2H); MS m/e MH$^+$ 238.

EXAMPLE 17

6-(1-Methyl-4-phenyl-1H-imidazol-5-yl)-7H-pyrrolo[2,3-d]pyrimidine

Potassium tert-butoxide (84 mg) was added to 5-[(1-methyl-4-phenyl-1H-imidazol-5-yl)ethynyl]pyrimidin-4-amine (intermediate 28) (41 mg) stirred in NMP (2 mL) and heated to 60° C. for 5 hours. After cooling to ambient temperature, water (3 mL) and then DCM (10 mL) was added. The reaction mixture was washed with water (4×10 mL), dried (MgSO$_4$), filtered and concentrated in vacuo. Purification by flash chromatography on silica eluting with DCM:MeOH (20:1 to 10:1) afforded the title compound as a white solid (13.6 mg, 33%);

$^1$H NMR (CDCl$_3$) δ 3.70 (s, 3H), 6.70 (s, 1H), 7.27-7.30 (m, 3H), 7.47-7.52 (m, 2H), 7.66 (s, 1H), 8.83 (s, 1H), 9.03 (s, 1H), 9.40 (s, 1H); MS m/e MH$^+$ 276.

The starting material used was prepared as follows:

Intermediate 28

5-[(1-Methyl-4-phenyl-1H-imidazol-5-yl)ethynyl]pyrimidin-4-amine

Copper(I) iodide (4 mg) and bis(triphenylphosphine)palladium dichloride (8 mg) were stirred in a mixture of DMF (6 mL) and NEt$_3$ (2 mL) then degassed with nitrogen for 30 minutes. 4-Amino5-iodopyrimidine (*Heterocycles*, 1984, 22, 1195-1210) (122 mg) and 5-ethynyl-1-methyl-4-phenyl-1H-imidazole (intermediate 26) (101 mg) were added and reaction mixture stirred for 30 minutes. Water (20 mL) was added, mixture extracted with EtOAc (3×15 mL), organics combined, dried (MgSO$_4$), filtered and concentrated in vacuo. Purification by flash chromatography on silica eluting with DCM:MeOH (40:1 to 20:1) afforded the title compound as an off-white solid (63.6 mg, 42%);

$^1$H NMR (CDCl$_3$) δ 3.77 (s, 3H), 5.48 (b s, 1H), 7.30-7.45 (m, 3H), 7.58 (s, 1H), 8.08-8.11 (m, 2H), 8.40 (s, 1H), 8.59 (s, 1H); MS m/e MH$^+$ 276

EXAMPLE 18

6-(4-Phenyl-1H-imidazol-5-yl)thieno[3,2-d]pyrimidine

The title compound was prepared using a similar process to that described for the preparation of Example 14 but using the compound of Example 13 as starting material. White solid (25 mg, 50%);
MS m/e MH$^+$ 279.

EXAMPLE 19

N-Methyl-6-(1-methyl-4-phenyl-1H-imidazol-5-yl)thieno[2,3-d]pyrimidin-4-amine

The title compound was prepared using a similar process to that described for the preparation of Example 8, but replacing NH$_3$ with methylamine in alcohol (33% w/v). White solid (74 mg, 90%);
MS m/e MH$^+$ 322.

EXAMPLE 20

N-[6-(1-Methyl-4-phenyl-1H-imidazol-5-yl)thieno[2,3-d]pyrimidin-4-yl]acetamide 6-(1-Methyl-4-phenyl-1H-imidazol-5-yl)thieno[2,3-d]pyrimidine-4-amine (Example 8) (29 mg), DMA (2 mL), DIPEA (0.05 mL) and acetic anhydride (0.01 mL) were heated at 82° C. for 1 day. The reaction mixture was cooled to ambient temperature, water (2 mL) added and then preparative RPHPLC (eluting with a gradient of MeCN and water containing 0.1% TFA) afforded the title compound as a colourless solid (25 mg, 76%);
MS m/e MH$^+$ 350.

EXAMPLE 21

6-[1-(4-Methoxybenzyl)-4-phenyl-1H-imidazol-5-yl]furo[2,3-d]pyrimidine

The title compound was prepared by the process described in Example 15 but using 5-ethynyl-1-(4-methoxybenzyl)-4-phenyl-1H-imidazole (Intermediate 31) in place of 5-ethynyl-1-methyl-4-phenyl-1H-imidazole (intermediate 26). White solid (110 mg, 40%);

$^1$H NMR (DMSO-d$_6$) δ 3.66 (s, 3H), 5.26 (s, 2H), 6.78 (d, 2H), 6.99 (d, 2H), 7.17 (s, 1H), 7.23-7.35 (m, 3H), 7.5 (d, 2H), 8.2 (s, 1H), 8.97 (s, 1H), 9.16 (s, 1H). MS m/e MH$^+$ 383.

The starting material was prepared as follows;

Intermediate 29

5-(Dimethoxymethyl)-1-(4-methoxybenzyl)-4-phenyl-1H-imidazole

The title compound was prepared by a similar process to that described for preparation of Intermediate 1, except that 4-methoxybenzylamine was used in place of methylamine and dimethoxyacetaldehyde in place of glycolaldehyde. Colourless oil (1.5 g, 74%);
MS m/e MH$^+$ 339.

Intermediate 30

1-(4-Methoxybenzyl)-4-phenyl-1H-imidazole-5-carbaldehyde 5-(Dimethoxymethyl)-1-(4-methoxybenzyl)-4-phenyl-1H-imidazole (Intermediate 29) (1.5 g) was dissolved in formic acid (10 mL) and water (10 mL) and stirred for 16 hours at ambient temperature. The solvents were evaporated in vacuo, the residue was azeotroped with toluene (2×10 mL) and the residual oil dried in vacuo over P$_2$O$_5$ to give the title compound as a colourless oil (1.29 g, 100%);
MS m/e MH$^+$ 293.

Intermediate 31

5-Ethynyl-1-(4-methoxybenzyl)-4-phenyl-1H-imidazole

The title compound was-prepared by a similar process to that described for intermediate 26 but using 1-(4-methoxybenzyl)-4-phenyl-1H-imidazole-5-carbaldehyde (Intermediate 30) in place of 1-methyl-4-phenyl-1H-imidazole-5-carbaldehyde (Intermediate 2). Colourless oil (420 mg, 33%);
MS m/e MH$^+$ 289.

EXAMPLE 22

2-[1-(4-Methoxybenzyl)-4-phenyl-1H-imidazol-5-yl]furo[3,2-c]pyridine

The title compound was prepared by-the process described in Example 15 but using 3-iodopyridin-4(1H)-one (SPECS chemical company) in place of 4-hydroxy-5-iodopyrimidine. White solid (1:15 mg, 58%);
MS m/e MH$^+$ 382.

EXAMPLE 23

2-(4-Phenyl-1H-imidazol-5-yl)[1,3]thiazolo[5,4-d]pyrimidin-7-amine

Phosphorous pentasulfide (175 mg) was added to N-(4-amino-6-hydroxypyrimidin-5-yl)-4-phenyl-1-{[2-(trimethylsilyl)ethoxy]methyl}-1H-imidazole-5-carboxamide and N-(4-amino-6-hydroxypyrimidin-5-yl)-5-phenyl-1-{[2-(trimethylsilyl)ethoxy]methyl}-1H-imidazole-4-carboxamide (Intermediate 34) (0.11 g) suspended in anhydrous pyridine (0.41 mL) under an inert atmosphere then heated at 110° C.

for 24 hours. The solvent was evaporated, the residue triturated with water (10 mL), and the precipitate isolated by filtration. Purification by RPHPLC chromatography (water: MeCN, 95:5 to 30:70, over 12 minutes), gave the title compound as a yellow gum (22 mg, 30%);

$^1$H NMR (DMSO-$d_6$) δ 7.4-7.48 (m, 2H), 7.52-7.58 (m, 2H), 8.0 (s, 1H), 8.08-8.12 (d, 2H), 8.32 (s, 1H); MS m/e MH$^+$ 295.

The starting material was prepared as follows.

Intermediate 32

Ethel 4-Phenyl-1-{[2-(trimethylsilyl)ethoxy]methyl}-1H-imidazole-5-carboxylate and ethyl 5-phenyl-1-{[2-(trimethylsilyl)ethoxyl]methyl}-1H-imidazole-4-carboxylate A solution of ethyl-4-phenyl-1H-imidazole-5-carboxylate (*J. Chem Soc.* 1925, 127, 576) (1 g) in THF (5 mL) was added to sodium hydride (60%) (0.20 g) in TBF (5 mL) at 0° C. 2-(Trimethylsilyl)ethoxymethyl chloride (0.90 mL) was added and the reaction was stirred for 2 hours before adding water (10 mL) and extracting with EtOAc (3×20 mL). The organic extracts were dried and the solvent removed in vacuo to give a 2:1 mixture of the title compounds, as a colourless gum (1.52 g, 95%);

MS m/e MH$^+$ 347

Intermediate 33

4-Phenyl-1-{[2-(trimethylsilyl)ethoxy]methyl}-1H-imidazole-5-carboxylic acid and 5-Phenyl-1-{[2-(trimethylsilyl)ethoxy]methyl}-1H-imidazole-4-carboxylic acid A solution of 2M NaOH (3.62 mL) and a few drops of MeOH were added to a 2:1 mixture of ethyl 4-phenyl-1-{[2-(trimethylsilyl)ethoxy]methyl}-1H-imidazole-5-carboxylate and ethyl 5-phenyl-1-{[2-(trimethylsilyl)ethoxy]methyl}-1H-imidazole-4-carboxylate (Intermediate 32) (1.0 g) in THF (7 mL) and the reaction heated at reflux for 48 hours. THF was evaporated in vacuo, water (25 mL) added and extracted into EtOAc (20 mL). The aqueous layer was acidified to pH 4 with AcOH and a white precipitate filtered and dried to give a 2:1 mixture of the title compounds as a white solid, (0.52 g, 56%);

MS m/e MH$^+$ 319

Intermediate 34

N-(4-Amino-6-hydroxypyrimidin-5-yl)-4-phenyl-1-{[2-(trimethylsilyl)ethoxy]methyl}-1H-imidazole-5-carboxamide and N-(4-amino-6-hydroxypyrimidin-5-yl)-5-phenyl-1-{[2-(trimethylsilyl)ethoxy]methyl}-1H-imidazole-4-carboxamide 4,5-Diamino-6-hydroxy-pyrimidine (119 mg) was added to a mixture of 4-phenyl-1-{[2-(trimethylsilyl)ethoxy]methyl}-1H-imidazole-5-carboxylic acid and 5-phenyl-1-{[2-(trimethylsilyl)ethoxy]methyl}-1H-imidazole-4-carboxylic acid (Intermediate 33) (0.20 g) in anhydrous DMF (4 mL). DMTMM (0.26 g) was added and the resulting solution heated at 50° C. for 24 hours. The reaction mixture was poured into water (15 mL) and stirred for 15 minutes until precipitation was complete. The solid was filtered off, washed with water and dried at 60° C. in vacuo to give the title compound as a pale yellow solid (111 mg, 41 %);

$^1$H NMR (DMSO-$d_6$) δ 0.81-0.86 (m, 2H), 3.41-3.48 (m, 2H), 5.27 (s, 2H), 6.36 (bs, 2H), 7.48-7.5 (m, 3H), 7.56-7.58 (m, 2H), 7.82 (s, 1H), 8.15 (s, 1H), 8.89 (s, 1H), 11.93 (bs, 1H). MS m/e MH$^+$ 427.

EXAMPLE 24

2-(4-Phenyl-1H-imidazol-5-yl)[1,3]thiazolo[5,4-d]pyrimidine

Phosphorous pentasulfide (109 mg) was added to a suspension of N-(4-hydroxypyrimidin-5-yl)-4-phenyl-1-{[2-(trimethylsilyl)ethoxy]methyl}-1H-imidazole-5-carboxamide and N-(4-hydroxypyrimidin-5-yl)-5-phenyl-1-{[2-(trimethylsilyl)ethoxy]-methyl}-1H-imidazole-4-carboxamide (Intermediate 35) (65 mg) in anhydrous pyridine (0.26 mL) and heated at 110° C. under an inert atmosphere for 24 hours. The solvent was evaporated and the residue purified by RPHPLC chromatography (water:MeCN, 95:5 to 30:70, over 12 minutes) to give the title compound as a yellow gum (9 mg, 20%);

$^1$H NMR (DMSO-$d_6$) δ 7.42-7.48 (m, 1H), 7.5-7.58 (m, 21), 7.9-8.4 (m, 2H), 9.05 (s, 1H), 9.1-9.15 (d, 1H), 9.23 (s, 1H); MS m/e MH$^+$ 280.

The starting material was prepared as follows.

Intermediate 35

N-(4-Hydroxypyrimidin-5-yl)-4-phenyl-1-{[2-(trimethylsilyl)ethoxy]methyl}-1H-imidazole-5-carboxamide and N-(4-hydroxypyrimidin-5-yl)-5-phenyl-1-{[2-(trimethylsilyl)ethoxy]methyl}-1H-imidazole-4-carboxamide 5-Aminopyrimidin-4-ol (*Collect. Czech. Chem. Commun.*; EN, 1986, 551, 1, 215-233) (105 mg) and DMTMM (0.26 g) were added to a mixture of 4-phenyl-1-{[2-(trimethylsilyl) ethoxy]methyl})-1H-imidazole-5-carboxylic acid and 5-phenyl-1-{[2-(trimethylsilyl)ethoxy]methyl}-1H-imidazole-4-carboxylic acid (Intermediate 33) (0.20 g) in anhydrous DMF (4 mL). The resulting mixture was heated at 50° C. for 24 hours. The reaction mixture was poured into water (15 mL) and stirred for 15 minutes until precipitation was complete. The solid was filtered off, washed with water and dried at 60° C. in vacuo to give the title compound as a yellow solid (65 mg, 25%);

MS m/e MH$^+$ 412.

EXAMPLE 25

8-(4-Phenyl-1H-imidazol-5-yl)-9H-purin-6-amine $P_2O_5$ (0.29 g) and $H_3PO_4$ (0.21 mL) were added to a mixture of N-(4,6-diaminopyrimidin-5-yl)-4-phenyl-1-{[2- trimethylsilyl)ethoxy]methyl}-1H-imidazole-5-carboxamide and N-(4,6-diaminopyrimidin-5-yl)-5-phenyl-1-{[2-(trimethylsilyl)ethoxy]methyl}-1H-imidazole-4-carboxamide (Intermediate 36) (65 mg) and heated at 160° C. for 24 hours. After cooling to ambient temperature, ice was added and the reaction mixture adjusted to pH 5 with NH$_3$ solution. The solvent was evaporated in vacuo to give a yellow oil. Purification by preparative RPHPLC (MeCN:water:TFA, 90:10: 0.1) gave the title compound as a colourless solid (2.6 mg, 6%);

$^1$H NMR (DMSO-$d_6$) δ 7.15 (d, 1H), 7.45 (m, 3H), 7.98 (m, 2H), 8.10 (s, 1H), 8.45 (s, 1H), 3.10 (bs, 2H); MS m/e MH$^+$ 278.

The starting materials used were prepared as follows:

Intermediate 36

N-(4,6-Diaminopyrimidin-5-yl)-4-phenyl-1-{[2-(trimethylsilyl)ethoxy]methyl}-1H-imidazole-5-carboxamide and N-(4,6-diaminopyrimidin-5-yl)-5-phenyl-1-{[2-(trimethylsilyl)ethoxy]methyl}-1H-imidazole-4-carboxamide DIPEA (0.09 mL) was added to a mixture of 4-phenyl-1-{[2-(trimethylsilyl)ethoxy]methyl}-1H-imidazole-5-carboxylic acid and 5-phenyl-1-{[3-(trimethylsilyl)propoxy]methyl}-1H-imidazole-4-carboxylic acid (Intermediate 33) (40 mg), 4,5,6-triaminopyrimidine sulfate hydrate (42 mg) and HATU (114 mg) in DMF (1 mL). The resulting mixture was stirred at ambient temperature for 24 hours. The reaction mixture was poured into water (5 mL) and extracted with EtOAc (3×10 mL), washed with brine (10 mL), dried and the solvent evaporated in vacuo to give a yellow oil. Purification by flash chromatography on silica eluting with DCM:MeOH (99:1) gave a 2:1 mixture of the title compounds as a yellow solid (53 mg, 99%);

MS m/e MH$^+$ 426.

EXAMPLE 26

2-(2-Bromo-1-methyl-4-phenyl-1H-imidazol-5-yl)[1,3]thiazolo[5,4-d]pyrimidin-7-amine The title compound was prepared by a similar process to that described for Example 8 but using 2-(2-bromo-1-methyl-4-phenyl-1H-imidazol-5-yl)-7-(methylsulfonyl)[1,3]thiazolo-[5,4-d]pyrimidine (Intermediate 38) in place of 6-(1-Methyl-4-phenyl-1H-imidazol-5-yl)-4-(methylsulfonyl)thieno[2,3-d]pyrimidine (Intermediate 17). Yellow solid (52 mg, 61%);

$^1$H NMR (CDCl$_3$) δ 3.95 (s, 3H), 5.71 (bs, 2H), 7.37 (m, 3H), 7.50 (m, 2H), 8.43 (s, 1H). MS m/e MH$^+$ 387, 389.

The starting materials used were prepared as follows:

Intermediate 37

2-(2-Bromo-1-methyl-4-phenyl-1H-imidazol-5-yl)-7-(methylthio)[1,3]thiazolo[5,4-d]pyrimidine A mixture of 2-(1-methyl-4-phenyl-1H-imidazol-5-yl)-7-(methylthio)[1,3]thiazolo-[5,4-d]pyrimidine (Intermediate 42) (0.25 g), N-bromosuccinimide (0.26 g) and AIBN (37 mg) in carbon tetrachloride (30 mL) was heated at 70° C. for 18 hours The suspension was filtered and the residue washed well with CCl$_4$. The solvent was evaporated in vacuo to give a yellow solid. Purification by flash chromatography on silica eluting with EtOAC:hexane (1:9) gave the title compound as a white solid (0.12 g, 39%);

$^1$H NMR (CDCl$_3$) δ 2.71 (s, 3H), 4.08 (s, 3H), 7.42 (m, 3H), 7.51 (m, 2H), 8.77 (s, 1H). MS m/e MH$^+$ 418, 420.

Intermediate 38

2-(2-Bromo-1-methyl-4-phenyl-1H-imidazol-5-yl)-7-(methylsulfonyl)[1,3]thiazolo[5,4-d]pyrimidine The title compound was prepared by a similar process to that described for Intermediate 17 but using 2-(2-bromo-1-methyl-4-phenyl-1H-imidazol-5-yl)-7-(methylthio)[1,3]thiazolo[5,4-d]pyrimidine (Intermediate 37) in place of 6-(1-methyl-4-phenyl-1H-imidazol-5-yl)-4-(methylthio)thieno[2,3-d]pyrimidine (example 7). Yellow oil (0.1 g, 93%);

MS m/e MH$^+$ 450, 452.

EXAMPLE 27

2-(2-Amino-1-methyl-4-phenyl-1H-imidazol-5-yl)[1,3]thiazolo[5,4-d]pyrimidin-7-amine A solution of 2-(2-bromo-1-methyl-4-phenyl-1H-imidazol-5-yl)-7-(methylthio)[1,3]-thiazolo[5,4-d]pyrimidine (Intermediate 37) (24 mg) in concentrated aqueous NH$_3$ (1 mL), 1,4-dioxane (1 mL) and aqueous ammonium chloride (2 drops) was heated under microwave conditions (CEM explorer, 170° C., 90 minutes hold). The solvent was evaporated in vacuo to give a yellow solid. Purification by flash chromatography on silica eluting with DCM:MeOH (9:1) gave the title compound as a yellow solid (2 mg, 9%);

$^1$H NMR (CDCl$_3$) δ 3.83 (s, 3H), 4.60 (bs, 2H), 5.65 (s, 2H), 7.40 (m, 3H), 7.51 (m, 2H), 8.38 (s, 1H); MS m/e MH$^+$ 324.

EXAMPLE 28

2-(2-Methoxy-1-methyl-4-phenyl-1H-imidazol-5-yl)[1,3]thiazolo[5,4-d]pyrimidin-7-amine Sodium methoxide (31 mg) was added to a solution of 2-(2-bromo-1-methyl-4-phenyl-1H-imidazol-5-yl)[1,3]thiazolo[5,4-d]pyrimidin-7-amine (Example 26) (22 mg) in MeOH (1 mL). The reaction was stirred and refluxed for 4 days with further sodium methoxide (31 mg) added each day. The solvent was evaporated in vacuo and water (5 mL) added. Extracted with DCM (2×5 mL) and the combined organics were dried over MgSO$_4$, filtered and the solvent evaporated in vacuo to give a white solid (15 mg, 78%);

$^1$H NMR (CDCl$_3$) δ 3.79 (s, 3H), 4.18 (s, 3H), 7.40 (m, 3H), 7.53 (m, 2H), 8.38 (s, 1H). MS m/e MH$^+$ 339.

EXAMPLE 29

2-(1-Methyl-2,4-diphenyl-1H-imidazol-5-yl)[1,3]thiazolo[5,4-d]pyrimidin-7-amine

The title compound was prepared by a similar process to that described for Example 8 but using 2-(1-Methyl-2,4-diphenyl-1H-imidazol-5-yl)-7-(methylsulfonyl)[1,3]thiazolo[5,4-d]pyrimidine (Intermediate 40) in place of 6-(1-Methyl-4-phenyl-1H-imidazol-5-yl)-4-(methylsulfonyl)thieno[2,3-d]pyrimidine (intermediate 17). Yellow solid (21 mg, 91%);

$^1$H NMR (CDCl$_3$) δ 3.98 (s, 3H), 5.77 (bs, 2H), 7.39 (m, 3H), 7.52 (m, 3H), 7.60 (m, 2H), 7.77 (m, 2H), 8.42 (s, 1H). MS m/e MH$^+$ 385.

The starting materials used were prepared as follows:

Intermediate 39

2-(1-Methyl-2,4-diphenyl-1H-imidazol-5-yl)-7-(methylthio)[1,3]thiazolo[5,4-d]pyrimidine A mixture of 2-(2-bromo-1-methyl-4-phenyl-1H-imidazol-5-yl)-7-(methylthio)-[1,3]thiazolo[5,4-d]pyrimidine (Intermediate 37) (50 mg), tetrakis(triphenylphosphino)palladium(0) (28 mg), sodium carbonate (33 mg) and phenylboronic acid (14 mg) in DME (2 mL) and water (1 mL) was heated at 90° C. for 2 hours. After cooling to ambient temperature and extraction into DCM (3×5 mL), the combined organics were dried, filtered and the solvent evaporated in vacuo to give a brown oil. Purification by flash chromatography on silica eluting with EtOAC:hexane (1:9) gave the title compound as a yellow solid (25 mg, 50%);

$^1$H NMR (CDCl$_3$) δ 2.71 (s, 3H), 4.10 (s, 3H), 7.43 (m, 3H), 7.50 (m, 3H), 7.60 (m, 2H), 7.75 (m, 2H), 8.77 (s, 1H). MS m/e MH$^+$ 416.

Intermediate 40

2-(1-Methyl-2,4-diphenyl-1H-imidazol-5-yl)-7-(methylsulfonyl)[1,3]thiazolo[5,4-d]pyrimidine The title compound was prepared by a similar process to that described for Intermediate 17 but using 2-(1-methyl-2,4-diphenyl-1H-imidazol-5-yl)-7-(methylthio)[1,3]thiazolo[5,4-d]pyrimidine (Intermediate 39) in place of 6-(1-methyl-4-phenyl-1H-imidazol-5-yl)-4-(methylthio)thieno[2,3-d]pyrimidine (example 7). Yellow solid (26 mg, 97%);

MS m/e MH$^+$ 448.

EXAMPLE 30

9-Cyclohexyl-8-(1-methyl-4-phenyl-1H-imidazol-5-yl)-9H-purin-6-amine

Diisopropyl azodicarboxylate (0.1 mL) was added to a solution of 8-(1-methyl-4-phenyl-1H-imidazol-5-yl)-9H-purin-6-amine (Example 3) (75 mg), cyclohexanol (0.07 mL) and triphenylphosphine (0.14 g) in THF (4 mL) under an inert atmosphere. After stirring at ambient temperature for 48 hours the reaction mixture was heated at 40° C. for 48 hours and then at 55° C. for 24 hours. The solvent was then evaporated in vacuo to give a brown oil. Purification by preparative LCMS gave the title compound as a white solid (11 mg, 11%);

$^1$H NMR (CDCl$_3$) δ 1.25 (m, 4H), 1.50 (m, 2H), 1.64 (m, 2H), 2.26 (m, 2H), 3.62 (s, 3H), 3.77 (m, 1H), 5.82 (bs, 2H), 7.27 (m, 3H), 7.40 (m, 2H), 7.72 (s, 1H), 8.37 (s, 1H). MS m/e MH$^+$ 374.

EXAMPLE 31

2-(1-Methyl-4-phenyl-1H-imidazol-5-yl)[1,3]thiazolo[5,4-d]pyrimidine-7-thiol

5-Aminopyrimidin-4,6-dithiol (Intermediate 41) (1.26 g) and 1-methyl-4-phenyl-1H-imidazole-5-carboxylic acid (Intermediate 3) (1.6 g) were dissolved/ suspended in pyridine (30 mL) and heated at 55° C. under an inert atmosphere. POCl$_3$ (1.55 mL) was added dropwise over 5 minutes, after 2 hours the reaction mixture was concentrated in vacuo and 2M NaOH (15 mL) added cautiously. After stirring for 15 minutes, concentrated HCl was added to acidify to pH 5, the precipitated solid was filtered, washed with water (40 mL), diethyl ether (50 mL) then dried under high vacuum to give the title compound as a yellow solid (1.83 g, 71%);

$^1$H NMR (DMSO-d$_6$) δ 3.93 (s, 3H), 7.35-7.43 (m, 3H), 7.50-7.55 (m, 2H), 8.00 (s, 1H), 8.24 (s, 1H); MS m/e MH$^+$ 326.

The starting material used was prepared as follows:

Intermediate 41

5-Aminopyrimidin-4,6-dithiol

A suspension of dichloroaminopyrimidine (28.9 g) and sodium hydrosulfide monohydrate (52.1 g) in water (700 mL) was heated at reflux under an inert atmosphere. After 3 hours additional sodium hydrosulfide monohydrate (19.5 g) was added, heating continued for 3 hours then cooled to ambient temperature. Concentrated HCl was added to adjust the pH to 6-7, the resulting pale yellow precipitate filtered off then the filtrate was concentrated in vacuo to ~500 mL. The filtrate was cooled (ice bath) and 2M HCl added to adjust the pH to 3, the resulting precipitate was filtered, washed with ice-cold water, dried under high-vacuum at 60° C. to give the title compound as a yellow solid (24 g, 86%);

MS m/e MH$^+$ 160.

EXAMPLE 32

2-(1-Methyl-4-phenyl-1H-imidazol-5-yl)[1,3]thiazolo[5,4-d]pyrimidin-7-one 2-(1-Methyl-4-phenyl-1H-imidazol-5-yl)-7-(methylthio)[1,3]thiazolo[5,4-d]pyrimidine (Intermediate 42) (1.26 g) was dissolved in DCM (60 mL), cooled to 0° C. then mCPBA (2.29 g) added in portions over 10 minutes. The reaction mixture was warmed to ambient temperature over 2 hours, then washed with saturated aqueous NaHCO$_3$ (1×40 mL), brine (1×30 mL), dried (MgSO$_4$), filtered and concentrated in vacuo to give the sulfone as a brown foam. The impure sulfone was dissolved in 1,4-dioxane, concentrated aqueous NH$_3$ (50 mL) added then stirred at ambient temperature for 1 hour. The reaction mixture was concentrated iii vacuo, diluted with saturated NaHCO$_3$ (60 mL), extracted with DCM (2×50 mL). The organic extracts were washed with brine (1×30 mL) and concentrated in vacuo to give a yellow solid. Purification by flash chromatography on silica eluting with 5% MeOH/DCM gave the compound of Example 2 as a colourless solid (0.65 g, 57%) (data reported previously). The aqueous layer was filtered, washed with diethyl ether, dried under high vacuum to give the title compound as a pale yellow solid (0.09 g, 8%);

$^1$H NMR (DMSO-d$_6$) δ 3.84 (s, 3H), 7.31-7.40 (m, 3H), 7.46-7.51 (m, 2H), 7.95 (s, 1H), 8.18 (s, 1H). MS m/e MH$^+$ 310

The starting materials used were prepared as follows:

Intermediate 42

2-(1-Methyl-4-phenyl-1H-imidazol-5-yl)-7-(methylthio)[1,3]thiazolo[5,4-d]pyrimidine 2-(1-Methyl-4-phenyl-1H-imidazol-5-yl)[1,3]thiazolo[5,4-d]pyrimidine-7-thiol (Example 31) (2.91 g) was dissolved in 2M NaOH (50 mL) then methyl iodide (0.67 mL) added under an inert atmosphere at ambient temperature. After 2.5 hours the reaction mixture was filtered, washed with water, dried under high-vacuum to give the title compound as a pale brown solid (2.9 g, 95%);

$^1$H NMR (DMSO-d$_6$) δ 2.66 (s, 3H), 3.96 (s, 3H), 7.39-7.45 (m, 3H), 7.51-7.56 (m, 2H), 8.05 s, 1H), 8.84 (s, 1H).

EXAMPLE 33

7-Methoxy-2-(1-methyl-4-phenyl-1H-imidazol-5-yl)[1,3]thiazolo[5,4-d]pyrimidine 2-(1-Methyl-4-phenyl-1H-imidazol-5-yl)-7-(methylthio)[1,3]thiazolo[5,4-d]pyrimidine (Intermediate 42) (2.88 g) was dissolved in DCM (120 mL), cooled to 0° C. then mCPBA (5.23 g) added in portions over 15 minutes. The reaction mixture was warmed to ambient temperature over 4 hours, then washed with saturated aqueous NaHCO$_3$ (2×60 mL), brine (60 mL), dried (MgSO$_4$), filtered and concentrated in vacuo to give the sulfone as a brown foam. The impure sulfone was dissolved in 7N NH$_3$/MeOH, stirred at ambient temperature overnight then filtered to give the title compound as a colourless solid. The filtrate was concentrated in vacuo, residue dissolved in DCM (150 mL), washed with saturated aqueous NaHCO$_3$ (100 mL), brine (40 mL) then dried (MgSO$_4$) and filtered. The filtrate was concentrated in vacuo, then purified by flash chromatography on silica eluting with.5% MeOH/DCM to give an additional batch of the tide compound (1.40 g in total, 50%);
$^1$H NMR (DMSO-d$_6$) δ 3.91 (s, 3H), 4.14 (s, 3H), 7.37-7.42 (m, 3H), 7.46-7.52 (m, 2H), 8.01 (s, 1H), 8.68 (s, 1H). MS m/e MH$^+$ 324.

EXAMPLE 34

2-[1-Methyl-4-phenyl-2-(3-thienyl)-1H-imidazol-5-yl][1,3]thiazolo[5,4-d]pyrimidin-7-amine 7-Methoxy-2-[1-methyl-4-phenyl-2-(3-thienyl)-1H-imidazol-5-yl][1,3]thiazolo[5,4-d]pyrimidine (Intermediate 44) (26 mg) was dissolved in 0.5M NH$_3$ in 1,4-dioxane (3 mL)/concentrated aqueous NH$_3$ (0.6 mL), sealed and heated under microwave conditions (CEM explorer, 150° C., 150 W) for 1 hour. After which the reaction mixture was concentrated in vacuo, dissolved in EtOAc (20 mL), washed: with 2M NaOH (2×10 mL) then brine (1×15 mL), dried (MgSO$_4$), filtered and concentrated in vacuo. Purification by flash chromatography on silica eluting with 4% MeOH/DCM gave the title compound as an off-white solid (17 mg, 68%);
$^1$H NMR (DMSO-d$_6$) δ 4.00 (s, 3H), 7.34-7.44 (m, 3H), 7.53-7.59 (m, 2H), 7.62 (m, 1H), 7.75 (m, 1H), 7.77 (bs, 2H), 8.01 (s, 1H), 8.68 (s, 1H). MS m/e MH$^+$ 391

The starting material used was prepared as follows:

Intermediate 43

2-(2-Bromo-1-methyl-4-phenyl-1H-imidazol-5-yl)-7-methoxy[1,3]thiazolo[5,4-d]pyrimidine The title compound was prepared by a similar process to that described for Intermediate 37 but using 7-Methoxy-2-(1-methyl-4-phenyl-1H-imidazol-5-yl)[1,3]thiazolo[5,4-d]pyrimidine (Example 33) in place of 2-(1-methyl-4-phenyl-1H-imidazol-5-yl)-7-(methylthio)[1,3]thiazolo[5,4-d]pyrimidine (Intermediate 42). Light brown solid (0.47 g, 45%);
$^1$H NMR (DMSO-d$_6$) δ 3.87 (s, 3H), 4.15 (s, 3H), 7.37-7.42 (m, 3H), 7.45-7.50 (m, 2H), 8.72 (s, 1H); MS m/e MH$^+$ 402, 404.

Intermediate 44

7-Methoxy-2-[1-methyl-4-phenyl-2-(3-thienyl)-1H-imidazol-5-yl][1,3]thiazolo[5,4-d]pyrimidine 2-(2-Bromo-1-methyl-4-phenyl-1H-imidazol-5-yl)-7-methoxy[1,3]thiazolo[5,4-d]pyrimidine (Intermediate 43) (50 mg), [1,1'-Bis(diphenylphosphino)ferrocene]dichloropalladium(II) (14 mg), thiophene-3-boronic acid (17 mg) and 2M potassium carbonate (0.25 mL) were heated in toluene (5 mL)/MeOH (1 mL) at 100° C. under an inert atmosphere. After 90 minutes the reaction mixture was cooled to ambient temperature, MgSO$_4$ added, filtered and concentrated in vacuo. Purification by flash chromatography on silica eluting with 35% EtOAc/iso-hexane gave the title compound as a colourless solid (40 mg, 82%);
$^1$H NMR (DMSO-d$_6$) δ 4.01 (s, 3H), 4.16 (s, 3H), 7.38-7.43 (m, 3H), 7.50-7.55 (m, 2H), 7.61 (m, 1H), 7.74 (m, 1H), 8.10 (s, 1H), 8.71 (s, 1H); MS m/e MH$^+$ 406.

EXAMPLE 35

2-(1-Methyl-4-phenyl-2-pyridin-4-yl-1H-imidazol-5-yl)[1,3]thiazolo[5,4-d]pyrimidin-7-amine 2-(2-Bromo-1-methyl-4-phenyl-1H-imidazol-5-yl)[1,3]thiazolo[5,4-d]pyrimidin-7-amine (Example 26) (20 mg), PdCl$_2$dppf (8 mg), pyridine-4-boronic acid (8 mg) and 2M sodium carbonate (2.0 mL) were heated in DMF (2.0 mL) at 100° C. under an inert atmosphere. After 3 hours the reaction mixture was cooled to ambient temperature, EtOAc (25 mL) added then washed with water (15 mL), brine (2×10 mL), dried (MgSO$_4$), filtered and concentrated in vacuo. Purification by flash chromatography on silica eluting with 6% MeOH/DCM gave a dark brown solid which was washed with diethyl ether then dried under high vacuum to give the title compound as light brown solid (6 mg, 31%);
$^1$H NMR (CDCl$_3$) δ 4.06 (s, 3H), 5.78 (bs, 2H), 7.35-7.42 (m, 3H), 7.54-7.59 (m, 3H), 7.74 (m, 2H), 8.45 (s, 1H), 8.82 (m, 1H); MS m/e MH$^+$ 386

EXAMPLE 36

2-(2-Ethyl-1-methyl-4-phenyl-1H-imidazol-5-yl)[1,3]thiazolo[5,4-d]pyrimidin-7-amine 10% Palladium on carbon (6 mg) was added to a solution of 2-(2-ethynyl-1-methyl-4-phenyl-1H-imidazol-5-yl)[1,3]thiazolo[5,4-d]pyrimidin-7-amine (Intermediate 46) (6 mg) in EtOAc (20 mL) under an inert atmosphere. The reaction mixture was then stirred under a hydrogen atmosphere for 11 hours, filtered and concentrated in vacuo. The impure product was triturated with diethyl ether and filtered to give the title compound as a colourless solid (2 mg, 30%);
MS m/e MH$^+$ 337

The starting material used was prepared as follows:

Intermediate 45

2-{1-Methyl-4-phenyl-2-[(trimethylsilyl)ethynyl]-1H-imidazol-5-yl}[1,3]thiazolo[5,4-d]pyrimidin-7-amine 2-(2-Bromo-1-methyl-4-phenyl-1H-imidazol-5-yl)[1,3]thiazolo[5,4-d]pyrimidin-7-amine (Example 26) (52 mg), PdCl$_2$dppf (10 mg), copper(I) iodide (2 mg), trimethylsilyl acetylene (0.11 mL) and triethylamine (0.2 mL) were heated in DMF (4 mL) at 80° C. for 1 hour under an inert atmosphere. The reaction mixture was concentrated in vacuo, EtOAc (20 mL)/MeOH (0.3 mL)/water (10 mL) added and the aqueous layer removed. The organic layer was dried (MgSO$_4$), filtered, concentrated in vacuo, then purification by flash chromatography on silica eluting with 4% MeOH/DCM gave the title compound as a light brown solid (48 mg, 100%);
$^1$H NMR (DMSO-d$_6$) δ 0.30 (s, 9H), 3.96 (s, 3H), 7.37-7.42 (m, 3H), 7.48-7.52 (m, 2H), 7.78 (bs, 2H), 8.27 (s, 1H); MS m/e MH$^+$ 405

Intermediate 46

2-(2-Ethynyl-1-methyl-4-phenyl-1H-imidazol-5-yl)[1,3]thiazolo[5,4-d]pyrimidin-7-amine 2-{1-Methyl-4-phenyl-2-[(trimethylsilyl)ethynyl]-1H-imidazol-5-yl}[1,3]thiazolo[5,4-d]pyrimidin-7-amine (Intermediate 45) (48 mg) was dissolved/suspended in MeOH (3 mL)/water (1 mL) and potassium carbonate (50 mg) added, then stirred for 90 minutes at ambient temperature. The reaction mixture was neutralised with 2M HCl, concentrated in vacuo, the residue diluted with water (10 mL) and extracted with DCM (3×10 mL). The organic extracts were dried (MgSO$_4$), filtered, concentrated in vacuo then purified by flash chromatography on silica eluting with 4% MeOH/DCM to give the title compound as a yellow solid (10 mg, 25%);
$^1$H NMR (DMSO-d$_6$) δ 3.99 (s, 3H), 4.89 (s, 1H), 7.37-7.45 (m, 3H), 7.49-7.54 (m, 2H), 7.79 (bs, 2H), 8.30 (s, 1H). MS m/e MH$^+$ 333.

EXAMPLE 37

2-[1-Methyl-4-phenyl-2-(propylthio)-1H-imidazol-5-yl][1,3]thiazolo[5,4-d]pyrimidin-7-amine 5-(7-Amino[1,3]thiazolo[5,4-d]pyrimidin-2-yl)-1-methyl-4-phenyl-1H-imidazole-2-thiol (Intermediate 47) (10 mg) was dissolved in 2M NaOH (0.5 mL), n-propyl iodide (2 drops) added then heated at 60° C. for 5 hours. The reaction mixture was cooled to ambient temperature, the solid precipitate filtered, washed with water (2 mL) and diethyl ether (2 mL) then dried under high vacuum to give the title compound as a colourless solid (5 mg, 43%);
MS m/e MH$^+$ 383.

The starting material used was prepared as follows:

Intermediate 47

5-(7-Amino[1,3]thiazolo[5,4-d]pyrimidin-2-yl)-1-methyl-4-phenyl-1H-imidazole-2-thiol 2-(2-Bromo-1-methyl-4-phenyl-1H-imidazol-5-yl)[1,3]thiazolo[5,4-d]pyrimidin-7-amine (Example 26) (80 mg) and sodium thiomethoxide (58 mg) in DMF (5 mL) were heated at 80° C. for 2 hours under an inert atmosphere. After cooling to ambient temperature the reaction mixture was concentrated in vacuo, then dissolved in 2M NaOH (5 mL) and washed with DCM (5 mL). The aqueous layer was acidified to pH 4 with 2M HCl, the solid precipitate washed with water (5 mL) then diethyl ether (10 mL) and dried under high vacuum to give the title compound as a yellow solid (44 mg, 65%);
$^1$H NMR (DMSO-d$_6$) δ 3.86 (s, 3H), 7.46-7.54 (m, 5H), 7.76 (bs, 2H), 8.26 (s, 1H), 13.15 (bs, 1H). MS m/e MH$^+$ 341.

EXAMPLE 38

2-{2-[(Methoxyethyl)thio]-1-methyl-4-phenyl-1H-imidazol-5-yl}[1,3]thiazolo-[5,4-d]pyrimidin-7-amine Using a similar procedure to that described above for Example 37, except exchanging n-propyl iodide for 2-bromo-ethyl methyl ether, gave the title compound as a colourless solid (8 mg, 40%);
$^1$H NMR (DMSO-d$_6$) δ 3.28 (s, 3H), 3.42 (t, 2H), 3.66 (t, 2H), 3.86 (s, 3H), 7.37-7.42 (m, 3H), 7.48-7.55 (m, 2H), 7.74 (bs, 2H), 8.25 (s, 1H). MS m/e MH$^+$ 399.

EXAMPLE 39

[5-(7-Amino[1,3]thiazolo[5,4-d]pyrimidin-2-yl)-1-methyl-4-phenyl-1H-imidazol-2-yl](5-methylisoxazol-3-yl)methanone 2-(1-Methyl-4-phenyl-1H-imidazol-5-yl)[1,3]thiazolo[5,4-d]pyrimidin-7-amine (Example 2). (50 mg) and 5-methyl-isoxazole-3-carbonyl chloride (140 mg) were stirred in MeCN (4 mL) for 15 minutes then triethylamine (0.14 mL) added and stirred at ambient temperature for 3.5 days under an inert atmosphere. The reaction mixture was concentrated in vacuo, 7N NH$_3$ in MeOH (5 mL)/concentrated aqueous NH$_3$ (5 mL) added then heated at 55° C. for 2.5 hours. The reaction mixture was concentrated in vacuo and purified on RPHPLC to give the title compound as a pale yellow solid (12 mg, 18%);
$^1$H NMR (DMSO-d$_6$) δ 2.56 (s, 3H), 4.19 (s, 3H), 7.01 (s, 1H), 7.40-7.45 (m, 3H), 7.63-7.68 (m, 2H), 8.01 (bs, 2H), 8.37 (s, 1H); MS m/e MH$^+$ 418.

EXAMPLE 40

[5-(7-Amino[1,3]thiazolo[5,4-d]pyrimidin-2-yl)-1-methyl-4-phenyl-1H-imidazol-2-yl](5-methylisoxazol-3-yl)methanol

[5-(7-Amino[1,3]thiazolo[5,4-d]pyrimidin-2-yl)-1-methyl-4-phenyl-1H-imidazol-2-yl](5-methylisoxazol-3-yl)methanone (Example 39) (6 mg) was dissolved in MeOH (2 mL), sodium borohydride (3 mg) added then stirred for 1 hour. Water (1 mL) was added, stirring continued for 20 minutes then concentrated in vacuo. The residue was diluted with water (5 mL), extracted with DCM (2×6 mL), organic extracts dried (MgSO$_4$), filtered and concentrated in vacuo to give the title compound as a pale yellow solid (3.6 mg, 60%); MS m/e MH$^+$ 420.

EXAMPLE 41

[5-(7-Amino[1,3]thiazolo[5,4-d]pyrimidin-2-yl)-1-methyl-4-phenyl-1H-imidazol-2-yl](2-furyl)methanone Using a similar procedure to that described for Example 39 above, except exchanging 5-methyl-isoxazole-3-carbonyl chloride for furan-2-carbonyl chloride gave the title compound as a pale yellow solid (5 mg, 8%);
$^1$H NMR (DMSO-d$_6$) δ 4.15 (s, 3H), 6.86 (m, 1H), 7.38-7.47 (m, 3H), 7.57-7.63 (m, 2H), 7.96 (bs, 2H), 8.15 (d, 1H), 8.19 (m, 1H), 8.36 (s, 1H). MS m/e MH$^+$ 403.

EXAMPLE 42

[5-(7-Amino[1,3]thiazolo[5,4-d]pyrimidin-2-yl)-1-methyl-4-phenyl-1H-imidazol-2-yl](2-furyl)methanol Using a similar ketone reduction procedure to that described for. Example 40 above, but using the compound of Example 41 gave the title compound as a pale yellow solid (3.4 mg, 68%);
MS m/e MH$^+$ 405.

EXAMPLE 43

[5-(7-Amino[1,3]thiazolo[5,4-d]pyrimidin-2-yl)-1-methyl-4-phenyl-1H-imidazol-2-yl](1,3-dimethyl-1H-pyrazol-5-yl)methanone Using a similar procedure to that described for Example 39 above, except substituting 5-methyl-isoxazole-3-carbonyl chloride for 1,3-dimethyl-1H-pyrazole-5-carbonyl chloride gave the title compound as a pale yellow solid (21 mg, 31%);
$^1$H NMR (DMSO-d$_6$) δ 2.27 (s, 3H), 4.11 (s, 3H), 4.14 (s, 3H), 7.38 (s, 1H), 7.40-7.47 (m, 3H), 7.56-7.61 (m, 2H), 7.98 (bs, 2H), 8.36 (s, 1H); MS m/e MH$^+$ 431.

EXAMPLE 44

[5-(7-Amino[1,3]thiazolo[5,4-d]pyrimidin-2-yl)-1-methyl-4-phenyl-1H-imidazol-2-yl](1,3-dimethyl-1H-pyrazol-5-yl)methanol Using a similar ketone reduction procedure described for Example 40 above, but using the compound of Example 43 above gave the title compound as a pale yellow solid (10 mg, 65%);
MS m/e MH$^+$ 433.

EXAMPLE 45

6-[1-(2-Fluoroethyl)-4-phenyl-1H-imidazol-5-yl]thieno[2,3-d]pyrimidin-4-amine

The title compound was prepared using the general method of Example 65 but replacing 3-aminopyrrolidine with 2-fluoroethylamine. Colourless solid (30 mg, 44%);
$^1$H NMR (DMSO-d6) 4.35 (dt, 2H), 4.67 (dt, 2H), 7.30 (t, 1H), 7.36 (t, 2H), 7.51 (d, 2H), 7.77 (s, 1H), 7.86 (bs, 2H), 8.38 (s, 1H), 8.56 (s, 1H); MS m/e MH$^+$ 340.

EXAMPLE 46

[5-(7-Amino[1,3]thiazolo[5,4-d]pyrimidin-2-yl)-1-methyl-4-phenyl-1H-imidazol-2-yl](2-thienyl)methanol Using a similar ketone reduction procedure described for Example 40 above, but using [5-(7-amino[1,3]thiazolo[5,4-d]pyrimidin-2-yl)-1-methyl-4-phenyl-1H-imidazol-2-yl](2-thienyl)methanone (Intermediate 48) gave the title compound as a colourless solid (9 mg, 89%);
$^1$H NMR (DMSO-d$_6$) δ 3.79 (s, 3H), 6.25 (d, 1H), 6.75 (d, 1H (exchangeable)), 6.95 (m, 1H), 7.01 (m, 1H), 7.30-7.39 (m, 3H), 7.45-7.50 (m, 3H), 7.77 (bs, 2H), 8.26 (s, 1H); MS m/e MH$^+$ 421.

The starting material used was prepared as follows:

Intermediate 48

[5-(7-Amino[1,3]thiazolo[5,4-d]pyrimidin-2-yl)-1-methyl-4-phenyl-1H-imidazol-2-yl](2-thienyl)methanone Using a similar procedure described for Example 39 above, except substituting 5-methyl-isoxazole-3-carbonyl chloride for 2-thiophene carbonyl chloride gave the title compound as a pale yellow solid (19 mg, 66%);
$^1$H NMR (DMSO-d$_6$) δ 4.12 (s, 3H), 7.32 (dd, 1H), 7.37-7.45 (m, 3H), 7.55-7.62 (m, 2H), 7.92 (bs, 2H), 8.13 (d, 1H), 8.34 (s, 1H), 8.47 (m, 1H); MS m/e MH$^+$ 419.

EXAMPLE 47

6-[4-(4-Fluorophenyl)-1-methyl-1H-imidazol-5-yl]thieno[2,3-d]pyrimidin-4-amine

The title compound was prepared by a similar process to that described for Example 8 but using 6-[4-(4-Fluorophenyl)-1-methyl-1H-imidazol-5-yl]-4-(methylsulfonyl)thieno[2,3-d]pyrimidine (Intermediate 50) in place of 6-(1-Methyl-4-phenyl-1H-imidazol-5-yl)-4-(methylsulfonyl)thieno[2,3-d]pyrimidine (intermediate 17). White solid (53 mg, 75%);
$^1$H NMR. (CDCl$_3$) δ 3.61 (s, 3H), 5.43 (br s, 2H), 6.93-7.00 (m, 2H), 7.09(s, 1H), 7.52-7.59 (m, 2H), 7.63 (s, 1H), 8.54 (s, 1H); MS m/e MH$^+$ 326.

The starting materials used were prepared as follows:

Intermediate 49

6-[4-(4-Fluorophenyl)-1-methyl-1H-imidazol-5-yl]-4-(methylthio)thieno[2,3-d]pyrimidine The title compound was prepared by a similar process to that described for Example 6 but using N-[4-(methylthio)thieno[2,3-d]pyrimidin-6-ylmethylidene]methanamine (Intermediate 16) in place of N-(3,4-Dimethoxybenzyl)-N-[thieno[2,3-d]pyrimidin-6-ylmethylidene]amine (intermediate 14) and using 4-fluorophenyl-tolylsulfonomethyl isocyanide in place of PhTosMIC. Pale yellow solid (105 mg, 67%);
$^1$H NMR (CDCl$_3$) δ 2.74 (s, 3H), 3.65 (s, 3H), 6.94-7.00 (m, 2H), 7.31 (s, 1H), 7.53-7.57 (m, 2H), 7.65 (s, 1H), 8.87 (s, 1H); MS m/e MH$^+$ 357.

Intermediate 50

6-[4-(4-Fluorophenyl)-1-methyl-1H-imidazol-5-yl]-4-(methylsulfonyl)thieno[2,3-d]pyrimidine The title compound was prepared by a similar process to that described for Intermediate 17 but using 6-[4-(4-fluorophenyl)-1-methyl-1H-imidazol-5-yl]-4-(methylthio)thieno[2,3-d]pyrimidine (Intermediate 49) in place of 6-(1-methyl-4-phenyl-1H-imidazol-5-yl)-4-(methylthio)thieno[2,3-d]pyrimidine (example 7). Yellow solid (80 mg, 73%);
$^1$H NMR (CDCl$_3$) δ 3.45 (s, 3H), 3.73 (s, 3H), 6.96-7.04 (m, 2H), 7.48-7.55 (m, 2H), 7.69 (s, 1H), 8.03 (s, 1H), 9.16 (s, 1H); MS m/e MH$^+$ 389.

EXAMPLE 48

6-(1-Benzyl-4-phenyl-1H-imidazol-5-yl)thieno[2,3-d]pyrimidine

The title compound was prepared by a similar process to that described for Example 6 but using N-benzyl-N-[thieno[2,3-d]pyrimidin-6-ylmethylidene]amine (Intermediate 51) in place of N-(3,4Dimethoxybenzyl)-N-[thieno[2,3-d]pyrimidin-6-ylmethylidene]amine (intermediate 14). Pale yellow solid (26 mg, 26%);
$^1$H NMR (CDCl$_3$) δ 5.13 (s, 2H), 7.00-7.03 (m, 2H), 7.10 (s, 1H), 7.21-7.32 (m, 6H), 7.55-7.58 (m, 2H), 7.75 (s, 1H), 9.03 (s, 1H), 9.10 (s, 1H); MS m/e MH$^+$ 429.

The starting material used was prepared as follows:

Intermediate 51

N-Benzyl-N-[thieno[2,3-d]pyrimidin-6-ylmethylidene]amine

The title compound was prepared by a similar process to that described for Intermediate 14 but using benzylamine in place of 3,4-dimethoxybenzylamine. Pale yellow solid (69 mg, 100%), which was used directly without further purification.

EXAMPLE 49

6-[4-(3-Iodophenyl)-1-methyl-1H-imidazol-5-yl]thieno[2,3-d]pyrimidin-4-amine

The title compound was prepared by a similar process to that described for Example 8 but using 6-[4-(3-Iodophenyl)-1-methyl-1H-imidazol-5-yl]-4-(methylsulfonyl)thieno[2,3-d]pyrimidine (Intermediate 55) in place of 6-(1-methyl-4-phenyl-1H-imidazol-5-yl)-4-(methylsulfonyl)thieno[2,3-d]pyrimidine (intermediate 17). White solid (136 mg, 78%);

¹H NMR (DMSO-d6) δ 3.58 (s, 3H), 7.06 (t, 1H), 7.42 (d, 1H), 7.56 (d, 1H), 7.65 (m, 3H), 7.95 (m, 2H), 8.32 (s, 1H). MS m/e MH⁺ 434.

The starting materials used were prepared as follows:

Intermediate 52

{(3-Iodophenyl)[(4-methylphenyl)sulfonyl]methyl}formamide

Trimethylsilylchloride (9.1 mL) was added to a stirred solution of 3-iodobenzaldehyde (15.1 g) and formamide (6.5 mL) in MeCN (34 mL) and toluene (34 mL) under an inert atmosphere. The reaction was then heated at 50° C. for 5 hours. Toluene sulfinic acid (15.3 g) was added and the reaction mixture was heated at 50° C. for a fisher 5 hours. The reaction mixture was cooled to ambient temperature, methyl t-butylether (55 mL) was added and stirred for 5 minutes. Water (275 mL) was added, the reaction cooled to 0° C. and stirred for 1 hour. The solid was filtered and the reaction flask was washed with MTBE (2×35 mL) and poured over the filtered cake. The solid was dried in a vacuum oven at 60° C. for 10 hours to afford impure title compound as a solid (14 g, 51%) which was used without further purification. A small sample was crystallised from EtOH;

¹H NMR (DMSO-d6) for major (6:1) rotamer δ; 2.43 (s, 3H), 6.42 (d, 1H), 7.15-8.00 (m, 9H), 9.73 (d, 1H). MS m/e MH⁺ 416.

Intermediate 53

(3-Iodophenyl)(isocyano)methyl 4-methylphenyl sulfone

POCl₃ (3.05 mL) was added to a stirred solution of {(3-iodophenyl)[(4-methylphenyl)sulfonyl]methyl}formamide (Intermediate 52) (6.23 g) in dry THF (35 mL) at 25° C. and stirred for 5 minutes. The reaction mixture was cooled to 0° C. and Et₃N (13.7 mL) was added dropwise over 45 minutes, keeping the internal temperature below 10° C. The reaction mixture was allowed to stir at 5-10° C. for a further 45 minutes. EtOAc (140 mL) and water (140 mL) was added and then stirred for 5 minutes. The organic phase was washed with water (2×140 mL), NaHCO3 (sat. aq., 140 mL) and then brine (140 mL). The organic phase was concentrated in vacuo to afford a dark brown gum. This was then passed through a pad of silica washing with DCM and concentrated in vacuo to afford a dark brown gum (ca. 70% pure 3.5 g, 58%);

¹H NMR (CDCl₃) δ 2.42 (s, 3H), 5.45 (s, 1H), 7.00-7.75 (m, 8H); MS m/e (M-H)⁻ 396.

Intermediate 54

6-[4-(3-Iodophenyl)-1-methyl-1H-imidazol-5-yl]-4-(methylthio)thieno[2,3-d]pyrimidine The title compound was prepared by a similar process to that described for Example 6 but using N-[4-(methylthio)thieno[2,3-d]pyrimidin-6-ylmethylidene]methanamine (Intermediate 16) in place of N-(3,4-Dimethoxybenzyl)-N-[thieno[2,3-d]pyrimidin-6-ylmethylidene]amine (intermediate 14) and using (3-iodophenyl)(isocyano)methyl 4-methylphenyl sulfone (Intermediate 53) in place of PhTosMIC. Pale yellow solid (1.50 g, 71%);

¹H NMR (DMSO-d6) δ 2.68 (s, 3H), 3.60 (s, 3H), 7.04 (t, 1H), 7.37 (d, 1H), 7.55 (d, 1H), 7.70 (s, 1H), 7.94 (m, 2H), 8.89 (s, 1H); MS m/e MH⁺ 465.

Intermediate 55

6-[4-(3-Iodophenyl)-1-methyl-1H-imidazol-5-yl]-4-(methylsulfonyl)thieno[2,3-d]pyrimidine The title compound was prepared by a similar process to that described for Intermediate 17 but using 6-[4-(3-iodophenyl)-1-methyl-1H-imidazol-5-yl]-4-(methylthio)thieno[2,3-d]pyrimidine (Intermediate 54) in place of 6-(1-methyl-4-phenyl-1H-imidazol-5-yl)-4-(methylthio)thieno[2,3-d]pyrimidine (example 7). Yellow solid (220 mg, 68%);

¹H NMR (DMSO-d6) δ 3.50 (s, 3H), 3.66 (s, 3H), 7.04 (t, 1H), 7.38 (d, 1H), 7.59 (d, 1H), 8.00 (m, 3H), 9.34 (s, 1H); MS m/e MH⁺ 497.

EXAMPLE 50

6-[4-(3-Bromophenyl)-1-methyl-1H-imidazol-5-yl]thieno[2,3-d]pyrimidin-4-amine

The title compound was prepared by a similar process to that described for Example 8 but using 6-[4-(3-Bromophenyl)-1-methyl-1H-imidazol-5-yl]-4-(methylsulfonyl)thieno[2,3-d]pyrimidine (Intermediate 59) in place of 6-(1-methyl-4-phenyl-1H-imidazol-5-yl)-4-(methylsulfonyl)thieno[2,3-d]pyrimidine (intermediate 17). Solid (357 mg, 58%);

¹H NMR (DMSO-d6) δ 3.60 (s, 3H), 7.26 (t, 1H), 7.40 (m, 2H), 7.65 (s, 2H), 7.69 (s, 1H), 7.77 (s, 1H), 7.95 (s, 1H), 8.33 (s, 1H); MS m/e MH⁺ 386, 388.

The starting materials used were prepared as follows:

Intermediate 56

{(3-Bromophenyl)[(4-methylphenyl)sulfonyl]methyl}formamide

The title compound was prepared by a similar process to that described for Intermediate 52 but using 3-bromobenzaldehyde in place of 3-iodobenzaldehyde. Solid (11 g, 28%);

¹H NMR (DMSO-d6) for major (5:1) rotamer δ 2.40 (s, 3H), 6.45 (d, 1H), 7.30-7.95 (m, 9H), 9.73 (d, 1H); MS m/e MNa⁺ 390, 392.

Intermediate 57

(3-Bromophenyl)(isocyano)methyl 4-methylphenyl sulfone

The title compound was prepared by a similar process to that described for Intermediate 53 but using {(3-bromophenyl)[(4-methylphenyl)sulfonyl]methyl}formamide (Intermediate 56) in place of {(3-iodophenyl)[(4-methylphenyl)sulfonyl]methyl}formamide (Intermediate 52). Light brown solid (3.2 g, 30%);

¹H NMR (DMSO-d6) δ 2.43 (s, 3H), 6.98 (s, 1H), 7.33-7.77 (m, 8H); MS m/e (M-H)⁻ 348, 350.

Intermediate 58

6-[4-(3-Bromophenyl)-1-methyl-1H-imidazol-5-yl]-4-(methylthio)thieno[2,3-d]pyrimidine The title compound was prepared by a similar process to that described for Example 6 but using N-[4-(methylthio)thieno[2,3-d]pyrimidin-6-ylmethylidene]methanamine (Intermediate 16) in place of N-(3,4Dimethoxybenzyl)-N-[thieno[2,3-d]pyrimidin-6-ylmethylidene]amine (intermediate 14) and using ((3-bromophenyl)(isocyano)methyl 4-methylphenyl sulfone (Intermediate 57) in place of PhTosMIC. Foam (1.9 g, 91%);

$^1$H NMR (DMSO-d6) δ 2.68 (s, 3H), 3.61 (s, 3H), 7.20 (t, 1H), 7.37 (m, 2H), 7.72 (m, 2H), 7.96 (s, 1H), 8.89 (s, 1H); MS m/e MH$^+$ 417, 419.

Intermediate 59

6-[4-(3-Bromophenyl)-1-methyl-1H-imidazol-5-yl]-4-(methylsulfonyl)thieno[2,3-d]pyrimidine The title compound was prepared by a similar process to that described for Intermediate 17 but using 6-[4-(3-bromophenyl)-1-methyl-1H-imidazol-5-yl]-4-(methylthio)thieno[2,3-d]pyrimidine (Intermediate 58) in place of 6-(1-methyl-4-phenyl-1H-imidazol-5-yl)-4-(methylthio)thieno[2,3-d]pyrimidine (example 7). Pale yellow foam (740 mg, 82%);

$^1$H NMR (DMSO-d6) δ 3.50 (s, 3H), 3.66 (s, 3H), 7.20 (t, 1H), 7.40 (m, 2H), 7.77 (s, 1H), 8.01 (s, 1H), 8.03 (s, 1H), 9.34 (s, 1H); MS m/e MH$^+$ 451, 449.

EXAMPLE 51

6-[4-(3-Butoxyphenyl)-1-methyl-1H-imidazol-5-yl]thieno[2,3-d]pyrimidin-4-amine

6-[4-(3-Iodophenyl)-1-methyl-1H-imidazol-5-yl]thieno[2,3-d]pyrimidin-4-amine (Example 49) (43 mg), 1,10-phenanthroline (4 mg), cesium carbonate (49 mg) and CuI (4 mg) in n-BuOH (1 mL) were heated under an inert atmosphere at 110° C. for 17 hours. The reaction mixture was allowed to cool and then diluted with EtOAc (10 mL) and water (10 mL). The organic layer was washed with water (10 mL), filtered and then applied to an MCX (1 g) column. The column was eluted with DCM:MeOH (1:1) and then 5% conc NH$_3$ in DCM:MeOH (1:1). The product fraction was evaporated and purified by flash chromatography on silica eluting with a gradient 0-100% EtOAc, then 0-20% MeOH, in DCM to afford the title compound as a gum (5 mg, 13%);

$^1$H NMR (CDCl$_3$) δ 0.90 (t, 3H), 1.38 (m, 2H), 1.65 (m, 2H), 3.56 (s, 3H), 3.84 (t, 2H), 5.60 (s, 2H), 6.75 (d, 1H), 7.10 (m, 3H), 7.20 (s, 1H), 7.63 (s, 1H), 8.50 (s, 1H); MS m/e MH$^+$ 380.

EXAMPLE 52

6-{1-Methyl-4-[3-(4-methylphenylthio)phenyl]-1H-imidazol-5-yl}thieno[2,3-d]pyrimidin-4-amine 6-[4-(3-Iodophenyl)-1-methyl-1H-imidazol-5-yl]thieno[2,3-d]pyrimidin-4-amine (Example 49) (43 mg), sodium para-toluene sulfinate (50 mg) and CuI (29 mg) in DMF (0.5 mL) were degassed and heated at 110° C. under an inert atmosphere for 17 hours. The reaction mixture was allowed to cool and then diluted with EtOAc (10 mL) and water (10 mL). The organic layer was washed with water (10 mL) and then concentrated. The residue was dissolved in DMSO and purified by preparative RPHPLC to afford the title compound as a solid (9 mg, 20%);

$^1$H NMR (CDCl$_3$) δ 2.30 (s, 3H), 3.52 (s, 3H), 5.60 (s, 2H), 6.95 (m, 3H), 7.14 (m, 4H), 7.43 (m, 2H), 7.60 (s, 1H), 8.52 (s, 1H); MS m/e MH$^+$ 430.

EXAMPLE 53

6-{4-[4-(Benzyloxy)phenyl]-1-methyl-1H-imidazol-5-yl}thieno[2,3d]pyrimidin-4-amine The title compound was prepared by a similar process to that described for Example 51 but using 6-[4-(4-Iodophenyl)-1-methyl-1H-imidazol-5-yl]thieno[2,3-d]pyrimidin-4-amine (Intermediate 64) in place of 6-[4-(3-Iodophenyl)-1-methyl-1H-imidazol-5-yl]thieno[2,3-d]pyrimidin-4-amine (Example 49) and using benzyl alcohol in place of n-BuOH. Solid (19 mg, 23%);

$^1$H NMR (CDCl$_3$) δ 3.51 (s, 3H), 5.02 (s, 2H), 5.60 (s, 2H), 6.87 (d, 2H), 7.03 (s, 1H), 7.35 (m, 5H), 7.50 (d, 2H), 7.59 (s, 1H), 8.51 (s, 1H); MS m/e MH$^+$ 414.

The starting materials used were prepared as follows:

Intermediate 60

{(4-Iodophenyl)[(4-methylphenyl)sulfonyl]methyl}formamide

The title compound was prepared by a similar process to that described for Intermediate 52 but using 4-iodobenzaldehyde in place of 3-iodobenzaldehyde. Solid (12.7 g, 57%);

$^1$H NMR (DMSO-d6) for major (5:1) rotamer δ 2.43 (s, 3H), 6.40 (d, 1H), 7.1-8.3 (m, 9H), 9.74 (d, 1H);

Intermediate 61

(4-Iodophenyl)(isocyano)methyl 4-methylphenyl sulfone

The title compound was prepared by a similar process to that described for Intermediate 53 but using {(4-iodophenyl)[(4-methylphenyl)sulfonyl]methyl}formamide (Intermediate 60) in place of {(3-iodophenyl)[(4-methylphenyl)sulfonyl]methyl}formamide (Intermediate 52). Brown gum (3.1 g, 20%);

$^1$H NMR (CDCl$_3$) δ 2.41 (s, 3H), 5.47 (s, 1H), 7.01 (d, 2H), 7.28 (d, 2H), 7.57 (d, 2H), 7.67 (d, 2H); MS m/e (M-H)$^-$ 396.

Intermediate 62

6-[4-(4-Iodophenyl)-1-methyl-1H-imidazol-5-yl]-4-(methylthio)thieno[2,3-d]pyrimidine The title compound was prepared by a similar process to that described for Example 6 but using N-[4-(methylthio)thieno[2,3-d]pyrimidin-6-ylmethylidene]methanamine (Intermediate 16) in place of N-(3,4-Dimethoxybenzyl)-N-[thieno[2,3-d]pyrimidin-6-ylmethylidene]amine (intermediate 14) and using (4-Iodophenyl)(isocyano)methyl 4-methylphenyl sulfone (Intermediate 61) in place of PhTosMIC. Solid (0.8 g, 37%);

$^1$H NMR (DMSO-d6) δ 2.68 (s, 3H), 3.60 (s, 3H), 7.27 (d, 2H), 7.62 (d, 2H), 7.68 (s, 1H), 7.94 (s, 1H), 8.90 (s, 1H); MS m/e MH$^+$ 465.

Intermediate 63

6-[4-(4-Iodophenyl)-1-methyl-1H-imidazol-5-yl]-4-(methylsulfonyl)thieno[2,3-d]pyrimidine The title compound was prepared by a similar process to that described for Intermediate 17 but using 6-[4-(4-iodophenyl)-1-methyl-1H-imidazol-5-yl]-4-(methylthio)thieno[2,3- d]pyrimidine (Intermediate 62) in place of 6-(1-methyl-4-phenyl-1H-imidazol-5-yl)-4-(methylthio)thieno[2,3-d]pyrimidine (example 7). Solid (200 mg, 100%);

$^1$H NMR (DMSO-d6) δ 3.50 (s, 3H), 3.66 (s, 3H), 7.29 (d, 2H), 7.64 (d, 2H), 8.02 (s, 2H), 9.34 (s, 1H); MS m/e MH$^+$ 497.

Intermediate 64

6-[4-(4-Iodophenyl)-1-methyl-1H-imidazol-5-yl]thieno[2,3-d]pyrimidin-4-amine

The title compound was prepared by a similar process to that described for Example 8 but using 6-[4-(4-Iodophenyl)-1-methyl-1H-imidazol-5-yl]-4-(methylsulfonyl)thieno[2,3-d]pyrimidine (Intermediate 63) in place of 6-(1-Methylphenyl-1H-imidazol-5-yl)-4-(methylsulfonyl)thieno[2,3-d]pyrimidine (intermediate 17). Solid (116 mg, 74%);

$^1$H NMR (DMSO-d6) δ 3.58 (s, 3H), 7.32 (d, 2H), 7.65 (m, 5H), 7.93 (s, 1H), 8.32 (s, 1H); MS m/e MH$^+$ 434.

EXAMPLE 54

6-{4-[4-Butoxyphenyl]-1-methyl-1H-imidazol-5-yl}thieno[2,3-d]pyrimidin-4-amine

The title compound was prepared by a similar process to that described for Example 51 but using 6-[4-(4-Iodophenyl)-1-methyl-1H-imidazol-5-yl]thieno[2,3-d]pyrimidin-4-amine (Intermediate 64) in place of 6-[4-(3-Iodophenyl)-1-methyl-1H-imidazol-5-yl]thieno[2,3-d]pyrimidin-4-amine (Example 49). Gum (5 mg, 13%);

$^1$H NMR (CDCl$_3$) δ 0.95 (t, 3H), 1.47 (m, 2H), 1.73 (m, 2H), 3.52 (s, 3H), 3.91 (t, 2H), 5.62 (s, 2H), 6.78 (d, 2H), 7.02 (s, 1H), 7.48 (d, 2H), 7.58 (s, 1H), 8.50 (s, 1H); MS m/e MH$^+$ 380.

EXAMPLE 55

N-{4-[5-(4-Aminothieno[2,3-d]pyrimidin-6-yl)-1-methyl-1H-imidazol-4-yl]phenyl}methanesulfonamide 6-[4-(4Bromophenyl)-1-methyl-1H-imidazol-5-yl]thieno[2,3-d]pyrimidin-4-amine (Intermediate 69) (38 mg), trans-1,2-cyclohexane diamine (11 mg), K$_3$PO$_4$ (42 mg), methanesulphonamide (19 mg) and CuI (10 mg) in dioxane (2 mL) were degassed and heated under an inert atmosphere at 100° C. for 12 hours. The reaction was cooled to ambient temperature and then MeOH, DCM and water added. The solution was introduced onto an MCX column. The column was eluted with DCM:MeOH (1:1) and then 5% conc NH$_3$ in DCM:MeOH (1:1). The product fraction was evaporated and purified by prep LCMS to afford the title compound as a gum (11 mg, 27%);

MS m/e MH$^+$ 401.

The starting materials used were prepared as follows:

Intermediate 65

{(4-Bromophenyl)[(4-methylphenyl)sulfonyl]methyl}formamide

The title compound was prepared by a similar process to that described for Intermediate 52 but using 4-bromobenzaldehyde in place of 3-iodobenzaldehyde. Solid (31 g, 80%);

$^1$H NMR (DMSO-d6) for major (4:1) rotamer δ 2.40 (s, 3H), 6.42 (d, 1H), 7.2-8.3 (m, 9H), 9.73 (d, 1H); MS m/e MNa$^+$ 390, 392.

Intermediate 66

(4-Bromophenyl)(isocyano)methyl 4-methylphenyl sulfone

The title compound was prepared by a similar process to that described for Intermediate 53 but using {(4-bromophenyl)[(4-methylphenyl)sulfonyl]methyl}formamide (Intermediate 65) in place of {(3-iodophenyl)[(4-methylphenyl)sulfonyl]methyl}formamide (Intermediate 52). Brown solid (3.1 g, 29%);

$^1$H NMR (DMSO-d6) δ 2.43 (s, 3H), 6.98 (s, 1H), 7.28 (d, 2H), 7.51 (d, 2H), 7.68 (m, 4H); MS m/e (M-H)$^-$ 348, 350.

Intermediate 67

6-[4-(4-Bromophenyl)-1-methyl-1H-imidazol-5-yl]-4-(methylthio)thieno[2,3-d]pyrimidine The title compound was prepared by a similar process to that described for Example 6 but using N-[4-(methylthio)thieno[2,3-d]pyrimidin-6-ylmethylidene]methanamine (Intermediate 16) in place of N-(3,4-Dimethoxybenzyl)-N-[thieno[2,3-d]pyrimidin-6-ylmethylidene]amine. (intermediate 14) and (4-bromophenyl)(isocyano)methyl 4-methylphenyl sulfone (Intermediate 66) in place of PhTosMIC. Pale yellow solid (1.7 g, 81%);

$^1$H NMR (DMSO-d6) δ 2.68 (s, 3H), 3.60 (s, 3H), 7.43 (m, 4H), 7.68 (s, 1H), 7.95 (s, 1H), 8.89 (s, 1H); MS m/e MH$^+$ 417, 419.

Intermediate 68

6-[4-(4-Bromophenyl)-1-methyl-1H-imidazol-5-yl]-4-(methylsulfonyl)thieno[2,3-d]pyrimidine The title compound was prepared by a similar process to that described for Intermediate 17 but using 6-[4-(4-bromophenyl)-1-methyl-1H-imidazol-5-yl]4-(methylthio)thieno[2,3-d]pyrimidine (Intermediate 67) in place of 6-(1-methyl-4-phenyl-1H-imidazol-5-yl)-4-(methylthio)thieno[2,3-d]pyrimidine (example 7). Pale yellow solid (715 mg, 79%);

$^1$H NMR (DMSO-d6) δ 3.51 (s, 3H), 3.67 (s, 3H), 7.45 (m, 4H), 7.99 (s, 1H), 8.02 (s, 1H), 9.34 (s, 1H); MS m/e MH$^+$ 449, 451.

Intermediate 69

6-[4-(4-Bromophenyl)-1-methyl-1H-imidazol-5-yl]thieno[2,3-d]pyrimidin-4-amine

The title compound was prepared by a similar process to that described for Example 8 but using 6-[4-(4-Bromophenyl)-1-methyl-1H-imidazol-5-yl]-4-(methylsulfonyl)thieno[2,3-d]pyrimidine (Intermediate 68) in place of 6-(1-Methyl-4-phenyl-1H-imidazol-5-yl)-4-(methylsulfonyl)thieno[2,3-d]pyrimidine (intermediate 17); Solid (568 mg, 95%);

$^1$H NMR (DMSO-d6) δ 3.58 (s, 3H), 7.48 (m, 4H), 7.66 (m, 3H), 7.94 (s, 1H), 8.33 (s, 1H); MS m/e MH$^+$ 386, 388.

EXAMPLE 56

6-(1-Ethyl-4-phenyl-1H-imidazol-5-yl)thieno[2,3-d]pyrimidin-4-amine mCPBA (70-75%, 160 mg) was added to a stirred solution of 6-(1-ethyl-4-phenyl-1H-imidazol-5-yl)-4-(methylthio)thieno[2,3-d]pyrimidine (Intermediate 70) (91 mg) in DCM (8 mL) and allowed to stir at ambient temperature for 45 minutes. $NH_3$ (0.5M in dioxane) (10 mL) was then added and the reaction was allowed to stir for 2 days with further $NH_3$ (0.5M in dioxane) (5 mL) added after 16 hours. The reaction mixture was concentrated in vacuo and the crude product purified by flash chromatography on silica eluting with isohexane:EtOAc (1:1) then 0-10% (7M $NH_3$ in MeOH) in EtOAc to afford the title compound as a solid (40 mg, 48%);

$^1$H NMR (DMSO-d6) δ 1.28 (t, 3H), 3.95 (q, 2H), 7.19 (t, 1H), 7.28 (t, 2H), 7.51 (d, 2H), 7.60 (s, 2H), 7.67 (s, 1H), 7.98 (s, 1H), 8.32 (s, 1H). MS m/e MH+ 322

The starting material used was prepared as follows:

Intermediate 70

6-(1-Ethyl-4-phenyl-1H-imidazol-5-yl)-4-(methylthio)thieno[2,3-d]pyrimidine 4-(Methylthio)thieno[2,3-d]pyrimidine-6-carbaldehyde (Intermediate 15) (105 mg) and ethylamine (70% aq.) (80 μL) in TBF (5 mL) were stirred at ambient temperature for 24 hours. PhTosMIC (203 mg) and piperazine (100 mg) were added and the reaction was allowed to stir for three days. A further portion of PhTosMIC (70 mg) was added and allowed to stir for 3 more days. The reaction mixture was concentrated in vacuo and the crude product purified by flash chromatography on silica eluting with Hex:EtOAc (4:1 to 100% EtOAc) to afford the title compound as a yellow gum (91 mg, 52%) (contains 33mol % of 1-ethyl-4,5-diphenyl-1H-imidazole);

MS m/e MH+ 353

The compounds of Examples 57 to 59 were prepared using the general method of Example 56 and Intermediate 70 but replacing ethylamine with the appropriate amine.

EXAMPLE 57

6-[1-(3-Methoxypropyl)-4-phenyl-1H-imidazol-5-yl]thieno[2,3-d]pyrimidin-4-amine

Yellow solid (40 mg, 51% yield); MS m/e MH+ 366 $^1$H NMR (DMSO-d6) δ 1.86 (m, 2H), 3.15 (s, 3H), 3.25-3.31 (m, 4H), 3.98 (t, 2H), 6.30 (s, 2H), 7.18 (t, 1H), 7.28 (t, 2H), 7.52 (d, 2H), 7.67 (s, 1H), 7.93 (s, 1H), 8.32 (s, 1H),

EXAMPLE 58

6-(1-Isobutyl-4-phenyl-1H-imidazol-5-yl)thieno[2,3-d]pyrimidin-4-amine

Yellow solid (60 mg, 51% yield); MS m/e MH+ 350. $^1$H NMR (DMSO-d6) δ 0.80 (d, 6H), 1.83-1.95 (m, 1H), 3.76 (d, 2H), 7.18 (t, 1H), 7.27 (t, 2H), 7.52 (d, 2H), 7.60 (s, 2H), 7.65 (s, 1H), 7.92 (s, 1H), 8.32 (s, 1H);

EXAMPLE 59

2-[5-(4-Aminothieno[2,3-d]pyrimidin-6-yl)-4-phenyl-1H-imidazol-1-yl]ethanol

Yellow solid (30 mg, 19% yield); MS m/e MH+ 338 $^1$H NMR (DMSO-d6) δ 3.56-3.60 (m, 2H), 3.95 (t, 2H), 4.99 (t, 1H), 7.18 (t, 1H), 7.28 (t, 2H), 7.52 (d, 2H), 7.60 (s, 2H), 7.64 (s, 1H), 7.91 (s, 1H), 9.31 (s, 1H);

EXAMPLE 60

6-(1-Cyclopropyl-4-phenyl-1H-imidazol-5-yl)thieno[2,3-d]pyrimidin-4-amine 6-(1-cyclopropyl-4-phenyl-1H-imidazol-5-yl)-4-(methylthio)thieno[2,3-d]pyrimidine (Intermediate 71) (25 mg), $NH_3$ (aq. conc) and $NH_4Cl$ (sat. aq.) in dioxane (2 mL) were heated under microwave conditions (CEM explorer, 170° C., 4 hours). The reaction mixture was diluted with DCM and water. The aqueous layer was extracted with DCM and then the combined organics were concentrated. The crude product was purified by flash chromatography on silica eluting with Hex:EtOAc (1:1 to 100% EtOAc, then MeOH:EtOAc 95:5) to afford the title compound as a solid (8 mg, 35%);

$^1$H NMR DMSO-d6) δ 0.87-0.93 (m, 2H), 0.98-1.02 (m, 2H), 3.30-3.45 (m, 1H), 7.20 (t, 1H), 7.29 (t, 2H), 7.52 (d, 2H), 7.58 (s, 2H), 7.70 (s, 1H), 7.91 (s, 1H), 8.31 (s, 1H); MS m/e MH+ 334

The starting material used was prepared as follows:

Intermediate 71

6-(1-Cyclopropyl-4-phenyl-1H-imidazol-5-yl)-4-(methylthio)thieno[2,3-d]pyrimidine The title compound was prepared by a similar process to that described for Intermediate 70 but using cyclopropylamine in place of ethylamine. Solid (25 mg, 14%) (contains 30% of 1-cyclopropyl-4,5-phenyl-1H-imidazole);

MS m/e MH+ 365.

The compounds of Examples 61 to 64 were prepared using the general method of Example 60 and Intermediate 70 but replacing ethylamine with the appropriate amine and the final compounds were purified by preparative LCMS instead of silica chromatography.

EXAMPLE 61

6-[1-(2-Methoxyethyl)-4-phenyl-1H-imidazol-5-yl]thieno[2,3-d]pyrimidin-4-amine

Yellow solid (11 mg, 16% yield); MS m/e MH+ 352.

EXAMPLE 62

6-(1-Butyl-4-phenyl-1H-imidazol-5-yl)thieno[2,3-d]pyrimidin-4-amine

Yellow solid (9 mg, 11% yield); MS m/e MH+ 350.

EXAMPLE 63

6-[4-Phenyl-1-(pyridin-3-ylmethyl)-1H-imidazol-5-yl]thieno[2,3-d]pyrimidin-4-amine Yellow solid (6 mg, 18% yield); MS m/e MH+ 385.

EXAMPLE 64

6-[1-(2,2-Dimethoxyethyl)-4-phenyl-1H-imidazol-5-yl]thieno[2,3-d]pyrimidin-4-amine Yellow solid (5 mg, 7% yield); MS m/e MH+ 382.

EXAMPLE 65

6-(4-Phenyl-1-pyrrolidin-3-yl-1H-imidazol-5-yl)thieno[2,3-d]pyrimidin-4-amine 3-Aminopyrrolidine (26 mg) in THF (1 mL) was added to 4-aminothieno[2,3-d]pyrimidine-6-carbaldehyde (Intermediate 73) (18 mg). The reaction mixture was allowed to stir at ambient temperature for 1.5 hours and then a solution of PhTosMIC (30 mg) and morpholine (20 μL) in THF (1 mL) was added. The reaction was stirred at ambient temperature for 6 days and then the solvent removed in vacuo. The crude product was purified by flash chromatography on silica eluting with EtOAc:7N $NH_3$ in MeOH (100:0 to 90:10) to afford the title compound (5 mg, 14%) as a pale yellow solid;

MS m/e $MH^+$ 363.

The starting materials used were prepared as follows:

Intermediate 72

6-(Diethoxymethyl)-4-(methylthio)thieno[2,3-d]pyrimidine 4-(Methylthio)thieno[2,3-d]pyrimidine-6carbaldehyde (Intermediate 15) (3.06 g), conc $H_2SO_4$ (0.25 mL) and $MgSO_4$ (7.6 g) were dissolved in EtOH (100 mL) and heated at 60° C. for 3 hours. The reaction was allowed to cool and then filtered through anhydrous $K_2CO_3$, washing with EtOH. The reaction mixture was concentrated in vacuo to afford crude product (3.95 g, 95%) (used in the next step without further purification);

$^1$H NMR ($CDCl_3$) δ 1.28 (t, 6H), 3.60-6.75 (m, 4H), 5.78 (s, 1H), 7.30 (s, 1H), 8.79 (s, 1H); MS m/e $MH^+$ 285

Intermediate 73

4-Aminothieno[2,3-d]pyrimidine-6-carbaldehyde $NaHCO_3$ (7.75 g) was added to a solution of crude 6-(diethoxymethyl)-4-(methylthio)thieno[2,3-d]pyrimidine (Intermediate 72) (3.95 g) and MCPBA (7.5 g) in DCM (125 mL). The reaction mixture was allowed to stir at ambient temperature for 3 hours and then further MCPBA (4.0 g) and $NaHCO_3$ (4.0 g) were added and allowed to stir overnight. The reaction mixture was filtered, washing well with DCM and then concentrated in vacuo. The residue was dissolved in dioxane (75 mL) and conc. $NH_3$ (100 mL) was added. The reaction mixture was allowed to stir at ambient temperature overnight. The reaction volume was concentrated to ca. 100 mL and then acidified with HCl (5 mL). The reaction mixture was allowed to stir at ambient temperature for 1.5 hours and then diluted with DCM (250 mL) and saturated aqueous $NaHCO_3$ (50 mL). The organic layer was separated and the aqueous layer extracted with DCM (3×50 mL). The combined organics were dried ($MgSO_4$), filtered and concentrated in vacuo. The product was triturated with ether to afford the title compound (1.74 g, 69%) as a pale yellow solid;

$^1$H NMR (DMSO-d6) δ 8.16 (s, 2H), 8.48 (s, 1H), 8.59 (s, 1H), 10.11 (s, 1H); MS m/e $MH^+$ 180.

The compounds of Examples 66 and 67 were prepared using the general method of Example 65 but replacing 3-aminopyrrolidine with the appropriate amine and the final compounds were purified by prep LCMS instead of silica chromatography.

EXAMPLE 66

2-[5-(4-aminothieno[2,3-d]pyrimidin-6-yl)-4-phenyl-1H-imidazol-1-yl]hexan-1-ol Yellow solid (6 mg, 15% yield); MS m/e $MH^+$ 394

EXAMPLE 67

2-[5-(4-Aminothieno[2,3-d]pyrimidin-6-yl)-4-phenyl-1H-imidazol-1-yl]butan-1-ol Yellow solid (5 mg, 14% yield); MS m/e $MH^+$ 366

EXAMPLE 68

6-{1-[2-(4-Methylpiperazin-1-yl)ethyl]-4-phenyl-1H-imidazol-5-yl}thieno[2,3-d]pyrimidin-4-amine

[5-(4-Aminothieno[2,3-d]pyrimidin-6-yl)-4-phenyl-1H-imidazol-1-yl]acetaldehyde (Intermediate 74) (100 mg) and N-methyl piperazine (100 μL) were stirred in AcOH (1 mL) for 15 minutes. $Na(AcO)_3BH$ (70 mg) was added and the reaction allowed to stir overnight. The reaction was made basic with 2M NaOH (50 mL) and then the product extracted with DCM (3×50 mL). The organics were washed with water (30 mL), brine (30 mL), dried ($MgSO_4$) and concentrated in vacuo. The product was purified by flash chromatography on silica eluting with DCM:7N $NH_3$ in MeOH. (95:5) to afford the title compound as a solid (32 mg, 28%);

$^1$H NMR (DMSO-d6) δ 2.12 (s, 3H), 2.20-2.40 (m, 8H), 3.30 (m, 2H, obscured by $H_2O$), 4.00 (t, 2H), 7.18 (t, 1H), 7.28 (t, 2H), 7.52 (d, 2H), 7.60 (s, 2H), 7.66 (s, 1H), 7.93 (s, 1H), 8.32 (s, 1H); MS m/e $MH^+$ 420.

The starting materials used were prepared as follows:

Intermediate 74

[5-(4-Aminothieno[2,3-d]pyrimidin-6-yl)-4-phenyl-1H-imidazol-1-yl]acetaldehyde 2M HCl (8 mL) and conc. $H_2SO_4$ (0.5 mL) were added to a solution of 6-[1-(2,2-dimethoxyethyl)-4-phenyl-1H-imidazol-5-yl]thieno[2,3-d]pyrimidin-4-amine (Example 64) (1.54 g) in THF (20 mL). The reaction was heated at 60° C. for 72 hours, allowed to cool to ambient temperature and then poured into $NaHCO_3$ (aq. 50% sat.) (100 mL). The resultant precipitate was filtered to afford the title compound as a pale yellow solid (1 g, 74%) (used without further purification);

MS m/e $MH^+$ 354.

EXAMPLE 69

2-(1-Ethyl-4-phenyl-1H-imidazol-5-yl)[1,3]thiazolo[5,4-d]pyrimidin-7-amine

The title compound was prepared by a similar process to that described for Example 56 but using 2-(1-ethyl-4-phenyl-1H-imidazol-5-yl)-7-(methylthio)[1,3]thiazolo[5,4-d]pyrimidine (Intermediate 78) in place of 6-(1-ethyl-4-phenyl-1H-imidazol-5-yl)-4-(methylthio)thieno-[2,3-d]pyrimidine (Intermediate 70). Yellow solid (60 mg, 64%);

$^1$H NMR (DMSO-d6) δ 1.30 (t, 3H), 4.39 (q, 2H), 7.35-7.42 (m, 3H), 7.50 (d, 2H), 7.74 (s, 2H), 8.02 (s, 1H), 8.29 (s, 1H); MS m/e $MH^+$ 323.

The starting materials used were prepared as follows:

Intermediate 75

(7-Mercapto[1,3]thiazolo[5,4-d]pyrimidin-2-yl)methanol

A cooled (ice bath) suspension of 5-aminopyrimidine-4,6-dithiol (Intermediate 41) (40.0 g) in pyridine (500 mL) was stirred under an inert atmosphere atmosphere. Acetoxyacetyl chloride (38 mL) was added over 10 minutes, the ice bath was removed and the mixture stirred at ambient temperature overnight. The mixture was concentrated in vacuo and azeotroped three times with toluene (200 mL). The residue was suspended in 2N HCl, and heated at 115° C. for 5 hours, and allowed to cool to ambient temperature overnight. The resulting suspension was filtered, washed with water (200 mL) and ether (200 mL) to give the title compound as a pale brown solid (48.3 g, 97%) (containing 10% of (7-mercapto[1,3]thiazolo[5,4-d]pyrimidin-2-yl)methyl acetate);

$^1$H NMR (DMSO-d6) δ 4.81 (d, 2H), 6.38 (s, br, 1H), 8.36 (s, 1H), 14.15 (s, br, 5H); MS m/e MH$^+$ 200.

Intermediate 76

[7-(Methylthio)[1,3]thiazolo[5,4-d]pyrimidin-2-yl]methanol

A solution of (7-mercapto[1,3]thiazolo[5,4-d]pyrimidin-2-yl)methanol (Intermediate 75) (48.3 g) and iodomethane (16.6 mL) in 2M NaOH (450 mL) was stirred at ambient temperature for 5 hours. The crude product was collected by filtration, suspended in water and acidified by addition of 2N HCl. The flocculant solid was collected by filtration, washed with water (200 mL) and ether (200 mL) and dried under vacuum over phosphorus pentoxide to give the title compound as a pale brown solid (27.5 g, 53%);

$^1$H NMR (DMSO-d6) δ 2.66 (s, 3H), 4.90 (d, 2H), 6.47 (s, br, 1H), 8.90 (s, 1H); MS m/e (MH)$^+$ 214.

Intermediate 77

7-Methylthio)[1,3]thiazolo[5,4-d]pyrimidine-2-carbaldehyde

A suspension of [7-(methylthio)[1,3]thiazolo[5,4-d]pyrimidin-2-yl]methanol (Intermediate 76) (25.0 g) and activated manganese dioxide (40.7 g) in dioxane (1200 mL) was heated at 100° C. for 24 hours. The mixture was filtered through celite, washed through with THF (2000 mL) and concentrated in vacuo to give the title compound as a yellow solid (22.5 g, 91%);

$^1$H NMR (DMSO-d6) δ 2.84 (s, 3H), 9.16 (s, 1H), 10.19 (s, 1H); MS m/e (MH+H$_2$O)$^+$ 230.

Intermediate 78

2-(1-Ethyl-4-phenyl-1H-imidazol-5-yl)-7-(methylthio)[1,3]thiazolo[5,4-d]pyrimidine The title compound was prepared by a similar process to that described for Intermediate 70 but using 7-(methylthio)[1,3]thiazolo[5,4-d]pyrimidine-2-carbaldehyde (Intermediate 77) in place of 4-(methylthio)thieno[2,3-d]pyrimidine-6-carbaldehyde (Intermediate 15). Yellow solid (103 mg, 58%);

MS m/e MH$^+$ 354

EXAMPLE 70

2-[1-(Cyclohexylmethyl)-4-phenyl-1H-imidazol-5-yl][1,3]thiazolo[5,4-d]pyrimidin-7-amine The title compound was prepared by a similar process to that described for Example 56 but using 2-[1-(cyclohexylmethyl)-4-phenyl-1H-imidazol-5-yl]-7-(methylthio)[1,3]-thiazolo[5,4-d]pyrimidine (Intermediate 79) in place of 6-(1-ethyl-4-phenyl-1H-imidazol-5-yl)-4-(methylthio)thieno[2,3-d]pyrimidine (Intermediate 70) and using NH$_3$ gas in place of NH$_3$ solution (0.5 M in dioxane). Solid (160 mg, 25%);

$^1$H NMR (DMSO-d6) δ 0.90-1.20 (6H, m), 1.40 (5H, m), 4.34 (d, 2H), 7.40-7.48 (m, 3H), 7.51-7.57 (m, 2H), 7.86 (s, br, 2H), 8.33 (s, 1H), 8.42 (s, 1H); MS m/e MH$^+$ 391.

The starting materials used were prepared as follows:

Intermediate 79

2-[1-(Cyclohexylmethyl)-4-phenyl-1H-imidazol-5-yl]-7-(methylthio)[1,3]thiazolo[5,4-d]pyrimidine The title compound was prepared by a similar process to that described for Example 65 but using 7-(methylthio)[1,3]thiazolo[5,4-d]pyrimidine-2-carbaldehyde (Intermediate 77) in place of 4-aminothieno[2,3-d]pyrimidine-6-carbaldehyde (Intermediate 73) and using cyclohexamethylamine in place of 3-aminopyrrolidine. Yellow solid (542 mg) (the product contained 33% of 1-(cyclohexylmethyl)-4,5-diphenyl-1H-imidazole but was used in subsequent steps without further purification);

MS m/e MH$^+$ 422.

EXAMPLE 71

6-(1-Methyl-4-phenyl-1H-imidazol-5-yl)furo[3,2-d]pyrimidin-4-amine

A mixture of 6-(1-methyl-4-phenyl-1H-imidazol-5-yl)-4-(methylthio)furo[3,2-d]pyrimidine (Intermediate 87) (50 mg) and saturated aqueous ammonium chloride solution (2 drops) in concentrated aqueous NH$_3$ (1 mL) and 1,4-dioxane (2 mL) was heated under microwave conditions (CEM explorer, 170° C., 150 minutes). Water (10 mL) was added, and the mixture extracted into EtOAc (2×20 mL). The combined organic phases were dried and concentrated in vacuo. Purification by flash chromatography on silica (0-5% MeOH in EtOAc) afforded the title compound as an off-white solid (38 mg, 84%);

$^1$H NMR (DMSO-d6) δ 3.69 (s, 3H), 7.10 (s, 1H), 7.20-7.34 (m, 4H), 7.53 (d, 1H), 7.93 (s, 1H), 8.25 (s, 1H); MS m/e MH$^+$ 292.

The starting materials used were prepared as follows:

Intermediate 80 tert-Butyl 3-furylcarbamate

Diphenylphosphoryl azide (78.9 mL) was added dropwise to a solution of 3-furoic acid (Aldrich) (27.2 g) in a mixture of toluene (400 mL), triethylamine (52.5 mL) and tert-butanol (35.1 mL). The solution was heated to reflux for 6 hours, cooled overnight and water added (500 mL). The mixture was extracted into EtOAc (3×500 mL) and the combined organics washed with water (400 mL), brine (400 mL), decolourised over activated charcoal, dried (MgSO$_4$), and the solvent removed to give 73 g of a brownish solid. Trituration with 1:1 DCM/isohexane gave the title compound as a white solid (31.5 g, 71%);

$^1$H NMR (CDCl$_3$) δ 1.50 (s, 9H), 6.22 (s, br, 1H), 6.27 (s, 1H), 7.26 (d, 1H), 7.69 (s, br, 1H); MS m/e MH$^+$ 184.

Intermediate 81

3-[(tert-Butoxycarbonyl)amino]-2-furoic acid

Butyl lithium (as 1.6 M in hexanes, 45 mL) was added slowly to a solution of tert-butyl 3-furylcarbamate (Intermediate 80) (5.49 g) in THF (60 mL) at −40° C., keeping the internal reaction temperature less than −35° C. The reaction was stirred at −40° C. for 4 hours, then poured onto solid CO$_2$ (100 mL) under a blanket of diethyl ether (300 mL). After warming to ambient temperature, the mixture was poured into water (300 mL) with stirring and an additional 100 mL diethyl ether added. The phases were separated and the organic phase was further extracted into water (2×100 mL). The combined organic phases were washed with ether, acidified by addition of aqueous HCl, and extracted into EtOAc (4×250 mL). The combined extracts were dried and evaporated to give a pale yellow solid (7.5 g). This was triturated with cyclohexane to afford the title compound as a white solid (4.80 g, 70%);

$^1$H NMR (DMSO-d6) δ 1.46 (s, 9H), 7.05 (s, 1H), 7.76 (s, 1H), 8.27 (s, 1H), 13.36 (s, br, 1H); MS m/e (M-H)$^-$ 226.

Intermediate 82 tert-Butyl 2-(aminocarbonyl)-3-furylcarbamate

Diisopropylethylamine (14.75 mL) was added to a suspension of PyBOP (10.4 g), ammonium chloride (1.81 g) and 3-[(tert-butoxycarbonyl)amino]-2-furoic acid (Intermediate 81) (3.83 g) in DMF (50 mL). The resulting mixture was stirred at ambient temperature for 90 minutes, poured into 0.4 M HCl (250 mL) and extracted into DCM (3×100 mL). The combined organics were washed with water (80 mL) and brine (80 mL), dried (MgSO$_4$), and evaporated The product was purified by flash chromatography on silica, eluting with 20-70% EtOAc in isohexane to afford the title compound as a white solid (3.38 g, 89%);

$^1$H NMR (DMSO-d6) δ 1.51 (s, 9H), 5.67 (s, br, 2H), 7.21 (s, 1H), 7.27 (d, 1H), 7.26 (s, 1H), 8.56 (s, 1H); MS m/e MH$^+$ 227.

Intermediate 83

Furo[3,2-d]pyrimidin-4-(3H)-one tert-Butyl 2-(aminocarbonyl)-3-furylcarbamate (Intermediate 82) (3.38 g) was stirred in DMF (25 mL) and DCM (25 mL) for 30 minutes. The solvent was removed and the crude product was heated at 80° C. in triethylorthoformate (20 mL) for 30 minutes. The mixture was cooled, poured into ether (100 mL) collected by filtration and washed with ether to afford a first crop of the title compound as a pale yellow solid (1.31 g, 65%). The filtrate was evaporated and triturated with EtOAc to afford a further crop (296 mg, 15%);

$^1$H NMR (DMSO-d6) δ 6.96 (d, 1H), 8.03 (s, 1H), 8.19 (d, 1H), 12.54 (s, br, 1H); MS m/e (M+MeCN)$^+$ 187.

Intermediate 84

4-Chlorofuro[3,2-d]pyrimidine

Furo[3,2-d]pyrimidin-4(3H)-one (Intermediate 83) (1.49 g) and phosphorus oxychloride (15 mL) were heated to 120° C. for 45 minutes, cooled to ambient temperature, and evaporated under high vacuum. The residue was added to 50% saturated sodium carbonate (100 mL) and extracted into DCM (3×100 mL). The combined organics were dried and the solvent removed to afford the title compound as an orange solid (1.32 g, 78%);

$^1$H NMR (CDCl$_3$) δ 7.07 (d, 1H), 8.03 (d, 1H), 8.88 (s, 1H); MS m/e (M+OH)$^-$ 171, 173.

Intermediate 85

4-(Methylthio)furo[3,2-d]pyrimidine

Sodium thiomethoxide (1.2 g) was added to a solution of 4-chlorofuro[3,2-d]pyrimidine (Intermediate 84) (1.32 g) in MeCN (100 mL). The mixture was heated to 90° C. for 60 minutes, cooled, and added to 50% sodium carbonate solution (100 ml). The resulting mixture was extracted into EtOAc (3×100 mL). The combined organics were dried (MgSO$_4$) and the solvent removed to afford the title compound as a pale orange solid (1.21 g, 85%);

$^1$H NMR (CDCl$_3$) δ 2.74 (s, 3H), 6.95 (d, 1H), 7.87 (d, 1H), 8.86 (s, 1H); MS m/e MH$^+$ 167.

Intermediate 86

4-(Methylthio)furo[3,2-d]pyrimidine-6-carbaldehyde

Butyl lithium (as 1.6 M in hexanes, 7 mL) was added to a solution of 4-(methylthio)furo[3,2-d]pyrimidine (Intermediate 85) (1.21 g) in THF (25 mL) at −70° C. The reaction was stirred for 5 minutes, DMF (5 mL) added, and the reaction mixture allowed to warm to ambient temperature. 30% Saturated ammonium chloride solution (50 mL) was added and the mixture extracted into EtOAc (3×50 mL). The combined organics were washed with 50% saturated sodium carbonate solution (50 mL), water (50 mL), dried and the solvent removed to afford the title compound as a pale yellow solid (1.02 g) (the product contained 20% unreacted starting material but was used without further purification in subsequents steps);

$^1$H NMR (DMSO-d6) δ 2.74 (s, 3H), 8.09 (s, 1H), 8.98 (s, 1H), 10.02 (s, 1H); MS m/e (M+MeOH+H)$^+$ 227.

Intermediate 87

6-(1-Methyl-4-phenyl-1H-imidazol-5-yl)-4-(methylthio)furo[3,2-d]pyrimidine

The title compound was prepared by a similar process to that described for Intermediate 70 but using 4-(methylthio)furo[3,2-d]pyrimidine-6-carbaldehyde (Intermediate 86) in place of 4-(methylthio)thieno[2,3-d]pyrimidine-6-carbaldehyde (Intermediate 15) and methylamine in place of ethylamine. Pale yellow solid (105 mg, 54%);

$^1$H NMR (DMSO-d6) δ 2.62 (s, 3H), 3.77 (s, 3H), 7.25-7.38 (m, 4H), 7.53 (d, 2H), 7.99 (s, 1H), 8.84 (s, 1H). MS m/e MH$^+$ 323.

EXAMPLE 72

6-(1-Methyl-4-phenyl-1H-imidazol-5-yl)-5H-pyrrolo[3,2-d]pyrimidin-4-amine

6-[(1-Methyl-4-phenyl-1H-imidazol-5-yl)ethynyl]pyrimidine-4,5-diamine (intermediate 90) (50 mg) and CuI (3 mg) in DMF (2 mL) were heated at 110° C. under an inert atmosphere for 4 hours. The reaction mixture was loaded on to a 1 g SCX column prewashed with DCM:MeOH (3:1). The column was eluted with DCM:MeOH (3:1) and then the product eluted with 7N NH$_3$/MeOH:DCM:MeOH (1:3:1).

The product fraction was concentrated and then purified by flash chromatography on silica eluting with DCM:MeOH (9:1) to afford the title compound as a yellow solid (3 mg, 6%);

$^1$H NMR (DMSO-D6) δ 3.60 (s, 3H), 6.65-6.66 (m, 3H), 7.17-7.31 (m, 3H), 7.47-7.49 (m, 2H), 7.92 (s, 1H), 8.18 (s, 1H), 11.19 (s, 1H). MS m/e MH$^+$ 291.

The starting materials used were prepared as follows:

Intermediate 88

6-Chloropyrimidine-4,5-diamine 4,5-Diamino-6-hydroxypyrimidine (1 g) and dimethylaniline (1 mL) in POCl$_3$ (10 mL) were heated at reflux under an inert atmosphere for 4 hours. The reaction mixture was concentrated in vacuo, carefully diluted with ice-water and then neutralised with NaHCO$_3$. The product was extracted with EtOAc (4×30 mL) and then the organics were dried (MgSO$_4$), filtered and concentrated in vacuo. The crude product was triturated with DCM to afford the product as a pale grey solid (168 mg, 15%);

$^1$H NMR (CDCl$_3$) δ 4.95 (br s, 2H), 6.73 (s, 2H), 7.65 (s, 1H); MS m/e (MH+MeCN)$^+$ 186.

Intermediate 89

6-Iodopyrimidine-4,5-diamine

6-Chloropyrimidine-4,5-diamine (Intermediate 88) (90 mg) was added slowly to HI (57%, aq) (2 mL) at 0° C. The reaction mixture was allowed to stir at 0° C. for 30 minutes and then at ambient temperature for 24 hours. NaHCO$_3$ (sat aq.) was added dropwise until the reaction mixture was pH 8. The product was extracted with EtOAc (3×15 mL). The combined organics were dried (MgSO$_4$), filtered and concentrated in vacuo to afford the title compound as a grey solid (144 mg, 98%);

$^1$H NMR (CDCl$_3$) δ 4.81 (bs, 2H), 6.66 (s, 2H), 7.61 (s, 1H); MS m/e MH$^+$ 237.

Intermediate 90

6-[(1-methyl-4-phenyl-1H-imidazol-5-yl)ethynyl]pyrimidine-4,5-diamine

6-Iodopyrimidine-4,5-diamine (Intermediate 89) (50 mg), CuI (2 mg), PdCl$_2$dppf (16 mag), 5-ethynyl-1-methyl-4-phenyl-1H-imidazole (intermediate 26) (77 mg), and triethylamine (0.33 mL) in DMF (7 mL) were mixed together and then degassed. The reaction mixture was allowed to stir at ambient temperature under an inert atmosphere for 24 hours. The reaction mixture was filtered through diatomaceous earth, washing well with DCM and then MeCN. The organics were concentrated and the residue purified by chromatography on silica eluting with DCM:MeOH (9:1) to afford the title compound as a yellow solid (47 mg, 76%);

$^1$H NMR (CDCl$_3$) δ 3.79 (s, 3H), 5.29 (s, 2H), 6.85 (s, 2H), 7.29-7.34 (m, 1H), 7.41-7.46 (m, 2H), 7.87 (s, 1H), 7.92 (s, 1H), 8.10-8.12 (m, 2H); MS m/e MH$^+$ 291.

EXAMPLE 73

6-[4-(2-Chlorophenyl)-1-methyl-1H-imidazol-5-yl]thieno[2,3-d]pyrimidin-4-amine 6-(4-Iodo-1-methyl-1H-imidazol-5-yl)thieno[2,3-d]pyrimidin-4-amine (Intermediate 95) (50 mg), 2-chlorophenylboronic acid (44 mg) and PdCl$_2$dppf (10 mg) in a solution of Na$_2$CO$_3$ (2M, aq.) (0.21 mL), EtOH (1.2 mL) and toluene (2 mL) were degassed and then heated at 80° C. under an inert atmosphere for 30 hours. The solvent was evaporated and the residue diluted with DCM (10 mL) and saturated aqueous NaHCO$_3$ (10 mL). The organic layer was separated and the aqueous layer extracted with DCM (10 mL). The combined organics were dried (MgSO$_4$), filtered and concentrated in vacuo. The crude product was purified by flash chromatography on silica eluting with DCM:MeOH (9:1) to afford the title compound as a yellow solid (15 mg, 31%);

$^1$H NMR (CDCl$_3$) δ 3.80 (s, 3H), 5.52 (bs, 2H), 7.01 (s, 1H), 7.22-7.27 (m, 2H), 7.34-7.42 (m, 2H), 7.66 (s, 1H), 8.43 (s, 1H); MS m/e MH$^+$ 342.

The starting materials were prepared as follows:

Intermediate 91

4-Methylthio-6-iodo-thieno[2,3-d]pyrimidine

Butyllithium (1.6 M in hexane, 32.8 mL) was added dropwise to a stirred solution of diisopropylamine (7.36 mL) in THF (170 mL) at −78° C. under an inert atmosphere. The reaction mixture was warmed to 0° C., stirred for 20 min, recooled to −78° C. and 4-(methylthio)thieno[2,3-d]pyrimidine (*J. Heterocycl. Chem.* 1975, 12, 921-924) (9.11 g) in THF (17 mL) added. A purple solution resulted and then iodine (19.0 g) in THF (20 mL) was added and stirring at −78° C. continued for 1 hours before warming to ambient temperature and stirring for a further 1.5 hr. Saturated aqueous NH$_4$Cl (3 mL), then water (500 mL) were added and the reaction mixture extracted with DCM (500 mL), the organic layer was washed with Na$_2$S$_2$O$_3$ (2M, aq) (2×50 mL), water (2×200 mL), dried (MgSO$_4$), filtered and concentrated in vacuo. The crude product was triturated with DCM (50 mL) to afford the title compound as a brown solid (11.8 g, 77%);

$^1$H NMR (CDCl$_3$) δ 2.70 (s, 3H), 7.60 (s, 1H), 8.74 (s, 1H); MS m/e MH$^+$ 309.

Intermediate 92

5-Tributylstannyl-4-iodo-1-methyl-1H-imidazole 4,5-Diiodo-1-methyl-1H-imidazole (40.0 g) was stirred in anhydrous THF (560 mL) at ambient temperature and ethylmagnesium bromide (3M in ether, 42.0 mL) was added over 20 minutes under an inert atmosphere. The resulting white precipitate was stirred for 30 minutes then tributyltin chloride (34.2 mL) added dropwise. The resulting clear solution was stirred for 1 hr, then saturated aqueous NH$_4$Cl (50 mL) and water (300 mL) were added. The reaction mixture was extracted with DCM (500 mL), washed with water (3×300 mL), dried (MgSO$_4$), filtered and concentrated in vacuo. The crude product was purified by flash chromatography on silica eluting with hexane:EtOAc (1:1) to afford the title compound as a colourless oil (45.1 g, 76%);

$^1$H NMR (CDCl$_3$) δ 0.89-0.95 (m, 9H), 1.21-1.29 (m, 6H), 1.30-1.40 (m, 6H), 1.51-1.60 (m, 6H), 3.66 (s, 3H), 7.45 (s, 1H); MS m/e MH$^+$ 499 ($^{120}$Sn), 497 ($^{118}$Sn), 495 ($^{116}$Sn).

Intermediate 93

6-(4-Iodo-1-methyl-1H-imidazol-5-yl)-4-methylthio-thieno[2,3-d]pyrimidine

4-Methylthio-6-iodo-thieno[2,3-d]pyrimidine (Intermediate 91) (949 mg), 5-tributylstannyl-4-iodo-1-methyl-1H-imidazole (Intermediate 92) (2.76 g) and tetrakis(triphenylphosphine)palladium(0) (178 mg) were stirred in anhydrous DMF (50 mL), degassed with nitrogen for 10 min, then heated to 100° C. for 18 hours under an inert atmosphere. The reaction mixture was concentrated in vacuo and the crude product triturated with DCM (20 mL) to afford the title compound as a yellow solid (805 mg, 67%);

$^1$H NMR (CDCl$_3$) δ 2.75 (s, 3H), 3.75 (s, 3H), 7.42 (s, 1H), 7.59 (s, 1H), 8.86 (s, 1H); MS m/e MH$^+$ 389.

Intermediate 94

6-(4-Iodo-1-methyl-1H-imidazol-5-yl)-4-(methylsulfonyl)thieno[2,3-d]pyrimidine

The title compound was prepared by a similar process to that described for Intermediate 17 but using 6-(4-iodo-1-methyl-1H-imidazol-5-yl)-4-(methylthio)thieno[2,3-d]pyrimidine (Intermediate 93) in place of 6-(1-methyl-4-phenyl-1H-imidazol-5-yl)-4-(methylthio)thieno[2,3-d]pyrimidine (example 7). Yellow solid (273 mg, 85%);

$^1$H NMR (CDCl$_3$) δ 3.46 (s, 3H), 3.82 (s, 3H), 7.63 (s, 1H), 8.10 (s, 1H), 9.20 (s, 1H); MS m/e MH$^+$ 421.

Intermediate 95

6-(4-iodo-1-methyl-1H-imidazol-5-yl)thieno[2,3-d]pyrimidin-4-amine

The title compound was prepared by a similar process to that described for Example 8 but using 6-(4-iodo-1-methyl-1H-imidazol-5-yl)-4-(methylsulfonyl)thieno[2,3-d]pyrimidine (Intermediate 94) in place of 6-(1-methyl-4-phenyl-1H-imidazol-5-yl)-4-(methylsulfonyl)thieno[2,3-d]pyrimidine (intermediate 17). Beige solid (143 mg, 85%);

$^1$H NMR (DMSO-D6) δ 3.72 (s, 3H), 7.66 (s, 2H), 7.73 (s, 1H), 7.88 (s, 1H), 8.32 (s, 1H); MS m/e MH$^+$ 358.

Examples 74 to Example 84 were prepared using the general method of Example 73 but using the appropriate boronic acid in place of 2-chlorophenylboronic acid.

EXAMPLE 74

6-[4-(3-Chlorophenyl)-1-methyl-1H-imidazol-5-yl]thieno[2,3-d]pyrimidin-4-amine

Beige solid (15 mg, 31%);
$^1$H NMR (CDCl$_3$) δ 3.61 (s, 3H), 5.43 (br s, 2H), 7.11 (1H, s), 7.15-7.18 (m, 2H), 7.35-7.38 (m, 1H), 7.65 (s, 1H), 7.70 (s, 1H), 8.54 (s, 1H); MS m/e MH$^+$ 342.

EXAMPLE 75

6-[4-(4-Chlorophenyl)-1-methyl-1H-imidazol-5-yl]thieno[2,3-d]pyrimidin-4-amine

Beige solid (12 mg, 25%); $^1$H NMR (CDCl$_3$) δ 3.58 (s, 3H), 5.63 (br s, 2H), 7.09 (1H, s), 7.22 (d, 2H), 7.51 (d, 2H), 7.64 (s, 1H), 8.53 (s, 1H); MS m/e MH$^+$ 342.

EXAMPLE 76

6-[1-Methyl-4-(2-naphthyl)-1H-imidazol-5-yl]thieno[2,3-d]pyrimidin-4-amine

Brown solid (18 mg, 36%); $^1$H NMR (CDCl$_3$) δ 3.55 (s, 3H), 5.63 (br s, 2H), 7.11 (1H, s), 7.39-7.76 (m, 7H), 8.14 (s, 1H), 8.53 (s, 1H); MS m/e MH$^+$ 358.

EXAMPLE 77

6-[4-(1-Benzothien-2-yl)-1-methyl-1H-imidazol-5-yl]thieno[2,3-d]pyrimidin-4-amine Beige solid (16 mg, 31%); $^1$H NMR (DMSO-D$_6$) δ 3.61 (s, 3H), 7.25-7.32 (m, 2H), 7.38 (s, 1H), 7.68 (br s, 2H), 7.73-7.75 (m, 1H), 7.82 (s, 1H), 7.87-7.89 (m, 1H), 7.97 (s, 1H), 8.37 (s, 1H); MS m/e MH$^+$ 364.

EXAMPLE 78

6-[4-(3-Fluorophenyl)-1-methyl-1H-imidazol-5-yl]thieno[2,3-d]pyrimidin-4-amine

Beige solid (23 mg, 50%); $^1$H NMR (CDCl$_3$) δ 3.59 (s, 3H), 5.53 (br s, 2H), 6.88-6.93 (m, 1H), 7.11 (s, 1H), 7.21 (td, 1H), 7.32-7.35 (m, 2H), 7.65 (s, 1H), 8.54 (s, 1H); MS m/e MH$^+$ 326.

EXAMPLE 79

6-[1-Methyl-4-(2-methylphenyl)-1H-imidazol-5-yl]thieno[2,3-d]pyrimidin-4-amine

Beige solid (17 mg, 38%); $^1$H NMR (CDCl$_3$) δ 2.19 (s, 3H), 3.79 (s, 3H), 5.36 (br s, 2H), 6.86 (1H, s), 7.11-7.14 (m, 1H), 7.18-7.26 (m, 3H), 7.64 (s, 1H), 8.43 (s, 1H); MS m/e MH$^+$ 322.

EXAMPLE 80

6-[4-(2,5-Difluorophenyl)-1-methyl-1H-imidazol-5-yl]thieno[2,3-d]pyrimidin-4-amine Beige solid (11 mg, 23%); $^1$H NMR (CDCl$_3$) δ 3.73 (s, 3H), 5.35 (br s, 2H), 6.91-6.97 (m, 2H), 7.01 (1H, s), 7.29-7.34 (m, 1H), 7.69 (s, 1H), 8.49 (s, 1H); MS m/e MH$^+$ 344.

EXAMPLE 81

6-[4-(2,5-Dichlorophenyl)-1-methyl-1H-imidazol-5-yl]thieno[2,3-d]pyrimidin-4-amine Green solid (9 mg, 17%); $^1$H NMR (CDCl$_3$) δ 3.80 (s, 3H), 5.41 (br s, 2H), 6.94 (1H, s), 7.22-7.30 (m, 2H), 7.48 (s, 1H), 7.68 (s, 1H), 8.46 (s, 1H); MS m/e MH$^+$ 376.

EXAMPLE 82

6-[1-Methyl-4-(1-naphthyl)-1H-imidazol-5-yl]thieno[2,3-d]pyrimidin-4-amine

Beige solid (18 mg, 36%); $^1$H NMR (CDCl$_3$) δ 3.79 (s, 3H), 5.39 (br s, 2H), 6.87 (1H, s), 7.33-7.47 (m, 4H), 7.71 (s, 1H), 7.78-7.84 (m, 2H), 8.07-8.10 (m, 1H), 8.46 (s, 1H); MS m/e MH$^+$ 358.

EXAMPLE 83

6-[4-(1H-Indol-5-yl)-1-methyl-1H-imidazol-5-yl]thieno[2,3-d]pyrimidin-4-amine

Beige solid (5 mg, 10%); $^1$H NMR (CDCl$_3$) δ 3.64 (s, 3H), 5.30 (br s, 2H), 6.49 (s, 1H), 7.10 (s, 1H), 7.18 (t, 1H), 7.30 (s, 1H), 7.41 (dt, 1H), 7.66 (s, 1H), 7.90 (s, 1H), 8.12 (s, 1H), 8.52 (s, 1H); MS m/e MH$^+$ 347.

EXAMPLE 84

6-{4-[4-(Benzyloxy)-2-methylphenyl]-1-methyl-1H-imidazol-5-yl}thieno[2,3-d]pyrimidin-4-amine Beige solid (14 mg, 23%); $^1$H NMR (CDCl$_3$) δ 2.15 (s, 3H), 3.76 (s, 3H), 5.04 (s, 2H), 5.50 (br s, 2H), 6.73 (dd, 1H), 6.82 (d, 1H), 6.90 (s, 1H), 7.15 (d, 1H), 7.31-7.43 (m, 5H), 7.61 (s, 1H), 8.42 (s, 1H); MS m/e MH$^+$ 428.

EXAMPLE 85

7-(Diisopropylamino)-2-(1-methyl-4-phenyl-1H-imidazol-5-yl)[1,3]thiazolo[5,4-d]pyrimidine-5-carbaldehyde A solution of 2-(1-methyl-4-phenyl-1H-imidazol-5-yl)-7-(methylthio)[1,3]thiazolo[5,4-d]pyrimidine (Intermediate 42) (0.1 g) in THF (4 mL) was added to a solution of LDA (2.2 eq) in THF (6 mL) at −78° C., under an inert atmosphere. The reaction mixture was stirred at −78° C. for 1 hours then DMF (0.4 mL) was added. The reaction mixture was stirred at −78° C. for a further 1 hours then poured into water (10 mL) and extracted with EtOAc (3×10 mL), washed with brine (10 mL), dried and the solvent evaporated in vacuo to give a brown oil. Purification by flash chromatography on silica, eluting with EtOAc:hexane (1:9) gave the title compound as a yellow oil (14 mg, 11%);

$^1$H NMR (CDCl$_3$) δ 1.32 (m, 12H), 3.65 (sept, 1H), 4.19 (s, 3H), 4.61 (sept, 1H), 7.35 (m, 3H), 7.57 (m, 2H), 7.68 (s, 1H), 9.91 (s, 1H); MS m/e MH$^+$ 421.

EXAMPLE 86

2-(2-{[2-(Dimethylamino)ethyl]thio}-1-methyl-4-phenyl-1H-imidazol-5-yl)[1,3]thiazolo[5,4-d]pyrimidin-7-amine A mixture of 5-(7-amino[1,3]thiazolo[5,4-d]pyrimidin-2-yl)-1-methyl-4-phenyl-1H-imidazole-2-thiol (Intermediate 47) (10 mg), N,N-diethyl-2-chloroethylamine hydrochloride (9 mg) and 2M NaOH (1 mL) was heated at 60° C. for 6 hours. After which the reaction mixture was cooled to ambient temperature and the title compound isolated by filtration as a yellow solid (6 mg, 50%);

$^1$H NMR (CDCl$_3$) δ 2.30 (s, 6H), 2.71 (t, 2H), 3.46 (t, 2H), 3.89 (s, 3H), 5.71 (bs, 2H), 7.38 (m, 3H), 7.51 (m, 2H), 8.39 (s, 1H); MS m/e MH$^+$ 412.

EXAMPLE 87

2-(1-Methyl-2-{[(methylthio)methyl]thio}-4-phenyl-1H-imidazol-5-yl)[1,3]thiazolo[5,4-d]pyrimidin-7-amine A mixture of 2-(2-bromo-1-methyl-4-phenyl-1H-imidazol-5-yl)[1,3]thiazolo[5,4-d]pyrimidin-7-amine (Example 26) (0.2 g), sodium thiomethoxide (0.14 g) and DMF (12 mL) was heated at 80° C., under an inert atmosphere, for 2 hours. The solvent was evaporated in vacuo, the residue dissolved in 1M NaOH (10 mL) then extracted into DCM (3×10 mL). The aqueous layer was acidified to pH 4 and extracted into EtOAc (3×10 mL). The organic layers were combined, dried and the solvent evaporated in vacuo to give a brown oil. Purification by flash chromatography on silica eluting with DCM:MeOH (9:1) gave the title compound as a yellow solid (26 mg, 15%);

$^1$H NMR (CDCl$_3$) δ 2.30 (s, 3H), 3.92 (s, 3H), 4.41 (s, 2H), 5.70 (bs, 2H), 7.40 (m, 3H), 7.52 (m, 2H), 8.41 (s, 1H); MS m/e MH$^+$ 401.

Examples 88 to Example 91 were prepared using the general method of Example 86 but using the appropriate alkyl halide in place of N,N-dimethyl-2-chloroethylamine hydrochloride.

EXAMPLE 88

2-(2-{[2-(1H-Imidazol-1-yl)ethyl]thio}-1-methyl-4-phenyl-1H-imidazol-5-yl)[1,3]thiazolo[5,4-d]pyrimidin-7-amine Yellow solid (9 mg, 99%); MS m/e MH$^+$ 435.

EXAMPLE 89

2-{1-Methyl-4-phenyl-2-[(pyridin-3-ylmethyl)thio]-1H-imidazol-5-yl}[1,3]thiazolo[5,4-d]pyrimidin-7-amine Yellow solid (8.5 mg, 99%); MS m/e MH$^+$ 432.

EXAMPLE 90

2-{2-[(Cyclopropylmethyl)thio]-1-methyl-4-phenyl-1H-imidazol-5-yl}[1,3]thiazolo[5,4-d]pyrimidin-7-amine Yellow solid (6.5 mg, 79%); MS m/e MH$^+$ 395.

EXAMPLE 91

2-[2-Benzylthio)-1-methyl-4-phenyl-1H-imidazol-5-yl][1,3]thiazolo[5,4-d]pyrimidin-7-amine Yellow solid (8.2 mg, 95%); MS m/e MH$^+$ 431.

EXAMPLE 92

2-[1-Methyl-2-(4-methylpiperazin-1-yl)-4-phenyl-1H-imidazol-5-yl][1,3]thiazolo[5,4-d]pyrimidin-7-amine A mixture of 2-(2-bromo-1-methyl-4-phenyl-1H-imidazol-5-yl)[1,3]thiazolo[5,4-d]pyrimidin-7-amine (Example 26) (0.02 g) and N-methylpiperazine (1 mL) were heated under microwave conditions (CEM explorer, 195° C., 1 hour). The solvent was evaporated in vacuo and the residue dissolved in EtOAc (10 mL), washed with water (2×10 mL), dried and the solvent evaporated in vacuo to give the title compound as a yellow solid (10 mg, 48%)

$^1$H NMR (CDCl$_3$) δ 2.39 (s, 3H), 2.63 (m, 4H), 3.29 (m, 4H), 3.78 (s, 3H), 5.72 (bs, 2H), 7.37 (m, 3H), 7.51 (m, 2H), 8.38 (s, 1H); MS m/e MH$^+$ 401.

EXAMPLE 93

2-{2-[(1-Aminocyclohexyl)ethynyl]-1-methyl-4-phenyl-1H-imidazol-5-yl}[1,3]thiazolo[5,4-d]pyrimidin-7-amine A mixture of 2-(2-bromo-1-methyl-4-phenyl-1H-imidazol-5-yl)[1,3]thiazolo[5,4-d]pyrimidin-7-amine (Example 26) (0.02 g), PdCl$_2$dppf (3.5 mg), triethylamine (0.1 mL), DMF (5 mL), copper(I) iodide (1 mg) and 1-ethynylcyclohexylamine (0.034 mL) was heated at 90° C., under an inert atmosphere, for 1.5 hours. The solvent was evaporated in vacuo then purification by flash chromatography on silica eluting with DCM:MeOH (9:1) gave the title compound as a beige solid (9 mg, 41%).

$^1$H NMR (CDCl$_3$) δ 1.30-2.10 (m, 10H), 4.08 (s, 3H), 5.80 (bs, 2H), 7.40 (m, 3H), 7.51 (m, 2H), 8.41 (s, 1H); MS m/e MH$^+$ 430.

Examples 94 to Example 98 were prepared using the general method of Example 93 but using the appropriate substituted alkyne in place of 1-ethynylcyclohexylamine

EXAMPLE 94

4-[5-(7-Amino[1,3]thiazolo[5,4-d]pyrimidin-2-yl)-1-methyl-phenyl-1H-imidazol-2-yl]but-3-yn-2-ol Yellow solid (2 mg, 9%); $^1$H NMR (CDCl$_3$) δ 1.61 (d, 3H), 2.25 (bs, 1H), 4.01 (s, 3H), 4.83 (m, 1H), 5.73 (bs, 2H), 7.40 (m, 3H), 7.51 (m, 2H), 8.42 (s, 1H); MS m/e MH$^+$ 377.

EXAMPLE 95

1-{[5-(7-Amino[1,3]thiazolo[5,4-d]pyrimidin-2-yl)-1-methyl-4-phenyl-1H-imidazol-2-yl]ethynyl}cyclohexanol Beige solid (7 mg, 29%); $^1$H NMR (CDCl$_3$) δ 1.50-1.81 (m, 8H), 2.09 (m, 2H), 2.54 (bs, 1H), 4.01 (s, 3H), 5.81 (bs, 2H), 7.38 (m, 3H), 7.51 (m, 2H), 8.41 (s, 1H); MS m/e MH$^+$ 431.

EXAMPLE 96

2-[1-Methyl-4-phenyl-2-(pyridin-2-ylethynyl)-1H-imidazol-5-yl][1,3]thiazolo[5,4-d]pyrimidin-7-amine Beige solid (9.4 mg, 44%); $^1$H NMR (CDCl$_3$) δ 4.17 (s, 3H), 5.81 (bs, 2H), 7.32 (m, 1H), 7.39 (m, 3H), 7.57 (m, 2H), 7.62 (d, 1H), 7.75 (t, 1H), 8.42 (s, 1H), 8.68 (s, 1H); MS m/e MH$^+$ 410.

EXAMPLE 97

2-[2-(3-Amino-3-methylbut-1-yn-1-yl)-1-methyl-4-phenyl-1H-imidazol-5-yl][1,3]thiazolo[5,4-d]pyrimidin-7-amine Yellow solid (7 mg, 33%); $^1$H NMR (CDCl$_3$) δ 1.40 (s, 6H), 4.01 (s, 3H), 5.76 (bs, 2H), 7.40 (m, 3H), 7.52 (m, 2H), 8.42 (s, 1H); MS m/e MH$^+$ 390.

EXAMPLE 98

2-[2-(3-Methoxyprop-1-yn-1-yl)-1-methyl-4-phenyl-1H-imidazol-5-yl][1,3]thiazolo[5,4-d]pyrimidin-7-amine Beige solid (9 mg, 45%); $^1$H NMR (CDCl$_3$) δ 3.51 (s, 3H), 4.04 (s, 3H), 4.43 (s, 2H), 5.91 (bs, 2H), 7.39 (m, 3H), 7.54 (m, 2H), 8.42 (s, 1H); MS m/e MH$^+$ 377.

EXAMPLE 99

2-(1-Methyl-2-morpholin-4-yl-4-phenyl-1H-imidazol-5-yl)[1,3]thiazolo[5,4-d]pyrimidin-7-amine The title compound was prepared by a similar process to that described for Example 92 but using morpholine in place of N-methylpiperazine. White solid (7 mg, 33%);
$^1$H NMR (CDCl$_3$) δ 3.25 (m, 4H), 3.81 (s, 3H), 3.90 (m, 4H), 5.63 (bs, 2H), 7.39 (m, 3H), 7.52 (m, 2H), 8.39 (s, 1H); MS m/e MH$^+$ 394.

EXAMPLE 100

2-(1-Methyl-4-phenyl-2-pyrimidin-5-yl-1H-imidazol-5-yl)[1,3]thiazolo[5,4-d]pyrimidin-7-amine The title compound was prepared by a similar process to that described for Example 35 but using 5-pyrimidyl boronic acid in place of pyridine-4-boronic acid. Colourless solid (6 mg, 15%);
MS m/e MH$^+$ 387.

EXAMPLE 101

2-{2-[3-(Dimethylamino)prop-1-yn-1-yl]-1-methyl-4-phenyl-1H-imidazol-5-yl}[1,3]thiazolo[5,4-d]pyrimidin-7-amine The title compound was prepared by a similar process to that described for Intermediate 45 but using 1-dimethylamino-2-propyne in place of trimethylsilyl acetylene. Colourless solid (25 mg, 64%);
$^1$H NMR (DMSO-d$_6$) δ 2.28 (s, 6H), 3.54 (s, 2H), 3.89 (s, 3H), 7.31-7.40 (m, 3H), 7.42-7.50 (m, 2H), 7.74 (bs, 2H), 8.23 (s, 1H). MS m/e MH$^+$ 390.

EXAMPLE 102 tert-Butyl 4-[5-(7-amino[1,3]thiazolo[5,4-d]pyrimidin-2-yl)-1-methyl-4-phenyl-1H-imidazol-2-yl]-3,6-dihydropyridine-1(2H)-carboxylate The title compound was prepared by a similar process to that described for Example 35 but using tert-butyl 4-(4,4,5,5-tetramethyl-1,3,2-dioxaborolan-2-yl)-3,6-dihydropyridine-1(2H)-carboxylate (Tetrahedron Lett., 2000, 41, 3705) in place of pyridine-4-boronic acid. Pale yellow foam (60 mg, 56%);
$^1$H NMR (DMSO-d$_6$) δ 1.46 (s, 9H), 2.58 (bs, 2H), 3.58 (m, 2H), 3.85 (s, 3H), 4.10 (bs, 2H), 6.23 (bs, 1H), 7.31-7.41 (m, 3H), 7.47-7.53 (m, 2H), 7.78 (bs, 2H), 8.29 (s, 1H). MS m/e MH$^+$ 490.

EXAMPLE 103

2-[1-Methyl-4-phenyl-2-(1,2,3,6-tetrahydropyridin-4-yl)-1H-imidazol-5-yl][1,3]thiazolo[5,4-d]pyrimidin-7-amine tert-Butyl 4-[5-(7-amino[1,3]thiazolo[5,4-d]pyrimidin-2-yl)-1-methyl-4-phenyl-1H-imidazol-2-yl]-3,6-dihydropyridine-1(2H)-carboxylate (Example 102) (20 mg) was dissolved in DCM (0.5 mL), TFA (2 mL) added, stirred at ambient temperature for 2 hours then concentrated in vacuo. The residue was diluted with saturated aqueous sodium bicarbonate, extracted with DCM (2×5 mL), organics dried, filtered and concentrated in vacuo. Purification by flash chromatography on silica gel eluting with 10% MeOH/DCM gave the title compound as a colourless solid (11 mg, 69%);
MS m/e MH$^+$ 390.

EXAMPLE 104

[5-(7-Amino[1,3]thiazolo[5,4-d]pyrimidin-2-yl)-1-methyl-4-phenyl-1H-imidazol-2-yl](phenyl)methanol

[5-(7-Amino[1,3]thiazolo[5,4-d]pyrimidin-2-yl)-1-methyl-4-phenyl-1H-imidazol-2-yl](phenyl)methyl dimethylcarbamate (Intermediate 97) (25 mg) was dissolved in THF (4 mL), TFA (0.1 mL) and water (0.1 mL) added then heated at reflux under an inert atmosphere. After 2 hours, cooled to ambient temperature, diluted with EtOAc (10 mL), washed with saturated aqueous NaHCO$_3$ (10 mL), organic layer dried (MgSO$_4$), filtered and concentrated in vacuo. Residue was purified by flash chromatography on silica eluting with 4% MeOH/DCM to give the title compound as a colourless foam (21 mg, 99%);

$^1$H NMR (DMSO-d$_6$) δ 3.72 (s, 3H), 6.06 (d, 1H), 6.47 (d, 1H, (exchangeable)), 7.24-7.76 (m, 9H), 7.74 (bs, 2H), 7.85 (m, 1H), 8.26 (s, 1H). MS m/e MH$^+$ 415.

The starting materials used were prepared as follows:

Intermediate 96

N-Benzoyl-N-[2-(1-methyl-4-phenyl-1H-imidazol-5-yl)[1,3]thiazolo[5,4-d]pyrimidin-7-yl]benzamide 2-(1-Methyl-4-phenyl-1H-imidazol-5-yl)[1,3]thiazolo[5,4-d]pyrimidin-7-amine (Example 2) (0.56 g) was dissolved in pyridine (10 mL), benzoyl chloride (0.44 mL) and triethylamine (0.28 mL) added then stirred at ambient temperature under an inert atmosphere. After 4 hours saturated aqueous NaHCO$_3$ (10 mL) was added, the reaction mixture filtered, washed with water, EtOAc, diethyl ether and dried under high-vacuum to give the title compound as a colourless solid (0.63 g, 68%);

$^1$H NMR (DMSO-d$_6$) δ 3.66 (s, 3H), 7.56-7.68 (m, 9H), 7.71-7.79 (m, 2H), 7.95 (m, 4H), 8.08 (s, 1H), 8.89 (s, 1H).

Intermediate 97

[5-(7-Amino[1,3]thiazolo[5,4-d]pyrimidin-2-yl)-1-methyl-4-phenyl-1H-imidazol-2-yl](phenyl)methyl dimethylcarbamate N-Benzoyl-N-[2-(1-methyl-4-phenyl-1H-imidazol-5-yl)[1,3]thiazolo[5,4-d]pyrimidin-7-yl]benzamide (Intermediate 96) (0.05 g) was dissolved/suspended in MeCN (5 mL), dimethylcarbamyl chloride (0.015 mL) added, then benzaldehyde (16 mg) and DIPEA (0.05 mL). The reaction mixture was heated at reflux for 24 hours then additional dimethylcarbamyl chloride (0.015 mL), benzaldehyde (16 mg) and DIPEA (0.05 mL) added. After heating for 5 days, the reaction mixture was concentrated in vacuo, diluted with saturated NaHCO$_3$ solution (5 mL) then extracted with DCM (2×10 mL). The combined organics were dried (MgSO$_4$), filtered and concentrated in vacuo to give a brown residue which was dissolved in MeOH (2 mL)/concentrated aqueous NH$_3$ (2 mL). The reaction mixture was heated at 55° C. for 1 hours then concentrated in vacuo, diluted with 2M NaOH (8 mL) and extracted with DCM (1×20 mL). The organic layer was dried (MgSO$_4$), filtered, concentrated in vacuo giving a residue which was purified by flash chromatography on silica (2% MeOH/DCM) to give the title compound as a colourless solid (0.033 g, 68%);

$^1$H NMR (DMSO-d$_6$) δ 2.84 (s, 3H), 2.99 (s, 3H), 3.81 (s, 3H), 6.96 (s, 1H), 7.26-7.53 (m, 8H), 7.78 (bs, 2H), 7.85 (m, 2H), 8.26 (s, 1H). MS m/e MH$^+$ 486.

EXAMPLE 105

[5-(7-Amino[1,3]thiazolo[5,4-d]pyrimidin-2-yl)-1-methyl-4-phenyl-1H-imidazol-2-yl](cyclopropyl)methanol The title compound was prepared by a similar process to that described for Example 104 but using [5-(7-amino[1,3] thiazolo[5,4-d]pyrimidin-2-yl)-1-methyl-4-phenyl-1H-imidazol-2-yl](cyclopropyl)methyl dimethylcarbamate. (Intermediate 98) in place of [5-(7-amino[1,3]thiazolo[5,4-d] pyrimidin-2-yl)-1-methyl-4-phenyl-1H-imidazol-2-yl] (phenyl)methyl dimethylcarbamate (Intermediate 97). Colourless solid (6 mg, 66%);

MS m/e MH$^+$ 379.

The starting materials used were prepared as follows:

Intermediate 98

[5-(7-Amino[1,3]thiazolo[5,4-d]pyrimidin-2-yl)-1-methyl-4-phenyl-1H-imidazol-2-yl](cyclopropyl) methyl dimethylcarbamate The title compound was prepared by a similar process to that described for Intermediate 97 but using cyclopropanecarboxaldehyde in place of benzaldehyde. Colourless gum (14 mg, 68%);

$^1$H NMR (CDCl$_3$) δ 0.42-0.50 (m, 1H), 0.61-0.76 (m, 3H), 1.86 (m, 1H), 2.83 (s, 3H), 2.98 (s, 3H), 3.96 (s, 3H), 5.26 (d, 1H), 5.74 (bs, 2H), 7.31-7.38 (m, 3H), 7.49-7.56 (m, 2H), 8.43 (s, 1H). MS m/e MH$^+$ 450.

EXAMPLE 106

[5-(7-Amino[1,3]thiazolo[5,4-d]pyrimidin-2-yl)-1-methyl-4-phenyl-1H-imidazol-2-yl](1,3-benzodioxol-4-yl)methanol The title compound was prepared by a similar process to that described for Example 104 but using [5-(7-amino[1,3] thiazolo[5,4-d]pyrimidin-2-yl)-1-methyl-4-phenyl-1H-imidazol-2-yl](1,3-benzodioxol-4-yl)methyl dimethylcarbamate (Intermediate 99) in place of [5-(7-amino[1,3]thiazolo[5, 4-d]pyrimidin-2-yl)-1-methyl-4-phenyl-1H-imidazol-2-yl] (phenyl)methyl dimethylcarbamate (Intermediate 97). Colourless solid (5 mg, 54%);

MS m/e MH$^+$ 459.

The starting materials used were prepared as follows:

Intermediate 99

[5-(7-Amino[1,3]thiazolo[5,4-d]pyrimidin-2-yl)-1-methyl-4-phenyl-1H-imidazol-2-yl](1,3-benzodioxol-4-yl)methyl dimethylcarbamate The title compound was prepared by a similar process to that described for Intermediate 97 but using 2,3-(methylenedioxy)benzaldehyde in place of benzaldehyde. Pale yellow oil (65 mg, 82%);

$^1$H NMR (CDCl$_3$) δ 2.95 (s, 3H), 3.06 (s, 3H), 4.01 (s, 3H), 5.74 (bs, 2H), 5.99 (d, 2H), 6.80 (m, 1H), 6.87 (m, 1H), 7.13 (s, 1H), 7.20 (d, 1H), 7.29-7.35 (m, 3H), 7.32-7.53 (m, 2H), 8.42 (s, 1H). MS m/e MH$^+$ 530.

EXAMPLE 107

1-[5-(7-Amino[1,3]thiazolo[5,4-d]pyrimidin-2-yl)-1-methyl-4-phenyl-1H-imidazol-2-yl]-3-methylbutan-1-ol The title compound was prepared by a similar process to that described for Example 104 but using 1-[5-(7-amino[1,3] thiazolo[5,4-d]pyrimidin-2-yl)-1-methyl-4-phenyl-1H-imidazol-2-yl]-3-methylbutyl dimethylcarbamate (Intermediate 100) in place of [5-(7-amino[1,3]thiazolo[5,4-d]pyrimidin-2- yl)-1-methyl-4-phenyl-1H-imidazol-2-yl](phenyl)methyl dimethylcarbamate (Intermediate 97). Colourless solid (5 mg, 63%);
MS m/e MH+ 394.
The starting materials used were prepared as follows:

Intermediate 100

1-[5-(7-Amino[1,3]thiazolo[5,4-d]pyrimidin-2-yl)-1-methyl-4-phenyl-1H-imidazol-2-yl]-3-methylbutyl dimethylcarbamate The title compound was prepared by a similar process to that described for Intermediate 97 but using isovaleraldehyde in place of benzaldehyde. Pale yellow oil (54 mg, 77%);
MS m/e MH+ 466.

EXAMPLE 108

[5-(7-Amino[1,3]thiazolo[5,4-d]pyrimidin-2-yl)-1-methyl-4-phenyl-1H-imidazol-2-yl](1-methyl-1H-imidazol-2-yl)methanol The title compound was prepared by a similar process to that described for Example 104 but using [5-(7-amino[1,3]thiazolo[5,4-d]pyrimidin-2-yl)-1-methyl-4-phenyl-1H-imidazol-2-yl](1-methyl-1H-imidazol-2-yl)methyl dimethylcarbamate (Intermediate 101) in place of [5-(7-amino[1,3]thiazolo[5,4-d]pyrimidin-2-yl)-1-methyl-4-phenyl-1H-imidazol-2-yl](phenyl)methyl dimethylcarbamate (Intermediate 97). Colourless solid (20 mg, 82%);
$^1$H NMR (DMSO-$d_6$) δ 3.77 (s, 3H), 3.92 (s, 3H), 6.24 (s, 1H), 6.93 (m, 1H), 7.26 (m, 1H), 7.31-7.39 (m, 3H), 7.41-7.47 (m, 2H), 7.82 (bs, 2H), 8.27 (s, 1H). MS m/e MH+ 419.
The starting materials used were prepared as follows:

Intermediate 101

[5-(7-Amino[1,3]thiazolo[5,4-d]pyrimidin-2-yl)-1-methyl-4-phenyl-1H-imidazol-2-yl](1-methyl-1H-imidazol-2-yl)methyl dimethylcarbamate The title compound was prepared by a similar process to that described for Intermediate 97 but using 1-methyl-2-imidazolecarboxaldehyde in place of benzaldehyde. Pale yellow oil (33 mg, 46%);
$^1$H (DMSO-$d_6$) δ 2.86 (s, 3H), 2.97 (s, 3H), 3.77 (s, 3H), 3.93 (s, 3H), 6.86 (s, 1H), 7.08 (s, 1H), 7.30-7.39 (m, 3H), 7.40-7.47 (m, 2H), 7.82 (bs, 2H), 8.29 (s, 1H). MS m/e MH+ 491.

EXAMPLE 109

6-[1-(Cyclohexylmethyl)-4-phenyl-1H-imidazol-5-yl]-thieno[2,3-d]pyrimidin-4-amine The title compound was prepared using the general method of Example 56 and Intermediate 70 but replacing ethylamine with the cyclohexylmethylamine. Solid (20 mg, 19%);
$^1$H NMR (DMSO-d6) 0.70-1.70 (m, 11H), 3.77 (d, 2H), 7.18 (t, 1H), 7.26 (t, 2H), 7.50 (d, 2H), 7.60 (s, br, 2H), 7.61 (s, 1H), 7.92 (s, 1H), 8.32 (s, 1H); MS m/e MH+ 390.

EXAMPLE 110

6-[1-[3-(4-Methyl-1-piperazinyl)propyl]-4-phenyl-1H-imidazol-5-yl]-thieno[2,3-d]pyrimidin-4-amine The title compound was prepared using the general method of Example 65 but replacing 3-aminopyrrolidine with 1-(3-aminopropyl)-4-methylpiperazine and using piperazine in place of morpholine. Solid (38 mg, 35%);
MS m/e MH+ 434.

EXAMPLE 111

6-[1-[3-(Hexahydro-1H-azepin-1-yl)propyl]-4-phenyl-1H-imidazol-5-yl]-thieno[2,3-d]pyrimidin-4-ol The title compound was prepared using the general method of Example 65 but replacing 3-aminopyrrolidine with 3-hexamethyleneimino-1-propylamine and using piperazine in place of morpholine. Solid (17 mg, 16%);
MS m/e MH+ 434.

Examples 112 to Example 169 were prepared using the general method of Example 65 but replacing 3-aminopyrrolidine with the appropropriate amine and using THF, DMA or DMSO as solvent (sol.).

| Example | Compound name | sol. | MH+ | $^1$H NMR (DMSO-d6) |
|---|---|---|---|---|
| Example 112 | 6-[4-phenyl-1-(tetrahydro-2,2-dimethyl-2H-pyran-4-yl)-1H-imidazol-5-yl]-thieno[2,3-d]pyrimidin-4-amine | THF | 406 | |
| Example 113 | 5-(4-aminothieno[2,3-d]pyrimidin-6-yl)-beta-methyl-4-phenyl-1H-imidazole-1-ethanol | THF | 352 | |
| Example 114 | 6-[1-(2-methoxy-1-methylethyl)-4-phenyl-1H-imidazol-5-yl]thieno[2,3-d]pyrimidin-4-amine | THF | 366 | |
| Example 115 | 6-[1-(1-methylethyl)-4-phenyl-1H-imidazol-5-yl]-thieno[2,3-d]pyrimidin-4-amine | THF | 336 | |
| Example 116 | 6-[1-(1,2-dimethylpropyl)-4-phenyl-1H-imidazol-5-yl]-thieno[2,3-d]pyrimidin-4-amine | THF | 364 | |
| Example 117 | 6-[1-(1,3-dimethylbutyl)-4-phenyl-1H-imidazol-5-yl]-thieno[2,3-d]pyrimidin-4-amine | THF | 378 | |

-continued

| Example | Compound name | sol. | MH+ | ¹H NMR (DMSO-d6) |
|---|---|---|---|---|
| Example 118 | 6-[1-(1-methylpropyl)-4-phenyl-1H-imidazol-5-yl]-thieno[2,3-d]pyrimidin-4-amine | THF | 350 | |
| Example 119 | 6-[4-phenyl-1-(2-propenyl)-1H-imidazol-5-yl]-thieno[2,3-d]pyrimidin-4-amine | THF | 334 | |
| Example 120 | 6-[4-phenyl-1-(2,2,6,6-tetramethyl-4-piperidinyl)-1H-imidazol-5-yl]-thieno[2,3-d]pyrimidin-4-amine | THF | 433 | |
| Example 121 | 4-[5-(4-aminothieno[2,3-d]pyrimidin-6-yl)-4-phenyl-1H-imidazol-1-yl]-cyclohexanol | THF | 392 | |
| Example 122 | 6-[4-phenyl-1-[(tetrahydro-2-furanyl)methyl]-1H-imidazol-5-yl]-thieno[2,3-d]pyrimidin-4-amine | THF | 378 | |
| Example 123 | 6-[1-[2-(4-morpholinyl)ethyl]-4-phenyl-1H-imidazol-5-yl]-thieno[2,3-d]pyrimidin-4-amine | THF | 407 | |
| Example 124 | 6-[1-[4-(diethylamino)-1-methylbutyl]-4-phenyl-1H-imidazol-5-yl]-thieno[2,3-d]pyrimidin-4-amine | THF | 435 | |
| Example 125 | 6-[1-[(2-fluorophenyl)methyl]-4-phenyl-1H-imidazol-5-yl]-thieno[2,3-d]pyrimidin-4-amine | THF | 402 | |
| Example 126 | 6-[1-[(2-methylphenyl)methyl]-4-phenyl-1H-imidazol-5-yl]-thieno[2,3-d]pyrimidin-4-amine | THF | 398 | |
| Example 127 | 6-[1-[(3-fluorophenyl)methyl]-4-phenyl-1H-imidazol-5-yl]-thieno[2,3-d]pyrimidin-4-amine | THF | 402 | |
| Example 128 | 5-(4-aminothieno[2,3-d]pyrimidin-6-yl)-alpha-methyl-4-phenyl-1H-imidazole-1-ethanol | THF | 352 | |
| Example 129 | 3-[5-(4-aminothieno[2,3-d]pyrimidin-6-yl)-4-phenyl-1H-imidazol-1-yl]-1,2-propanediol | THF | 368 | |
| Example 130 | 6-[1-(2-methylbutyl)-4-phenyl-1H-imidazol-5-yl]-thieno[2,3-d]pyrimidin-4-amine | THF | 364 | |
| Example 131 | 6-[4-phenyl-1-[2-(phenylamino)ethyl]-1H-imidazol-5-yl]-thieno[2,3-d]pyrimidin-4-amine | THF | 413 | |
| Example 132 | 5-(4-aminothieno[2,3-d]pyrimidin-6-yl)-4-phenyl-1H-imidazole-1-propanol | THF | 352 | |
| Example 133 | 6-[1-[3-(dimethylamino)-2,2-dimethylpropyl]-4-phenyl-1H-imidazol-5-yl]-thieno[2,3-d]pyrimidin-4-amine | THF | 407 | |
| Example 134 | 6-[1-(2-methyl-2-propenyl)-4-phenyl-1H-imidazol-5-yl]-thieno[2,3-d]pyrimidin-4-amine | THF | 348 | |
| Example 135 | N-[2-[5-(4-aminothieno[2,3-d]pyrimidin-6-yl)-4-phenyl-1H-imidazol-1-yl]ethyl]-4-hydroxy-benzeneacetamide | THF | 471 | |
| Example 136 | 6-[1-(2-methoxy-2-methylpropyl)-4-phenyl-1H-imidazol-5-yl]-thieno[2,3-d]pyrimidin-4-amine | THF | 380 | |
| Example 137 | 6-[4-phenyl-1-(spiro[bicyclo[2.2.1]hept-2-ene-7,1'-cyclopropan]-5-ylmethyl)-1H-imidazol-5-yl]-thieno[2,3-d]pyrimidin-4-amine | THF | 426 | |
| Example 138 | 6-[1-[2-(3,5-dimethyl-1H-pyrazol-4-yl)ethyl]-4-phenyl-1H-imidazol-5-yl]-thieno[2,3-d]pyrimidin-4-amine | THF | 416 | |
| Example 139 | 6-[1-[2-(1H-imidazol-1-yl)ethyl]-4-phenyl-1H-imidazol-5-yl]-thieno[2,3-d]pyrimidin-4-amine | THF | 388 | |
| Example 140 | 6-[1-[2-[[(4-fluorophenyl)methyl]amino]ethyl]-4-phenyl-1H-imidazol-5-yl]-thieno[2,3-d]pyrimidin-4-amine | THF | 446 | |

-continued

| Example | Compound name | sol. | MH+ | ¹H NMR (DMSO-d6) |
|---|---|---|---|---|
| Example 141 | 6-[1-[(3,4-dihydro-1H-2-benzopyran-1-yl)methyl]-4-phenyl-1H-imidazol-5-yl]-thieno[2,3-d]pyrimidin-4-amine | THF | 440 | |
| Example 142 | 6-[1-[2-(methylsulfonyl)ethyl]-4-phenyl-1H-imidazol-5-yl]-thieno[2,3-d]pyrimidin-4-amine | THF | 400 | |
| Example 143 | N-[2-[5-(4-aminothieno[2,3-d]pyrimidin-6-yl)-4-phenyl-1H-imidazol-1-yl]ethyl]-2-[(2-chloro-3-pyridinyl)oxy]-acetamide | THF | 505, 507 | |
| Example 144 | 6-[4-phenyl-1-[2-[(tetrahydro-1,1-dioxido-3-thienyl)amino]ethyl]-1H-imidazol-5-yl]-thieno[2,3-d]pyrimidin-4-amine | THF | 455 | |
| Example 145 | 5-(4-aminothieno[2,3-d]pyrimidin-6-yl)-4-phenyl-alpha-(trifluoromethyl)-1H-imidazole-1-ethanol | THF | 406 | |
| Example 146 | 5-(4-aminothieno[2,3-d]pyrimidin-6-yl)-4-phenyl-alpha-[3-(trifluoromethyl)phenyl]-1H-imidazole-1-ethanol | THF | 482 | |
| Example 147 | 6-[4-phenyl-1-[2-(2-propenylamino)ethyl]-1H-imidazol-5-yl]-thieno[2,3-d]pyrimidin-4-amine | THF | 377 | |
| Example 148 | N-[5-[5-(4-aminothieno[2,3-d]pyrimidin-6-yl)-4-phenyl-1H-imidazol-1-yl]pentyl]-4-morpholinecarboxamide | THF | 492 | |
| Example 149 | 5-(4-aminothieno[2,3-d]pyrimidin-6-yl)-alpha-(2,3-dihydro-1,4-benzodioxin-6-yl)-4-phenyl-1H-imidazole-1-ethanol | THF | 472 | |
| Example 150 | 6-[1-[3-[4-(2-methoxyphenyl)-1-piperazinyl]propyl]-4-phenyl-1H-imidazol-5-yl]-thieno[2,3-d]pyrimidin-4-amine | THF | 526 | |
| Example 151 | N'-[2-[5-(4-aminothieno[2,3-d]pyrimidin-6-yl)-4-phenyl-1H-imidazol-1-yl]ethyl]-N,N-dimethyl-sulfamide | THF | 444 | |
| Example 152 | 6-[1-[6-(8-oxa-3-azabicyclo[3.2.1]oct-3-yl)hexyl]-4-phenyl-1H-imidazol-5-yl]-thieno[2,3-d]pyrimidin-4-amine | THF | 489 | |
| Example 153 | 6-[1-[[2-4-morpholinyl)phenyl]methyl]-4-phenyl-1H-imidazol-5-yl]-thieno[2,3-d]pyrimidin-4-amine | THF | 469 | 2.45-2.50(m, 4H), 4.06-4.10(m, 4H), 5.36(s, 2H), 6.90(dd, 1H), 6.96(d, 1H), 7.03(t, 1H), 7.21-7.38(m, 4H), 7.44(s, 1H), 7.46-7.52(m, 2H), 7.83(s, br, 2H), 8.29(s, 1H), 8.96(s, 1H); |
| Example 154 | 6-[1-(1,4-dioxan-2-ylmethyl)-4-phenyl-1H-imidazol-5-yl]-thieno[2,3-d]pyrimidin-4-amine | THF | 394 | 3.17(dd, 1H), 3.43(dt, 1H), 3.53(dt, 1H), 3.63(dd, 2H), 3.69-3.76(m, 2H), 3.90-4.00(m, 2H), 7.19(t, 1H), 7.27(t, 2H), 7.50(d, 2H), 7.61(s, br, 2H), 7.65(s, 1H), 7.91(s, 1H), 8.33(s, 1H) |
| Example 155 | 2-[[5-(4-aminothieno[2,3-d]pyrimidin-6-yl)-4-phenyl-1H-imidazol-1-yl]methyl]-,(1S,2R)-cyclohexanol | THF | 406 | 0.70-1.20(m, 5H), 1.32-1.54(m, 3H), 1.64-1.70(m, 1H), 2.92-2.96(m, 1H), 3.58(dd, 1H), 4.24(dd, 1H), 4.53(s, br, 1H), 7.07(t, 1H), 7.16(t, 2H), 7.40(d, 2H), 7.48(s, br, 2H), 7.53(s, 1H), 7.78(s, 1H), 7.78(s, 1H), 8.21(s, 1H); |
| Example 156 | 6-[1-(cycloheptylmethyl)-4-phenyl-1H-imidazol-5-yl]-thieno[2,3-d]pyrimidin-4-amine | THF | 404 | 1.03-1.85(m, 13H), 3.76(d, 2H) 7.18(t, 1H), 7.27(t, 2H), 7.51(d, 2H), 7.61(s, br, 2H), 7.64(s, 1H), 7.94(s, 1H), 8.32(s, 1H); |

-continued

| Example | Compound name | sol. | MH+ | $^1$H NMR (DMSO-d6) |
|---|---|---|---|---|
| Example 157 | 6-[1-[[(1S,5S)-6,6-dimethylbicyclo[3.1.1]hept-2-yl]methyl]-4-phenyl-1H-imidazol-5-yl]-thieno[2,3-d]pyrimidin-4-amine | THF | 430 | 0.70-2.30(m, 17H), 3.92(d, 2H), 7.18(t, 1H), 7.28(t, br, 2H), 6.76(s, 1H), 8.00(s, 1H), 8.32(s, 1H); |
| Example 158 | 1-[[5-(4-aminothieno[2,3-d]pyrimidin-6-yl)-4-phenyl-1H-imidazol-1-yl]methyl]-cyclohexaneacetic acid | THF | 448 | 1.07-1.51(m, 10H), 2.25(s, 2H), 4.23(s, 2H), 7.26(t, 1H), 7.35(t, 2H), 7.56(d, 2H), 7.68(s, br, 2H), 7.76(s, 1H), 8.12(s, 1H), 8.39(s, 1H), CO2H exchanges into baseline; |
| Example 159 | 6-[4-phenyl-1-(phenylmethyl)-1H-imidazol-5-yl]-thieno[2,3-d]pyrimidin-4-amine | DMSO | 384 | 5.33(s, 2H), 7.07(dd, 2H), 7.26-7.38(m, 6H), 7.51(d, 2H), 7.66(s, 1H), 7.87(s, br, 2H), 8.35(s, 1H), 8.79(s, 1H); |
| Example 160 | 6-[1-[(2-methoxyphenyl)methyl]-4-phenyl-1H-imidazol-5-yl]-thieno[2,3-d]pyrimidin-4-amine | DMA | 414 | 3.65(s, 3H), 5.22(s, 2H), 6.84-6.87(m, 2H), 6.96(d, 1H), 7.26-7.40(m, 4H), 7.50-7.57(m, 2H), 7.65(s, 1H), 7.78(s, br, 2H), 8.34(s, 1H), 8,59(s, 1H); |
| Example 161 | 6-[4-phenyl-1-[[2-(1-piperidinyl)phenyl]methyl]-1H-imidazol-5-yl]-thieno[2,3-d]pyrimidin-4-amine | DMA | 467 | |
| Example 162 | 6-[4-phenyl-1-[[2-(2-pyridinyloxy)phenyl]methyl]-1H-imidazol-5-yl]-thieno[2,3-d]pyrimidin-4-amine | DMA | 477 | |
| Example 163 | 6-[1-[[2-(4-methyl-1-piperazinyl)phenyl]methyl]-4-phenyl-1H-imidazol-5-yl]-thieno[2,3-d]pyrimidin-4-amine | DMA | 482 | |
| Example 164 | 1-[2-[[5-(4-aminothieno[2,3-d]pyrimidin-6-yl)-4-phenyl-1H-imidazol-1-yl]methyl]phenyl]-4-piperidinemethanol | DMA | 497 | |
| Example 165 | 6-[1-[(2-aminophenyl)methyl]-4-phenyl-1H-imidazol-5-yl]-thieno[2,3-d]pyrimidin-4-amine | DMA | 399 | |
| Example 166 | N-[2-[[5-(4-aminothieno[2,3-d]pyrimidin-6-yl)-4-phenyl-1H-imidazol-1-yl]methyl]phenyl]-2,4-dichloro-benzenesulfonamide | DMA | 607, 609, 611 | 5.37(s, 2H), 6.56(d, 1H), 6.83(d, 1H), 7.14-7.36(m, 5H), 7.46-7.51(m, 3H), 7.57(s, 1H), 7.73(d, 1H), 7.77-7.81(m, 3H), 8.31(s, 1H), 8.48(s, br, 1H), 9.87(s, br, 1H); |
| Example 167 | 6-[1-(1H-imidazol-2-ylmethyl)-4-phenyl-1H-imidazol-5-yl]-thieno[2,3-d]pyrimidin-4-amine | DMA | 374 | |
| Example 168 | 6-[1-[(6-fluoro-4H-1,3-benzodioxin-8-yl)methyl]-4-phenyl-1H-imidazol-5-yl]-thieno[2,3-d]pyrimidin-4-amine | DMA | 460 | |
| Example 169 | 6-[1-(imidazo[1,2-a]pyridin-2-ylmethyl)-4-phenyl-1H-imidazol-5-yl]-thieno[2,3-d]pyrimidin-4-amine | DMA | 424 | |

EXAMPLE 170

N-Benzyl-6-(1-methyl-4-phenyl-1H-imidazol-5-yl)thieno[2,3-d]pyrimidin-4-amine

The title compound was prepared by a similar process to that described for Example 8 but using benzylamine in place of NH$_3$. Colourless solid (7 mg, 18%);
MS m/e MH$^+$ 398.

EXAMPLE 171

6-[1-(1-Methylpyrrolidin-3-yl)-4-phenyl-1H-imidazol-5-yl]thieno[2,3-d]pyrimidin-4-amine A mixture of lithium aluminium hydride in THF (1M, 0.1 mL), THF (2 mL) and tert-butyl 3-[5-(4-aminothieno[2,3-d]pyrimidin-6-yl)-4-phenyl-1H-imidazol-1-yl]pyrrolidine-1-carboxylate (intermediate 102) (31 mg) was refluxed for 4 hours under an inert atmosphere. After addition of water and TFA (1 drop), the mixture was evaporated and the residue was purified by preparative RPHPLC (eluting with a gradient of MeCN and water containing 0.1% TFA) to afford the title compound as a colourless solid (5 mg, 28%).

MS m/e MH$^+$ 377.

Intermediate 102 and Examples 172 and 173 was prepared by a similar process to that described for Example 65 but using the appropriate amine in place of 3-aminopyrrolidine followed by purification by preparative RPHPLC.

Intermediate 102 tert-Butyl 3-[5-(4-aminothieno[2,3-d]pyrimidin-6-yl)-4-phenyl-1H-imidazol-1-yl]pyrrolidine-1-carboxylate Colourless solid (96 mg, 14%); MS m/e MH$^+$ 463.

EXAMPLE 172 tert-Butyl {2-[5-(4-aminothieno[2,3-d]pyrimidin-6-yl)-4-phenyl-1H-imidazol-1-yl]ethyl}carbamate Colourless solid (30 mg, 65%); MS m/e MH$^+$ 437.

EXAMPLE 173 tert-Butyl {4-[5-(4-aminothieno[2,3-d]pyrimidin-6-yl)-4-phenyl-1H-imidazol-1-yl]butyl}carbamate Colourless solid (35 mg, 75%); MS m/e MH$^+$ 465.

EXAMPLE 174

2-[5-(7-Amino[1,3]thiazolo[5,4-d]pyrimidin-2-yl)-4-phenyl-1H-imidazol-1-yl]ethanol mCPBA (50 mg) was added to a solution of 2-[5-(7-methylthio[1,3]thiazolo[5,4-d]pyrimidin-2-yl)-4-phenyl-1H-imidazol-1-yl]ethanol (Intermediate 103) (52 mg) in DCM (40 mL) over dry MgSO$_4$ (0.5 g). After 16 hours the mixture was filtered and the solid washed with DCM (2×10 mL). The combined filtrate and washings were evaporated and the residual crude sulfone was dissolved in 1,4-dioxane (20 mL) and saturated with gaseous NH$_3$. After 48 hours, the mixture was evaporated and the title compound was obtained by preparative RPHPLC as a colourless solid (34 mg, 72%);
MS m/e MH$^+$ 339.

The starting material used was prepared as follows:

Intermediate 103

2-[5-(7-Methylthio[1,3]thiazolo[5,4-d]pyrimidin-2-yl)-4-phenyl-1H-imidazol-1-yl]ethanol The title compound was prepared by a similar process to that described for Intermediate 70 but using 7-(methylthio)[1,3]thiazolo[5,4-d]pyrimidine-2-carbaldehyde (Intermediate 78) in place of 4-(methylthio)thieno[2,3-d]pyrimidine-6-carbaldehyde (Intermediate 15) and ethanolamine in place of ethylamine. Colourless solid (52 mg, 56%);
MS m/e MH$^+$ 370.

The compounds of Examples 175 to 178 were prepared using the general method of Example 174 and Intermediate 103 but replacing ethanolamine with the appropriate amine.

EXAMPLE 175

2-[1-(2-Methoxyethyl)-4-phenyl-1H-imidazolo-5-yl][1,3]thiazolo[5,4-d]pyrimidin-7-amine Colourless solid (46 mg, 90%); MS m/e MH$^+$ 353.

EXAMPLE 176

2-[5-(7-Amino[1,3]thiazolo[5,4-d]pyrimidin-2-yl)-4-phenyl-1H-imidazol-1-ylbutan-1-ol Colourless solid (20 mg, 56%); MS m/e MH$^+$ 367.

EXAMPLE 177

2-(1-Butyl-4-phenyl-1H-imidazol-5-yl)[1,3]thiazolo[5,4-d]pyrimidin-7-amine

Colourless solid (42 mg, 80%); MS m/e MH$^+$ 351.

EXAMPLE 178

2-[1-(1,4-Dioxaspiro[4,5]dec-8-ylmethyl)-4-phenyl-1H-imidazol-5-yl][1,3]thiazolo[5,4-d]pyrimidin-7-amine Colourless solid (1.35 g, 88%); MS m/e MH$^+$ 449.

EXAMPLE 179

4-{[5-(7-Amino[1,3]thiazolo[5,4-d]pyrimidin-2-yl)-4-phenyl-1H-imidazol-1-yl]methyl}cyclohexanone 2-[1-(1,4-Dioxaspiro[4,5]dec-8-ylmethyl)-4-phenyl-1H-imidazol-5-yl][1,3]thiazolo[5,4-d]pyrimidin-7-amine (Example 178) (634 mg) was dissolved in MeCN (10 mL) and water (10 mL) and TFA (0.5 mL) was added. After 48 hours at ambient temperature, the title compound was obtained by preparative RPHPLC (eluting with a gradient of water and MeCN containing 0.1% TFA) as a colourless solid (570 mg, 99%);
MS m/e MH$^+$ 405.

EXAMPLE 180

4-{[5-(7-Amino[1,3]thiazolo[5,4-d]pyrimidin-2-yl)-4-phenyl-1H-imidazol-1-yl]methyl}cyclohexanol 4-{[5-(7-Amino[1,3]thiazolo[5,4-d]pyrimidin-2-yl)-4-phenyl-1H-imidazol-1-yl]methyl}cyclohexanone (Example 179), (100 mg) was treated with sodium triacetoxyborohydride (160 mg) and 1-methylpiperazine (150 mg) in MeCN (20 mL) for 4 days at ambient temperature. The mixture was filtered and the solids washed with MeCN (2×5 mL). The combined filtrate and washes were evaporated and the residue was purified by preparative RPHPLC (eluting with a gradient of water and MeCN containing 0.1% TFA) to afford the title alcohol as a colourless solid (15 mg, 16%);
MS m/e MH$^+$ 407.

EXAMPLE 181

6-{4-[3-(Benzyloxy)phenyl]-1-methyl-1H-imidazol-5-yl}thieno[2,3-d]pyrimidin-4-amine The title compound was prepared by a similar process to that described for Example 51 but using benzyl alcohol in place of n-butanol. Gum (20 mg);
$^1$H NMR (CDCl$_3$) 3.55 (s, 3H), 4.95 (s, 2H), 5.50 (bs, 2H), 6.85 (m, 1H), 7.06 (s, 1H), 7.15 (m, 2H), 7.35 (m, 6H), 7.62 (s, 1H), 8.52 (s, 1H). MS m/e MH$^+$ 414.

EXAMPLE 182

4-[5-(4-Aminothieno[2,3-d]pyrimidin-6-yl)-1-methyl-1H-imidazol-4-yl]phenol

6-{4-[4-(Benzyloxy)phenyl]-1-methyl-1H-imidazol-5-yl}thieno[2,3-d]pyrimidin-4-amine (Example 53) (19 mg) was refluxed with TFA (3 mL) and water (0.05 mL) for 6 hr.

The mixture was diluted with 1:1 DCM/MeOH and passed through an acidic extraction cartridge (Waters Oasis® MCX 1 g). The cartridge was washed with 1:1 DCM/MeOH, then eluted with concentrated aqueous $NH_3$/DCM/MeOH 4:48:48. Fractions were evaporated to give the title compound as a solid (10 mg, 67%);

$^1$H NMR (DMSO-$d_6$) 3.56 (s, 3H), 6.68 (d, 2H), 7.32 (d, 2H), 7.55 (bs, 2H), 7.62 (s, 1H), 7.82 (s, 1H), 8.30 (s, 1H), 9.36 (bs, 1H). MS m/e MH$^+$ 324.

EXAMPLE 183

3-[5-(4-Aminothieno[2,3-d]pyrimidin-6-yl)-1-methyl-1H-imidazol-4-yl]benzonitrile 6-[4-(3-Bromophenyl)-1-methyl-1H-imidazol-5-yl]thieno[2,3-d]pyrimidin-4-amine (Example 50) (192 mg) was stirred with zinc cyanide (118 mg) and tetrakis(triphenylphosphine)palladium (116 mg) in DMF (7 mL), degassed, then heated under an inert atmosphere at 80° C. for 20 hours. The solvent was evaporated and the residue was purified by flash chromatography on silica using 0-100% EtOAc in DCM then 0-20% MeOH in DCM as eluent. Further purification by preparative RPBPLC using an MeCN/water/formic acid gradient gave the title compound as a solid (28 mg, 16%);

$^1$H NMR (DMSO-$d_6$) 3.60 (s, 3H), 7.50 (m, 1H), 7.60 (bs, 2H), 7.66 (m, 1H), 7.70 (s, 1H), 7.76 (m, 1H), 7.94 (m, 1H), 7.99 (s, 1H), 8.33 (s, 1H). MS m/e MH$^+$ 333.

EXAMPLE 184 tert-Butyl {3-[5-(4-aminothieno[2,3-d]pyrimidin-6-yl)-1-methyl-1H-imidazol-4-yl]phenyl}carbamate 6-[4-(3-Iodophenyl)-1-methyl-1H-imidazol-5-yl]thieno[2,3-d]pyrimidin-4-amine (Example 49) (43 mg) was stirred with tert-butyl carbamate (24 mg), N,N'-dimethylethylenediamine (9 mg), copper(I) iodide (10 mg), and potassium phosphate (42 mg) in 1,4-dioxane (2 mL), degassed, and heated under an inert atmosphere at 100° C. for 24 hours. The mixture was partitioned between EtOAc and dilute aqueous $NH_3$. The organic phase was dried and evaporated. The residue was purified by flash chromatography on silica using a gradient of 0-100% EtOAc in DCM then 0-20% MeOH in DCM as eluent. Fractions were evaporated to give the title compound as a gum (4 mg, 9%);

MS m/e MH$^+$ 423.

EXAMPLE 185

6-(4-{4-[(3,4-Dichlorobenzyl)oxy]phenyl}-1-methyl-1H-imidazol-5-yl)thieno[2,3-d]pyrimidin-4-amine To a suspension of 4-[5-(4-aminothieno[2,3-d]pyrimidin-6-yl)-1-methyl-1H-imidazol-4-yl]phenol (intermediate 108) (25 mg) in MeCN (2 mL) was added 4-chlorobenzyl bromide (14 mg), potassium carbonate (53 mg) and 1,4,7,10,13,16-hexaoxacycloocatadecane (7 mg). The reaction mixture was heated under microwave conditions (CEM explorer, 140° C., 10 minutes) then diluted with EtOAc (10 mL) followed by $H_2O$ (10 mL). The organic layer was separated and washed with brine (10 mL), dried, then concentrated in vacuo and the crude product purified by flash chromatography on silica eluting with DCM: MeOH (0-10%) to afford the title compound (42 mg, 56%);

$^1$H NMR (DMSO-$d_6$) δ 3.56 (s, 3H), 5.1 (s, 2H), 6.92-6.96 (d, 2H), 7.4-7.46 (m, 3H), 7.58 (bs, 2H), 7.61-7.65 (m, 2H), 7.68 (s, 1H), 7.85 (s, 1H), 8.30 (s, 1H); MS m/e MH$^+$ 482.

The starting materials used were prepared as follows:

Intermediate 104

Isocyano(4-methoxyphenyl)methyl 4-methylphenyl sulfone

The title compound was prepared by a similar process to that described for Intermediate 53 but using (4-methoxyphenyl)(phenylsulfonyl)methylformamide (Tetrahedron Lett., 1996, 37 (45), 8113) in place of {(3-iodophenyl)[(4-methylphenyl)sulfonyl]methyl}formamide (Intermediate 52). Tan solid (26.15 g, 97%)

$^1$H NMR (CDCl$_3$) δ 2.56 (s, 3H), 3.92 (s, 3H), 5.62 (s, 1H), 6.97-7.00 (d, 2H), 7.31-7.36 (d, 2H), 7.40-7.44 (d, 2H), 7.70-7.73 (d, 2H).

Intermediate 105

6-[4-(4-Methoxyphenyl)-1-methyl-1H-imidazol-5-yl]-4-(methylthio)thieno[2,3-d]pyrimidine The title compound was prepared by a similar process to that described for Example 6 but using isocyano(4-methoxyphenyl)methyl 4-methylphenyl sulfone (Intermediate 104) in place of PhTosMIC and N-[4-(methylthio)thieno[2,3-d]pyrimidin-6-ylmethylidene]methanamine (intermediate 16) in place of N-(3,4-dimethoxybenzyl)-N-[thieno[2,3-d]pyrimidin-6-ylmethylidene]amine (intermediate 14) to afford the title compound as a solid (2.69 g, 39%);

$^1$H NMR (CDCl$_3$) δ 2.72 (s, 3H), 3.63 (s, 3H), 3.78 (s, 3H), 6.79-6.84 (d, 2H), 7.30 (s, 1H), 7.49-7.53 (d, 2H), 7.63 (s, 1H), 8.85 (s, 1H); MS m/e MH$^+$ 369.

Intermediate 106

6-[4-(4-Methoxyphenyl)-1-methyl-1H-imidazol-5-yl]-4-(methylsulfonyl)thieno[2,3-d]pyrimidine The title compound was prepared by a similar process to that described for Intermediate 17 but using 6-[4-(4-methoxyphenyl)-1-methyl-1H-imidazol-5-yl]-4-(methylthio)thieno[2,3-d]pyrimidine (Intermediate 105) in place of 6-(1-methyl-4-phenyl-1H-imidazol-5-yl)-4-(methylthio)thieno[2,3-d]pyrimidine (Example 7). Brown gum (3.13 g, 100%);

$^1$H NMR (CDCl$_3$) δ 3.44 (s, 3H), 3.72 (s, 3H), 3.81 (s, 3H), 6.83-6.87 (d, 2H), 7.46-7.48 (d, 2H), 7.69 (s, 1H), 8.02 (s, 1H), 9.15 (s, 1H); MS m/e MH$^+$ 401.

Intermediate 107

6-[4-(4-Methoxyphenyl)-1-methyl-1H-imidazol-5-yl]thieno[2,3-d]pyrimidin-4-amine

The title compound was prepared by a similar process to that described for Example 8 but using 6-[4-(4-methoxyphenyl)-1-methyl-1H-imidazol-5-yl]-4-(methylsulfonyl)thieno[2,3-d]pyrimidine (intermediate 106) in place of 6-(1-methyl-4-phenyl-1H-imidazol-5-yl)-4-(methylsulfonyl)thieno[2,3-d]pyrimidine (Intermediate 17) followed by flash chromatography on silica eluting with DCM:MeOH (0-10%) then 1% $NH_3$. Tan solid (0.91 g, 36%);

$^1$H NMR (DMSO-d$_6$) δ 3.56 (s, 3H), 3.70 (s, 3H), 6.77-6.87 (d, 2H), 7.41-7.44 (d, 2H), 7.57 (bs, 2H), 7.63 (s, 1H), 7.84 (s, 1H), 8.29 (s, 1H); MS m/e MH$^+$ 338.

Intermediate 108

4-[5-(4-Aminothieno[2,3-d]pyrimidin-6-yl)-1-methyl-1H-imidazol-4-yl]phenol

Boron tribromide (1.0M in DCM) (10.1 mL) was added dropwise to 6-[4-(4-methoxyphenyl)-1-methyl-1H-imidazol-5-yl]thieno[2,3-d]pyrimidin-4-amine (Intermediate 107) (0.91 g) in DCM (20 mL) then stirred for 5 days at ambient temperature. The reaction mixture was concentrated in vacuo and the residue partitioned between DCM and water. The aqueous layer was separated and extracted with DCM (3×20 mL), the aqueous layer was then adjusted to pH 9 with concentrated aqueous NH$_3$, the resultant solid filtered and dried in vacuo to give the title compound as a brown solid (623 mg, 71%);
$^1$H NMR (DMSO-d$_6$) δ 3.56 (s, 3H), 6.65-6.67 (d, 2H), 7.29-7.33 (d, 2H), 7.55-7.58 (bs, 2H), 7.61 (s, 1H), 7.82 (s, 1H), 8.29 (s, 1H), 9.36 (s, 1H); MS m/e MH$^+$ 324.

EXAMPLE 186

N-{3-[5-(4-Aminothieno[2,3-d]pyrimidin-6-yl)-1-methyl-1H-imidazol-4-yl]phenyl}-N'-phenylurea Phenyl isocyanate (28 mg) was added to a stirred suspension of 6-[4-(3-aminophenyl)-1-methyl-1H-imidazol-5-yl]thieno[2,3-d]pyrimidin-4-amine (Intermediate 110) (40 mg) in THF (6 mL) under an inert atmosphere. After 30 minutes methylethylenediamine-polystyrene (200 mg) was added, the reaction mixture filtered, filtrate loaded onto a MCX column washed with DCM/MeOH (1:1) then eluted with 5% triethylamine in DCM/MeOH (1:1) to give the title compound as a colourless solid (35 mg, 67%);
$^1$H NMR (DMSO-d$_6$) δ 3.59 (s, 3H), 6.93-6.97 (m, 1H), 7.09-7.11 (m, 1H), 7.15-7.19 (m, 1H), 7.24-7.32 (m, 3H), 7.36-7.39 (m, 2H), 7.57 (bs, 2H), 7.66 (s, 1H), 7.74-7.75 (m, 1H), 7.90 (s, 1H), 8.32 (s, 1H), 8.53 (s, 1H), 8.57 (s, 1H); MS m/e MH$^+$ 442.

The starting material was prepared as follows:

Intermediate 109

6-(4-{3-[(Diphenylmethylene)amino]phenyl}-1-methyl-1H-imidazol-5-yl)thieno[-2,3-d]pyrimidin-4-amine 6-[4-(3-Iodophenyl)-1-methyl-1H-imidazol-5-yl]thieno[2,3-d]pyrimidin-4-amine (Example 49), benzophenone imine (549 mg), 1,1'-bis(diphenylphosphino)ferrocene (120 mg), bis(benzylideneacetone)palladium (100 mg) and sodium tert-butoxide (960 mg) in dioxane (40 mL) was degassed then heated at 90° C. under an inert atmosphere. After 17 hours the reaction mixture was cooled, diluted with water (50 mL), extracted with EtOAc (2×30 mL), organic extracts washed with brine, dried, filtered and concentrated in vacuo. Purification by flash chromatography on silica eluting with DCM/MeOH (0-10%) gave the title compound (0.48 g, 50%);
$^1$H NMR (CDCl$_3$) δ 3.32 (s, 3H), 5.75 (bs, 2H), 6.40-6.45 (m, 1H), 6.85-6.94 (m, 4H), 6.83-7.15 (m, 5H), 7.28-7.32 (m, 2H), 7.35-7.40 (m, 1H), 7.48 (s, 1H), 7.57-7.62 (m, 2H), 8.40 (s, 1H); MS m/e MH$^+$ 487.

Intermediate 110

6-[4-(3-Aminophenyl)-1-methyl-1H-imidazol-5-yl]thieno[2,3-d]pyrimidin-4-amine

2M HCl (0.75 mL) was added to a solution of 6-(4-{3-[(diphenylmethylene-amino]phenyl}-1-methyl-1H-imidazol-5-yl)thieno[2,3-d]pyrimidin-4-amine (Intermediate 109) (0.45 g) in THF (15 mL), stirred for 10 minutes, then partitioned between water and EtOAc. The aqueous layer was separated, adjusted to pH 9 with concentrated aqueous NH$_3$, extracted with DCM (3×30 mL), combined organics dried, filtered and concentrated in vacuo to give the title compound as a colourless solid (0.33 g, 100%);
$^1$H NMR (DMSO-d$_6$) δ 3.54 (s, 3H), 4.96 (bs, 2H), 6.36-6.39 (m, 1H), 6.55-6.57 (m, 1H), 6.83-6.88 (m, 2H), 7.56 (bs, 2H), 7.59 (s, 1H), 7.82 (s, 1H), 8.28 (s, 1H); MS m/e MH$^+$ 323.

EXAMPLE 187

N-{3-[5-(4-Aminothieno[2,3-d]pyrimidin-6-yl)-1-methyl-1H-imidazol-4-yl}phenyl]-N'-benzylurea The title compound was prepared by a similar process to that described for Example 186 but using benzyl isocyanate in place of phenyl isocyanate. Colourless solid (16 mg, 57%);
$^1$H NMR (DMSO-d$_6$) δ 3.56 (s, 3H), 4.26 (d, 2H), 6.50 (t, 1H), 6.95-6.99 (m, 1H), 7.10 (t, 1H), 7.22-7.36 (m, 6H), 7.57 (bs, 2H), 7.63-7.65 (m, 2H), 7.89 (s, 1H), 8.30 (s, 1H), 8.46 (s, 1H); MS m/e MH$^+$ 456.

EXAMPLE 188

N-{3-[5-(4-Aminothieno[2,3-d]pyrimidin-6-yl)-1-methyl-1H-imidazol-4-yl]phenyl}-N'-[2-fluoro-5-(trifluoromethyl)phenyl]urea The title compound was prepared by a similar process to that described for Example 186 but using 2-fluoro-5-trifluoromethylphenylisocyanate in place of phenyl isocyanate. Colourless solid (59 mg, 90%);
$^1$H NMR (DMSO-d$_6$) δ 3.57 (s, 3H), 7.06-7.09 (m, 1H), 7.15-7.21 (m, 1H), 7.33-7.38 (m, 2H), 7.43-7.50 (m, 1H), 7.57 (bs, 2H), 7.65 (s, 1H), 7.71-7.73 (m, 1H), 7.90 (s, 1H), 8.29 (s, 1H), 8.54-8.58 (m, 1H), 8.76-8.78 (s, 1H), 9.09 (s, 1H); MS m/e MH$^+$ 527.

EXAMPLE 189

N-{4-[5-(4-Aminothieno[2,3-d]pyrimidin-6-yl)-1-methyl-1H-imidazol-4-yl]phenyl}-N'-phenylurea The title compound was prepared by a similar process to that described for Example 186 but using 6-[4-(4-aminophenyl)-1-methyl-1H-imidazol-5-yl]thieno[2,3-d]pyrimidin-4-amine (Intermediate 112) in place of 6-[4-(3-aminophenyl)-1-methyl-1H-imidazol-5-yl]thieno[2,3-d]pyrimidin-4-amine (Intermediate 110). Yellow solid (15 mg, 56%);
$^1$H NMR (DMSO-d$_6$) δ 3.57 (s, 3H), 6.94-6.98 (m, 1H), 7.18-7.55 (m, 8H), 7.56-7.65 (m, 3H), 7.87 (s, 1H), 8.31 (s, 1H), 8.67 (s, 1H), 8.69 (s, 1H); MS m/e MH$^+$ 442.

The starting material was prepared as follows:

Intermediate 111

6-(4-{4-[(Diphenylmethylene)amino]phenyl}-1-methyl-1H-imidazol-5-yl)thieno[2,3-d]pyrimidin-4-amine The title compound was prepared by a similar process to that described for Intermediate 109 but using 6-[4-(4-iodophenyl)-1-methyl-1H-imidazol-5-yl]thieno[2,3-d]pyrimidin-4-amine (Intermediate 64) in place of 6-[4-(3-iodophenyl)-1-methyl-1H-imidazol-5-yl]thieno[2,3-d]pyrimidin-4-amine (Example 49). Colourless solid (31 mg, 64%);
$^1$H NMR (CDCl$_3$) δ 3.53 (s, 3H), 6.52-6.50 (m, 2H), 6.62 (bs, 2H), 7.01-7.03 (m, 1H), 7.17-7.20 (m, 3H), 7.31-7.34 (m, 4H), 7.38-7.39 (m, 1H), 7.44-7.45 (m, 2H), 7.55 (s, 1H), 7.62-7.64 (m, 2H), 8.33 (s, 1H); MS m/e MH$^+$ 487.

Intermediate 112

6-[4-(4-Aminophenyl)-1-methyl-1H-imidazol-5-yl]thieno[2,3-d]pyrimidin-4-amine

The title compound was prepared by a similar process to that described for Intermediate 110 but using 6-(4-{4-[(diphenylmethylene)amino]phenyl}-1-methyl-1H-imidazol-5-yl)thieno[2,3-d]pyrimidin-4-amine (Intermediate 111) in place of 6-(4-{3-[(diphenylmethylene)amino]phenyl}-1-methyl-1H-imidazol-5-yl)thieno[2,3-d]pyrimidin-4-amine (Intermediate 109). Colourless solid (276 mg, 87%);
$^1$H NMR (DMSO-d$_6$) δ 3.54 (s, 3H), 5.04 (bs, 2H), 6.42-6.47 (m, 2H), 7.15-7.19 (m, 2H), 7.54 (bs, 2H), 7.59 (s, 1H), 7.77 (s, 1H), 8.28 (s, 1H); MS m/e MH$^+$ 323.

EXAMPLE 190

N-{4-[5-(4-Aminothieno[2,3-d]pyrimidin-6-yl)-1-methyl-1H-imidazol-4-yl]phenyl}-N'-benzylurea The title compound was prepared by a similar process to that described for Example 186 but using 6-[4-(4-aminophenyl)-1-methyl-1H-imidazol-5-yl]thieno[2,3-d]pyrimidin-4-amine (Intermediate 112) in place of 6-[4-(3-aminophenyl)-1-methyl-1H-imidazol-5-yl]thieno[2,3-d]pyrimidin-4-amine (Intermediate 110) and using benzyl isocyanate in place of phenyl isocyanate. Yellow solid (10 mg, 36%);
$^1$H NMR (DMSO-d$_6$) δ 3.57 (s, 3H), 4.26-4.29 (m, 2H), 6.56-6.59 (m, 1H), 7.19-7.39 (m, 9H), 7.58 (s, 2H), 7.63 (s, 1H), 7.85 (s, 1H), 8.28 (s, 1H), 8.50 (s, 1H); MS m/e MH$^+$ 456.

EXAMPLE 191

N-{4-[5-(4-Aminothieno[2,3-d]pyrimidin-6-yl)-1-methyl-1H-imidazol-4-yl]phenyl}-N'-[2-fluoro-5-(trifluoromethyl)phenyl]urea The title compound was prepared by a similar process to that described for Example 186 but using 6-[4-(4-aminophenyl)-1-methyl-1H-imidazol-5-yl]thieno[2,3-d]pyrimidin-4-amine (Intermediate 112) in place of 6-[4-(3-aminophenyl)-1-methyl-1H-imidazol-5-yl]thieno[2,3-d]pyrimidin-4-amine (Intermediate 110) and using 2-fluoro-5-trifluoromethylphenyl isocyanate in place of phenyl isocyanate. Colourless solid (48 mg, 73%);
$^1$H NMR (DMSO-d$_6$) δ 3.57 (s, 3H), 7.36-7.47 (m, 6H), 7.58 (bs, 2H), 7.64 (s, 1H), 7.86 (s, 1H), 8.30 (s, 1H), 8.57-8.62 (m, 1H), 8.86-8.89 (m, 1H), 9.12 (s, 1H); MS m/e MH$^+$ 527.

The following compounds are prepared by analogous methods:

EXAMPLE 192

6-[1-(4-Aminobutyl)-4-phenyl-1H-imidazol-5-yl]-thieno[2,3-d]pyrimidin-4-amine tert-Butyl {4-[5-(4-aminothieno[2,3-d]pyrimidin-6-yl)-4-phenyl-1H-imidazol-1-yl]butyl}carbamate (Example 173) (23 mg) was added to a mixture of TFA, water and triisopropyl silane (5:5:1) (5 ml) and stirred at ambient temperature for 1 hour. The reaction mixture was concentrated in vacuo and the residue purified by preparative RPHPLC (eluting with a gradient of MeCN and water containing 0.1% TFA) to give the title compound as a colourless solid (18 mg, 90%);
MS m/e MH$^+$ 365.

EXAMPLE 193

6-[1-(3-Methylbut-2-en-1-yl)-4-phenyl-1H-imidazol-5-yl]-thieno[2,3-d]pyrimidin-4-amine The title compound was prepared using the general method of Example 65 but replacing 3-aminopyrrolidine with 3-methylbut-2-en-1-amine. Colourless solid (45 mg, 62%);
$^1$H NMR (DMSO-d6) 1.48 (s, 3H), 1.65 (s, 3H), 4.65 (d, 2H), 5.25 (t, 1H), 7.33 (t, 1H), 7.38 (t, 2H), 7.50 (d, 2H), 7.76 (s, 1H), 7.80 (s, br, 2H), 8.36 (s, 1H), 8.69 (s, 1H); MS m/e MH$^+$ 362.

EXAMPLE 194

2-[1-(2-Morpholin-4-ylbenzyl)-4-phenyl-1H-imidazol-5-yl][1,3]thiazolo[5,4-d]pyrimidin-7-amine

EXAMPLE 195

6-[4-(4-Fluorophenyl)-1 (2-morpholin-4-ylbenzyl)-1H-imidazol-5-yl]thieno[2,3-d]pyrimidin-4-amine The title compound was prepared by using the general method of Example 65 but replacing 3-aminopyrrolidine and PhTosMIC with the appropropriate reagents. Colourless solid (24 mg, 25%);
$^1$H NMR (DMSO-d6) 2.40-2.50 (m, 4H), 3.50-3.60 (m, 4H), 5.23 (s, 2H), 6.78 (d, 1H), 6.94 (d, 1H), 7.02 (t, 1H), 7.09 (t, 2H), 7.21 (t, 1H), 7.35 (s, 1H), 7.49 (s, br, 2H), 7.53 (dd, 2H), 8.13 (s, 1H), 8.22 (s, 1H); MS m/e MH$^+$ 487.

EXAMPLE 196

Benzyl {3-[5-(4-aminothieno[2,3-d]pyrimidin-6-yl)-1-methyl-1H-imidazol-4-yl]phenyl}carbamate Benzylchloroformate (0.027 mL) was added to a solution of 6-[4-(3-aminophenyl)-1-methyl-1H-imidazol-5-yl]thieno[2,3-d]pyrimidin-4-amine (Intermediate 110) (40 mg) and pyridine (0.02 mL) in THF (7 mL). The mixture was stirred under an inert atmosphere for 1 hour, then quenched with H$_2$O (10 mL) and extracted EtOAc (3×10 mL). The combined organics were dried (MgSO$_4$), filtered and concentrated in vacuo. Purification by flash chromatography on silica eluting with CH$_2$Cl$_2$:MeOH (0-10%) gave the title compound as a gum (16 mg, 28%);
$^1$H NMR (DMSO-d$_6$) δ 3.47-3.57 (m, 3H), 5.03 5.12 (m, 2H), 7.05-7.23 (m, 2H), 7.29-7.40 (m, 6H), 7.55 (bs, 2H), 7.63 (s, 1H), 7.75-7.77 (m, 1H), 7.87 (s, 1H), 8.29 (s, 1H), 9.68 (bs, 1H); MS m/e MH+ 457.

EXAMPLE 197

Phenyl {3-[5-(4-aminothieno[2,3-d]pyrimidin-6-yl)-1-methyl-1H-imidazol-4-yl]phenyl}carbamate The title compound was prepared by a similar process to that described for Example 196 but using phenylchloroformate in place of benzylchloroformate. Pale yellow solid (9 mg, 16%);
$^1$H NMR (DMSO-d$_6$) δ 3.58 (s, 3H), 6.7-6.75 (d, 1H), 7.1-7.25 (m, 3H), 7.37-7.50 (m, 5H), 7.55-7.6 (bs, 2H), 7.65 (s, 1H), 7.87 (s, 1H), 8.30 (s, 1H), 10.2 (bs, 1H); MS m/e MH+ 443.

What is claimed is:
1. A compound of the Formula I:

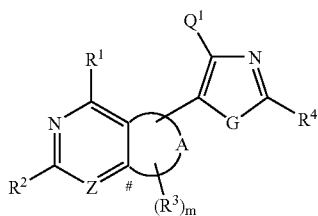

Formula I wherein:
A together with the carbon atoms to which it is attached forms a fused 5-membered heteroaryl ring, wherein said heteroaryl ring contains 1 or 2 heteroatoms selected from O, N and S,
  and wherein the 5-membered ring containing G is linked to the ring formed by A in the meta position to the bridgehead carbon marked # in Formula I;
G is selected from O, S and NR$^5$;
Z is selected from N and CR$^6$;
Q$^1$ is selected from aryl and heteroaryl, wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked,
  and wherein Q$^1$ is optionally substituted by one or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, 3-(1-6C)alkylureido, (1-6C)alkoxycarbonylamino from a group of the formula:

—X$^1$—R$^7$ wherein X$^1$ is a direct bond or is selected from O and N(R$^8$), wherein R$^8$ is hydrogen or (1-6C)alkyl, and R$^7$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and from a group of the formula:

—X$^2$-Q$^2$ wherein X$^2$ is a direct bond or is selected from O, S, SO, SO$_2$, N(R$^9$), CO, CH(OR$^9$), CON(R$^9$), N(R$^9$)CO, N(R$^9$)CON(R$^9$), SO$_2$N(R$^9$), N(R$^9$)SO$_2$, C(R$^9$)$_2$O, C(R$^9$)$_2$S and N(R$^9$)C(R$^9$)$_2$, wherein R$^9$ is hydrogen or (1-6C)alkyl, and Q$^2$ is aryl, aryl-(1-6C)alkyl, heteroaryl, heteroaryl-(1-6C)alkyl, heterocyclyl or heterocyclyl-(1-6C)alkyl wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked and wherein said heterocyclyl group is selected from a non-aromatic saturated and partially saturated 3 to 10 membered monocyclic and bicyclic ring which is bridged or spiro with up to five heteroatoms selected from oxygen, nitrogen and sulfur, which may be carbon or nitrogen linked, wherein a ring sulfur atom may be oxidized to form the S-oxide(s),
  and wherein Q$^2$ optionally bears 1, 2 or 3 substituents, which may be the same or different, selected from trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X$^3$—R$^{10}$ wherein X$^3$ is a direct bond or is selected from O and N(R$^{11}$), wherein R$^{11}$ is hydrogen or (1-6C)alkyl, and R$^{10}$ is halogeno-(1-6C)alkyl, hydroxy-(1-6C)alkyl, (1-6C)alkoxy-(1-6C)alkyl, cyano (1-6C)alkyl, amino-(1-6C)alkyl, (1-6C)alkylamino-(1-6C)alkyl or di-[(1-6C)alkyl]amino-(1-6C)alkyl,
and any heterocyclyl group within Q$^2$ optionally bears 1 or 2 oxo or thioxo substituents; and
wherein Q$^1$ is a group of the formula:

-Q$^{1a}$-X$^2$-Q$^2$ wherein Q$^{1a}$ is phenyl which is optionally substituted by 1 or 2 substituents which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl and X$^2$ is a direct bond or is selected from O, S, SO$_2$, N(R$^9$), CO, CON(R$^9$), N(R$^9$)CO, N(R$^9$)CON(R$^9$), SO$_2$N(R$^9$), N(R$^9$)$_2$O, C(R$^9$)S and N(R$^9$)C(R$^9$)$_2$, wherein R$^9$ is hydrogen or (1-3C)alkyl, and $Q^2$ is phenyl, phenyl-(1-3C)alkyl, thienyl, or thienyl-(1-3C)alkyl, and wherein $Q^2$ optionally bears 1, 2 or 3 substituents, which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl;

$R^1$ is selected from hydrogen, halogeno, trifluoromethyl, trifluoromethoxy, cyano, nitro, hydroxy, amino, mercapto, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, $R^2$ is selected from hydrogen, amino, hydroxy, halogeno, (1-6C)alkyl, (1-6C)alkoxy, formyl, (1-6C)alkylamino and di-[(1-6C)alkyl]amino;

$R^3$ is, independently, as defined for $R^4$ and $R^6$, provided that $R^3$ is not hydrogen, and when $R^3$ is attached to a nitrogen atom in A, $R^3$ is not halogeno;

$R^5$ is, independently, as defined for $R^4$ and $R^6$, provided that $R^5$ is not halogeno;

$R^4$ and $R^6$ which may be the same or different, are selected from hydrogen, halogeno, trifluoromethyl, trifluoromethoxy, cyano, isocyano, nitro, hydroxy, mercapto, amino, formyl, carboxy, carbamoyl, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$Q^4$-$X^5$— wherein $X^5$ is a direct bond or is selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, $CO(R^{12})_2$, $SC(R^{12})_2$ and $N(R^{12})C(R^{12})_2$, wherein $R^{12}$ is hydrogen or (1-6C)alkyl, and $Q^4$ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl, wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked and wherein said heterocyclyl group is selected from a non-aromatic saturated and partially saturated 3 to 10 membered monocyclic and bicyclic ring which is bridged or spiro with up to five heteroatoms selected from oxygen, nitrogen and sulfur, which may be carbon or nitrogen linked, wherein a ring sulfur atom may be oxidized to form the S-oxide(s), and wherein adjacent carbon atoms in any (2-6C)alkylene chain within a $R^3$, $R^4$, $R^5$ or $R^6$ substituent are optionally separated by the insertion into the chain of a group selected from O, S, SO, $SO_2$, $N(R^{13})$, CO, $CH(OR^{13})$, $CON(R^{13})$, $N(R^{13})CO$, $SO_2N(R^{13})$, $N(R^{13})SO_2$, CH=CH and C≡C wherein $R^{13}$ is hydrogen or (1-6C)alkyl, and wherein any $CH_2$=CH— or HC≡C— group within a $R^3$, $R^4$, $R^5$ or $R^6$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$Q^5$-$X^6$— wherein $X^6$ is a direct bond or is selected from CO and $N(R^{14})CO$, wherein $R^{14}$ is hydrogen or (1-6C)alkyl, and $Q^5$ is aryl, aryl-(1-6C)alkyl, (3-11C)cycloalkyl, heteroaryl, heteroaryl-(1-6C)alkyl, heterocyclyl or heterocyclyl-(1-6C)alkyl, wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked and wherein said heterocyclyl group is selected from a non-aromatic saturated and partially saturated 3 to 10 membered monocyclic and bicyclic ring which is bridged or spiro with up to five heteroatoms selected from oxygen, nitrogen and sulfur, which may be carbon or nitrogen linked, wherein a ring sulfur atom may be oxidized to form the S-oxide(s), and wherein any $CH_2$ or $CH_3$ group within a $R^3$, $R^4$, $R^5$ or $R^6$ substituent optionally bears on each said $CH_2$ or $CH_3$ group one or more halogeno or (1-6C)alkyl substituents or a substituent selected from oxo, hydroxy, cyano, amino, carboxy, carbamoyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, (1-6C)alkoxycarbonylamino, aminosulfonylamino, (1-6C)alkylaminosulfonylamino, di-[(1-6C)alkyl]aminosulfonylamino, or from a group of the formula:

—$X^7$-$Q^6$ wherein $X^7$ is a direct bond or is selected from O, S, SO, $SO_2$, $N(R^{15})$, CO, $CH(OR^{15})$, $CON(R^{15})$, $N(R^{15})CO$, $SO_2N(R^{15})$, $N(R^{15})SO_2$, $C(R^{15})_2O$, $C(R^{15})_2S$ and $N(R^{15})C(R^{15})_2$, wherein $R^{15}$ is hydrogen or (1-6C)alkyl, and $Q^6$ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl, wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked and wherein said heterocyclyl group is selected from a non-aromatic saturated and partially saturated 3 to 10 membered monocyclic and bicyclic ring which is bridged or spiro with up to five heteroatoms selected from oxygen, nitrogen and sulfur, which may be carbon or nitrogen linked, wherein a ring sulfur atom may be oxidized to form the S-oxide(s), and wherein any aryl, heteroaryl, heterocyclyl, cycloalkyl or cycloalkenyl group within a substituent on $R^3$, $R^4$, $R^5$ or $R^6$ optionally bears 1 or more substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, from a group of the formula:

—$X^8$—$R^{16}$ wherein $X^8$ is a direct bond or is selected from O and N($R^{17}$), wherein $R^{17}$ is hydrogen or (1-6C)alkyl, and $R^{16}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

—$X^9$-$Q^7$ wherein $X^9$ is a direct bond or is selected from O, S, SO, $SO_2$, N($R^{18}$), CO, CH(O$R^{18}$), CON($R^{18}$), N($R^{18}$)CO, $SO_2$N($R^{18}$), N($R^{18}$)$SO_2$, C($R^{18}$)$_2$O, C($R^{18}$)$_2$S and N($R^{18}$)C($R^{18}$)$_2$, wherein $R^{18}$ is hydrogen or (1-6C)alkyl, and $Q^7$ is aryl, aryl-(1-6C)alkyl, (3-11C)cycloalkyl, (3-11C)cycloalkyl-(1-6C)alkyl, (3-11C)cycloalkenyl, (3-11C)cycloalkenyl-(1-6C)alkyl, heteroaryl, heteroaryl-(1-6C)alkyl, heterocyclyl or heterocyclyl-(1-6C)alkyl, wherein said aryl is selected from phenyl and naphthyl and said heteroaryl is selected from an aromatic 5- or 6-membered monocyclic ring and a 9- or 10-membered bicyclic ring, with up to five ring heteroatoms selected from oxygen, nitrogen and sulfur, which may be carbon or nitrogen linked and wherein said heterocyclyl group is selected from a non-aromatic saturated and partially saturated 3 to 10 membered monocyclic and bicyclic ring which is bridged or spiro with up to five heteroatoms selected from oxygen, nitrogen and sulfur, which may be carbon or nitrogen linked, wherein a ring sulfur atom may be oxidized to form the S-oxide(s), and wherein any aryl, heteroaryl, heterocyclyl, cycloalkyl or cycloalkenyl group optionally bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or when G is N$R^5$, $R^4$ and $R^5$ together with the atoms to which they are attached form a fused 5- or 6- membered heteroaryl or heterocyclyl ring, and wherein said fused 5- or 6-membered ring optionally bears one or more substituents as defined for $R^4$, and any fused 5- or 6- membered heterocyclyl ring so formed optionally bears 1 or 2 oxo or thioxo substituents, and wherein any heterocyclyl group within any $R^3$, $R^4$, $R^5$ or $R^6$ substituent optionally bears 1 or 2 oxo or thioxo substituents;

m is 0, 1 or 2, and wherein the values of $R^3$ may be the same or different;

or a pharmaceutically-acceptable salt thereof.

2. A compound according to claim 1 in which A is —N═C*—S—, $R^2$ is H, Z is N, m is 0 and G is N$R^5$.

3. A compound according to claim 1 in which A is —CH═C*—S—, $R^2$ is H, Z is N, m is 0 and G is N$R^5$.

4. A compound according to claim 1 which is selected from one or more of the following:

8-(1-methyl-4-phenyl-1H-imidazol-5-yl)-9H-purin-6-amine 9-methyl-8-(1-methyl-4-phenyl-1H-imidazol-5-yl)-9H-purin-6-amine 7-methyl-8-(1-methyl-4-phenyl-1H-imidazol-5-yl)-7H-purin-6-amine 8-(4-phenyl-1H-imidazol-5-yl)-9H-purin-6-amine 6-(1-methyl-4-phenyl-1H-imidazol-5-yl)-4-(methylthio)thieno[3,2-d]pyrimidine 6-(1-methyl-4-phenyl-1H-imidazol-5-yl)thieno[3,2-d]pyrimidin-4-amine 5-[4-(methylthio)thieno[3,2-d]pyrimin-6-yl]-1H-imidazol-1-ol 9-Cyclohexyl-8-(1-methyl-4-phenyl-1H-imidazol-5-yl)-9H-purin-6-amine 6-(1-methyl-4-phenyl-1H-imidazol-5-yl)furo[2,3-d]pyrimidine 6-(1-methyl-4-phenyl-1H-imidazol-5-yl)furo[2,3-d]pyrimidin-4-amine 6-[1-(4-methoxybenzyl)-4-phenyl-1H-imidazol-5-yl]furo[2,3-d]pyrimidine 6-(1-methyl-4-phenyl-1H-imidazol-5-yl)-7H-pyrrolo[2,3-d]pyrimidine 6-(4-phenyl-1H-imidazol-5-yl)thieno[3,2-d]pyrimidine 2-(1-methyl-4-phenyl-1H-imidazol-5-yl)[1,3]oxazolo[5,4-d]pyrimidin-7-amine 2-[1-(4-methoxybenzyl)-4-phenyl-1H-imidazol-5-yl]furo[3,2-c]pyridine 6-(1-Methyl-4-phenyl-1H-imidazol-5-yl)-5H-pyrrolo[3,2-d]pyrimidin-4-amine 2-(1-methyl-4-phenyl-1H-imidazol-5-yl)[1,3]thiazolo[5,4-d]pyrimidin-7-amine
2-(4-phenyl-1H-imidazol-5-yl)[1,3]thiazolo[5,4-d]pyrimidin-7-amine
2-(4-phenyl-1H-imidazol-5-yl)[1,3]thiazolo[5,4-d]pyrimidine
2-(2-Bromo-1-methyl-4-phenyl-1H-imidazol-5-yl)[1,3]thiazolo[5,4-d]pyrimidin-7-amine
2-(2-Amino-1-methyl-4-phenyl-1H-imidazol-5-yl)[1,3]thiazolo[5,4-d]pyrimidin-7-amine
2-(2-Methoxy-1-methyl-4-phenyl-1H-imidazol-5-yl)[1,3]thiazolo[5,4-d]pyrimidin-7-amine
2-(1-Methyl-2,4-diphenyl-1H-imidazol-5-yl)[1,3]thiazolo[5,4-d]pyrimidin-7-amine
2-(1-methyl-4-phenyl-1H-imidazol-5-yl)[1,3]thiazolo[5,4-d]pyrimidine-7-thiol
7-methoxy-2-(1-methyl-4-phenyl-1H-imidazol-5-yl)[1,3]thiazolo[5,4-d]pyrimidine
2-[1-methyl-4-phenyl-2-(3-thienyl)-1H-imidazol-5-yl][1,3]thiazolo[5,4-d]pyrimidin-7-amine
2-(1-methyl-4-phenyl-2-pyridin-4-yl-1H-imidazol-5-yl)[1,3]thiazolo[5,4-d]pyrimidin-7-amine
2-(2-ethyl-1-methyl-4-phenyl-1H-imidazol-5-yl)[1,3]thiazolo[5,4-d]pyrimidin-7-amine
2-[1-methyl-4-phenyl-2-(propylthio)-1H-imidazol-5-yl][1,3]thiazolo[5,4-d]pyrimidin-7-amine
2-{2-[(methoxymethyl)thio]-1-methyl-4-phenyl-1H-imidazol-5-yl}[1,3]thiazolo-[5,4-d]pyrimidin-7-amine
[5-(7-amino[1,3]thiazolo[5,4-d]pyrimidin-2-yl)-1-methyl-4-phenyl-1H-imidazol-2-yl](5-methylisoxazol-3-yl)methanone
[5-(7-amino[1,3]thiazolo[5,4-d]pyrimidin-2-yl)-1-methyl-4-phenyl-1H-imidazol-2-yl](5-methylisoxazol-3-yl)methanol
[5-(7-amino[1,3]thiazolo[5,4-d]pyrimidin-2-yl)-1-methyl-4-phenyl-1H-imidazol-2-yl](2-furyl)methanone
[5-(7-amino[1,3]thiazolo[5,4-d]pyrimidin-2-yl)-1-methyl-4-phenyl-1H-imidazol-2-yl](2-furyl)methanol
[5-(7-amino[1,3]thiazolo[5,4-d]pyrimidin-2-yl)-1-methyl-4-phenyl-1H-imidazol-2-yl](1,3-dimethyl-1H-pyrazol-5-yl)methanone
[5-(7-amino[1,3]thiazolo[5,4-d]pyrimidin-2-yl)-1-methyl-4-phenyl-1H-imidazol-2-yl](1,3-dimethyl-1H-pyrazol-5-yl)methanol or
[5-(7-amino[1,3]thiazolo[5,4-d]pyrimidin-2-yl)-1-methyl-4-phenyl-1H-imidazol-2-yl](2-thenyl)methanol
2-(1-Ethyl-4-phenyl-1H-imidazol-5-yl)[1,3]thiazolo[5,4-d]pyrimidin-7-amine
2-[1-(cyclohexylmethyl)-4-phenyl-1H-imidazol-5-yl][1,3]thiazolo[5,4-d]pyrimidin-7-amine
7-(Diisopropylamino)-2-(1-methyl-4-phenyl-1H-imidazol-5-yl)[1,3]thiazolo[5,4-d]pyrimidine-5-carbaldehyde
2-(2-{[2-(Dimethylamino)ethyl]thio}-1-methyl-4-phenyl-1H-imidazol-5-yl)[1,3]thiazolo[5,4-d]pyrimidin-7-amine
2-(1-Methyl-2-{[(methylthio)methyl]thio}-4-phenyl-1H-imidazol-5-yl)[1,3]thiazolo[5,4-d]pyrimidin-7-amine
2-(2-{[2-(1H-Imidazol-1-yl)ethyl]thio}-1-methyl-4-phenyl-1H-imidazol-5-yl)[1,3]thiazolo[5,4-d]pyrimidin-7-amine
2-{1-Methyl-2-[(pyridin-3-ylmethyl)thio]-1H-imidazol-5-yl}[1,3]thiazolo[5,4-d]pyrimidin-7-amine
2-{2-[(Cyclopropylmethyl)thio]-1-methyl-4-phenyl-1H-imidazol-5-yl}[1,3]thiazolo[5,4-d]pyrimidin-7-amine
2-[2-(Benzylthio)-1-methyl-4-phenyl-1H-imidazol-5-yl][1,3]thiazolo[5,4-d]pyrimidin-7-amine
2-[1-Methyl-2-(4-methylpiperazin-1-yl)-4-phenyl-1H-imidazol-5-yl][1,3]thiazolo[5,4-d]pyrimidin-7-amine
2-{2-[(1-Aminocyclohexyl)ethynyl]-1-methyl-4-phenyl-1H-imidazol-5-yl}[1,3]thiazolo[5,4-d]pyrimidin-7-amine
4-[5-(7-Amino[1,3]thiazolo[5,4-d]pyrimidin-2-yl)-1-methyl-4-phenyl-1H-imidazol-2-yl]but-3-yn-2-ol
1-{[5-(7-Amino[1,3]thiazolo[5,4-d]pyrimidin-2-yl)-1-methyl-4-phenyl-1H-imidazol-2-yl]ethynyl}cyclohexanol
2-[1-Methyl-4-phenyl-2-(pyridin-2-ylethynyl)-1H-imidazol-5-yl][1,3]thiazolo[5,4-d]pyrimidin-7-amine
2-[2-(3-Amino-3-methylbut-1-yn-1-yl)-1-methyl-4-phenyl-1H-imidazol-5-yl][1,3]thiazolo[5,4-d]pyrimidin-7-amine
2-[2-(3-Methoxyprop-1-yn-1-yl)-1-methyl-4-phenyl-1H-imidazol-5-yl][1,3]thiazolo[5,4-d]pyrimidin-7-amine
2-(1-Methyl-2-morpholin-4-yl-4-phenyl-1H-imidazol-5-yl)[1,3]thiazolo[5,4-d]pyrimidin-7-amine
2-(1-Methyl-4-phenyl-2-pyrimidin-5-yl-1H-imidazol-5-yl)[1,3]thiazolo[5,4-d]pyrimidin-7-amine
2-{2-[3-(Dimethylamino)prop-1-yn-1-yl]-1-methyl-4-phenyl-1H-imidazol-5-yl}[1,3]thiazolo[5,4-d]pyrimidin-7-amine
tert-Butyl 4-[5-(7-amino[1,3]thiazolo[5,4-d]pyrimidin-2-yl)-1-methyl-4-phenyl-1H-imidazol-2-yl]-3,6-dihydropyridine-1(2H)-carboxylate
2-[1-Methyl-4-phenyl-2-(1,2,3,6-tetrahydropyridin-4-yl)-1H-imidazol-5-yl][1,3]thiazolo[5,4-d]pyrimidin-7-amine
[5-(7-Amino[1,3]thiazolo[5,4-d]pyrimidin-2-yl)-1-methyl-4-phenyl-1H-imidazol-2-yl](phenyl)methanol
[5-(7-Amino[1,3]thiazolo[5,4-d]pyrimidin-2-yl)-1-methyl-4-phenyl-1H-imidazol-2-yl](cyclopropyl)methanol
[5-(7-Amino[1,3]thiazolo[5,4-d]pyrimidin-2-yl)-1-methyl-4-phenyl-1H-imidazol-2-yl](1,3-benzodioxol-4-yl)methanol
1-[5-(7-Amino[1,3]thiazolo[5,4-d]pyrimidin-2-yl)-1-methyl-4-phenyl-1H-imidazol-2-yl]-3-methylbutan-1-ol
[5-(7-Amino[1,3]thiazolo[5,4-d]pyrimidin-2-yl)-1-methyl-4-phenyl-1H-imidazol-2-yl](1-methyl-1H-imidazol-2-yl)methanol
2-[5-(7-Amino[1,3]thiazolo[5,4-d]pyrimidin-2-yl)-4-phenyl-1H-imidazol-1-yl]ethanol
2-[1-(2-Methoxyethyl)-4-phenyl-1H-imidazolo-5-yl][1,3]thiazolo[5,4-d]pyrimidin-7-amine
2-[5-(7-Amino[1,3]thiazolo[5,4-d]pyrimidin-2-yl)-4-phenyl-1H-imidazol-1-ylbutan-1-ol
2-(1-Butyl-4-phenyl-1H-imidazol-5-yl)[1,3]thiazolo[5,4-d]pyrimidin-7-amine
2-[1-(1,4-Dioxaspiro[4,5]dec-8-ylmethyl)-4-phenyl-1H-imidazol-5-yl][1,3]thiazolo[5,4-d]pyrimidin-7-amine
4-{[5-(7-Amino[1,3]thiazolo[5,4-d]pyrimidin-2-yl)-4-phenyl-1H-imidazol-1-yl]methyl}cyclohexanol
4-{[5-(7-Amino[1,3]thiazolo[5,4-d]pyrimidin-2-yl)-4-phenyl-1H-imidazol-1-yl]methyl}cyclohexanone
2-[1-(2-morpholin-4-ylbenzyl)-4-phenyl-1H-imidazol-5-yl][1,3]thiazolo[5,4-d]pyrimidin-7-amine
2-{1-[(2-morpholin-4-ylcyclohexyl)methyl]-4-phenyl-1H-imidazol-5-yl)}[1,3]thiazolo[5,4-d]pyrimidin-7-amine
6-[1-(3,4-Dimethoxybenzyl)-4-phenyl-1H-imidazol-5-yl]thieno[2,3-d]pyrimidine
6-(1-Methyl-4-phenyl-1H-imidazol-5-yl)-4-(methylthio)thieno[2,3-d]pyrimidine 6-(1-Methyl-4-phenyl-1H-imidazol-5-yl)thieno[2,3-d]pyrimidin-4-amine
6-[1-(3,4-dimethoxybenzyl)-4-phenyl-1H-imidazol-5-yl]-4-(methylthio)thieno[2,3-d]pyrimidine
6-[1-(3,4-Dimethoxybenzyl)-4-phenyl-1H-imidazol-5-yl]thieno[2,3-d]pyrimidin-4-amine
N-methyl-6-(1-methyl-4-phenyl-1H-imidazol-5-yl)thieno[2,3-d]pyrimidin-4-amine
N-[6-(1-methyl-4-phenyl-1H-imidazol-5-yl)thieno[2,3-d]pyrimidin-4-yl]acetamide
6-[4-(4-Fluorophenyl)-1-methyl-1H-imidazol-5-yl]thieno[2,3-d]pyrimidin-4-amine
6-(1-Benzyl-4-phenyl-1H-imidazol-5-yl)thieno[2,3-d]pyrimidine
6-[4-(3-Iodophenyl)-1-methyl-1H-imidazol-5-yl]thieno[2,3-d]pyrimidin-4-amine
6-[4-(3-Bromophenyl)-1-methyl-1H-imidazol-5-yl]thieno[2,3-d]pyrimidin-4-amine
6-[4-(3-Butoxyphenyl)-1-methyl-1H-imidazol-5-yl]thieno[2,3-d]pyrimidin-4-amine
6-{1-Methyl-4-[3-(4-methylphenylthio)phenyl]-1H-imidazol-5-yl}thieno[2,3-d]pyrimidin-4-amine
6-{4-[4-(Benzyloxy)phenyl]-1-methyl-1H-imidazol-5-yl}thieno[2,3-d]pyrimidin-4-amine
6-{4-[4-Butoxyphenyl]-1-methyl-1H-imidazol-5-yl}thieno[2,3-d]pyrimidin-4-amine
N-{4-[5-(4-aminothieno[2,3-d]pyrimidin-6-yl)-1-methyl-1H-imidazol-4-yl]phenyl}methanesulfonamide
6-(1-ethyl-4-phenyl-1H-imidazol-5-yl)thieno[2,3-d]pyrimidin-4-amine
6-[1-(3-Methoxypropyl)-4-phenyl-1H-imidazol-5-yl]thieno[2,3-d]pyrimidin-4-amine
6-(1-Isobutyl-4-phenyl-1H-imidazol-5-yl)thieno[2,3-d]pyrimidin-4-amine
2-[5-(4-Aminothieno[2,3-d]pyrimidin-6-yl)-4-phenyl-1H-imidazol-1-yl]ethanol
6-(1-Cyclopropyl-4-phenyl-1H-imidazol-5-yl)thieno[2,3-d]pyrimidin-4-amine
6-[1-(2-Methoxyethyl)-4-phenyl-1H-imidazol-5-yl]thieno[2,3-d]pyrimidin-4-amine
6-(1-Butyl-4-phenyl-1H-imidazol-5-yl)thieno[2,3-d]pyrimidin-4-amine
6-[4-Phenyl-1-(pyridin-3-ylmethyl)-1H-imidazol-5-yl]thieno[2,3-d]pyrimidin-4-amine
6-[1-(2,2-Dimethoxyethyl)-4-phenyl-1H-imidazol-5-yl]thieno[2,3-d]pyrimidin-4-amine
6-(4-Phenyl-1-pyrrolidin-3-yl-1H-imidazol-5-yl)thieno[2,3-d]pyrimidin-4-amine
2-[5-(4-aminothieno[2,3-d]pyrimidin-6-yl)-4-phenyl-1H-imidazol-1-yl]hexan-1-ol
2-[5-(4-Aminothieno[2,3-d]pyrimidin-6-yl)-4-phenyl-1H-imidazol-1-yl]butan-1-ol
6-{1-[2-(4-Methylpiperazin-1-yl)ethyl]-4-phenyl-1H-imidazol-5-yl}thieno[2,3-d]pyrimidin-4-amine
2-(1-Ethyl-4-phenyl-1H-imidazol-5-yl)[1,3]thiazolo[5,4-d]pyrimidin-7-amine
2-[1-(cyclohexylmethyl)-4-phenyl-1H-imidazol-5-yl][1,3]thiazolo[5,4-d]pyrimidin-7-amine
6-(1-methyl-4-phenyl-1H-imidazol-5-yl)furo[3,2-d]pyrimidin-4-amine
6-[1-(2-Fluoroethyl)-4-phenyl-1H-imidazol-5-yl]thieno[2,3-d]pyrimidin-4-amine
6-[4-(2-Chlorophenyl)-1-methyl-1H-imidazol-5-yl]thieno[2,3-d]pyrimidin-4-amine
6-[4-(3-Chlorophenyl)-1-methyl-1H-imidazol-5-yl]thieno[2,3-d]pyrimidin-4-amine
6-[4-(4-Chlorophenyl)-1-methyl-1H-imidazol-5-yl]thieno[2,3-d]pyrimidin-4-amine
6-[1-Methyl-4-(2-naphthyl)-1H-imidazol-5-yl]thieno[2,3-d]pyrimidin-4-amine
6-[4-(1-Benzothien-2-yl)-1-methyl-1H-imidazol-5-yl]thieno[2,3-d]pyrimidin-4-amine
6-[4-(3-Fluorophenyl)-1-methyl-1H-imidazol-5-yl]thieno[2,3-d]pyrimidin-4-amine
6-[1-Methyl-4-(2-methylphenyl)-1H-imidazol-5-yl]thieno[2,3-d]pyrimidin-4-amine
6-[4-(2,5-Difluorophenyl)-1-methyl-1H-imidazol-5-yl]thieno[2,3-d]pyrimidin-4-amine
6-[4-(2,5-Dichlorophenyl)-1-methyl-1H-imidazol-5-yl]thieno[2,3-d]pyrimidin-4-amine
6-[1-Methyl-4-(1-naphthyl)-1H-imidazol-5-yl]thieno[2,3-d]pyrimidin-4-amine
6-[4-(1H-Indol-5-yl)-1-methyl-1H-imidazol-5-yl]thieno[2,3-d]pyrimidin-4-amine
6-{4-[4-(Benzyloxy)-2-methylphenyl]-1-methyl-1H-imidazol-5-yl}thieno[2,3-d]pyrimidin-4-amine
6-[1-(Cyclohexylmethyl)-4-phenyl-1H-imidazol-5-yl]-thieno[2,3-d]pyrimidin-4-amine
6-[1-[3-(4-Methyl-1-piperazinyl)propyl]-4-phenyl-1H-imidazol-5-yl]-thieno[2,3-d]pyrimidin-4-amine
6-[1-[3-(Hexahydro-1H-azepin-1-yl)propyl]-4-phenyl-1H-imidazol-5-yl]-thieno[2,3-d]pyrimidin-4-ol
6-[4-phenyl-1-(tetrahydro-2,2-dimethyl-2H-pyran-4-yl)-1H-imidazol-5-yl]-thieno[2,3-d]pyrimidin-4-amine
5-(4-aminothieno[2,3-d]pyrimidin-6-yl)-beta-methyl-4-phenyl-1H-imidazole-1-ethanol
6-[1-(2-methoxy-1-methylethyl)-4-phenyl-1H-imidazol-5-yl]thieno[2,3-d]pyrimidin-4-amine
6-[1-(1-methylethyl)-4-phenyl-1H-imidazol-5-yl]-thieno[2,3-d]pyrimidin-4-amine
6-[1-(1,2-dimethylpropyl)-4-phenyl-1H-imidazol-5-yl]-thieno[2,3-d]pyrimidin-4-amine
6-[1-(1,3-dimethylbutyl)-4-phenyl-1H-imidazol-5-yl]-thieno[2,3-d]pyrimidin-4-amine
6-[4-phenyl-1-(2-propenyl)-1H-imidazol-5-yl]-thieno[2,3-d]pyrimidin-4-amine
6-[4-phenyl-1-(2,2,6,6-tetramethyl-4-piperidinyl)-1H-imidazol-5-yl]-thieno[2,3-d]pyrimidin-4-amine
6-[1-(1-methylpropyl)-4-phenyl-1H-imidazol-5-yl]-thieno[2,3-d]pyrimidin-4-amine
4-[5-(4-aminothieno[2,3-d]pyrimidin-6-yl)-4-phenyl-1H-imidazol-1-yl]-cyclohexanol
6-[4-phenyl-1-[(tetrahydro-2-furanyl)methyl]-1H-imidazol-5-yl]-thieno[2,3-d]pyrimidin-4-amine
6-[1-[2-(4-morpholinyl)ethyl]-4-phenyl-1H-imidazol-5-yl]-thieno[2,3-d]pyrimidin-4-amine
6-[1-[4-(diethylamino)-1-methylbutyl]-4-phenyl-1H-imidazol-5-yl]-thieno[2,3-d]pyrimidin-4-amine
6-[1-[(2-fluorophenyl)methyl]-4-phenyl-1H-imidazol-5-yl]-thieno[2,3-d]pyrimidin-4-amine
6-[1-[(2-methylphenyl)methyl]-4-phenyl-1H-imidazol-5-yl]-thieno[2,3-d]pyrimidin-4-amine
6-[1-[(3-fluorophenyl)methyl]-4-phenyl-1H-imidazol-5-yl]-thieno[2,3-d]pyrimidin-4-amine
5-(4-aminothieno[2,3-d]pyrimidin-6-yl)-alpha-methyl-4-phenyl-1H-imidazole-1-ethanol
3-[5-(4-aminothieno[2,3-d]pyrimidin-6-yl)-4-phenyl-1H-imidazol-1-yl]-1,2-propanediol
6-[1-(2-methylbutyl)-4-phenyl-1H-imidazol-5-yl]-thieno[2,3-d]pyrimidin-4-amine
6-[4-phenyl-1-[2-(phenylamino)ethyl]-1H-imidazol-5-yl]-thieno[2,3-d]pyrimidin-4-amine 5-(4-aminothieno[2,3-d]pyrimidin-6-yl)-4-phenyl-1H-imidazole-1-propanol
6-[1-[3-(dimethylamino)-2,2-dimethylpropyl]-4-phenyl-1H-imidazol-5-yl]-thieno[2,3-d]pyrimidin-4-amine
6-[1-(2-methyl-2-propenyl)-4-phenyl-1H-imidazol-5-yl]-thieno[2,3-d]pyrimidin-4-amine
N-[2-[5-(4-aminothieno[2,3-d]pyrimidin-6-yl)-4-phenyl-1H-imidazol-1-yl]ethyl]-4-hydroxy-benzeneacetamide
6-[1-(2-methoxy-2-methylpropyl)-4-phenyl-1H-imidazol-5-yl]-thieno[2,3-d]pyrimidin-4-amine
6-[4-phenyl-1-(spiro[bicyclo[2.2.1]hept-2-ene-7,1'-cyclopropan]-5-ylmethyl)-1H-imidazol-5-yl]-thieno[2,3-d]pyrimidin-4-amine
6-[1-[2-(3,5-dimethyl-1H-pyrazol-4-yl)ethyl]-4-phenyl-1H-imidazol-5-yl]-thieno[2,3-d]pyrimidin-4-amine
6-[1-[2-(1H-imidazol-1-yl)ethyl]-4-phenyl-1H-imidazol-5-yl]-thieno[2,3-d]pyrimidin-4-amine
6-[1-[2-[[(4-fluorophenyl)methyl]amino]ethyl]-4-phenyl-1H-imidazol-5-yl]-thieno[2,3-d]pyrimidin-4-amine
6-[1-[(3,4-dihydro-1H-2-benzopyran-1-yl)methyl]-4-phenyl-1H-imidazol-5-yl]-thieno[2,3-d]pyrimidin-4-amine
6-[1-[2-(methylsulfonyl)ethyl]-4-phenyl-1H-imidazol-5-yl]-thieno[2,3-d]pyrimidin-4-amine
N-[2-[5-(4-aminothieno[2,3-d]pyrimidin-6-yl)-4-phenyl-1H-imidazol-1-yl]ethyl]-2-[(2-chloro-3-pyridinyl)oxy]-acetamide
6-[4-phenyl-1-[2-[(tetrahydro-1,1-dioxido-3-thienyl)amino]ethyl]-1H-imidazol-5-yl]-thieno[2,3-d]pyrimidin-4-amine
5-(4-aminothieno[2,3-d]pyrimidin-6-yl)-4-phenyl-alpha-(trifluoromethyl)-1H-imidazole-1-ethanol
5-(4-aminothieno[2,3-d]pyrimidin-6-yl)-4-phenyl-alpha-[3-(trifluoromethyl)phenyl]-1H-imidazole-1-ethanol
6-[4-phenyl-1-[2-(2-propenylamino)ethyl]-1H-imidazol-5-yl]-thieno[2,3-d]pyrimidin-4-amine
N-[5-[5-(4-aminothieno[2,3-d]pyrimidin-6-yl)-4-phenyl-1H-imidazol-1-yl]pentyl]-4-morpholinecarboxamide
5-(4-aminothieno[2,3-d]pyrimidin-6-yl)-alpha-(2,3-dihydro-1,4-benzodioxin-6-yl)-4-phenyl-1H-imidazole-1-ethanol
6-[1-[3-[4-(2-methoxyphenyl)-1-piperazinyl]propyl]-4-phenyl-1H-imidazol-5-yl]-thieno[2,3-d]pyrimidin-4-amine
N'-[2-[5-(4-aminothieno[2,3-d]pyrimidin-6-yl)-4-phenyl-1H-imidazol-1-yl]ethyl]-N,N-dimethyl-sulfamide
6-[1-[6-(8-oxa-3-azabicyclo[3.2.1]oct-3-yl)hexyl]-4-phenyl-1H-imidazol-5-yl]-thieno[2,3-d]pyrimidin-4-amine
6-[1-[[2-(4-morpholinyl)phenyl]methyl]-4-phenyl-1H-imidazol-5-yl]-thieno[2,3-d]pyrimidin-4-amine
6-[1-(1,4-dioxan-2-ylmethyl)-4-phenyl-1H-imidazol-5-yl]-thieno[2,3-d]pyrimidin-4-amine
2-[[5-(4-aminothieno[2,3-d]pyrimidin-6-yl)-4-phenyl-1H-imidazol-1-yl]methyl]-(1S,2R)-cyclohexanol
6-[1-(cycloheptylmethyl)-4-phenyl-1H-imidazol-5-yl]-thieno[2,3-d]pyrimidin-4-amine
6-[1-[[(1S,5S)-6,6-dimethylbicyclo[3.1.1]hept-2-yl]methyl]-4-phenyl-1H-imidazol-5-yl]-thieno[2,3-d]pyrimidin-4-amine
1-[[5-(4-aminothieno[2,3-d]pyrimidin-6-yl)-4-phenyl-1H-imidazol-1-yl]methyl]-cyclohexaneacetic acid
6-[4-phenyl-1-(phenylmethyl)-1H-imidazol-5-yl]-thieno[2,3-d]pyrimidin-4-amine
6-[1-[(2-methoxyphenyl)methyl]-4-phenyl-1H-imidazol-5-yl]-thieno[2,3-d]pyrimidin-4-amine
6-[4-phenyl-1-[[2-(1-piperidinyl)phenyl]methyl]-1H-imidazol-5-yl]-thieno[2,3-d]pyrimidin-4-amine
6-[4-phenyl-1-[[2-(2-pyridinyloxy)phenyl]methyl]-1H-imidazol-5-yl]-thieno[2,3-d]pyrimidin-4-amine
6-[1-[[2-(4-methyl-1-piperazinyl)phenyl]methyl]-4-phenyl-1H-imidazol-5-yl]-thieno[2,3-d]pyrimidin-4-amine
1-[2-[[5-(4-aminothieno[2,3-d]pyrimidin-6-yl)-4-phenyl-1H-imidazol-1-yl]methyl]phenyl]-4-piperidinemethanol
6-[1-[(2-aminophenyl)methyl]-4-phenyl-1H-imidazol-5-yl]-thieno[2,3-d]pyrimidin-4-amine
N-[2-[[5-(4-aminothieno[2,3-d]pyrimidin-6-yl)-4-phenyl-1H-imidazol-1-yl]methyl]phenyl]-2,4-dichloro-benzenesulfonamide
6-[1-(1H-Imidazol-2-ylmethyl)-4-phenyl-1H-imidazol-5-yl]-thieno[2,3-d]pyrimidin-4-amine
6-[1-[(6-fluoro-4H-1,3-benzodioxin-8-yl)methyl]-4-phenyl-1H-imidazol-5-yl]-thieno[2,3-d]pyrimidin-4-amine
6-[1-(imidazo[1,2-a]pyridin-2-ylmethyl)-4-phenyl-1H-imidazol-5-yl]-thieno[2,3-d]pyrimidin-4-amine
N-Benzyl-6-(1-methyl-4-phenyl-1H-imidazol-yl)thieno[2,3-d]pyrimidin-4-amine
6-[1-(1-Methylpyrrolidin-3-yl)-4-phenyl-1H-imidazol-5-yl]thieno[2,3-d]pyrimidin-4-amine
tert-Butyl {2-[5-(4-aminothieno[2,3-d]pyrimidin-6-yl)-4-phenyl-1H-imidazol-1-yl]ethyl}carbamate
tert-Butyl {4-[5-(4-aminothieno[2,3-d]pyrimidin-6-yl)-4-phenyl-1H-imidazol-1-yl]butyl}carbamate
6-{4-[3-(Benzyloxy)phenyl]-1-methyl-1H-imidazo-5-yl}thieno[2,3-d]pyrimidin-4-amine
4-[5-(4-Aminothieno[2,3-d]pyrimidin-6-yl)-1-methyl-1H-imidazol-4-yl]phenol
3-[5-(4-Aminothieno[2,3-d]pyrimidin-6-yl)-1-methyl-1H-imidazol-4-yl]benzonitrile
tert-Butyl {3-[5-(4-aminothieno[2,3-d]pyrimidin-6-yl)-1-methyl-1H-imidazol-4-yl]phenyl}carbamate
6-(4-{4-[(3,4-Dichlorobenzyl)oxy]phenyl}-1-methyl-1H-imidazol-5-yl)thieno[2,3-d]pyrimidin-4-amine
N-{3-[5-(4-Aminothieno[2,3-d]pyrimidin-6-yl)-1-methyl-1H-imidazol-4-yl]phenyl}-N'-phenylurea
N-{3-[5-(4-Aminothieno[2,3-d]pyrimidin-6-yl)-1-methyl-1H-imidazol-4-yl]phenyl}-N'-benzylurea
N-{3-[5-(4-Aminothieno[2,3-d]pyrimidin-6-yl)-1-methyl-1H-imidazol-4-yl]phenyl}-N'-[2-fluoro-5-(trifluoromethyl)phenyl]urea
N-{3-[5-(4-Aminothieno[2,3-d]pyrimidin-6-yl)-1-methyl-1H-imidazol-4-yl]phenyl}-N'-phenylurea
N-{3-[5-(4-Aminothieno[2,3-d]pyrimidin-6-yl)-1-methyl-1H-imidazol-4-yl]phenyl}-N'-benzylurea
N-{4-[5-(4-Aminothieno[2,3-d]pyrimidin-6-yl)-1-methyl-1H-imidazo1-4-yl]phenyl}-N'-[2-fluoro-5-(trifluoromethyl)phenyl]urea
6-[1-(4-aminobutyl)-4-phenyl-1H-imidazol-5-yl]-thieno[2,3-d]pyrimidin-4-amine
6-[1-(3-methylbut-2-en-1-yl)-4-phenyl-1H-imidazol-5-yl]-thieno[2,3-d]pyrimidin-4-amine
6-[4-(4-fluorophenyl)-1-(2-morpholin-4-ylbenzyl)-1H-imidazol-5-yl]thieno[2,3-d]pyrimidin-4-amine
phenyl {3-[5-(4-aminothieno[2,3-d]pyrimidin-6-yl)-1-methyl-1H-imidazol-4-yl]phenyl}carbamate or
benzyl {3-[5-(4-aminothieno[2,3-d]pyrimidin-6-yl)-1-methyl-1H-imidazol-4-yl]phenyl}carbamate
or a pharmaceutically acceptable salt thereof.

5. A pharmaceutical composition which comprises a compound of the Formula I, or a pharmaceutically acceptable salt thereof, as defined in claim 1 in association with a pharmaceutically-acceptable diluent or carrier.

6. A compound according to claim 1 in which A is selected from —CH=C*—O—, —O—C*=CH—, —CH=C*—S—, —S—C*=CH—, —CH=C*—NH—, —NH—C*=CH—, —N=C*—NH—, —NH—C*=N—, —O—C*=N—, —N=C*—O—, —S—C*=N— and —N=C*—S— wherein * indicates the atom which forms the bond to the ring containing G in Formula I.

7. A compound according to claim 1 in which A is selected from —CH=C*—O—, —O—C*=CH, —CH=C*—S—, —S—C*=CH—, —NH—C*=CH—, —N=C*—NH—, —NH—C*=N—, —O—C*=N—, —N=C*—O—, —S—C*=N— and —N=C*—S— wherein * indicates the atom which forms the bond to the ring containing G in Formula I.

8. A compound according to claim 1 in which A is selected from —CH=C*—S—, —N=C*—NH— and —N=C*—S— wherein * indicates the atom which forms the bond to the ring containing G in Formula I.

9. A compound according to claim 1 in which G is $NR^5$.

10. A compound according to claim 1 in which Z is N.

11. A compound according to claim 1 in which $Q^1$ is selected from phenyl and naphthyl optionally substituted by 1, 2 or 3 substituents selected from fluoro, chloro, bromo, methyl, ethyl, methoxy and ethoxy.

12. A compound according to claim 1 in which $Q^1$ is phenyl.

13. A compound according to claim 1 in which $R^1$ is selected from hydrogen, cyano, hydroxy, amino, mercapto, (1-6C)alkyl, (1-6C)alkoxy, (1-6C)alkylthio, (1-6C)alkylsulfinyl, (1-6C)alkylsulfonyl and (1-6C)alkylamino.

14. A compound according to claim 1 in which $R^2$ is selected from hydrogen and (1-3C)alkyl.

15. A compound according to claim 1 in which $R^4$ and $R^6$, which may be the same or different, are selected from hydrogen, cyano, nitro, hydroxy, halogeno, mercapto, amino, carbamoyl, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino.

16. A compound according to claim 1 in which $R^4$ is hydrogen.

17. A compound according to claim 1 in which $R^6$ is hydrogen.

18. A compound according to claim 1, wherein $Q^1$ is a group of the formula:

$-Q^{1a}-X^2-Q^2$ wherein $Q^{1a}$ is phenyl which is optionally substituted by 1 or 2 substituents which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl; and $X^2$ is a direct bond or is selected from O, S, $SO_2$, $N(R^9)$, CO, $CON(R^9)$, $N(R^9)CO$, $N(R^9)CON(R^9)$, $SO_2N(R^9)$, $N(R^9)SO_2$, $C(R^9)_2O$, $C(R^9)_2S$ and $N(R^9)C(R^9)_2$, wherein $R^9$ is hydrogen or (1-3C)alkyl, and $Q^2$ is phenyl, phenyl-(1-3C)alkyl, thienyl, orthienyl-(1-3C)alkyl, and wherein $Q^2$ optionally bears 1, 2 or 3 substituents, which may be the same or different, selected from fluoro, chloro, bromo, trifluoromethyl, trifluoromethoxy, cyano, nitro, hydroxy, amino, carboxy, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, N-(1-3C)alkylsulfamoyl and N,N-di-[(1-3C)alkyl]sulfamoyl.

\* \* \* \* \*